US012637691B2

(12) United States Patent
Doudna et al.

(10) Patent No.: US 12,637,691 B2
(45) Date of Patent: *May 26, 2026

(54) RNA-GUIDED NUCLEIC ACID MODIFYING ENZYMES AND METHODS OF USE THEREOF

(71) Applicant: The Regents of the University of California, Oakland, CA (US)

(72) Inventors: Jennifer A. Doudna, Berkeley, CA (US); Jillian F. Banfield, Berkeley, CA (US); David Burstein, Berkeley, CA (US); Lucas Benjamin Harrington, Berkeley, CA (US); Steven C. Strutt, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/513,347

(22) Filed: Nov. 17, 2023

(65) Prior Publication Data

US 2024/0167052 A1     May 23, 2024

Related U.S. Application Data

(63) Continuation of application No. 16/335,516, filed as application No. PCT/US2017/054081 on Sep. 28, 2017, now Pat. No. 11,873,504.

(60) Provisional application No. 62/402,846, filed on Sep. 30, 2016.

(51) Int. Cl.
| | |
|---|---|
| *C12N 15/85* | (2006.01) |
| *C07K 19/00* | (2006.01) |
| *C12N 9/10* | (2006.01) |
| *C12N 9/22* | (2006.01) |
| *C12N 15/10* | (2006.01) |
| *C12N 15/113* | (2010.01) |
| *C12N 15/52* | (2006.01) |
| *C12N 15/62* | (2006.01) |
| *C12N 15/74* | (2006.01) |
| *C12N 15/86* | (2006.01) |
| *C12N 15/88* | (2006.01) |
| *C12N 15/90* | (2006.01) |

(52) U.S. Cl.
CPC .......... *C12N 15/8509* (2013.01); *C07K 19/00* (2013.01); *C12N 9/1007* (2013.01); *C12N 9/1025* (2013.01); *C12N 9/22* (2013.01); *C12N 15/102* (2013.01); *C12N 15/113* (2013.01); *C12N 15/52* (2013.01); *C12N 15/62* (2013.01); *C12N 15/74* (2013.01); *C12N 15/85* (2013.01); *C12N 15/86* (2013.01); *C12N 15/88* (2013.01); *C12N 15/902* (2013.01); *C07K 2319/02* (2013.01); *C07K 2319/03* (2013.01); *C07K 2319/06* (2013.01); *C07K 2319/09* (2013.01); *C07K*

*2319/20* (2013.01); *C12N 2310/20* (2017.05); *C12N 2740/13043* (2013.01); *C12N 2740/16043* (2013.01); *C12N 2750/14143* (2013.01)

(58) Field of Classification Search
CPC .............. C12N 15/8509; C12N 9/1007; C12N 9/1025; C12N 9/22; C12N 15/102; C12N 15/113; C12N 15/52; C12N 15/62; C12N 15/74; C12N 15/85; C12N 15/86; C12N 15/88; C12N 15/902; C12N 2310/20; C12N 2740/13043; C12N 2740/16043; C12N 2750/14143; C12N 15/63; C07K 19/00; C07K 2319/02; C07K 2319/03; C07K 2319/06; C07K 2319/09; C07K 2319/20

See application file for complete search history.

(56) References Cited

U.S. PATENT DOCUMENTS

| | | | |
|---|---|---|---|
| 6,773,885 | B1 | 8/2004 | Walder et al. |
| 8,597,886 | B2 | 12/2013 | Smith et al. |
| 8,815,782 | B2 | 8/2014 | Zeiner et al. |
| 9,730,967 | B2 | 8/2017 | Kovarik et al. |
| 9,790,490 | B2 | 10/2017 | Zhang et al. |

(Continued)

FOREIGN PATENT DOCUMENTS

| | | |
|---|---|---|
| CN | 1886512 A | 12/2006 |
| CN | 101283089 A | 10/2008 |

(Continued)

OTHER PUBLICATIONS

Hendel et al. "Chemically modified guide RNAs enhance CRISPR-Cas genome editing in human primary cells." Nature biotechnology 33.9 (2015): 985-989 (Year: 2015).*

(Continued)

*Primary Examiner* — Alexander W Nicol
(74) *Attorney, Agent, or Firm* — Shweta Chandra; Bozicevic, Field & Francis LLP

(57) ABSTRACT

The present disclosure provides CasX proteins, nucleic acids encoding the CasX proteins, and modified host cells comprising the CasX proteins and/or nucleic acids encoding same. CasX proteins are useful in a variety of applications, which are provided. The present disclosure provides CasX guide RNAs that bind to and provide sequence specificity to the CasX proteins, nucleic acids encoding the CasX guide RNAs, and modified host cells comprising the CasX guide RNAs and/or nucleic acids encoding same. CasX guide RNAs are useful in a variety of applications, which are provided. The present disclosure provides archaeal Cas9 polypeptides and nucleic acids encoding same, as well as their associated archaeal Cas9 guide RNAs and nucleic acids encoding same.

22 Claims, 58 Drawing Sheets

Specification includes a Sequence Listing.

(56) References Cited

U.S. PATENT DOCUMENTS

| | | | |
|---|---|---|---|
| 10,253,365 | B1 | 4/2019 | Doudna et al. |
| 10,266,886 | B2 | 4/2019 | Abudayyeh et al. |
| 10,316,324 | B2 | 6/2019 | Begemann et al. |
| 10,337,051 | B2 | 7/2019 | Doudna et al. |
| 10,494,664 | B2 | 12/2019 | Doudna et al. |
| 10,570,415 | B2 | 2/2020 | Doudna et al. |
| 11,180,743 | B2 | 11/2021 | Doudna et al. |
| 11,371,031 | B2 | 6/2022 | Doudna et al. |
| 11,371,062 | B2 | 6/2022 | Doudna et al. |
| 11,441,137 | B2 | 9/2022 | Doudna et al. |
| 11,453,866 | B2 | 9/2022 | Doudna et al. |
| 11,459,599 | B2 | 10/2022 | Doudna et al. |
| 11,459,600 | B2 | 10/2022 | Doudna et al. |
| 11,739,335 | B2 | 8/2023 | Chevessier-Tünnesen et al. |
| 11,795,472 | B2 | 10/2023 | Doudna et al. |
| 11,827,919 | B2 | 11/2023 | Doudna et al. |
| 11,840,725 | B2 | 12/2023 | Doudna et al. |
| 11,873,504 | B2 | 1/2024 | Doudna et al. |
| 11,970,719 | B2 | 4/2024 | Doudna et al. |
| 2012/0252876 | A1 | 10/2012 | Tenenbaum et al. |
| 2013/0123129 | A1 | 5/2013 | Zeiner et al. |
| 2013/0261196 | A1 | 10/2013 | Diamond et al. |
| 2014/0068797 | A1 | 3/2014 | Doudna et al. |
| 2014/0093883 | A1 | 4/2014 | Maples et al. |
| 2014/0273226 | A1 | 9/2014 | Wu |
| 2015/0020223 | A1 | 1/2015 | Zhang et al. |
| 2015/0211058 | A1 | 7/2015 | Carstens |
| 2016/0017366 | A1 | 1/2016 | Chen et al. |
| 2016/0138008 | A1 | 5/2016 | Charpentier et al. |
| 2016/0208243 | A1 | 7/2016 | Zhang et al. |
| 2016/0289659 | A1 | 10/2016 | Doudna et al. |
| 2017/0037432 | A1 | 2/2017 | Donohoue et al. |
| 2017/0051276 | A1 | 2/2017 | May et al. |
| 2017/0175104 | A1 | 6/2017 | Doudna et al. |
| 2017/0198277 | A1 | 7/2017 | Kmiec et al. |
| 2017/0211142 | A1 | 7/2017 | Smargon et al. |
| 2017/0233756 | A1* | 8/2017 | Begemann ........... C12N 15/102 800/295 |
| 2017/0306335 | A1 | 10/2017 | Zhang et al. |
| 2017/0321198 | A1 | 11/2017 | Severinov et al. |
| 2017/0321214 | A1 | 11/2017 | Zhang et al. |
| 2017/0362644 | A1 | 12/2017 | Doudna et al. |
| 2017/0369870 | A1* | 12/2017 | Gill ................... C12N 15/1065 |
| 2018/0148735 | A1 | 5/2018 | Begemann et al. |
| 2018/0201921 | A1 | 7/2018 | Malcolm |
| 2018/0208976 | A1 | 7/2018 | Doudna et al. |
| 2018/0208977 | A1 | 7/2018 | Doudna et al. |
| 2018/0320163 | A1 | 11/2018 | Koonin et al. |
| 2018/0340218 | A1 | 11/2018 | Abudayyeh et al. |
| 2019/0177775 | A1 | 6/2019 | Doudna et al. |
| 2019/0185933 | A1 | 6/2019 | Zhang et al. |
| 2019/0276842 | A1 | 9/2019 | Doudna et al. |
| 2019/0300908 | A1 | 10/2019 | Doudna et al. |
| 2020/0010878 | A1 | 1/2020 | Doudna et al. |
| 2020/0010879 | A1 | 1/2020 | Doudna et al. |
| 2020/0017879 | A1 | 1/2020 | Doudna et al. |
| 2020/0087640 | A1 | 3/2020 | Doudna et al. |
| 2020/0115688 | A1 | 4/2020 | Doudna et al. |
| 2020/0172886 | A1 | 6/2020 | Doudna et al. |
| 2020/0255858 | A1 | 8/2020 | Doudna et al. |
| 2020/0299660 | A1 | 9/2020 | Doudna et al. |
| 2020/0339967 | A1 | 10/2020 | Doudna et al. |
| 2020/0370028 | A1 | 11/2020 | Doudna et al. |
| 2021/0017508 | A1 | 1/2021 | Doudna et al. |
| 2021/0024942 | A1 | 1/2021 | Chen et al. |
| 2021/0166783 | A1 | 6/2021 | Shmakov et al. |
| 2021/0209981 | A1 | 7/2021 | Wang |
| 2021/0214697 | A1 | 7/2021 | Doudna et al. |
| 2021/0284981 | A1 | 9/2021 | Doudna et al. |
| 2021/0309981 | A1 | 10/2021 | Doudna et al. |
| 2022/0396812 | A1 | 12/2022 | Doudna et al. |
| 2023/0332218 | A1 | 10/2023 | Rauch et al. |
| 2023/0348872 | A1 | 11/2023 | Doudna et al. |
| 2024/0182953 | A1 | 6/2024 | Doudna et al. |
| 2024/0301376 | A1 | 9/2024 | Doudna et al. |

FOREIGN PATENT DOCUMENTS

| | | | |
|---|---|---|---|
| CN | 103088128 | A | 5/2013 |
| CN | 104620107 | A | 5/2015 |
| CN | 106701830 | A | 5/2017 |
| EP | 1580273 | A1 | 9/2005 |
| EP | 3009511 | A2 | 4/2016 |
| EP | 2825654 | B1 | 4/2017 |
| EP | 3546573 | A1 | 10/2019 |
| EP | 3283625 | B1 | 12/2019 |
| EP | 3665279 | A1 | 6/2020 |
| JP | 2004521606 | A | 7/2004 |
| WO | WO 2014065596 | A1 | 5/2014 |
| WO | WO 2015/071474 | | 5/2015 |
| WO | WO 2015089486 | A2 | 6/2015 |
| WO | WO 2015/139139 | | 9/2015 |
| WO | WO 2015/191693 | | 12/2015 |
| WO | WO 2016/094872 | | 12/2015 |
| WO | WO 2016/106236 | | 12/2015 |
| WO | WO 2016/028843 | | 2/2016 |
| WO | WO 2016/094867 | | 6/2016 |
| WO | WO 2016/205711 | | 6/2016 |
| WO | WO 2016/123243 | | 8/2016 |
| WO | WO 2016166340 | A1 | 10/2016 |
| WO | WO 2016183402 | A2 | 11/2016 |
| WO | WO 2016/205613 | | 12/2016 |
| WO | WO 2016/205749 | | 12/2016 |
| WO | WO 2016/205764 | | 12/2016 |
| WO | WO 2017/070605 | | 4/2017 |
| WO | WO 2017/205668 | | 5/2017 |
| WO | WO 2017/120410 | | 7/2017 |
| WO | WO 2017/147345 | | 8/2017 |
| WO | WO 2017/176529 | | 10/2017 |
| WO | WO 2017/218573 | | 12/2017 |
| WO | WO 2017/219027 | | 12/2017 |
| WO | WO 2017/223538 | | 12/2017 |
| WO | WO 2017207589 | | 12/2017 |
| WO | WO 2018027078 | A1 | 2/2018 |
| WO | WO 2018035250 | A1 | 2/2018 |
| WO | WO 2018/064352 | | 4/2018 |
| WO | WO 2018/064371 | | 4/2018 |
| WO | WO 2018/107129 | | 6/2018 |
| WO | WO 2018152418 | A1 | 8/2018 |
| WO | WO 2018/172556 | | 9/2018 |
| WO | WO 2018/195545 | | 10/2018 |
| WO | WO 2018202800 | | 11/2018 |
| WO | WO 2019/030695 | | 2/2019 |
| WO | WO 2019/089796 | | 5/2019 |
| WO | WO 2019/089804 | | 5/2019 |
| WO | WO 2019/089808 | | 5/2019 |
| WO | WO 2019/089820 | | 5/2019 |
| WO | WO 2019/126577 | | 6/2019 |
| WO | WO 2019222555 | A1 | 11/2019 |
| WO | WO 2020023529 | A1 | 1/2020 |
| WO | WO 2020098772 | A1 | 5/2020 |

OTHER PUBLICATIONS

Pausch, et al., "DNA Interference States of the Hypercompact CRISPR-Casɸ Effector", Nat Struct Mol Biol., Aug. 2021, 28(8):652-661.

Abudayyeh, et al.; "C2c2 is a single-component programmable RNA-guided RNA-targeting CRISPR effector; Supplementary Information"; Science; vol. 353, vol. 6299, 31 pages (Aug. 5, 2016).

Abudayyeh, et al.; "C2c2 is a single-component programmable RNA-guided RNA-targeting CRISPR effector"; Science; vol. 353, No. 6299, 23 pages (Aug. 5, 2016).

Abudayyeh, et al.; "RNA targeting with CRISPR-Cas13"; Nature; vol. 550, 18 pages (Oct. 12, 2017).

Ambion; "RnaseAlert Lab Test Kit v2, User Guide"; 12 pages (Mar. 1, 2013).

Anantharaman, et al.; "Thousands of microbial genomes shed light on interconnected biogeochemical processes in an aquifer system"; Nature Communications; vol. 7, No. 13210, 11 pages (Oct. 24, 2016).

Applied Biosystems/Ambion; "RNaseAlert Lab Test Kit"; 12 pages (2008).

(56)     References Cited

OTHER PUBLICATIONS

Armitage, et al.; "Hairpin-Forming Peptide Nucleic Acid Oligomers"; Biochemistry; vol. 37, No. 26, pp. 9417-9425 (1998).

Baker, et al.; "Enigmatic, ultrasmall, uncultivated Archaea"; PNAS; vol. 107, No. 19, pp. 8806-8811 (May 11, 2010).

Barrangou, et al.; "Expanding the CRISPR Toolbox: Targeting RNA with Cas13b"; Molecular Cell; vol. 65, No. 4, pp. 582-584 (Feb. 16, 2017).

Bautista, et al.; "Virus-Induced Dormancy in the Archaeon Sulfolobus islandicus"; mBio; vol. 6, No. 2, 8 pages (2015).

Burstein, et al.; "Major bacterial lineages are essentially devoid of CRISPR-Cas viral defence systems"; Nature Communications; vol. 7, No. 10613, 8 pages (Feb. 3, 2016).

Burstein, et al.; "New CRISPR-Cas systems from uncultivated microbes"; Nature; vol. 542, No. 7640, pp. 237-241 (Feb. 9, 2017).

Chen, et al.; "CRISPR-Cas12a target binding unleashes indiscriminate single-stranded DNase activity"; Science; vol. 360, pp. 436-439 (2018).

Choudhury, et al.; "CRISPR-dCas9 mediated TET1 targeting for selective DNA demethylation at BRCA1 promoter"; Oncotarget; vol. 7, No. 29, pp. 46545-46556 (2016).

Chylinski, et al.; "Classification and evolution of type II CRISPR-Cas systems"; Nucleic Acids Research; vol. 42, No. 10, pp. 6091-6105 (2014).

Clustl; "Omega Multiple Sequence Alignment. https://www.ebi.ac.uk/Tools/msa/clustalo/" [Retrieved from internet Feb. 2, 2022]. Alignment and Percent identity matrix. (Year: 2022).

Cong, et al.; "Multiplex Genome Engineering Using CRISPR/Cas Systems"; Science; vol. 339, No. 6121, pp. 819-823 (Feb. 15, 2013).

Cox, et al.; "RNA editing with CRISPR-Cas13"; Science; vol. 358, No. 6366, 15 pages (Nov. 24, 2017).

CRZ3554.1 (hypothetical protein HHT344_2368 [Herbinix hemicellulosilytica], Gen Bank Accession sequence, priority to Jul. 24, 2015, 1 page) (Year: 2015).

Deltcheva, et al.; "CRISPR RNA maturation by trans-encoded small RNA and host factor RNase III"; Nature; vol. 471, pp. 1-19 (Mar. 31, 2011).

East-Seletsky, et al.; "RNA Targeting by Functionally Orthogonal Type VI-A CRISPR-Cas Enzymes"; Molecular Cell; vol. 66, pp. 373-383 (May 4, 2017).

East-Seletsky, et al.; "Two distinct Rnase activities of CRISPR-C2c2 enable guide-RNA processing and RNA detection"; Nature; vol. 538, Issue 7624, pp. 270-273 (Oct. 13, 2016).

Extended European Search Report for European Patent Application No. 17857442.2 with a mailing date of Jan. 1, 2020.

Fonfara, et al.; "Phylogeny of Cas9 determines functional exchangeability of dual-RNA and Cas9 among orthologous type II CRISPR-Cas systems"; Nucleic Acids Research; vol. 42, No. 4, pp. 2577-2590 (2014).

GenBank CRL33181.1; Hypothetical protein T1815_05231 [[Eubacterium] rectale], priority to Apr. 6, 2016, 2 pages (Year: 2016).

GenBank CRZ35554 1; "Hypothetical protein HHT355_2368 [Herbinix hemicellulosilytica]"; 1 page (Oct. 11, 2018).

GenBank KU516197.1; "Uncultured bacterium GWB1_scaffold_10668 CRISPR-Cas system-like gene, complete sequence"; 4 pages (2016).

GenBank OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).

Gootenberg, et al.; "Multiplexed and portable nucleic acid detection platform with Cas13, Cas12a, and Csm6"; Science; vol. 360, pp. 439-444 (2018).

Gootenberg, et al.; "Nucleic acid detection with CRISPR-Cas13a/C2c2"; Science; 9 pages (Apr. 13, 2017).

Hale, et al.; "RNA-Guided RNA Cleavage by a CRISPR RNA-Cas Protein Complex"; Cell; vol. 139, No. 5, pp. 945-956 (Nov. 25, 2009).

Hale, et al.; "Target RNA capture and cleavage by the Cmr type III-B CRISPR-Cas effector complex"; Genes & Development; vol. 28, No. 21, pp. 2432-2443 (Nov. 1, 2014).

Harrington, et al.; "Programmed DNA destruction by miniature CRISPR-Cas14 enzymes"; Science; vol. 362, pp. 839-842 (Nov. 16, 2018).

Hooton et al. "The Bacteriophage Carrier State of Campylobacter jejuni Features Changes in Host Non-coding RNAs and the Acquisition of New Host-derived CRISPR Spacer Sequences," Frontiers in Microbiology; vol. 7, Article 355, pp. 1-8 (Mar. 23, 2016).

Hyun, et al.; "Site-directed mutagenesis in Arabidopsis thaliana using dividing tissue-targeted RGEN of the CRISPR/Cas system to generate heritable null alleles"; Planta; vol. 241, pp. 271-284 (Jan. 2015).

Karvelis, et al.; "PAM recognition by miniature CRISPR-Cas12f nucleases triggers programmable double-stranded DNA target cleavage"; Nucleic Acids Research; pp. 1-8 (2020).

Kelemen, et al.; "Hypersensitive substrate for ribonucleases"; Nucleic Acids Research; vol. 27, No. 18, pp. 3696-3701 (1999).

Kim, et al.; "Specific and sensitive detection of nucleic acids and RNases using gold nanoparticle-RNA-fluorescent dye conjugates"; Chemical Communications; vol. 14, No. 42, pp. 4342-4344 (Sep. 19, 2007).

Knott, et al.; "Guide-bound structures of an RNA-targeting A-cleaving CRISPR-Cas13a enzyme"; Nature Structural & Molecular Biology; vol. 24, No. 10, 13 pages (Oct. 2017).

Kodak (Gel Logic 100 System User's Guide, 2005, 98 pages) (Year: 2005).

Koonin, et al.; "CRISPR-Cas: an adaptive immunity system in prokaryotes"; F1000 Biology Reports; vol. 1, No. 95, 6 pages (Dec. 9, 2009).

Koonin, et al.; "Diversity, classification and evolution of CRISPR-Cas systems"; Current Opinion in Microbiology; vol. 37, pp. 67-78 (2017).

Koonin, et al.; "Origins and evolution of CRISPR-Cas systems"; Phil. Trans. R. Soc. B.; vol. 374, No. 1772, 6 pages (Mar. 25, 2019).

Lander et al.; "Genome Editing by CRISPR/Cas9: a Game Change in the Genetic Manipulation of Protists"; J Eukaryot Microbial.; vol. 63, No. 5, pp. 679-690 (Sep. 2016).

Le Cong, et al.; "Multiplex Genome Engineering Using CRISPR/Cas Systems"; Science; vol. 339, pp. 819-823 (Feb. 15, 2013).

Li, et al.; "Using molecular beacons as a sensitive fluorescence assay for enzymatic cleavage of single-stranded DNA"; Nucleic Acids Research; vol. 28, No. 11, 6 pages (2000).

Liu, et al.; "Delivery strategies of the CRISPR-Cas9 gene-editing system for therapeutic applications"; Journal of Controlled Release; vol. 266, pp. 17-26 (2017).

Liu, et al.; "CasX enzymes comprise a distinct family of RNA-guided genome editors"; Nature; vol. 566, pp. 23 pages (Feb. 14, 2019).

Liu, et al.; "The Molecular Architecture for RNA-Guided RNA Cleavage by Cas13a"; Cell; vol. 170, pp. 714-126 (Aug. 10, 2017).

Liu, et al.; "Two Distant Catalytic Sites Are Responsible for C2c2 RNase Activities"; Cell; vol. 168, pp. 121-134 (Jan. 12, 2017).

Makarova, et al.; "An updated evolutionary classification of CRISPR-Cas systems"; Nat. Rev. Microbiol.; vol. 13, No. 11, pp. 722-736 (Nov. 2015).

Makarova, et al.; "Evolutionary classification of CRISPR-Cas systems: a burst of class 2 and derived variants"; Nature Reviews Microbiology; vol. 18, pp. 67-83 (Feb. 2020).

Makarova, et al.; "SnapShot: Class 2 CRISPR-Cas Systems"; Cell; vol. 168, 2 pages (Jan. 12, 2017).

Mohanraju, et al.; "Diverse evolutionary roots and mechanistic variations of the CRISPR-Cas systems"; Science; vol. 353, No. 6299, 14 pages (Aug. 5, 2016).

NCBI Accession No. KZX85786 (May 2, 2016), May 2, 2016, 2 pages.

NCBI Reference Sequence: WP_012985477.1 (May 18, 2013).

NCBI Reference Sequence: WP_015770004.1 (May 20, 2013).

NCBI Reference Sequence: WP_021746003.1 (Sep. 24, 2013).

NCBI Reference Sequence: WP_021746774.1 (Sep. 24, 2013).

NCBI Reference Sequence: WP_021747205.1 (Sep. 24, 2013).

NCBI Reference Sequence: WP_023911507.1 (Oct. 23, 2013).

(56)          References Cited

OTHER PUBLICATIONS

NCBI Reference Sequence: WP_034560163.1 (Oct. 22, 2015).

Ngo, et al.; "Computational Complexity, Protein Structure Prediction, and the Levinthal Paradox"; The Protein Folding Problem and Tertiary Structure Prediction; pp. 433 and 492-495 (1994).

O'Connell; "Molecular Mechanisms of RNA Targeting by Cas13-containing Type VI CRISPR-Cas Systems"; J Mol Biol; vol. 431, pp. 66-87 (2019).

OHA03494.1 (hypothetical protein A3J58_03210 [Candidatus Sung bacteria bacterium RIFCSPH IGHO2_02_FULL_52_23], NCBI Reference Sequence, priority to Oct. 21, 2016, 2 pages) (Year: 2016).

Price, et al.; "Cas9-mediated targeting of viral RNA in eukaryotic cells"; PNAS; vol. 112, No. 19, pp. 6164-6169 (May 12, 2015).

RNaseAlert Lab Test Kit (Applied Biosystems, Fluorometric RNase Detection Assay, 2008, 12 pages). (Year: 2008).

Sampson, et al.; "A CRISPR/Cas system mediates bacterial innate immune evasion and virulence"; Nature; vol. 497, No. 7448; pp. 254-257 (May 9, 2013).

Sato, et al.; "Highly Sensitive Nuclease Assays Based on Chemically Modified DNA or RNA"; Sensors; vol. 14, No. 7, pp. 12437-12450 (2014).

Sawamura, et al.; "Generation of biallelic FO mutants in medaka using theCRISPR/Cas9 system"; Genes to Cells; No. 22, pp. 756-763 (2017).

Shmakov, et al.; "Discovery and functional characterization of diverse Class 2 CRISPR-Cas systems"; Mol. Cell.; vol. 60, No. 3, pp. 385-397 (Nov. 5, 2015).

Shmakov, et al.; "Diversity and evolution of class 2 CRISPR-Cas systems"; Nature Reviews Microbiology; vol. 15, pp. 169-182 (2017).

Smargon, et al.; "Cas13b is a Type VI-B CRISPR-associated RNA-Guided RNAse differentially regulated by accessory proteins Csx27 and Csx28"; Molecular Cell; vol. 65, No. 4, pp. 618-630 (Feb. 16, 2017).

Stella, et al.; "Class 2 CRISPR-Cas RNA-guided endonucleases: Swiss Army knives of genome editing"; Nature Structural & Molecular Biology; vol. 24, No. 11, pp. 882-892 (Nov. 2017).

Stephen Floor; "CV"; 6 pages (Jun. 11, 2018).

Stephen Floor; "Tweets cited in third party observation filed on Oct. 15, 2018"; 1 page (date of tweets are May 21, 2016).

Strauß, et al.; "Zinc Fingers, TAL Effectors, or Cas9-Based DNA Binding Proteins: What's Best for Targeting Desired Genome Loci?"; Molecular Plant; vol. 6, No. 5, pp. 1384-1387 (Sep. 2013).

Third Party Observations filed on Oct. 15, 2018 in UK patent application No. GB 1804822.3 (18 pages).

Wright, et al.; "Biology and Applications of CRISPR Systems: Harnessing Nature's Toolbox for Genome Engineering"; Cell; vol. 164, pp. 29-44 (2016).

Wright, et al.; "Rational design of a split-Cas9 enzyme complex"; PNAS; vol. 112, No. 10, pp. 2984-2989 (Mar. 10, 2015).

Xie et al. "RNA-Guided Genome Editing in Plants Using a CRISPR-Cas System." Molecular Plant, vol. 6, No. 6 , pp. 1975-1983, Nov. 2013.

Yamano, et al.; "Crystal Structure of Cpf1 in Complex with Guide RNA and Target DNA"; Cell; vol. 165, pp. 949-962 (2016).

Yan, et al.; "Cas13d Is a Compact RNA-Targeting Type VI CRISPR Effector Positively Modulated by a WYL-Domain-Containing Accessory Protein"; Molecular Cell; vol. 70, pp. 327-339 (2018).

Yang, et al.; "Using Molecular Beacons for Sensitive Fluorescence Assays of the Enzymatic Cleavage of Nucleic Acids"; Methods in Molecular Biology, Fluorescent Energy Transfer Nucleic Acid Probes: Designs and Protocols; vol. 335, pp. 71-81 (2006).

Yang, et al.; "New CRISPR-Cas systems discovered"; Cell Res.; vol. 27, pp. 313-314 (Feb. 21, 2017).

Zetsche, et al.; "Cpf1 Is a Single RNA-Guided Endonuclease of a Class 2 CRISPR-Cas System"; Cell; vol. 163, pp. 759-771 (Oct. 22, 2015).

Zhang, et al.; "Design of a Molecular Beacon DNA Probe with Two Fluorophores"; Angew. Chem.; vol. 113, No. 2, pp. 416-419 (2001).

Harrington et al., (2020) "A scoutRNA Is Required for Some Type V CRISPRCas Systems." Molecular Cell, vol. 79, pp. 416-424.

"How to Choose the Right Cas Variant for Every CRISPR Experiment", Synthego, Chapter 5, Retrieved from the internet <https://www.synthego.com/guide/how-to-use-crispr/cas9-nuclease-variants> on Sep. 11, 2024, , 17 pages.

"Transposase", JGI Accession No. (Taxon ID:Gene ID) 3300013127.a:Ga0172365_100044211, Nov. 5, 2021, 2 pages.

"Transposase", JGI Accession No. (Taxon ID:Gene ID) 3300013123.a:Ga0172368_100090142, Nov. 5, 2021, 2 pages.

"Transposase", JGI Accession No. (Taxon ID:Gene ID) 3300025317.a:Ga0209541_ 1000016152, Nov. 5, 2021, 2 pages.

"Transposase", JGI Accession No. (Taxon ID:Gene ID) 3300025317.a:Ga0209541_1000046133, Nov. 5, 2021, 1 pages.

"Transposase", JGI Accession No. (Taxon ID:Gene ID) 3300013125.a:Ga0172369_100104642, Nov. 5, 2021, 2 pages.

"Transposase", JGI Accession No. (Taxon ID:Gene ID) 3300013130.a:Ga0172363_100165517, Nov. 5, 2021, 2 pages.

"Transposase", JGI Accession No. (Taxon ID:Gene ID) 3300025317.a:Ga0209541_100217848, Nov. 5, 2021, 2 pages.

"Transposase", JGI Accession No. (Taxon ID:Gene ID) 3300025323.a:Ga0209542_100271699, Nov. 5, 2021, 2 pages.

"Transposase", JGI Accession No. 3300025142.a:Ga0210019_10421012, Sep. 1, 2021, 2 pages.

"Transposase", JGI Accession No. 3300025308.a:Ga0209211_100536734, Nov. 9, 2021, 2 pages.

"Transposase", JGI Accession No. 3300025317.a:Ga0209541_100096836, Nov. 9, 2021, 2 pages.

"Transposase", JGI Accession No. 3300025323.a:Ga0209542_1000010711, Nov. 9, 2021, 2 pages.

"Transposase", JGI Accession No. 3300025323.a:Ga0209542_10000107204, Nov. 9, 2021, 2 pages.

"Transposase and inactivated derivatives", JGI Accession No. (Taxon ID: Gene ID) 3300000353.a:ElkS_mat_MD6ADRAFT_10068983, Nov. 5, 2021, 2 pages.

"Transposase and inactivated derivatives", JGI Accession No. 3300002105.a:C687J26635_100228363, Nov. 9, 2021, 2 pages.

"Transposase and inactivated derivatives", JGI Accession No. (Taxon ID:Gene ID) 3300002966.a:JGI24721J44947_100297402, Nov. 5, 2021, 2 pages.

"Transposase and inactivated derivatives", JGI Accession No. (Taxon ID:Gene ID) 3300002502.a:C687J35174_100502431, Nov. 5, 2021, 2 pages.

"Transposase and inactivated derivatives", JGI Accession No. (Taxon ID:Gene ID) 3300001245.a:JGI12048J13642_102012859, Nov. 5, 2021, 2 pages.

"Transposase and inactivated derivatives", JGI Accession No. (Taxon ID:Gene ID) 3300001245.a:JGI12048J13642_102012865, Nov. 5, 2021, 2 pages.

"Transposase and inactivated derivatives", JGI Accession No. (Taxon ID:Gene ID) 3300001256.a:JGI12210J13797_103875826, Nov. 5, 2021, 2 pages.

"Transposase and inactivated derivatives", JGI Accession No. (Taxon ID:Gene ID) 3300001256.a:JGI12210J13797_103875833, Nov. 5, 2021, 2 pages.

"Transposase and inactivated derivatives", JGI Accession No. (Taxon ID:Gene ID) 3300005573.a:Ga0078972_100101520, Nov. 5, 2021, 1 page.

"Transposase and inactivated derivatives", JGI Accession No. 3300002502.a:C687J35174_100538264, Sep. 1, 2021, 2 pages.

Bhattacharya et al., "Impact of genetic variation on three dimensional structure and function of proteins", PLoS One, Mar. 15, 2017, 12(3):e0171355:1-22.

Bork et al., "Go hunting in sequence databases but watch out for the traps", Trends in Genetics, Oct. 1996, 12(10):425-427.

Bork, P., "Powers and pitfalls in sequence analysis: the 70% hurdle", Genome Research, Apr. 2000, 10(4):398-400.

Brenner et al., "Errors in genome annotation", Outlook, Apr. 1, 1999, 15(4):132-133.

Doerks et al., "Protein annotation: detective work for function prediction", Trends in Genetics, Jan. 2000, 14(6):248-50.

(56) References Cited

OTHER PUBLICATIONS

Fenton et al., "Rheostat positions: A new classification of protein positions relevant to pharmacogenomics", Med Chem Res., Jul. 2020, 9(7):1133-1146.

Genbank, "Rec Name: Full=CRISPR-associated endonuclease Cas12a; AltName: Full=AsCpf1; AltName: Full=CRISPR-associated endonuclease Cpf1", Genbank U2UMQ6.1, UniProtKB reviewed Jun. 2023, 11 pages.

Genbank, "Type VI-a CRISPR-Associated RNA-Guided Ribonuclease Cas13a [Leptotrichia Buccalis]", GenBank: WP_015770004, Retrieved from: https://www.ncbi.nlm.nih.gov/protein/WP_015770004.1, Sep. 28, 2020, 2 pages.

Liu et al., "Synthetic chimeric nucleases function for efficient genome editing", Nat Commun., Dec. 2019, 10(5524):11 pages.

Pausch et al., "CRISPR-Casφ from huge phages is a hypercompact genome editor", Science, Jul. 17, 2020, 369(6501):333-337.

Skolnick et al., "From genes to protein structure and function: novel applications of computational approaches in the genomic era", Trends in Biotechnology, Jan. 1, 2000, 18(1):34-39.

Smith et al., "The challenges of genome sequence annotation or "the devil is in the details"", Nature Biotechnology, Nov. 1, 1997, 15(12):1222-1223.

Thorne, et al., "Illuminating Insights into Firefly Luciferase and Other Bioluminescent Reporters Used in Chemical Biology", Chemistry and Biology, Jun. 25, 2010, 17(6):646-657.

Tokuriki et al., "Stability effects of mutations and protein evolvability", Current Opinion in Structural Biology, Oct. 2009, 19(5):596-604.

Xie et al., "sgRNAcas9: A Software Package for Designing CRISPR sgRNA and Evaluating Potential Off-Target Cleavage Sites", PLoS One, Jun. 23, 2014, 9(6):e100448, 9 pages.

* cited by examiner

FIG. 1A

>CasX1
MEKRINKIRKKLSADNATKPVSRSGPMKTLLVRVMTDDLKKRLEKRRKKPEVMPQVISNNAANN
LRMLLDDYTKMKEAILQVYWQEFKDDHVGLMCKFAQPASKKIDQNKLKPEMDEKGNLTTAGFAC
SQCGQPLFVYKLEQVSEKGKAYTNYFGRCNVAEHEKLILLAQLKPEKDSDEAVTYSLGKFGQRA
LDFYSIHVTKESTHPVKPLAQIAGNRYASGPVGKALSDACMGTIASFLSKYQDIIIEHQKVVKG
NQKRLESLRELAGKENLEYPSVTLPPQPHTKEGVDAYNEVIARVRMWVNLNLWQKLKLSRDDAK
PLLRLKGFPSFPVVERRENEVDWWNTINEVKKLIDAKRDMGRVFWSGVTAEKRNTILEGYNYLP
NENDHKKREGSLENPKKPAKRQFGDLLLYLEKKYAGDWGKVFDEAWERIDKKIAGLTSHIEREE
ARNAEDAQSKAVLTDWLRAKASFVLERLKEMDEKEFYACEIQLQKWYGDLRGNPFAVEAENRVV
DISGFSIGSDGHSIQYRNLLAWKYLENGKREFYLLMNYGKKGRIRFTDGTDIKKSGKWQGLLYG
GGKAKVIDLTFDPDDEQLIILPLAFGTRQGREFIWNDLLSLETGLIKLANGRVIEKTIYNKKIG
RDEPALFVALTFERREVVDPSNIKPVNLIGVDRGENIPAVIALTDPEGCPLPEFKDSSGGPTDI
LRIGEGYKEKQRAIQAAKEVEQRRAGGYSRKFASKSRNLADDMVRNSARDLFYHAVTHDAVLVF
ENLSRGFGRQGKRTFMTERQYTKMEDWLTAKLAYEGLTSKTYLSKTLAQYTSKTCSNCGFTITT
ADYDGMLVRLKKTSDGWATTLNNKELKAEGQITYYNRYKRQTVEKELSAELDRLSEESGNNDIS
KWTKGRRDEALFLLKKRFSHRPVQEQFVCLDCGHEVHADEQAALNIARSWLFLNSNSTEFKSYK
SGKQPFVGAWQAFYKRRLKEVWKPNA    (SEQ ID NO: 1)

>CasX2
MQEIKRINKIRRRLVKDSNTKKAGKTGPMKTLLVRVMTPDLRERLENLRKKPENIPQPISNTSR
ANLNKLLTDYTEMKKAILHVYWEEFQKDPVGLMSRVAQPAPKNIDQRKLIPVKDGNERLTSSGF
ACSQCCQPLYVYKLEQVNDKGKPHTNYFGRCNVSEHERLILLSPHKPEANDELVTYSLGKFGQR
ALDFYSIHVTRESNHPVKPLEQIGGNSCASGPVGKALSDACMGAVASFLTKYQDIILEHQKVIK
KNEKRLANLKDIASANGLAFPKITLPPQPHTKEGIEAYNNVVAQIVIWVNLNLWQKLKIGRDEA
KPLQRLKGFPSFPLVERQANEVDWWDMVCNVKKLINEKKEDGKVFWQNLAGYKRQEALLPYLSS
EEDRKKGKKFARYQFGDLLLHLEKKHGEDWGKVYDEAWERIDKKVEGLSKHIKLEEERRSEDAQ
SKAALTDWLRAKASFVIEGLKEADKDEFCRCELKLQKWYGDLRGKPFAIEAENSILDISGFSKQ
YNCAFIWQKDGVKKLNLYLIINYFKGGKLRFKKIKPEAFEANRFYTVINKKSGEIVPMEVNFNF
DDPNLIILPLAFGKRQGREFIWNDLLSLETGSLKLANGRVIEKTLYNRRTRQDEPALFVALTFE
RREVLDSSNIKPMNLIGIDRGENIPAVIALTDPEGCPLSRFKDSLGNPTHILRIGESYKEKQRT
IQAAKEVEQRRAGGYSRKYASKAKNLADDMVRNTARDLLYYAVTQDAMLIFENLSRGFGRQGKR
TFMAERQYTRMEDWLTAKLAYEGLPSKTYLSKTLAQYTSKTCSNCGFTITSADYDRVLEKLKKT
ATGWMTTINGKELKVEGQITYYNRYKRQNVVKDLSVELDRLSEESVNNDISSWTKGRSGEALSL
LKKRFSHRPVQEKFVCLNCGFETHADEQAALNIARSWLFLRSQEYKKYQTNKTTGNTDKRAFVE
TWQSFYRKKLKEVWKPAV    (SEQ ID NO: 2)

FIG. 1B

>CasX3
MDNANKPSTKSLVNTTRISDHFGVTPGQVTRVFSFGIIPTKRQYAIIERWFAAVEAARERLYGM
LYAHFQENPPAYLKEKFSYETFFKGRPVLNGLRDIDPTIMTSAVFTALRHKAEGAMAAFHTNHR
RLFEEARKKMREYAECLKANEALLRGAADIDWDKIVNALRTRLNTCLAPEYDAVIADFGALCAF
RALIAETNALKGAYNHALNQMLPALVKVDEPEEAEESPRLRFFNGRINDLPKFPVAERETPPDT
ETIIRQLEDMARVIPDTAEILGYIHRIRHKAARRKPGSAVPLPQRVALYCAIRMERNPEEDPST
VAGHFLGEIDRVCEKRRQGLVRTPFDSQIRARYMDIISFRATLAHPDRWTEIQFLRSNAASRRV
RAETISAPFEGFSWTSNRTNPAPQYGMALAKDANAPADAPELCICLSPSSAAFSVREKGGDLIY
MRPTGGRRGKDNPGKEITWVPGSFDEYPASGVALKLRLYFGRSQARRMLTNKTWGLLSDNPRVF
AANAELVGKKRNPQDRWKLFFHMVISGPPPVEYLDFSSDVRSRARTVIGINRGEVNPLAYAVVS
VEDGQVLEEGLLGKKEYIDQLIETRRRISEYQSREQTPPRDLRQRVRHLQDTVLGSARAKIHSL
IAFWKGILAIERLDDQFHGREQKIIPKKTYLANKTGFMNALSFSGAVRVDKKGNPWGGMIEIYP
GGISRTCTQCGTVWLARRPKNPGHRDAMVVIPDIVDDAAATGFDNVDCDAGTVDYGELFTLSRE
WVRLTPRYSRVMRGTLGDLERAIRQGDDRKSRQMLELALEPQPQWGQFFCHRCGFNGQSDVLAA
TNLARRAISLIRRLPDTDTPPTP (SEQ ID NO: 3)

FIG. 2

+Target spacer

Antibiotic selection for targeted plasmid

*E. coli* containing CasX
CRISPR locus
or
Control plasmid without
CRISPR locus

+Non-target spacer

CRISPR Plasmid

Figure 4C:
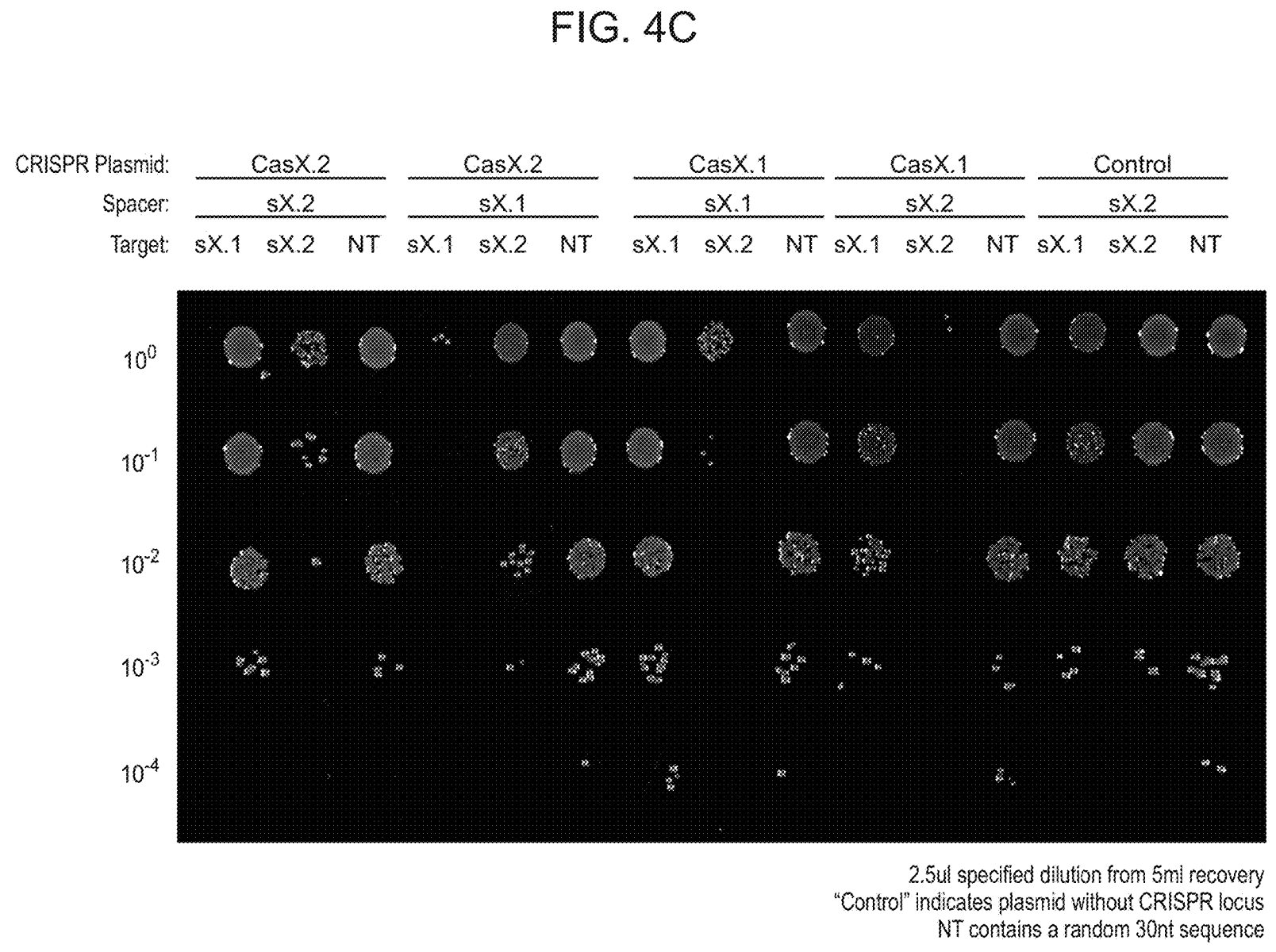

FIG. 4C 2.5ul specified dilution from 5ml recovery
"Control" indicates plasmid without CRISPR locus
NT contains a random 30nt sequence E. coli containing CasX
CRISPR locus Transformation with targeting containing
randomized PAM sequence E. coli containing Control
Plasmid Determine depleted
PAM sequences Antibiotic selection for PAM plasmid and sequence remaining PAMs

FIG. 6A
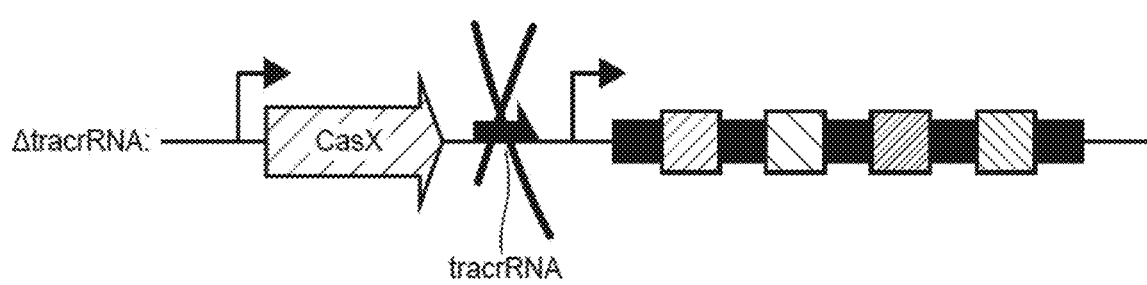
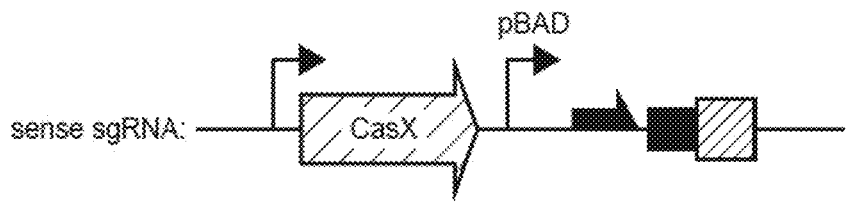
FIG. 6B
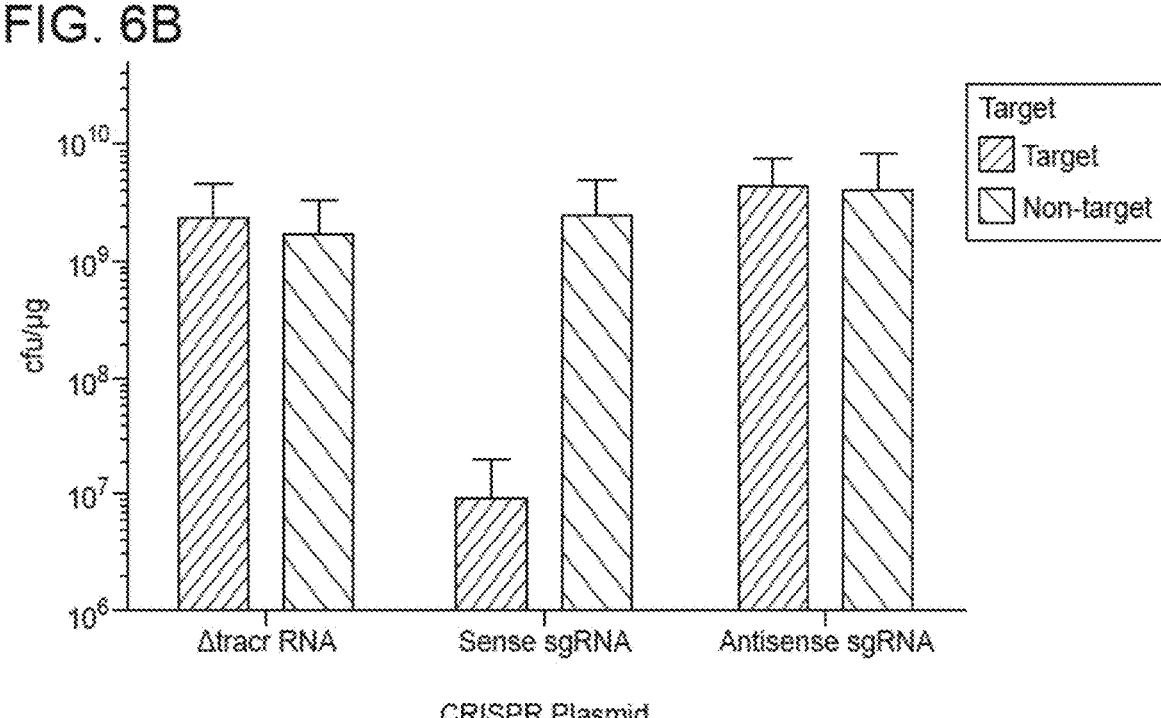

Single guide RNA

Dual guide RNA

FIG. 8
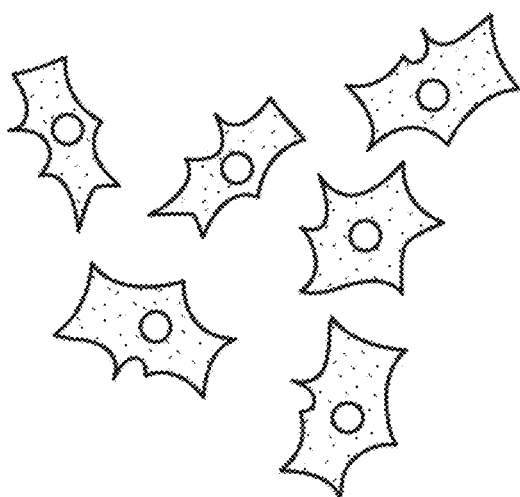
HEK293FT Cells expressing
destabilized GFP
Delivery of CasX by RNP nucleofection
or
lipofection of
CasX expressing plasmid
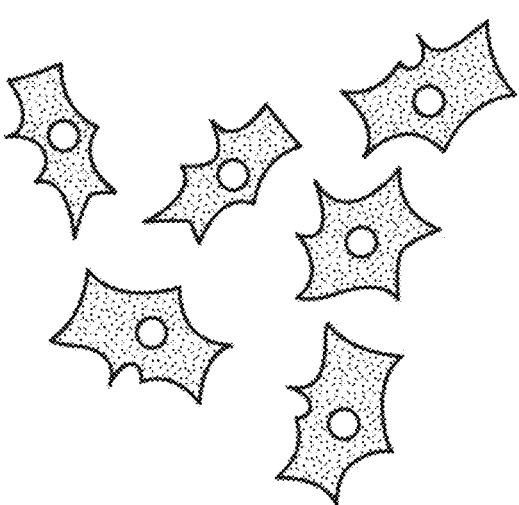
Analysis by
flow cytometry
and T7E1 Assay

FIG. 9
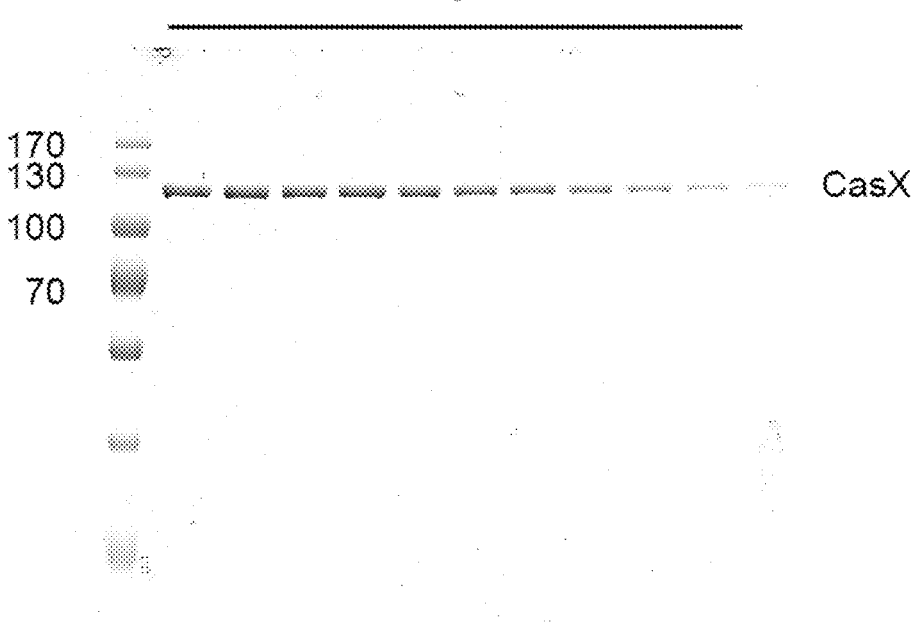
Elution from S200 gel filtration column
170
130 — CasX
100
70
FIG. 10
FIG. 11
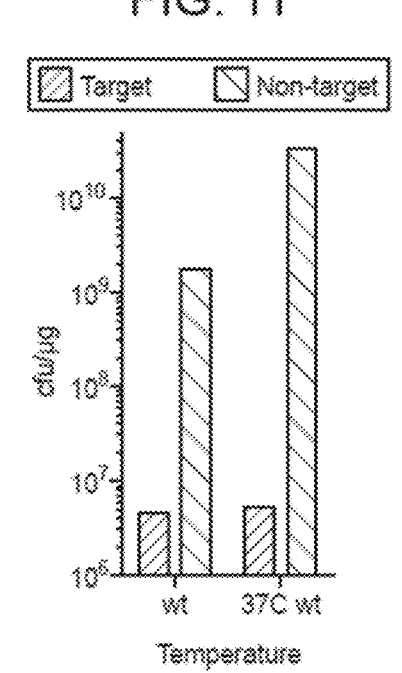

FIG. 13

\>Archaeal Cas9_ARMAN-1
MRDSITAPRYSSALAARIKEFNSAFKLGIDLGTKTGGVALVKDNKVLLAK
TFLDYHKQTLEERRIHRRNRRSRLARRKRIARLRSWILRQKIYGKQLPDP
YKIKKMQLPNGVRKGENWIDLVVSGRDLSPEAFVRAITLIFQKRGQRYEE
VAKEIEEMSYKEFSTHIKALTSVTEEEFTALAAEIERRQDVVDTDKEAER
YTQLSELLSKVSESKSESKDRAQRKEDLGKVVNAFCSAHRIEDKDKWCKE
LMKLLDRPVRHARFLNKVLIRCNICDRATPKKSRPDVRELLYFDTVRNFL
KAGRVEQNPDVISYYKKIYMDAEVIRVKILNKEKLTDEDKKQKRKLASEL
NRYKNKEYVTDAQKKMQEQLKTLLFMKLTGRSRYCMAHLKERAAGKDVEE
GLHGVVQKRHDRNIAQRNHDLRVINLIESLLFDQNKSLSDAIRKNGLMYV
TIEAPEPKTKHAKKGAAVVRDPRKLKEKLFDDQNGVCIYTGLQLDKLEIS
KYEKDHIFPDSRDGPSIRDNLVLTTKEINSDKGDRTPWEWMHDNPEKWKA
FERRVAEFYKKGRINERKRELLLNKGTEYPGDNPTELARGGARVNNFITE
FNDRLKTHGVQELQTIFERNKPIVQVVRGEETQRLRRQWNALNQNFIPLK
DRAMSFNHAEDAAIAASMPPKFWREQIYRTAWHFGPSGNERPDFALAELA
PQWNDFFMTKGGPIIAVLGKTKYSWKHSIIDDTIYKPFSKSAYYVGIYKK
PNAITSNAIKVLRPKLLNGEHTMSKNAKYYHQKIGNERFLMKSQKGGSII
TVKPHDGPEKVLQISPTYECAVLTKHDGKIIVKFKPIKPLRDMYARGVIK
AMDKELETSLSSMSKHAKYKELHTHDIIYLPATKKHVDGYFIITKLSAKH
GIKALPESMVKVKYTQIGSENNSEVKLTKPKPEITLDSEDITNIYNFTR \>Archaeal Cas9_ARMAN-4
MLGSSRYLRYNLTSFEGKEPFLIMGYYKEYNKELSSKAQKEFNDQISEFN
SYYKLGIDLGDKTGIAIVKGNKIILAKTLIDLHSQKLDKRREARRNRRTR
LSRKKRLARLRSWVMRQKVGNQRLPDPYKIMHDNKYWSIYNKSNSANKKN
WIDLLIHSNSLSADDFVRGLTIIFRKRGYLAFKYLSRLSDKEFEKYIDNL
KPPISKYEYDEDLEELSSRVENGEIEEKKFEGLKNKLDKIDKESKDFQVK
QREEVKKELEDLVDLFAKSVDNKIDKARWKRELNNLLDKKVRKIRFDNRF
ILKCKIKGCNKTPKKEKVRDFELKMVLNNARSDYQISDEDLNSFRNEVI
NIFQKKENLKKGELKGVTIEDLRKQLNKTFNKAKIKKGIREQIRSIVFEK
ISGRSKFCKEHLKEFSEKPAPSDRINYGVNSAREQHDFRVLNFIDKKIFK
DKLIDPSKLRYITIESPEPETEKLEKGQISEKSFETLKEKLAKETGGIDI
YTGEKLKKDFEIEHIFPRARMGPSIRENEVASNLETNKEKADRTPWEWFG
QDEKRWSEFEKRVNSLYSKKKISERKREILLNKSNEYPGLNPTELSRIPS
TLSDFVESIRKMFVKYGYEEPQTLVQKGKPIIQVVRGRDTQALRWRWHAL
DSNIIPEKDRKSSFNHAEDAVIAACMPPYYLRQKIFREEAKIKRKVSNKE
KEVTRPDMPTKKIAPNWSEFMKTRNEPVIEVIGKVKPSWKNSIMDQTFYK
YLLKPFKDNLIKIPNVKNTYKWIGVNGQTDSLSLPSKVLSISNKKVDSST
VLLVHDKKGGKRNWVPKSIGGLLVYITPKDGPKRIVQVKPATQGLLIYRN
EDGRVDAVREFINPVIEMYNNGKLAFVEKENEEELLKYFNLLEKGQKFER
IRRYDMITYNSKFYYVTKINKNHRVTIQEESKIKAESDKVKSSSGKEYTR
KETEELSLQKLAELISI

FIG. 15
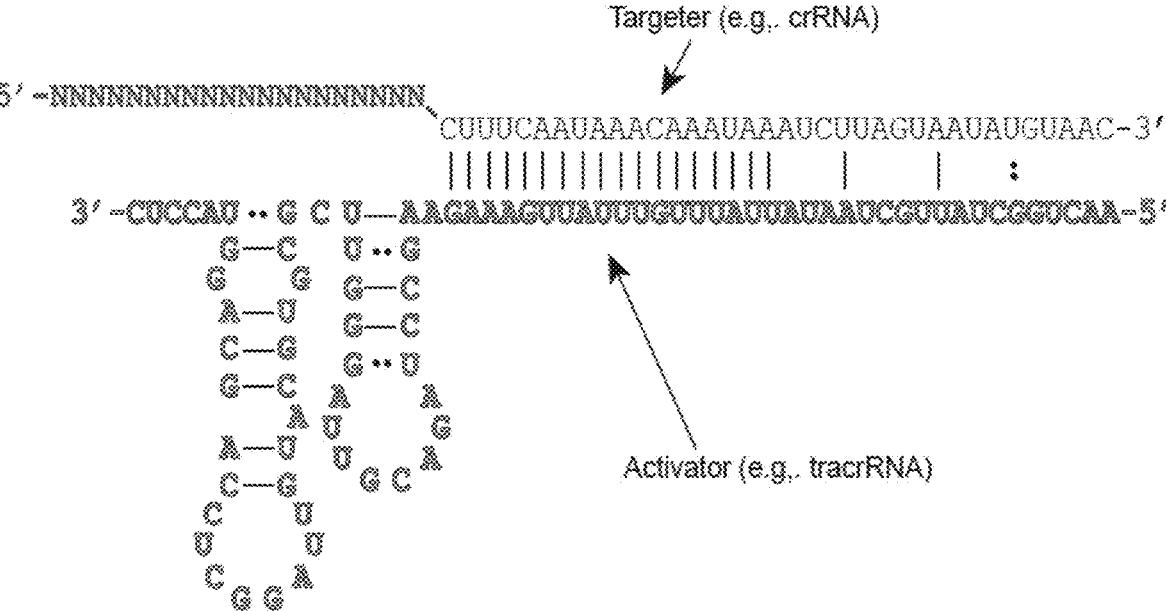
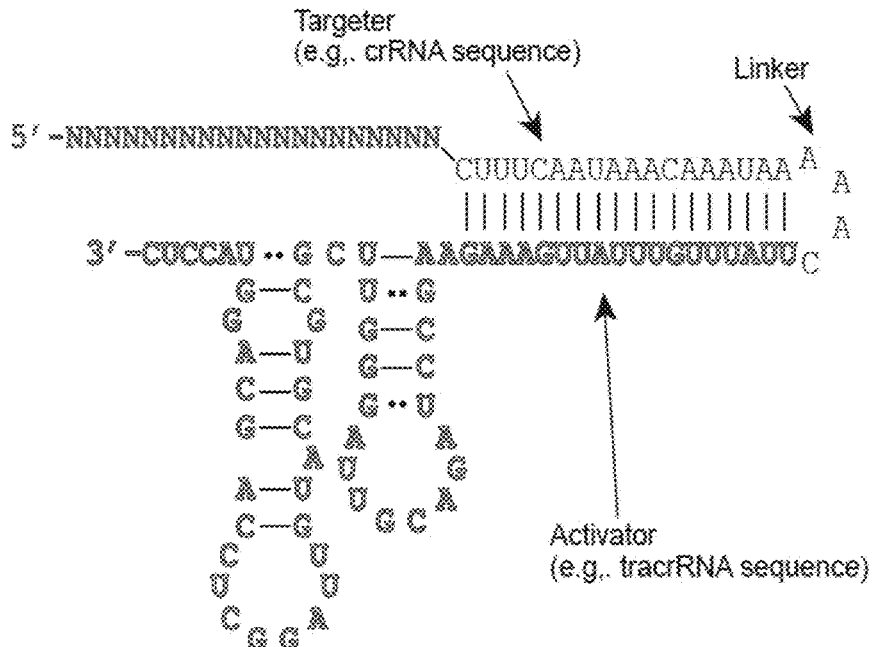

FIG. 16

>Lindowbacteria Cas9
VSATRKGQGSGAPISRTEAPQIALMATELEQRLNEFLDSLRLGIDFGEDYGGIALVQANRVLHAETFVDFHQAT
LKDRRRNRRGRRTRHARKMRLARLRSWILRQKLPGGQRLPDPYGVMHWPFKTKKGHTIKTGLASRQDGKRTIIQ
KCKIGTATPEEFVCSLTLLFQKRGFVWEGSDLCELSDQELAEELMTVRITEAVAAAIKEEIERRKKEPEDNKEG
EIENLETVLCDAVKRARSPRTPEHRSIVESDLKDIVDGWTRKNCPQMTDMWKKELSCLLNKHVRPARFENRIVA
GCSWCGKMVPRKSKVRELAYKVVVKNIRVEDFTSRQPLTAQEAEYFSQLWVDKEAKPPARTAIENKLKKLKASP
KMANQLYELLAPSEPKGHTNLCQQHLEMAARGAFMCNRHHAICENNNGDHQTIDSVKEGRKRAGPRNPCREDRD
RRMIRRLEQILFETPGKPGKPSHSIPRLITIEFPKPNTAQTAGCPHCKEKLSLDARVRWKMARPMKLEASNDST
PFFCPSCAAGIKITLYKKMRIKEKEIVQKYSPKDTDVLVRKTAAGGLKKLKYDMYLKETDGTCVYCGTSIGSGQ
IDHIFPQSRGGPNIDYNLISCCRTCNGNLKKNKSPWEWFGNIDQRWREFEDRVKKLPAPQRKKAILLSRESAYP
ENPTALARVGARTKEFIGRIKQMLLANGVKENEIADNYEKDKIVIQTIDGWMTSRLRGCWRTFPDGTANFPPKN
DADKRNHAQDAVLIAACPPHTWRERIFTWKPENPYFSVLQKIAPRWKDHQATMKILGRYFPRWHNQNSDIQFVH
QHKTQNGTSYTMRDTVESIDVGTDKKGGSIERIYSKSFRDFFSRTFKSLGIKMAMNEIPKLKSQWLNERRAAWM
KKNPATPVPNQRERAWEASFPRRLQFDMGYGEDVAEVNPKNGPSRFVRAQPVNDRIEVWTNDVRQAQIRTVKNR
ILFRHIQDNSPQGRTLERIFRRNDMIQLDAVQKRGRKGITGKSYEAGEYMVVKIEKGGKFTAVPAHRGKGRENQ
RQVSQREIAKLCGVSLSPKRRKPSRSTSESG (SEQ ID NO: 135)

>Deltaproteobacteria Cas9
VAAASLILQRGGLVALHPRLERKIKEFLPTYRLGVDLGEAAGGLALIHNNNILHAETFTDFHEATLETKRALRR
GRRTRHAKKMRLARLRSWILRQCIPAHVTGAEIKDSYSRLPDPYRLMKDKKYQTLPGFYEVKGQNPEKSPTWID
KAKAGEVDAEGFVIALTHILQKRGYKYDGKEFSDYDDSRLIDFIDSCAMLAEAPEMRKALEDEIMRREVGEKEK
PKLHEAFDNALNRQRERKKALPRQVREKDMEDMVDVFGRRWQLSQEIIANWKSQLTGLLNKVVREARYDNRLKS
GCSWCGKKTPRLAKPEIRELAFEAAVGNLRIRERDGRDRPISDEERNPLRGWFQRRRENHDYSRATKNTPIEER
APSEDNIRTYLEQIGVKKAWIRKKKGKEKWKFDFAMLPQLDNLINKEARKGRARLCVEHMRMQAEGKTMKDADV
DWQSMRKRNAPNPRREQHDARVLKRIERLIFNRGKKGTDAWRHGPIAVITLEVPMPVDLERAREKEQVERKPLN
LRQRLHAETEGVCIYCGENVHDRTMHLEHIVPQAKGGPDVQMNRIASCPKCNADRDTGKKDMLPSEWLTGDKWN
VFKSRVMSLNLPPLKKQLLLLEPGSKYPNDPTPLARVSARWRAFAADIMWLFDEYSVPVPTLNYEKDKPHIQVV
RGNLTSRLRRDWRWKDHEATVENFPDKRRTDLYNHAQDAAILAAIPPHTWQEQIFSDMAVRPCAKKDEQGNILK
NEKEMRPRPGIAALALAPEWADYERTQKELKRPMVHTLGKLKATWRRQIMDLSFYQNPTDNDGPLFIRKVDAKT
GKRETKEVQKGGLVVQVPHYDGTSGKRKVQIKPIQSNAIILWHDPSGRKDNLNISIERPAAIKKFVKHPVDPPI
ASDAIILGRIERASTLWLREGKGTVELKADKKSVRSSVVMPEGIYRVKELGSNGVIVVQENAVSKELANKLGIS
DDQFSKVPERALGKKELAEYFKGNQRSG (SEQ ID NO: 136)

FIG. 17A

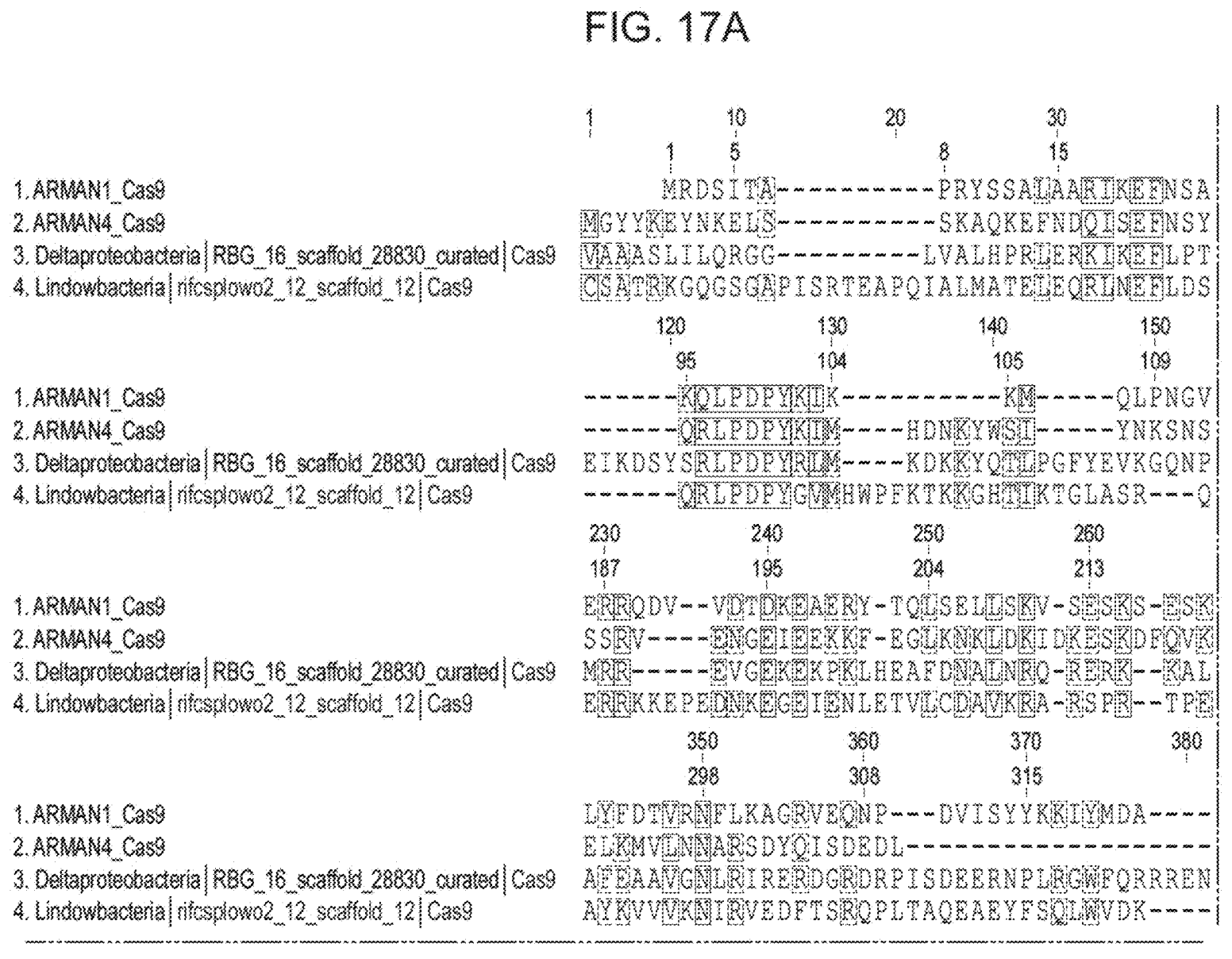

1. ARMAN1_Cas9
2. ARMAN4_Cas9
3. Deltaproteobacteria|RBG_16_scaffold_28830_curated|Cas9
4. Lindowbacteria|nfcsplowo2_12_scaffold_12|Cas9

Figure 17C:
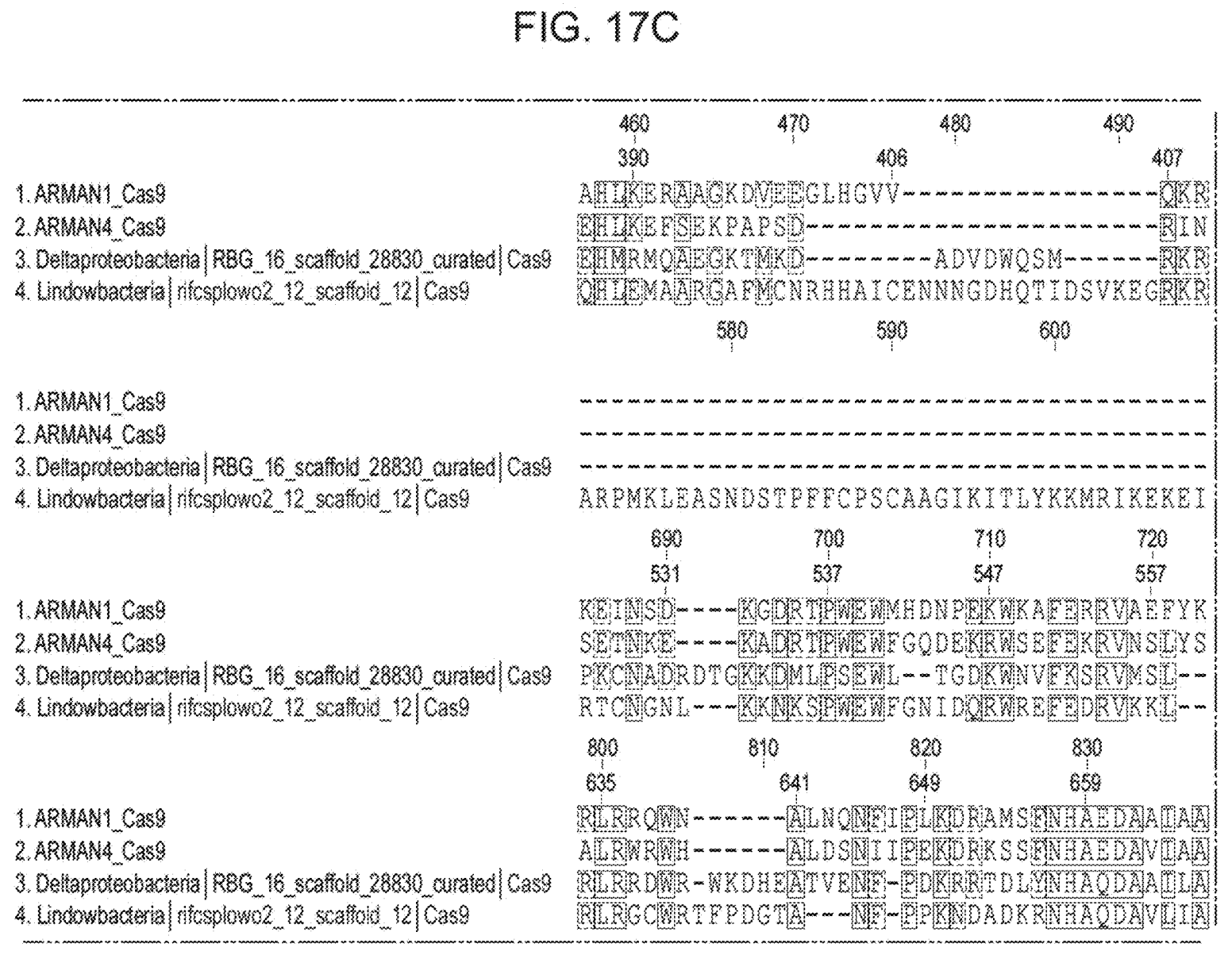

```
                    460       470       480       490
                    390       408               407
1. ARMAN1_Cas9      AHLKERDAGKDVEEGLHGVV--------------QKR
2. ARMAN4_Cas9      EHLKEFISEKPAPSD-------------------BIN
3. Deltaproteobacteria|RBG_16_scaffold_28830_curated|Cas9   EHMRMQAECKTMKD---------ADVDWQSM----RKR
4. Lindowbacteria|rifcsplowo2_12_scaffold_12|Cas9   QHLEMAIRGAFMCNRHHAICENNGDHQTIDSVKEGRKR
```

```
                    580       590       600
                    531       537       547
1. ARMAN1_Cas9      --
2. ARMAN4_Cas9      --
3. Deltaproteobacteria|RBG_16_scaffold_28830_curated|Cas9   --
4. Lindowbacteria|rifcsplowo2_12_scaffold_12|Cas9   ARPMKLEASNDSTPFFCPSCAAGIKITLYKKMRIKEKEI
```

```
                    690       700       710       720
                    531       537       547       557
1. ARMAN1_Cas9      KETINSD-----EGDRTIPWEWMHDNPEKWKAEERVAEFYK
2. ARMAN4_Cas9      SEHNKE------EADRTIPWEWFGQDEKKWSEEKRVNSLYS
3. Deltaproteobacteria|RBG_16_scaffold_28830_curated|Cas9   PKCNADRDTGKKDMLIPSEWL--TGDKNNVERSRVMSL--
4. Lindowbacteria|rifcsplowo2_12_scaffold_12|Cas9   RTCNGNL----KKNKSIPWEWFGNIDQRWREEDRVKKL--
```

```
                    800       810       820       830
                    635       641       649       659
1. ARMAN1_Cas9      RLRRQMN----ALNQNEIPLKDRAMSENHAEDAAILAI
2. ARMAN4_Cas9      ALRWRWH----ALDSNIIPERDRKSENHAEDAVILAI
3. Deltaproteobacteria|RBG_16_scaffold_28830_curated|Cas9   RLRRDWR-WKDHEATVENE--PDKRNITDLYNHAQDAAILIAI
4. Lindowbacteria|rifcsplowo2_12_scaffold_12|Cas9   RLRGCWRTFPDGTA----NE--PFKNDADKRNHAQDAVILIAI
```

1. ARMAN1_Cas9
2. ARMAN4_Cas9
3. Deltaproteobacteria|RBG_16_scaffold_28830_curated|Cas9
4. Lindowbacteria|rifcsplowo2_12_scaffold_12|Cas9

Figure 17E:
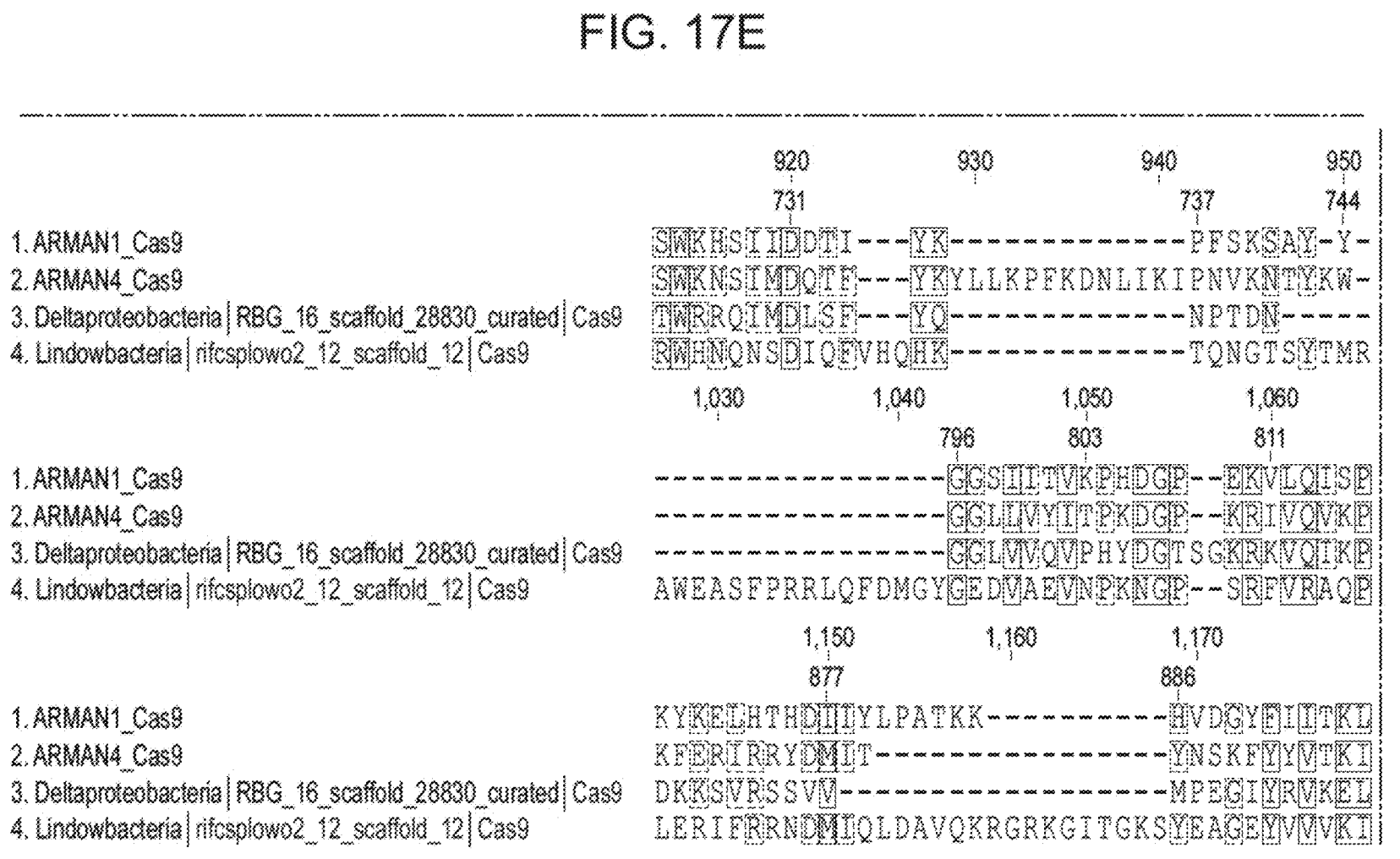

1. ARMAN1_Cas9
2. ARMAN4_Cas9
3. Deltaproteobacteria | RBG_16_scaffold_28830_curated | Cas9
4. Lindowbacteria | rifcspiowo2_12_scaffold_12 | Cas9

1. ARMAN1_Cas9
2. ARMAN4_Cas9
3. Deltaproteobacteria | RBG_16_scaffold_28830_curated | Cas9
4. Lindowbacteria | rifcspiowo2_12_scaffold_12 | Cas9

1. ARMAN1_Cas9
2. ARMAN4_Cas9
3. Deltaproteobacteria | RBG_16_scaffold_28830_curated | Cas9
4. Lindowbacteria | rifcspiowo2_12_scaffold_12 | Cas9

FIG. 17F

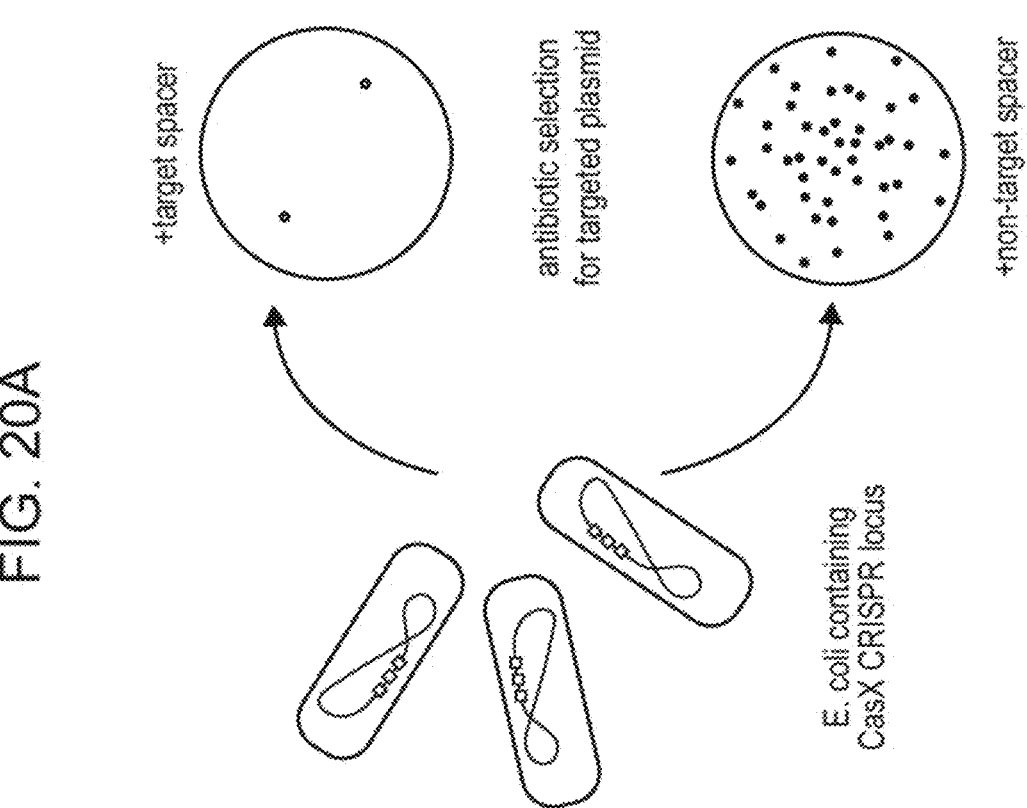

Cas1-based phylogeny of CRISPR system

FIG. 25E

Thermoplasmatales archaeon I-plasma

| Protein | Guide |
|---|---|
| AR1-Cas9<br>AR1-dCas9 | crRNA<br>sgRNA-69<br>sgRNA-104<br>sgRNA-179 |
| AR4-Cas9<br>AR4-dCas9 | crRNA<br>sgRNA-75<br>sgRNA-122 |

*In vivo E. coli* targeting assay

*In vitro* cleavage conditions assayed for Cas9 from ARMAN-1

| Protein Purification | Buffer | Salt (mM) | Metal | Guide | Target | Temperature |
|---|---|---|---|---|---|---|
| AR1-Cas9 #1 | Tris ph 7.5 | 300 | $Mg^{2+}$ $Mn^{2+}$ $Zn^{2+}$ | crRNA cr:69 cr:69 cr:69 | dsDNA ssDNA DNA Bubble ssRNA dsDNA | 37 |
| AR1-Cas9 #1 | Tris ph 7.5 | 100-500 | $Mg^{2+}$ | cr:69 cr:104 cr:179 | dsDNA | 37 |
| AR1-Cas9 #1 | Tris ph 7.5 | 300 | $Mg^{2+}$ $Mn^{2+}$ $Zn^{2+}$ | cr:69 cr:104 cr:179 | dsDNA | 30-48 |
| AR1-Cas9 #1 | MOPS pH 6 pH 6.5 pH 7.0 pH 7.5 | 300 | $Mg^{2+}$ | cr:69 cr:104 cr:179 | dsDNA | 37 |
| AR1-Cas9 #1 | Citrate pH 5 pH 5.5 pH 6 | 300 | $Mg^{2+}$ | cr:69 cr:104 cr:179 | dsDNA | 37 |
| AR1-Cas9 #1 | Tris ph 7.5 | 300 | $Mg^{2+}$ $Mn^{2+}$ $Zn^{2+}$ | cr:69 cr:104 cr:179 | plasmid | 37-50 |
| AR1-Cas9 #2 | Tris ph 7.5 | 300 | $Mg^{2+}$ $Mn^{2+}$ $Zn^{2+}$ | cr:69 cr:104 cr:179 | dsDNA | 37 |
| AR1-Cas9 #3 | Tris ph 7.5 | 300 | $Mg^{2+}$ $Mn^{2+}$ $Zn^{2+}$ | cr:69 cr:104 cr:179 | dsDNA | 37 |
| AR1-Cas9 #4 | Tris ph 7.5 | 300 | $Mg^{2+}$ $Mn^{2+}$ $Zn^{2+}$ | cr:69 cr:104 cr:179 | dsDNA | 37 |
| AR1-Cas9 #5 | Tris ph 7.5 | 300 | $Mg^{2+}$ $Mn^{2+}$ $Zn^{2+}$ | cr:69 cr:104 cr:179 | dsDNA | 37 |
| AR1-Cas9 #6 | Tris ph 7.5 | 300 | $Mg^{2+}$ $Mn^{2+}$ $Zn^{2+}$ | cr:69 cr:104 cr:179 | ssDNA dsDNA | 37 |
| AR4-Cas9 #1 | Tris ph 7.5 | 300 | $Mg^{2+}$ $Mn^{2+}$ $Zn^{2+}$ | sgRNA-122 | dsDNA | 37 |
| AR4-Cas9 #2 | Tris ph 7.5 | 300 | $Mg^{2+}$ $Mn^{2+}$ $Zn^{2+}$ | sgRNA-122 | dsDNA | 37 |
| AR4-Cas9 #3 | Tris ph 7.5 | 300 | $Mg^{2+}$ $Mn^{2+}$ $Zn^{2+}$ | sgRNA-122 | dsDNA | 37 |
| AR4-Cas9 #4 | Tris ph 7.5 | 300 | $Mg^{2+}$ $Mn^{2+}$ $Zn^{2+}$ | sgRNA-122 | dsDNA | 37 |

SEQUENCE LISTING

```
Sequence total quantity: 141
SEQ ID NO: 1          moltype = AA  length = 986
FEATURE               Location/Qualifiers
REGION                1..986
```

-continued

```
                        note = identified from meta-transcriptomics sequence data
                          from unknown deltaproteobacter
source                  1..986
                        mol_type = protein
                        organism = unidentified
SEQUENCE: 1
MEKRINKIRK KLSADNATKP VSRSGPMKTL LVRVMTDDLK KRLEKRRKKP EVMPQVISNN  60
AANNLRMLLD DYTKMKEAIL QVYWQEFKDD HVGLMCKFAQ PASKKIDQNK LKPEMDEKGN  120
LTTAGFACSQ CGQPLFVYKL EQVSEKGKAY TNYFGRCNVA EHEKLILLAQ LKPEKDSDEA  180
VTYSLGKFGQ RALDFYSIHV TKESTHPVKP LAQIAGNRYA SGPVGKALSD ACMGTIASFL  240
SKYQDIIIEH QKVVKGNQKR LESLRELAGK ENLEYPSVTL PPQPHTKEGV DAYNEVIARV  300
RMWVNLNLWQ KLKLSRDDAK PLLRLKGFPS FPVVERRENE VDWWNTINEV KKLIDAKRDM  360
GRVFWSGVTA EKRNTILEGY NYLPNENDHK KREGSLENPK KPAKRQFGDL LLYLEKKYAG  420
DWGKVFDEAW ERIDKKIAGL TSHIEREEAR NAEDAQSKAV LTDWLRAKAS FVLERLKEMD  480
EKEFYACEIQ LQKWYGDLRG NPFAVEAENR VVDISGFSIG SDGHSIQYRN LLAWKYLENG  540
KREFYLLMNY GKKGRIRFTD GTDIKKSGKW QGLLYGGGKA KVIDLTFDPD DEQLIILPLA  600
FGTRQGREFI WNDLLSLETG LIKLANGRVI EKTIYNKKIG RDEPALFVAL TFERREVVDP  660
SNIKPVNLIG VDRGENIPAV IALTDPEGCP LPEFKDSSGG PTDILRIGEG YKEKQRAIQA  720
AKEVEQRRAG GYSRKFASKS RNLADDMVRN SARDLFYHAV THDAVLVFEN LSRGFGRQGK  780
RTFMTERQYT KMEDWLTAKL AYEGLTSKTY LSKTLAQYTS KTCSNCGFTI TTADYDGMLV  840
RLKKTSDGWA TTLNNKELKA EGQITYYNRY KRQTVEKELS AELDRLSEES GNNDISKWTK  900
GRRDEALFLL KKRFSHRPVQ EQFVCLDCGH EVHADEQAAL NIARSWLFLN SNSTEFKSYK  960
SGKQPFVGAW QAFYKRRLKE VWKPNA                                      986

SEQ ID NO: 2            moltype = AA   length = 978
FEATURE                 Location/Qualifiers
REGION                  1..978
                        note = identified from meta-transcriptomics sequence data
                          from unknown Planctomycetes
source                  1..978
                        mol_type = protein
                        organism = unidentified
SEQUENCE: 2
MQEIKRINKI RRRLVKDSNT KKAGKTGPMK TLLVRVMTPD LRERLENLRK KPENIPQPIS  60
NTSRANLNKL LTDYTEMKKA ILHVYWEEFQ KDPVGLMSRV AQPAPKNIDQ RKLIPVKDGN  120
ERLTSSGFAC SQCCQPLYVY KLEQVNDKGK PHTNYFGRCN VSEHERLILL SPHKPEANDE  180
LVTYSLGKFG QRALDFYSIH VTRESNHPVK PLEQIGGNSC ASGPVGKALS DACMGAVASF  240
LTKYQDIILE HQKVIKKNEK RLANLKDIAS ANGLAFPKIT LPPQPHTKEG IEAYNNVVAQ  300
IVIWVNLNLW QKLKIGRDEA KPLQRLKGFP SFPLVERQAN EVDWWDMVCN VKKLINEKKE  360
DGKVFWQNLA GYKRQEALLP YLSSEEDRKK GKKFARYQFG DLLLHLEKKH GEDWGKVYDE  420
AWERIDKKVE GLSKHIKLEE ERRSEDAQSK AALTDWLRAK ASFVIEGLKE ADKDEFCRCE  480
LKLQKWYGDL RGKPFAIEAE NSILDISGFS KQYNCAFIWQ KDGVKKLNLY LIINYFKGGK  540
LRFKKIKPEA FEANRFYTVI NKKSGEIVPM EVNFNFDDPN LIILPLAFGK RQGREFIWND  600
LLSLETGSLK LANGRVIEKT LYNRRTRQDE PALFVALTFE RREVLDSSNI KPMNLIGIDR  660
GENIPAVIAL TDPEGCPLSR FKDSLGNPTH ILRIGESYKE KQRTIQAAKE VEQRRAGGYS  720
RKYASKAKNL ADDMVRNTAR DLLYYAVTQD AMLIFENLSR GFGRQGKRTF MAERQYTRME  780
DWLTAKLAYE GLPSKTYLSK TLAQYTSKTC SNCGFTITSA DYDRVLEKLK KTATGWMTTI  840
NGKELKVEGQ ITYYNRYKRQ NVVKDLSVEL DRLSEESVNN DISSWTKGRS GEALSLLKKR  900
FSHRPVQEKF VCLNCGFETH ADEQAALNIA RSWLFLRSQE YKKYQTNKTT GNTDKRAFVE  960
TWQSFYRKKL KEVWKPAV                                               978

SEQ ID NO: 3            moltype = AA   length = 855
FEATURE                 Location/Qualifiers
REGION                  1..855
                        note = identified from meta-transcriptomics sequence data
                          from Candidatus Sungbacteria bacterium
source                  1..855
                        mol_type = protein
                        organism = unidentified
SEQUENCE: 3
MDNANKPSTK SLVNTTRISD HFGVTPGQVT RVFSFGIIPT KRQYAIIERW FAAVEAARER  60
LYGMLYAHFQ ENPPAYLKEK FSYETFFKGR PVLNGLRDID PTIMTSAVFT ALRHKAEGAM  120
AAFHTNHRRL FEEARKKMRE YAECLKANEA LLRGAADIDW DKIVNALRTR LNTCLAPEYD  180
AVIADFGALC AFRALIAETN ALKGAYNHAL NQMLPALVKV DEPEEAEESP RLRFFNGRIN  240
DLPKFPVAER ETPPDTETII RQLEDMARVI PDTAEILGYI HRIRHKAARR KPGSAVPLPQ  300
RVALYCAIRM ERNPEEDPST VAGHFLGEID RVCEKRRQGL VRTPFDSQIR ARYMDIISFR  360
ATLAHPDRWT EIQFLRSNAA SRRVRAETIS APFEGFSWTS NRTNPAPQYG MALAKDANAP  420
ADAPELCICL SPSSAAFSVR EKGGDLIYMR PTGGRRGKDN PGKEITWVPG SPDEYPASGV  480
ALKLRLYFGR SQARRMLTNK TWGLLSDNPR VFAANAELVG KKRNPQDRWK LFFHMVISGP  540
PPVEYLDFSS DVRSRARTVI GINRGEVNPL AYAVVSVEDG QVLEEGLLGK KEYIDQLIET  600
RRRISEYQSR EQTPPRDLRQ RVRHLQDTVL GSARAKIHSL IAFWKGILAI ERLDDQFHGR  660
EQKIIPKKTY LANKTGFMNA LSFSGAVRVD KKGNPWGGMI EIYPGGISRT CTQCGTVWLA  720
RRPKNPGHRD AMVVIPDIVD DAAATGFDNV DCDAGTVDYG ELFTLSREWV RLTPRYSRVM  780
RGTLGDLERA IRQGDDRKSR QMLELALEPQ PQWGQFFCHR CGFNGQSDVL AATNLARRAI  840
SLIRRLPDTD TPPTP                                                  855

SEQ ID NO: 4            moltype = AA   length = 4
FEATURE                 Location/Qualifiers
source                  1..4
```

-continued

```
                                 mol_type = protein
                                 organism = synthetic construct
SEQUENCE: 4
AAAA                                                                          4

SEQ ID NO: 5              moltype = AA  length = 4
FEATURE                   Location/Qualifiers
source                    1..4
                          mol_type = protein
                          organism = synthetic construct
SEQUENCE: 5
AAAA                                                                          4

SEQ ID NO: 6              moltype = AA  length = 4
FEATURE                   Location/Qualifiers
source                    1..4
                          mol_type = protein
                          organism = synthetic construct
SEQUENCE: 6
AAAA                                                                          4

SEQ ID NO: 7              moltype = AA  length = 4
FEATURE                   Location/Qualifiers
source                    1..4
                          mol_type = protein
                          organism = synthetic construct
SEQUENCE: 7
AAAA                                                                          4

SEQ ID NO: 8              moltype = AA  length = 4
FEATURE                   Location/Qualifiers
source                    1..4
                          mol_type = protein
                          organism = synthetic construct
SEQUENCE: 8
AAAA                                                                          4

SEQ ID NO: 9              moltype = AA  length = 4
FEATURE                   Location/Qualifiers
source                    1..4
                          mol_type = protein
                          organism = synthetic construct
SEQUENCE: 9
AAAA                                                                          4

SEQ ID NO: 10             moltype = AA  length = 4
FEATURE                   Location/Qualifiers
source                    1..4
                          mol_type = protein
                          organism = synthetic construct
SEQUENCE: 10
AAAA                                                                          4

SEQ ID NO: 11             moltype = RNA  length = 23
FEATURE                   Location/Qualifiers
source                    1..23
                          mol_type = other RNA
                          organism = synthetic construct
SEQUENCE: 11
ccgataagta aaacgcatca aag                                                    23

SEQ ID NO: 12             moltype = RNA  length = 37
FEATURE                   Location/Qualifiers
source                    1..37
                          mol_type = other RNA
                          organism = synthetic construct
SEQUENCE: 12
atttgaaggt atctccgata agtaaaacgc atcaaag                                     37

SEQ ID NO: 13             moltype = RNA  length = 26
FEATURE                   Location/Qualifiers
source                    1..26
                          mol_type = other RNA
                          organism = synthetic construct
SEQUENCE: 13
tctccgataa ataagaagca tcaaag                                                 26

SEQ ID NO: 14             moltype = RNA  length = 25
FEATURE                   Location/Qualifiers
```

-continued

```
source                  1..25
                        mol_type = other RNA
                        organism = synthetic construct
SEQUENCE: 14
gtttacacac tccctctcat agggt                                      25

SEQ ID NO: 15           moltype = RNA   length = 25
FEATURE                 Location/Qualifiers
source                  1..25
                        mol_type = other RNA
                        organism = synthetic construct
SEQUENCE: 15
gtttacacac tccctctcat gaggt                                      25

SEQ ID NO: 16           moltype = RNA   length = 25
FEATURE                 Location/Qualifiers
source                  1..25
                        mol_type = other RNA
                        organism = synthetic construct
SEQUENCE: 16
ttttacatac cccctctcat gggat                                      25

SEQ ID NO: 17           moltype = RNA   length = 25
FEATURE                 Location/Qualifiers
source                  1..25
                        mol_type = other RNA
                        organism = synthetic construct
SEQUENCE: 17
gtttacacac tccctctcat ggggg                                      25

SEQ ID NO: 18           moltype = RNA   length = 10
FEATURE                 Location/Qualifiers
source                  1..10
                        mol_type = other RNA
                        organism = synthetic construct
SEQUENCE: 18
aaaaaaaaaa                                                       10

SEQ ID NO: 19           moltype =    length =
SEQUENCE: 19
000

SEQ ID NO: 20           moltype =    length =
SEQUENCE: 20
000

SEQ ID NO: 21           moltype = RNA   length = 81
FEATURE                 Location/Qualifiers
source                  1..81
                        mol_type = other RNA
                        organism = synthetic construct
SEQUENCE: 21
acatctggcg cgtttattcc attactttgg agccagtccc agcgactatg tcgtatggac   60
gaagcgctta tttatcggag a                                          81

SEQ ID NO: 22           moltype = RNA   length = 78
FEATURE                 Location/Qualifiers
source                  1..78
                        mol_type = other RNA
                        organism = synthetic construct
SEQUENCE: 22
acatctggcg cgtttattcc attactttgg agccagtccc agcgactatg tcgtatggac   60
gaagcgctta tttatcgg                                              78

SEQ ID NO: 23           moltype = RNA   length = 65
FEATURE                 Location/Qualifiers
source                  1..65
                        mol_type = other RNA
                        organism = synthetic construct
SEQUENCE: 23
ttattccatt actttggagc cagtcccagc gactatgtcg tatggacgaa gcgcttattt   60
atcgg                                                            65

SEQ ID NO: 24           moltype = RNA   length = 93
FEATURE                 Location/Qualifiers
source                  1..93
                        mol_type = other RNA
                        organism = synthetic construct
SEQUENCE: 24
```

-continued

```
aagtagtaaa ttacatctgg cgcgtttatt ccattacttt ggagccagtc ccagcgacta   60
tgtcgtatgg acgaagcgct tatttatcgg aga                                 93

SEQ ID NO: 25          moltype = RNA   length = 68
FEATURE                Location/Qualifiers
source                 1..68
                       mol_type = other RNA
                       organism = synthetic construct
SEQUENCE: 25
ttattccatt actttggagc cagtcccagc gactatgtcg tatggacgaa gcgcttattt   60
atcggaga                                                             68

SEQ ID NO: 26          moltype = RNA   length = 69
FEATURE                Location/Qualifiers
source                 1..69
                       mol_type = other RNA
                       organism = synthetic construct
SEQUENCE: 26
ttatctcatt actttgagag ccatcaccag cgactatgtc gtatgggtaa agcgcttatt   60
tatcggaga                                                            69

SEQ ID NO: 27          moltype = RNA   length = 66
FEATURE                Location/Qualifiers
source                 1..66
                       mol_type = other RNA
                       organism = synthetic construct
SEQUENCE: 27
ttatctcatt actttgagag ccatcaccag cgactatgtc gtatgggtaa agcgcttatt   60
tatcgg                                                               66

SEQ ID NO: 28          moltype = RNA   length = 230
FEATURE                Location/Qualifiers
source                 1..230
                       mol_type = other RNA
                       organism = synthetic construct
SEQUENCE: 28
taaatttttt gagccctatc tccgcgagga agacagggct cttttcatga gaggaagctt   60
ttatacccga ccggtaatcc ggtcggggga ttggccgttg aaacgatttt aaagcggcca  120
atgggccct ctatatggat actacttata taaggagctt ggggaagaag atagcttaat   180
cccgctatct tgtcaagggg ttggggggagt atcagtatcc ggcaggcgcc             230

SEQ ID NO: 29          moltype =    length =
SEQUENCE: 29
000

SEQ ID NO: 30          moltype =    length =
SEQUENCE: 30
000

SEQ ID NO: 31          moltype = RNA   length = 45
FEATURE                Location/Qualifiers
source                 1..45
                       mol_type = other RNA
                       organism = synthetic construct
SEQUENCE: 31
gtttacacac tccctctcat agggtnnnnn nnnnnnnnnn nnnnn                     45

SEQ ID NO: 32          moltype = RNA   length = 45
FEATURE                Location/Qualifiers
source                 1..45
                       mol_type = other RNA
                       organism = synthetic construct
SEQUENCE: 32
gtttacacac tccctctcat gaggtnnnnn nnnnnnnnnn nnnnn                     45

SEQ ID NO: 33          moltype = RNA   length = 45
FEATURE                Location/Qualifiers
source                 1..45
                       mol_type = other RNA
                       organism = synthetic construct
SEQUENCE: 33
ttttacatac ccctctcat gggatnnnnn nnnnnnnnnn nnnnn                      45

SEQ ID NO: 34          moltype = RNA   length = 45
FEATURE                Location/Qualifiers
source                 1..45
                       mol_type = other RNA
                       organism = synthetic construct
SEQUENCE: 34
```

```
gtttacacac tccctctcat gggggnnnnn nnnnnnnnnn nnnnn                          45

SEQ ID NO: 35          moltype =   length =
SEQUENCE: 35
000

SEQ ID NO: 36          moltype =   length =
SEQUENCE: 36
000

SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype =   length =
SEQUENCE: 40
000

SEQ ID NO: 41          moltype = RNA  length = 92
FEATURE                Location/Qualifiers
source                 1..92
                       mol_type = other RNA
                       organism = synthetic construct
SEQUENCE: 41
ttattccatt actttggagc cagtcccagc gactatgtcg tatggacgaa gcgcttattt     60
atcgggaaac cgataagtaa aacgcatcaa ag                                   92

SEQ ID NO: 42          moltype = RNA  length = 108
FEATURE                Location/Qualifiers
source                 1..108
                       mol_type = other RNA
                       organism = synthetic construct
SEQUENCE: 42
acatctggcg cgtttattcc attactttgg agccagtccc agcgactatg tcgtatggac     60
gaagcgctta tttatcggag agaaaccgat aagtaaaacg catcaaag                  108

SEQ ID NO: 43          moltype = RNA  length = 96
FEATURE                Location/Qualifiers
source                 1..96
                       mol_type = other RNA
                       organism = synthetic construct
SEQUENCE: 43
ttatctcatt actttgagag ccatcaccag cgactatgtc gtatgggtaa agcgcttatt     60
tatcgggaaa tctccgataa ataagaagca tcaaag                               96

SEQ ID NO: 44          moltype =   length =
SEQUENCE: 44
000

SEQ ID NO: 45          moltype =   length =
SEQUENCE: 45
000

SEQ ID NO: 46          moltype =   length =
SEQUENCE: 46
000

SEQ ID NO: 47          moltype =   length =
SEQUENCE: 47
000

SEQ ID NO: 48          moltype =   length =
SEQUENCE: 48
000

SEQ ID NO: 49          moltype =   length =
SEQUENCE: 49
000

SEQ ID NO: 50          moltype =   length =
SEQUENCE: 50
```

-continued

```
000

SEQ ID NO: 51           moltype = DNA   length = 25368
FEATURE                 Location/Qualifiers
source                  1..25368
                        mol_type = other DNA
                        organism = synthetic construct
SEQUENCE: 51
ctggaaggac gcatggcaga aatcgttttt tactgttttt gccgataggg atagttttg    60
cttcttgaca tgcttttca tagatgacag attaaggact tttacaagag gctaacattg   120
ctttgttttt caaaaacaac ttaagaagat agtctatcat gcaaaaatct atagaggtta   180
ttgatgttat aaagatatac aagatgggag atgtagattt tccagcgctt caaggggttt   240
ctcttgagat agacaaaggg gaattcgtgg cagtaatggg gccgtcaggt tctggaaaat   300
ctacattcat gaacatcata ggctgtctcg atacgcctac tgccgaaaa tattggttgg    360
ataggcagga agtcgggcaa ttaagcaaag atgtgttggc aattatacgc aataaaaata   420
tagggtttgt atttcagagc tttaacctgc tgccaaggat aactgcaatg gaaaatgttg   480
aactccccct tttgtataac ggtttgccgt caagggagag aagacaaagg tctctttcag   540
cattgaggtc tgttgggctt gaagggaggg aatatcacaa atccaatcaa ttatcaggcg   600
ggcagcaaca gagggttgcc atagcaaggg cattggtaaa taatccatct ctcattctgg   660
ctgatgaacc aaccggcaat cttgattccc aaacaagcaa tgaacttatg acgctttta    720
agcggctcaa taaggaaaac ggcataacta ttgttatggt aacccatgag gcagatgttg   780
cccggtatgc tgacaggcat attgttttta aggacggaag ggtggtaaaa gacgataaaa   840
ttacgaatta atcttgcaat tccctgtagc ttgctgcagg gttactttat agttccctcc   900
cccttgatgg gggagggtta gggtgggggt gatagaatgt tgtttccacc ctcccctttg   960
tcccctcccg tcaagagagg ggagatttta ggataccccg cagcttgccg cggggaggtt  1020
cattaactac gaattttaaa aaaaccattc agatgtctta gcaggctgtt gaaaaagtca  1080
tcaacagcct tgattacaca gattataaaa aatgattaca cagatatttc aaggagtttc  1140
aatctgtgta atccaatctt ttctctgtgt aatcagagat tgttgagttt ttcaacaatc  1200
tgttaatttt taattcttac ttcataattg ctttcctatg aacataatcg caaccattaa  1260
aatagccgcc aatgccctgg gcataaataa aatgaggtca ggccttacca tgcttggcat  1320
aataatcggc gtggccgctg ttatagccat gctctctgta ggctcaggcg caaggactca  1380
gatttctaaa gagattgcca gcctcggctc caacctttg ataattctgc ctggcgcgcc   1440
caccagcggc ggactcagaa tgggtttttg aacagcgccc acgttgacat ccgatgatgc  1500
aaaggcaata cctcaggaaa tatctaatgt tgcatttgca gcgccgattt taggcggcac  1560
agcgcagata gtatacgaa atcaaaactg gagcaccatt gtgacaggca caacaccggg   1620
tttttttgat atacgggaat ggcagcttga ctcaggcgct ctgtttaccc agaaggatgt  1680
tgatggcgca acaaaggttg cattggttgg ccagactgtt acggaaaacc tttttggata  1740
tgaggaccca ttgggaaaga ttataagaat aaaaaagata ccatttagag tcatcggggt  1800
cttatccaga aaagggcagt ctcctattgg ccaggatcag gatgacagca tatatatacc  1860
ggtaacaact gcgcaaaaga ggcttttttg cacaacattt cccggcatgg tgaggatgat  1920
aaccgtaaag gcgaaaacct ctgatgcaat caaagatgct gaaaaggaga ttgcggcatt  1980
actgagacag agacatcata ttacagccgg gagggacgaa gatgatttca gcgtccgcaa  2040
tcttagtgaa atgatggctg catctgaaca ggcggcaaaa atcatgtcca tcctcctcgg  2100
ctctattgcg tcggtatctt taatagtcgg cggcataggc attatgaaca tcatgcttgt  2160
ctctgtaaca gaaaggacaa gagagatagg catccgcatg gcagtcggcg caaggcccag  2220
agatatactc atgcagtttc ttatagaagc catagtcctt gctgtcattg gcggcagtat  2280
aggtattctg tgcggcgccg gaggctcatg gcttatttca tactttgccg gctgggagat  2340
agccatatcc tctgttgcta tagttcttgc attcggtttt tccgcgttag tcggaatatt  2400
cttcggtttt tatccggcca gaaaggcgtc ccgccttgcg ccggtggagt gtttgaggta  2460
tgaataagtt gtggtttgca ggcaaactcc attttcgttt tataatccgg agcggactgg  2520
gtttgtctgg ctgggttgcg gcattacaga ggaagtaaat ttgggaaact gttataaaaa  2580
aggttgaaat acatatcgt tctgcttata ataagaatat cagataatca gaaaggagga   2640
atttatatgc ctgttgtcaa aatgagggaa aggggacaac taaccatccc atacgaatac  2700
aggaaagatc tcggcattgg caaggaagat atgctcaatg tcttaaaaat cggcgatgtg  2760
cttatccttg tgccgaaaca gcttgccgga gatatcgtat ccaagaaaat tgaagggacg  2820
atgaagaaaa aagggctgac acttgataac cttctaagca atctcaggga gcagagaaaa  2880
agatattcca aagagacata tgccaaagca aagacctaaa gtttttcttg acacaagcgc  2940
attgattgcc ggcatagcat cttcaagggg cgcagcaagg gctgtgctgc agcttgctga  3000
aatcggttcg atacaggtct ttgtctcaag gcaggtcatt gtggaagcag aggaaatat   3060
tgaagaaaaa ctgccggaga tgctgaatga atacagagaa tttatcaaac tcctatcacc  3120
cgtgttagtt gatgacccaa gccacaagga agttgcaaaa tatttatcag taatcaattc  3180
ggatgacgcg cctatccttg cctctgcaat aacctcacac gctgatttcc ttatcacatg  3240
ggacagaaag catttcatcg gcaaaaatat ccgtatccac ttaaacctga aaatcgttac  3300
tccgggagat tttttgaagt atttcaggaa atatattgga taaaagccca cctctttggc  3360
aaagagggga atggcatttg tttgagggac gaggggactg tcccagacaa aataaaattat  3420
ttttaaccgt tttttggatg tgtgttatat tctgtgaata aggagggatt gccatggatg  3480
ataaagacaa ggatttaatg ctggaattta gaaaaaggct ttcatcggat ttagcaaatc  3540
atataacacg tctcatagta ttcgggtcaa gggcgaaagg tgaagtagca gaggattctg  3600
atcttgatgt aattgccata gttgatgaaa aaaactctgc gattgaaaaa agtcttgaag  3660
atatagcgta tcggattatg tgggatcatg acttcaggcc aatcatatca ctcaaagtgc  3720
tctctgaagc ccaattcagt gacgcccttc gtagagggt ttcttttttac aggcatgtgg   3780
aaaaagaggg ggtttggta tgaccgagga agtaaaaaag ctgattgaaa aagctgaaca   3840
cgcccttgag gtagccgaaa agttaatgaa tgacggttat ccatcagatg ccgcaagcaa  3900
aatctattat tcaatgtatt atgcagcaca tgccccttta aaaacagaag gaattgatgt  3960
catcaagcac tcagccgttg aatcagcctt cgggtattac tttgcgaaga ctggaaagat  4020
taatcccaaa caccacagga tgctaataga cgcaagaaag attcgtgaaa tagccgatta  4080
tgatattcag gaagagattg ttgagccaac tgcatcgcta aaaattaaag aggggaagtc  4140
ttttttgtct gcaatcagaa aaattcttgg cagcctgtag caatggactt gacaagcgaa  4200
gtgggactgt ccaggattta cggacagagc gaagcggagt cccgaatcca atggttgtgg  4260
```

-continued

```
tttgcgggca ggcattattt tcgtttttata atctggaaag aaaaaaggaa aaccccttat  4320
ggaaaagaga ataaacaaga tacgaaagaa actatcggcc gataatgcca caaagcctgt  4380
gagcaggagc ggcccccatga aaacactcct tgtccgggtc atgacggacg acttgaaaaa  4440
aagactggag aagcgtcgga aaaagccgga agttatgccg caggttattt caaataacgc  4500
agcaaacaat cttagaatgc tccttgatga ctatacaaag atgaaggagg cgatactaca  4560
agtttactgg caggaattta aggacgacca tgtgggcttg atgtgtcaaat ttgcccagcc  4620
tgcttccaaa aaaattgacc agaacaaact aaaaccggaa atggatgaaa aaggaaatct  4680
aacaactgcc ggttttgcat gttctcaatg cggtcagccg ctatttgttt ataagcttga  4740
acaggtgagt gaaaaaggca aggcttatac aaattacttc ggccggtgta atgtggccga  4800
gcatgagaaa ttgattcttc ttgctcaatt aaaacctgaa aaagacagtg acgaagcagt  4860
gacatactcc cttggcaaat tcggccagag ggcattggac tttattcaa tccacgtaac  4920
aaaagaatcc acccatccag taaagcccct ggcacagatt gcgggcaacc gctatgcaag  4980
cggacctgtt ggcaaggccc tttccgatgc ctgtatgggc actatagcca gttttctttc  5040
gaaatatcaa gacatcatca tagaacatca aaaggttgtg aagggtaatc aaaagaggtt  5100
agagagtctc agggaattgg cagggaaaga aaatcttgag tacccatcgg ttacactgcc  5160
gccgcagccg catacgaaag aagggggttga cgcttataac gaagttattg caagggtacg  5220
tatgtgggtt aatcttaatc tgtggcaaaa gctgaagctc agccgtgatg acgcaaaacc  5280
gctactgcgg ctaaaaggat tcccatcttt ccctgttgtg gagcggcgtg aaaacgaagt  5340
tgactggtgg aatacgatta atgaagtaaa aaaactgatt gacgctaaac gagatatggg  5400
acgggtattc tggagcggcg ttaccgcaga aaagagaaat accatccttg aaggatacaa  5460
ctatctgcca aatgagaatg accataaaaa gagagagggc agtttggaaa accctaagaa  5520
gcctgccaaa cgccagtttg gagacctcct gctgtatcct gaaaagaaat atgccggaga  5580
ctggggaaag gtcttcgatg aggcatggga gaggatagat aagaaaatag ccggactcac  5640
aagccatata gagcgcgaag aagcaagaaa cgcgggaagac gctcaatcca aagccgtact  5700
tacagactgg ctaagggcaa aggcatcatt tgttcttgaa agactgaagg aaatggatga  5760
aaaggaattc tatgcgtgtg aaatccaact tcaaaaatgg tatggcgatc ttcgaggcaa  5820
cccgtttgcc gttgaagctg agaatagagt tgttgatata agcggtgttt ctatcggaag  5880
cgatggccat tcaatccaat acagaaatct ccttgcctgg aaatatctgg agaacggcaa  5940
gcgtgaattc tatctgttaa tgaattatgg caagaaaggg cgcatcagat ttacagatgg  6000
aacagatatt aaaaagagcg gcaaatggca gggactatta tatggcggtg gcaaggcaaa  6060
ggttattgat ctgactttcg accccgatga tgaacagttg ataatcctgc cgctggcctt  6120
tggcacaagg caaggccgcg agtttatctg gaacgatttg ctgagtcttg aaacaggcct  6180
gataaagctc gcaaacggaa gagttatcga aaaaacaatc tataacaaaa aaatagggcg  6240
ggatgaaccg gctctattcg ttgccttaac atttgagcgc cgggaagttg ttgatccatc  6300
aaatataaag cctgtaaacc ttataggcgt tgaccgcgagc gaaaacatcc cggcggttat  6360
tgcattgaca gaccctgaag gttgtccttt accggaattc aaggattcat cagggggccc  6420
aacagacatc ctgcgaatag gagaaggata taaggaaaag cagagggcta ttcaggcagc  6480
aaaggaggta gagcaaaggc gggctggcgg ttattcacgg aagtttgcat ccaagtcgag  6540
gaacctggcg gacgacatgg tgagaaattc agcgcgagac ctttttacc atgccgttac  6600
ccacgatgcc gtccttgtct ttgaaaacct gagcaggggg tttggaaggc agggcaaaag  6660
gaccttcatg acggaaagac aatatacaaa gatggaagac tggctgacag cgaagctcgc  6720
atacgaaggt cttacgtcaa aaacctacct ttcaaagacg ctggcgcaat atacgtcaaa  6780
aacatgctcc aactgcgggt ttactataac gactgccgat tatgacggga tgttggtaag  6840
gcttaaaaag acttctgatg gatgggcaac taccctcaac aacaaagaat taaaagccga  6900
aggcagata acgtattata accggtataa aaggcaaacc gtggaaaaag aactctccgc  6960
agagcttgac aggctttcag aagagtcggg caataatgat atttctaagt ggaccaaggg  7020
tcgccgggac gaggcattat ttttgttaaa gaaaagattc agccatcggc ctgttcagga  7080
acagtttgtt tgcctcgatt gcggccatga agtccacgcc gatgaacagg cagccttgaa  7140
tattgcaagg tcatggcttt ttctaaactc aaattcaaca gaattcaaaa gttataaatc  7200
gggtaaacag cccttcgttg gtgcttggca ggccttttac aaaaggaggc ttaaagaggt  7260
atggaagccc aacgcctgat attgccgata agcaccgtaa tggaatccat ctactgcccg  7320
cgcaacgcat ggtatgcctt tgtgggcgag cggcggaata tggctaaaag cgttcacttt  7380
acggaggccg tccatgcaca cagggcggtg gatgaatcca cgcagagaat ccgcactgat  7440
tgcaagcaga ttacagggat gtatatttat agcaataagc ttggcctgac agggcgggcg  7500
gatacagttg agtggctgta tggaatccct ataccggttg agacaaagac cggcgcaatc  7560
agggattttg agaacttccg ggtacagatt gcattacagg ccttgtgcct ggaagagatg  7620
tttaatgtga acatcccata cggtgagata tttttctgtg aaaccatgcg gcggcacgaa  7680
atagctgtag acgaagacct tagaacgcat agcacggcaa ttgtggtgga gttgagagaa  7740
aggtttctgt cttttgacat caaccgcttc caaagggtaa atgaccatag atgcccaaag  7800
tgtcaatatt tggagtcatg ccttcctccg agtcttgagt tgtgaggttc ctttatgacg  7860
gcgataacag acaggataac cctttacatc acagcggatg aatccagcat ttcacgccga  7920
ggcgatgcat tcctgatcca aaaggcaggc gaggaaaaag ggcaaaagat accagccgatg  7980
aaagtaaaag atatagtagt cgttggtcac gttacgcttg acagccgtct gattggactt  8040
tgcagggaag agtcaattcc gatccatttt ctaagcggaa ggtgggaata tcagggtagc  8100
cttcagttcg agccggtcaa gaatctattt atccgcaggg cgcagataaa aaaacatttc  8160
gacccggaaa agaaactgga tatatccaaa aaaatagtcg gtggaaaaat ccgaaatcag  8220
caggccatgc tggataaaata ccggaaaaat ctgaagttgg cgtgcccgca aattgattca  8280
gtgggcgata tggaaaccct gcgagggatt gagggtgtgg tggcaaagga gtattacggc  8340
ttctatcccg ccataataaa aaattcggag ttcacgttta cacgcaggac aaagcgtccg  8400
ccggaggatg aaataaacgc gctcctaagc ctgctgtata ccctcatttt caacgagata  8460
cactctaccg cattgctcgt agggctggac ccggcctttg ggtatctcca cgacgtctat  8520
tacgacgac catcgttgat ttgcgatctt cttgaagaat ggcggccatt ggccgaccgg  8580
tttgtgctga atatgataaa caggaaagag gtcacaccgg aagatttcag gaaagagacc  8640
gaccaaaagg gcgtgtggtt aagcaaggac ggatatccaa aggtgataaa gaaatggcac  8700
cagttttttca agatggatga acaaaacaca agcattctga gccgccccat aacatatcaa  8760
cacgcaattg aaaggcaggt caggaccttc agccagtatc tcatggatga caaagacaat  8820
tataagacga tagagctttg ataatgcgcc atctcatctg ttatgacata gaggaggata  8880
aggtaagggc acggcttgta aagctcttgg aagcctacgg cgtcaggatt caatattctg  8940
tttttgaatt caacctttca aaggcgcgct ggacagacct taagctgaat ttgaaagaaa  9000
```

-continued

```
aagggttcct tgacggctcc attagcattg tcatctatcc attatccgca gaggcttatg  9060
agctggtgga acgttatggc gctgcctcta tatgggatga gggggatatg gttttcgatt  9120
gattttctt gactgcaatc tgtcataagt agtaaattac atctggcgcg tttattccat  9180
tactttggag ccagtcccag cgactatgtc gtatggacga agcgcttatt tatcggagat  9240
agctccgggt gcaaactcgg agctgttttt ttacgaaaca gctaatttta gccaaaagtt  9300
ctttgaaaac ctgatattac ggtttttttg tttgtaaaag ggtttacagt gcagatctcc  9360
ttataattat tgaaaatgtg tttcgttact cttaatattc gagaatttcg acttccggaa  9420
ctcattgata tatctgggtt gttggtattt gaaggtatct ccgataagta aaacgcatca  9480
aaggtctcac tcaagatgac gaggagatac ttgagaattt gaaggtatct ccgataagta  9540
aaacgcatca aagatccaga aaaatacggc cttctttacc atttcctatt tgaaggtatc  9600
tccgataagt aaaacgcatc aaagtacccc tgcacccatt agatttagat gcaggataat  9660
ttgaaggtat ctccgataag taaaacgcat caaagagctc tgctttgtag atgcctgctg  9720
caagggttga tttgaaggta tctccgataa gtaaaacgca tcaaagtcct gcagcagaaa  9780
atcaaagaca atgaatatta tttgaaggta tctccgataa gtaaaacgca tcaaaggccg  9840
ctctgaaaaa ggaaaagctc ggactaaaat tatatttggg cgggaagcaa cgtaaagcct  9900
tcttttcttg ctgcatctct cagttttgaa tcaaggcaga cgaaataatg accttttggc  9960
cttttttcctg cccatacgag cgcggcagat agttgcaagg catctgcggc acggagaggg  10020
tgcagcataa gaagtcttcc tgcaaatatcc cgtatgtctt cgccgggttc aatctctgtc  10080
catgtatccg aaagaagggt gaggagatgc cgcacaccgt cttcttcctc aggtttgagg  10140
aatcccttgc gccgcaagcg ggcaaaggct gaacagcact ctatgaagct gccccaccat  10200
actgcaatag cgtgatcttt tctcacaagc tgttagacag cctttgtttg tggttcgtca  10260
atgcataatg ggatgatagc agaagaatcc cagaacatca tcttccttcc tcccgttccc  10320
gtaaaagggc attaagagcc cgtccttttt tatcctttgg tctgggcata ttccaaaaat  10380
ctgccggcag tctgcctgcg ccgatgcgga caagccctgc cttctccaac gttaatagat  10440
gcgccggtat ttcaatatct cctctttca aaggaataat cttggctata ggctttcccc  10500
tgtcagtgac aagaacctct tctccagcct ttaccttga caggtattcg ctgatagatg  10560
cctttaattc agaaaccttt gcggtcttca taggttatc ctccgtgact atatggatat  10620
gaccgatata gtcttattcc atagccctgt caaatgaaaa aaacgaataa cagttacttt  10680
atcgtatgaa acataagctc agcatgattt aatgaaccgc ttttatcaag aatgagtttc  10740
aggagaaaag ggcgtcttgg cggaagcgag ttaaaccgca ggtcaaaata ttccaccata  10800
tatccttcgc cctcctcttt tacggttacc acaggaaatc tggcaaacca gagatatgtc  10860
tttacaatct ccagttttc aacctttca ataatgttat ttccctccgg tccctgattt  10920
aagccttcag ggagatgctt tttctcaaag gaattaaatg gcgagatgct tttcagcgca  10980
tcaacatcaa cctgataaaa cctttatca tcctctatat acacagacca tctgaaaggg  11040
gagaaggga ggggaattgc ctcaactctt ttgccggtta tgccaagttt ttgagcctcg  11100
gccttagcgc tttcaatagc aatggttctc catgtgtagg caatccccag atagattatt  11160
atacctgcaa cagaactcaa ggctataacc tttgtccatt cccgtttgaa ctttattatg  11220
accaatggga taagcatcaa ggcggtgaaa taaaaatcta tgataaagac aaggtcaaga  11280
gagtatcttt tgtcggtgaa aggaaagaaa actaaagtcc cgtaagatgt gatgaggtca  11340
aggaagatat gggtgtatat gcctaataaa aacaggccaa aggttgttag atagcctaat  11400
ttttctctaa atcgttctat tgaacagaca atacctgcca tgatagcggc gattacaaaa  11460
ctgccgataa tggagtgcgt aaatccccga tggtatttga gataggcgag gggacctgca  11520
agcctcaggg ttaagtggtc aatatcaggt attagtgcga caacaataaa gattatggtg  11580
gcaggtctgc caaatctctg atagaatcct gttctggaca gaacgacacc ggagaggccg  11640
tgtgttattg gatccatagg tttagataag tatattatat ataatggtat taaacaacag  11700
gggattttat cgttaccttt ttatgagaac aattaaaaga acagtttgtt cagcctttgt  11760
tttatttatc ttattctcgt cagatgctgt tgccgacctt tatcagtggc aggatgaaaa  11820
aggggatatc catgttgtag atgatatgct cctggttccg ccgcaatata aagataaggc  11880
aaagaaatta aaggcaaggc cttcaaggca aaccccttct ccccaacaaa atgttcaacc  11940
ccctgtgccg cctcaaacat cttcagaaca agaagagctg tatggggatt atcctttgag  12000
ttggtggaaa aatgagttca gcagtaaaaa aaacgagatt tctaaacttg aaaatactat  12060
aaaagagcag aaaaattta tagctgatta tgaaagaggg aggaggcttt atcgattata  12120
cagcaaggaa gatacggata aatacgaaac ctataaaaaa gagctgtctg ataatgagaa  12180
ccaattgaac aaactcaaaa cagatttgga cgaattcagg cgcaaggcgc aaatctacgg  12240
cgttccgagg gcaatcagag aatagtaatt aacaggctgt tgaaaaaggc atcaacagcc  12300
ttgattacac agattaggaa aaacgattac acagatattt caatgagttt taatctgtga  12360
aatctaatct tttatccgtg taattgaagt ttgttgagtt tttcaacaaa ctgttaatat  12420
ggtaaaacct gttatcagtt gtagggcaag ccttcaggct tgcttatttg cagggctaaa  12480
gccctgccct catcaagtt atttatcaag ttatttattg ccttcactat aatatggtaa  12540
aacctattat cagaaatagc attgcatatc tcttatgttt atgcctcctt tacccgtga  12600
ctaaggtttt tggtgtggat gacgatgcta taacaatagt ggcagcagga gacctttatc  12660
ttggaggctc tgccaatcca tacttaaaac agcgcggata ttcatatcca tttgaatcaa  12720
ccaaggatgt tttgcatagc gcggatatcg cagttgtcaa tctcgaagcg cccttgacca  12780
acaagacgga aatatttatg aataaagagt ttgtccttaa ggctaaccct gattcaagtg  12840
aggcgataaa ggctgtgggt tttgatgtgg cgacattggc aaataatcac attatggatt  12900
acgggcaaga gggattgaaa gatacgataa ccgcacttaa taagagaggg gtaagctata  12960
ctggcgcagg agaagactta aataatgcaa ggaagcctgc catccttaat gttaaaaata  13020
aaaagaattgc ctttcttgca tattccaggg tctttccaga agaattctat gctaccgata  13080
tctctggcgg aacagcgccc ggtttatttg aatatataag ggacgatatt aaaaagataa  13140
agaaagatgc tgatattgtt gttgtttctt ttcactggag tgaagagctg ttgaaatatc  13200
ccaaagaata ccaaattaaa cttgcccatc ttgccattga cagcgggca aatctaatca  13260
taggccatca cccgcatgtg attcagggta tagagaaata taaaaacggc ctcatctttt  13320
acagtcttgg gaattttgcc tttggatcta tcagccaatc atcgccagag ggtatattgg  13380
ccgctgtccg gtttaagggt aaccaaatca tctcggctga gataattcca ttaaatgtca  13440
ataataaaga ggttttttttt cagccaaagg tttttggaagg agaaaggggcg gaagttgcaa  13500
tgaggaatat tcaagaaata tcagacagat tcaaattaac cattatggct agggaaggaa  13560
agggctacat acagcttaac gaggagttaa aatcagcctc gcttccgtga ataggggttg  13620
ttgttacaag tagagttaag tcagatatta tgtaaacgtg tgatcccttg ctatgcaagt  13680
ttacataata tatcttatgc gacaataaaa tttagttagc cttaatggcc tgtttgggct  13740
```

-continued

```
aaaaatccct atattccatt cgttttgccc cctgttatct ttatcccgct tttcttatt    13800
gcgctttta tcatctttag tttccaatcc ctatgcgcat taattgtaga gagaacctct    13860
ctggggttat cggttatttt aacgaggtct aaatcttccg gagatattgt atcttccttt    13920
aacatcgttg ttttcatcca gtggataaga ccattccaat aatccttgcc aaccagaatt    13980
aaaggcaatg gatatatctt atgagtctga acaagcgtaa gcgcctcaaa aaattcatca    14040
agggttccaa atccgccagg catacagaca tagcccatgg catactttat aaacatcacc    14100
tttctggcaa aaaagtattt aaaggttaat gatttattct gaaatgggtt cggcttctgc    14160
tcctttggca gaaggatgtt gagtcctacc gaacctccgc cattcttggc agcgcctctg    14220
ttggcagcct ccataatgcc gggaccgccg ccggttatga tggtatagcc atcctttgca    14280
agcagtgtgg ctatatcttc ggccattttg tagtatgtat gattttagg aaatcttgcg    14340
gagccgaata tagatacagc cggccctatg gcagaaagtt cttcaaaacc ctccacgaac    14400
tcgctcatta ttttaaatat acgccatgtt tcctgacctc ttaaatcttc aaccatttt    14460
atttactccc attctatagt actcggggt tttgtgctga tatcataaac caccctgttg    14520
atgccgcgca cttcatttat aatccttgag gagatccttg ccattaaatc ataggggaagc    14580
tttacccagt ctgccgtcat tccatccatg ctttctacag cccttattgc ggcaacattc    14640
tcatatgtcc tctcatcacc catgacaccc actgtcctta cgggcaaaag cactgcaaac    14700
gcctgccaca tctttgtgta aaggccggcc tttttttatct cttcaagcac aatactgtct    14760
gcctttctta gtatatcaca tctctctttt gtaacctcgc ctaaaattct tatagcaagg    14820
cctgggcctg gaaatgggtg tctgtttatt atttcctcag acatgccaag ttctttaccc    14880
agtatccgca cttcatcctt aaacaattcg cgaagaggtt cgacaagttt gagtttcatt    14940
ttttttagaa gaccgccgac attatggtgg cttttttattg tcgctgaagg gcctttgaag    15000
gatacactct caatcacatc cggataaaga gtgccttgtc caagaaagct cacttcctgc    15060
cttttgcctc cgcctctggc ggatgaggcg gatgccccct gtttttaactt catggcctct    15120
tcttcaaaga cccttacaaa ttcattgcct attattttttc tcttcttttc agggtcctcg    15180
atacctttga gcttgtttaa aaatctttga gaggcgtcaa tacatttaaa attcatacga    15240
aaatgcttct ttaatgtctc ttcaaccttc tttgcctcac cctgcctcaa tacgccgttg    15300
tctacaaaga tacaggtaag tttgtttcct atggccttat gcattaatac cgctgcaact    15360
gctgaatcca caccccgct tatgccgcat accaccccc tgcccctac cctttccctt    15420
atatcctta cagcagtgtc tacaaatgcc tccatggtcc agataggttt gcatccacat    15480
atcttgaaaa ggaaatttct aattatctgc aagcccttg gcgtatgaac tacttccgga    15540
tgaaactgca cgccaaagat ttttcttttg gcatccttca tagcacagat tggagaatta    15600
ctactgcggg caatagatgt gaatccatta ggcatctttc ttacacggtc gccgtggctc    15660
atccatacag gcgtgaggtg tgaggcgtaa ggcgtgaggc gtgacaacaa atcattacta    15720
tcatcaatta ccagttcagc gcttccgtat tctctgtgtg atgattttttc aacctttccg    15780
cctaaaaggt aggctgtaag ctgcatgccg tagcatatgc cgaggattgg aatgtccaga    15840
ttgaagagtt cttttggaat aagaggggcg ttttttatcgt agacgcttga cggcccgccg    15900
gagaggatta tgccttttgg gtgaaaagcc ctgatctttt caaggcctat attataagga    15960
tgtatctcgc agtagacctt ttgttcccgc accctccttg caataagctg ggtatattgg    16020
gaaccaaagt ctaaaataag gattttttgc tgatgtatgt tttgcattag gggaatattt    16080
tattaaagtt aaaaaaatat atcttaaaaa aaccaaatag acaatagaaa aatcatgcgt    16140
gtaaaaaacc tctttcttga cagtatccat tctgttatga taagaacagc tcttttttta    16200
tacagaacaa gactgaatct tacgatagaa tcattaagca aatcatatag tttaataggt    16260
aggacacttc atgtttcaat ttgttaagat agcagcgcta tcctttataa taattatagc    16320
accttgggat tcatttaaac caacatataa tagcgatata tttcagttta taataacctc    16380
tttcagttca gttgacctgc catttgtatc aagcagtctg catagagagg aattggaaca    16440
agcctctgtc ttttggaagt atttctttct attaatcttt ttcctgtctg ttgatggatt    16500
caaaatattg attgaaattt ataaacgtcc ggtcttacga acttatactt ccaaccctca    16560
ggatgtaaca gcattaatcg catgctacaa tagcgctaaa acaataaagt ttacgattga    16620
tgaccttcaa aagatttgt ctaatgatag gattattgtt gtggatgacg gcagcactga    16680
taatacattt aatattgcaa agaatatggg cgttcaggta tatcggtttg aaatgaataa    16740
aggaaaagtt gcagccatta attttggaat ctaccgtgtt aaaactaagt atactttgct    16800
attagatgat gatacaaggg taggcccttt gtctcctcca acctctttgc tggaggaagg    16860
gtacaccgga gtggccttta acctttttacc ttgccgtaga acacgagact tgactaatgg    16920
gaaaaacttt gtaagctgcc ttcagagata cgagtacagt aaatccatgg agattggcaa    16980
aagattccaa gacggcgcat tgagcgtcag ctgcatatcc ggcgcagtag gcctgttttt    17040
gacttcacgg ctcaattctt tccatcattt acactcaacg gtatttcagg gagaagattt    17100
ggagagaacc ttaatagatt tattaaaagg cggaaaggtt gcctttgtaa atcaaaatgt    17160
ttggacctttt gccccggata actggttgag tctcacaaag caacggcttt ttaactggta    17220
ccctgggttt taccgcaata tagaccattt cttccatata ctctttgaca aacaacttcc    17280
gttaaggctc aaaggtgaaa tgtttttataa catctttgta attctgactg atcctctaag    17340
gatatattca tttttttgccc tgtttattta taagcagtgg gctatgcttc ttttcgtata    17400
tctcttttat ttagctatag agatataccc ctttattgta gtggaaaaat atcttcctgt    17460
cgcaagatat tatatgcccg ccctcatcgc atatcccata tatggaattt ataataccct    17520
attgcgctct cttgctttat tcgtatggtt gtataataga tttataacaa aacggatgag    17580
accaaaagga cgcccgggggg atagaattgc ttaggaatgc ctttctgatt gctgtatttc    17640
tactatggct gccaaatgtt gtaatgggcg ctgacagctt aactatcaca aatgattata    17700
ttatagatat caaagatggc ggggataaaa catataacga cacatatatc cgcttagatt    17760
ataaacagct ctacgcagtg ggctatcttg gagagtggca gcatggcttt gaaataggcg    17820
ggtttataaa agatgaacgg atgtctgcgt atagcgcaat gttgcgggct cgtgggaaatg    17880
atcagaccta tcaggtggga accgatcagg tgttaggaat gggttttgtg ggaaaggttg    17940
atttacgata catccatatt gaagaattag aaaaaaccgg agataaacac gacctttttg    18000
tttatggttt gggatttgat aaatattatg gtgattacaa ctatttgact gctgtgattt    18060
ataacgaccc ccggaagagt gatagattct ctgtagtcat cagtaacacc cttgccaatc    18120
agaactctta tctgagatta ggtgtcgttc cgagaagcga cggcacattg ggctattttg    18180
gaacaataaa ataccactgg attgtggccg gatatgccta tacgcgagaa tttgactttta    18240
ctacccttga taggaaggtt tttaccttag cgctccagat acccttttgat ttaaagtgga    18300
acagagaaga acaataaccc gaaaagtgca taatgcctgt ctgcaaacaa ctactccacc    18360
accttataat tcggcgcctc ttttgtgatt acgacatcat ggacatgact ttcacgaagc    18420
cctgcaatgc ttattctgac taatttggca ttctttctaa gctcagaaat agtcctgcac    18480
```

-continued

```
ccgcaataac ccataccgga ttttaggccg cctataagct gaaatatact tgaagatacc   18540
ggccccttgt gaggcaccct cccctcaatg ccttccggca caagcttaag ctcgctctca   18600
acatcatcct gaaagtatct gtctttgctc cctttcttca tagcttcaat agatcccatt   18660
cctctataca tcttataggt tcgcccttga taaagaactg tctccccagg gctttcatct   18720
gtgcctgcaa ataaccctcc tatcataacc gaatcagcgc cggcagcgag ggcctttaca   18780
atatcgcctg aaaactttat gccgccgtcg gcaataaccg gtatgttctt ttttctggca   18840
acagccgcac aatccatgat ggctgttatc tgcggaacgc ctacccctgt cactatcctg   18900
gtggtgcata ttgagccggg gccaatgcca atctttacag catcaacgtc agcctttatc   18960
agagcatttg cgccatcgga tgtcccaaca ttgcctgcta tcagctggca ttttggaaag   19020
tttttcttgg tatctttaac agcggtgagc accccttgc tgtggccgtg ggctgtatca   19080
ataacaataa catcagcgcc tgcctttaaa agcgcatcta tccttgcctc gcggtcaaat   19140
gatacgccaa ctgcagcgcc aaccattaat cgcccgagtt tatccttgca agagtttgga   19200
tattttccc gttttcttat gtcagagatg gttatcaggc ctttcaactg cccattttta   19260
tcaattaacg gcagttttc tatcctgtgg cggtgaagca tatcctttgc cttttctatt   19320
gatgtgccgg ccggagctgt tacaagtttt tttgtcatta cctcggatat tttttttgtta   19380
gggttcttct caaatcttaa gtccctgttg gtaaggatgc cgaccaatac cccgttttta   19440
actataggga aactggatat ctgctctatt tttttaatct gcaatgcatc ggcaatgcgc   19500
tggtctggct ccagtgtcct tggtttcatt attacaacac tttcgtattt ttttactttg   19560
tcaacctcta tggcctgttc ttctatggtc aggtttttat ggattatgcc cataccgcct   19620
tcctgggcta ttgcaattgc catgcgggat tccgttactg tatccatagc ggagcttaaa   19680
agaggtatat ttaatctgat ggtatttgta aggcgggtag aggtatctac atccctcggc   19740
aaagcttccg aaaatgccgg tatcagtaaa acatcgtcaa aggcaagacc ttgtttaata   19800
ttttttctg gcataaataa aacctccaac agaaattgat tgaggctgga ggcaagaggt   19860
gcgaggcaaa cgacactacc tccatcctcc aacctctaac ctgtcttctc caatagtatc   19920
ccttccaaaa gccccgcatc gcttaccgtc attttatcaa aaccaaaacc ttccattgcc   19980
tttaaaacaa tagctgcgcc tgggattatt atgtcttccc tccccttttc aagagagaga   20040
atttcctctc tctgttttaa aggcaataag gcaaggtgtt gatatatctt tctgatagcc   20100
tcataactta atatgtaatt gtttatcttg cctgactcat atttctcaag tccctgatca   20160
atagcagcaa gcgtggtaat agtacctgct gttcctacaa ataaggcgga ggctgaaggt   20220
aaacagccat ctcttttcat caaatccttt aaatctgcaa taacacctct tatctcattt   20280
tccattgcgt ctaactcact gtgagtcggc gggtctgtct tgagataatt ttctgtgaga   20340
tgcaccaccc ccatctcaag actccacgca ccaagcatcc ttccggcatc tgttgcaata   20400
aactcggtgc tccctccgcc aatatcaacg acaaggcatt tggggataga ttttaaatct   20460
gtccccactt ttatgactga cagaacccca agcaaagaaa gccttgcctc ttcatcgcct   20520
gatattatct ttatctctat ccctgtcctt ttcaggacac tgttcagaaa ttcttccctg   20580
ttctttgccc tgcgtaccac actggttgca actgccctta cctctttat atcatactct   20640
tttatctttt cagaaaaaaa ctcaagcgcc tttattgtcc tttcctgagc cttcctgttt   20700
atgccaatat cttctttata accgccgcca agccttgtga tggttcgttt taagtaaaca   20760
ggctgaaggt ttttattatc tatctctgca atcagtaacc ttaaggtgtt tgtgccaata   20820
tcaatggagg cgtattttgt tgacatagct gtatcattgc ttaattcagt ttatgctcaa   20880
aaaatatccca gatgcaaggc gccgaggagc gagcagcgga gcatacgccc tcaggtatgt   20940
gagcagcgca gtgacgaagg caacgctagca gatgggtatt tttcagcata aactatttcc   21000
tttccggctc tattgcgata gataacttct ctgccccggc gcgcttggca atatccaaaa   21060
cctttacaac tatgccgtgg agaacatctt tatctgcctt tattattacg attttatcag   21120
ctcgagatgt aatatctgtt tttatagcgt caaaaagcat ttctatgccg attgttttgt   21180
tgttaatata tataatacct cccggagcaa tggagatagt tatacccttc cctgtttcag   21240
tgtctgccgt aaccgccttt ggcagcttta ttttgaatga ttccattatc agaagcggcg   21300
ttgtcaccat aaaaatcaca agcaagacaa gcatgacatc agtcaatgga gtgatattta   21360
tctcagagat aatcttatcc ctattacctg caagactcca tttttttcatt tattgtcctc   21420
aaaaagcgca tcaataaatt ctgctgccct gccttctatt tcaactgccg cgctgtttat   21480
ttttcttgta aagtaattat atgcaataac cgccggcaca gccacaaaaa gacctgctgc   21540
ggttgccaca agggcctctg caatcccatc tgccacaaca gaaggccctg cccccctctgc   21600
tatggcgagg tcatggaatg ccctgataat tccaagcact gtgccaaaga gccccacaaa   21660
gggggctgtg cttccagtgg ttccaagaac gcctaaatac cgctctaaat aaagaagctc   21720
ttgtttttgct gccagctcca ttgcctctcc aaccgctgtt ttgccttctt tatattttgt   21780
aagccctgcc ttaaaaatcc ttgccagagg ttcttccttc ccgcagatgg taaatgccgc   21840
ctccctgtta ccatcccttta aagccttttc aatttgcaaa gaaatatttt tagaacctct   21900
tcggaattta aataaagccc aaagtctctc catcatcacg ccgacagaga gaacagaaaa   21960
gaaggcgagg acaattaccg taacgccgcc tttttgaagc agggatataa gaccaagatt   22020
atcaaacata tttatatttc taaacctaat gtaatctgcc gatttatcgg ctattcaaag   22080
ttacgcaata gaaatacgcc cataaatggg caactacctt ttatactcct tagaatattc   22140
aatgtagttt tttgcggatt tcaaaatcct tgccacttct tcatctttaa gctgtcggac   22200
aacctttccc ggcagcccca tgacaaggct tttcggcggg attatgctct tttcagtaac   22260
gagtgcgccc gctcctatga tggaatcttc gccgattgta acgccatcaa gattattga   22320
acccatgccg atgaggcacc tatctttgat cacacagccg tgcagcgtaa cattgtgccc   22380
gacagtaata tcattgccaa gcatcacagg ccaaacacct tttgtgccgt gaaggacgca   22440
attatcctgg atatttgtcc ttgcgccaag cttaatatga tgaacatcgc ctctcagaac   22500
agcgttcac caaatgctgg aatattcgcc tatctccaca tcgccgatta cctgggcgct   22560
gtcttcaata taggctgtag catgtatttt tggatttatg tttttgtaag gtcttatcat   22620
aagaaattac agattgtgat atgccttata aatatagtat aaggtctttt cttcggtaga   22680
tattctcttc attaacgccg ctcttattgc aataatgcca tttataaaac cggtttcgtc   22740
tgctgtaatg gcttttttcat tttcatacct tgaaagaaaa tcaaaaatat tcttggaaat   22800
atctttcatg ccgtctataa aaatatcaag cgcaggcagc agtgcgtctt gtttaagctc   22860
tatggcttt tgcctcatag cagggtaaaa cttattgtcc tcatcccgga gatgattaat   22920
gaggatagtt ttaagctgtt caataatttt caatacataa gcagtgtcac ggatgtcctt   22980
gttttctata ataggctcta atttcttgaa tgccttctct atcattgcat gttcttttc   23040
taaacccta ataaattttt catgctccat aacaatgccc ctctaaataa agacaccaat   23100
aaaggtgtaa aactataaca aaaacacca tctttgcgca agattttgct gccacccaga   23160
aaatcaaagt ctattttttt gtatcacttt ctgggcgtct ttacagatgc gataaattca   23220
```

```
gcgctgaaaa gcaatataac tgccgaataa aatatccata aaaagcattat cataatagcg  23280
ccaagagagc catacatctt attaaaactc ccaaagtgtg cgaggtataa ggcaaagagg  23340
tgttttgctg tctcccataa aacagagaat attacgctgc ctaaaatagc atgtcttgcc  23400
tttatgttct tcccggccat tattttgaat ataaaggcga cggcaataat cataattaca  23460
actggcagga aatatttaaa ggttatactc tttgcaacat agtaggatat atctatgccc  23520
aagacagcta tttttactct gcctaaaatc tctgcggcaa tcggaagacc tatagaaata  23580
agaaaaactg cgcaccagat aaaaaatata ccccatacaa ctatcctggt tttttatgaag  23640
cccatcttct ctgcttctcc aaaaatgagg ttcattgcat cccttatcgc gagtattaca  23700
aactcagcgc tccagatgag cgtgataatg ccaatccagc caaaaacctt tctgttagct  23760
ataagcccttt taatatcatc tacgatgctg tcgctcaaat atggaaggct ctcctttaca  23820
aattctaaaa tccgttcaaa aagccgtgtc tccgttccga gaatagagcc tataaaagag  23880
aagagcagaa acatgagcgg gagcagagag aataaggcat aaaatgatat tgccgcagcc  23940
atagtaagac aattatcata agaaaatgcc ctaatgctgt cagttataat tacaaaaagt  24000
cgtttcataa ttatttctgc ctctttctaa aataaagccg tatgacaacc ttatcaaggc  24060
caaaggcctc tctcatttga tttacaagga accgttcata ggaaaagtga ataccttccg  24120
ggtaattggc aaagccgaca aatgtaggcg gttttatgtc agtctgggtt atataataaa  24180
ttttcagcaa tttcccctta tacatcggag gctgatggtg cttattgaag gtgctaaaaa  24240
atttgttaag ctgtgcagtt ggtatccttt tcgtaagctg cgccaatacc tcttctacca  24300
attcaaggat tttaaaaatc ctctggcctg taagcgctga cacaaagatg acaggggcga  24360
actgcaaaaa ttttaccttc caccgtatac gttctgcata ttgttttgcc gtgtttgtct  24420
cttttttcagg caaatcccat ttattgacaa caataataca tcccttaccc ctttcatagg  24480
caaggcctgc tatctttca tcctgctctg tcatgccgct cattgcatct ataaccaata  24540
atgcaacatc gcatctatca atacacttga ttgccgacat aactgaatac tgttcaagcg  24600
ccatgcctat ccttgccttt tttcttatac cggctgtatc aacaagcaga taattttct  24660
tattataatt gaattgcgta tcaatggcat ctctggttgt gccaggaata tcgcttacca  24720
caaccctctc atagccgaga agcctgttaa caagggaaga cttgccgaca tttggtcttc  24780
caactactgc caattttatc ctctcttctt tttcttcttt gacagcagcc cttggaataa  24840
ggcttattgc tttatctaat aattcatcaa cccccccttcc ctgttcagat gaaacgagaa  24900
agagattttc catgccgaga ctgaagaaat cagaaacccc ctgttcttgc ttggtagtat  24960
ctattttatt cacagcataa actattggtt tgccggattt tctcagtatg tctgccacat  25020
ccctatctga cggaagaaat ccatctctgc catccatgag aagtataata acatcagcct  25080
cctcaatggc gagcatggcc tgctctctta ccttggcagg gatagttaaa tccctcctat  25140
cacccttttct ggggacagtc cgcatttggc ggatgaaatc tgttcccata gggcgagcgg  25200
ggattgcctc gaaaccgcct gtgtcaataa gggtaaatgt tgttcctcgt tcaaccacat  25260
cccataatt caagtctctg gttacaccag gctcatttt tacaatggcc tttctttttcc  25320
caatgagcg gttgaagagg gttgacttgc cgacattcgg cctgccta                 25368
```

SEQ ID NO: 52        moltype = DNA  length = 7832
FEATURE             Location/Qualifiers
source              1..7832
                  mol_type = other DNA
                  organism = synthetic construct
SEQUENCE: 52

```
gctatcttta atctcaattc ttttcataca cgcataatac cataaatctg tattatgcgc  60
aatatattat gtcgttatgt ataataagct gataaatacc gatccgagac ccatttcatg  120
taaaaaggca catatttttc tttaactagt ggcttctgaa tgagatgctc tttaaaagcc  180
aaaagcataa caggatcaaa caattatcgt aattcagtat aataataaat atcctatttc  240
ttatctaaaa tatctccaag ttttcaacat aatgctgtcg attttggatt gacatccgct  300
aagtaatacg atattcctta acacttcaat ctctttctga aaattttatc tctttatggt  360
cttgccattg ctctatactt tatctatttc tcattgcttg caattgaaat atgaaggtga  420
ccccaatctc ccgccatgaa aacttagtca aatatattta ttgcatggag atttcatctg  480
tagtaaaatc ctgaaaatgc tgggatgaaa gatatttatc gaattttgcc atctatttaa  540
atagccacca aactatatac ttattaaaga attgggggta aagatgcagg aaataaaaag  600
gataaataaa atacgaagga gattggtaaa ggatagcaac acgaaaaaag ccggcaaaac  660
cggccctatg aaaaccttgc tcgttcgggt tatgacacct gacctgagag aaaggttaga  720
gaatcttcgc aaaaagccgg aaaacattcc tcagcccatt tcaaatactt cacgtgcaaa  780
tttaaataaa ctcctcactg actatacgga aatgaagaaa gcaatcctgc atgtttattg  840
ggaagagttc caaaaagacc ctgtcggatt gatgagcagg gttgcacaac cagcgcccaa  900
gaatattgat cagagaaaat tgattccggt gaaggacgga aatgagagac taacaagttc  960
tggatttgcc tgttctcagt gctgtcaacc cctctatgtt tataagcttg aacaagtgaa  1020
tgacaagggt aagccccata caaattactt tggccgttgt aatgtctccg agcatgaacg  1080
tttgatattg ctctcgccgc ataaaccgga ggcaaatgac gagctagtaa cgtattcgtt  1140
ggggaagttc ggtcaaaggg cattggactt ttattcaatc cacgtaacaa gagaatcgaa  1200
ccatcctgta aagccgctag aacagatcgg tggcaatagc tgcgcaagtg gtcccgttga  1260
taaggcttta tctgatgcct gtatgggagc agtagccagt ttccttacaa agtaccagga  1320
catcatcctc gaacaccaaa aggttataaa aaaaaacgaa aagagattgg caaatctaaa  1380
ggatatagca agtgcaaacg ggcttgcatt tcctaaaatc actcttccac cgcaaccgca  1440
tacaaaagaa gggattgaag cttataacaa tgttgttgct cagatagtga tctgggtaaa  1500
cctgaatctt tggcagaaac tcaaaattgg cagggatgag gcaaagccct tacagcggct  1560
taagggtttt ccgtccttcc ctcttgttga acgccaggcg aatgaggttg attggtggga  1620
tatggtctgt aatgtcaaaa agttgattaa cgaaaagaaa gaggacggga aggtcttctg  1680
gcaaaatctt gctggatata aaaggcagga agccttgctt ccatatcttt cgtctgaaga  1740
agaccgtaaa aaaggaaaaa agtttgcgcg ttatcagttt ggtgacccttt tgcttcacct  1800
tgaaaagaaa cacggtgaag attggggcaa agtttatgat gaggcatggg aaagaatagaa  1860
taaaaaagtg gaaggtctga gtaagcacat aaagttggag gaagaaagaa ggtctgaaga  1920
tgctcaatca aaggctgccc tcactgattg gctcagggca aaggcctctt ttgttattga  1980
agggctcaaa gaagctgata aggatgagtt ttgcaggtgt gagttaaagc ttcaaaagtg  2040
gtatggagat ttgagaggaa aaccatttgc tatagaagca gagaacagca ttttagatat  2100
aagcggattt tctaaacagt ataattgtgc atttatatgg cagaaagacg gcgtaaagaa  2160
```

-continued

```
gttaaatctt tatttaataa taaattactt caaaggtggt aagctacgct tcaaaaaaat  2220
caagccagaa gctttgaag caaataggtt ttatacagta attaataaaa aaagcggtga  2280
gattgtgcct atggaggtca acttcaattt tgatgacccg aatttgataa ttctgccttt  2340
ggcctttgga aaaaggcagg ggagggagtt tatctggaac gacctattga gccttgagac  2400
gggttcattg aaactcgcca atggcagggt tattgaaaaa acgctctata acagaaggac  2460
gagacaggat gaaccagcac tttttgttgc cctgacattt gaaagaagag aggtgcttga  2520
ctcatcgaat ataaaaccga tgaatctgat aggaatagac cggggagaaa atatcccggc  2580
agtcatagca ttaacagacc cggaaggatg ccccttgtca agattcaaag attcattggg  2640
caatccaacg catattttgc gaataggaga aagttataag gaaaaacaac ggactattca  2700
ggctgctaaa gaagttgaac aaaggcgggc aggcggatat tcgagaaaat atgcatcaaa  2760
ggcgaagaat ctggcggacg atatggtaag aaatacagct cgtgacctct tatattatgc  2820
tgttactcaa gatgcaatgc tcatttttga aaatctttcc cgcggttttg gtagacaagg  2880
caagaggact tttatggcgg aaaggcagta cacgaggatg gaagactggc tgactgcaaa  2940
gcttgcctat gaaggtctgc catcaaaaac ctatctttca aagactctgg cacagtatac  3000
ctcaaagaca tgttctaatt gtggttttac aatcacaagt gcagattatg acagggtgct  3060
cgaaaagctc aagaagacgg ctactggatg gatgactaca atcaatggaa aagagttaaa  3120
agttgaagga cagataacat actataaccg gtataaaagg cagaatgtgg taaaagacct  3180
ctctgtagag ctggatagac tttcggaaga gtcggtaaat aatgatattt ctagttggac  3240
aaaaggccgc agtggtgaag ctttatctct gctaaaaaag agatttagtc acaggccggt  3300
gcaggaaaag tttgtttgcc tgaactgtgg ttttgaaacc catgcagacg aacaagcagc  3360
actgaatatt gcaaggtcgt ggctctttct ccgttctcaa gaatataaga agtatcaaac  3420
caataaaacg accggaaata ctgacaaaag ggcatttgtt gaaacatggc aatccttta  3480
cagaaagaag ctcaaagaag tatggaaacc agccgtctga tattgcacat cagcacggta  3540
atggagtcaa tctattgtcc gcgcaatgca tggtatgcct ttgttggaga acggcgtaat  3600
atggctaaga gcatccactt tacagaggcc atacacgcgc acaggcggt ggataaatca  3660
tcgcagagaa gctgccctga ttgtaagcag gtaacaggcg tgtatcttta cagcaataag  3720
ctcggtttgg caggccgggc agaccttatc gagtggaggg atgggatacc gattcctatc  3780
gaaacaaaga cagggaaggt aagggatttt gagaacttcc acgttcagat tgggttacag  3840
gcaatttgcc ttgaagagat gtataatgtc aatataccag ttggtgaaat attttttctgt  3900
gaaacacgga gacggaaaga aattgttata gataaaaccc tgaaagtgcg ttgtgtagaa  3960
gttgttacaa atctgcgaga ctgcttcttg tcctttgata taagcaggtt tcccaaggtt  4020
gatgaccata ggtgtccgca gtgccagtat agtgaatcgt gtcttccttc aatacttggt  4080
tagaaaaata aaaggcttac tgatgaccgc tataaccgac aggataaccc tctatctcac  4140
gggtgatgaa ttcattttgg attgtcgtgg tcgggcattt ctcataaaaa aggacaatga  4200
agagaagggg cagaagattc ccgcaatgaa ggtaaaagat atcgtggtag ttggccgggat  4260
taccctcgat agccgtgtta ttagcctttg cagagaagaa tctataccga tacatttctt  4320
tagcggcaga tgggaatatc aagggagcct tcaatttgaa cccgtcaaaa atctgtttat  4380
tcgtcgggcg caaattcata agcattttga tccccacaaa aaacttgaaa ttgcaaaaag  4440
tatcgttgcc ggtaagatca aaaaccagca atcattactt gataaatata gacttggttt  4500
gagaatcgag tgtaccgaaa tcaacgccgt cactgattta gagaccttgc gtggaataga  4560
aggcgcaaca acaaggcagt attatggcaa ttttttcggct atcttaaagc atccaagctt  4620
tgttttttgtg cgccgtacca agagacctcc tgaggatgaa atcaacgcca tgatgagcct  4680
tatctacacc ctcctgttca acgaaataca ttcgactgca ttactcgtcg gttttgaccc  4740
ggccttttggt tacttgcatg acgtctatta tggtcgtccc tctttaatat gcgatcttct  4800
ggaggagtgg cggccgttgg ctgaccgttt tgtgatcaat ttgataaata gaagggaagt  4860
ggatacagac gatttcagga aagaaactga ccaaaaaggt gtttggctga ataaggatgc  4920
ctatccaaaa gtaatcaaaa aatggcatca attctttaag gtagatgagc agaaaaccaa  4980
tttacttatc caatcaataa cgtatcagca cgcagttgag cggcaggtta ggttgtttag  5040
ccagcatatt caagatgata gggaatgtta taagcctata gagctttaaa atgcgacatc  5100
tcatttgtta tgatattgaa gatgataagg tcagggcacg gttagttaaa cttctggaag  5160
cctatggtgt tcggattcaa tattctgtct ttgagtttaa cctttcaaaa gcaaggtagg  5220
ctgatctaaa gctcaacctt aaagaaaaag gatttatgga tggctctata agtctggtaa  5280
tttatcctct ctcagaggag atatatgaac ggatagaaag gtacggaagc gctgctattt  5340
ggaatgaagg ggatatggtc tttgattgat tttaagcttg acgaaaggat ttgtgaatag  5400
taaattatta ctggcgcttt tatctcatta ctttgagagc catcaccagc gactatgtcg  5460
tatgggtaaa gcgcttattt atcggagagt tctggatgca aacccagagc tgtttttttta  5520
gattcttata aattacataa gaagttcttt gaaaatctga tgttaaagct ttttgtgaga  5580
agaacaggtt tacagtgcgt aactctgcta aattattaaa ggtatcctcc gcaacttgta  5640
aaatattgaa aatacaattt ccagaagtca ttgaaaaatc tggatatgcg gggtttgaag  5700
atatctccga taaataagaa gcatcaaagt taatccccaa atagacgggc taaaatacgt  5760
atcgtttgaa gatatctccg ataaataaga agcatcaaag cttatatata tacaatctttt  5820
gcaggtttct gtgtttgaag atatctccga taaataagaa gcatcaaagt tatctaatct  5880
tgatgtcttt ctcaatacat tacgtttgaa gatatctccg ataaataaga agcatcaaag  5940
agccagagga tatgcctgta aaatgggcaa tgtttgaaga tatctccgat aaataagaag  6000
catcaaagaa tattaatggt tcaccattgc catgttgatg gtgtttgaag atatctccga  6060
taaataagaa gcatcaaaga aataataggc gcataattcc acgatttcag tttgaagata  6120
tctccgataa ataagaagca tcaaagtatt aaatactcgt attgctgttc gattatgttt  6180
gaagatatct ccgataaaata agaagcatca aagaacaag cagaatatat tacacggaca  6240
aatcatgtga ttaggaagat aaaggctttg gggtagatat aatgagcttt acacgagtag  6300
attgcctttc cttgattcaa aagatttcag aagagatagg cgctttgtgc cttaaatccc  6360
cagaatcaac aattcagaga cacgtggaaa aacccagccc cataaaaaat cctttagact  6420
tagccccatt aattgagcat accttattga aaccggaggc aacccatagg gatataacga  6480
ggctttgcga tgaggcaagg cgattccatt ttcgtggcgt ctgtgtgaat cctgtctttg  6540
ttaaagaagt ccaaaaccaa ttagcagaaa cagattgttt gattgttact gttgtgggtt  6600
tcccactagg tgctaattta acagctacaa aggttgagga aacgaaacat gttataaatc  6660
taggtgcgaa tgaggtggat atggttattg cactcggtgc attgaaagag ggcaattaca  6720
aaactgtcta taatgacatc cgtgcggtcg ttaaatctgt agaatcaata cctgttaagg  6780
taattgtaga ggcaggactt ctgaatgaaa gagaaaagat agccgcttgt ctgttagcag  6840
aacgggctgg cgcatcgttt gttaaaacct ctactggttt tactgcacgt agtgcgacgg  6900
```

-continued

```
taggagatgt cagattaatg aaggcagtag taggagacag actcggcata aaagccgcag   6960
gtgggatacg tgattttcag actgcctgcg ctatggtgga ggcaggggca gtgcgtttgg   7020
gctgttcggc atcggtagca attgtgacag aacacatata aaaaagcatt gtgagatatt   7080
tttgtatata atgtttaaca atagaatttt ttaaatattt ctgtttgttt actattttgg   7140
caagtttaag tatgtatctt ttgttatttc ttcttcgtgc tgaacaagct atattgacca   7200
tctttaaaac agtatgtccc tataacattg ggagcttctg gatttttaaa ggatatgaca   7260
aatttaagac gtgaataacc agcggtttca gatgaaggtt ctacctctac gtaggtcaag   7320
tgcgccttat gctcaaggct aatgatattc cactgaattc ccttattatc gggaaactca   7380
gcttctgcca acctggtaat attgtctttc agaaacgatt ccctctttgc ctcttcgctg   7440
acaaaggttg tttcctgttt tggttgcaca atgtcgggct ttgcctcgct agtctgcgtt   7500
atttcttcag tagctttctg caaatcttcg gacttagtct gttcactgat tacggctgtt   7560
tcctcttttg gtggtgcgat atcagtattt acttcgccgg tctgtgttgt ttcttcaaga   7620
ccttcctgtg tattttcagc cattgccttt tctatttcct cgatgccttt cttgattccc   7680
tctcccacag ccttgccaag acctttcacc atctcaccca ctgcgcctcc aaacattgac   7740
atcattgtct tgtcagcatc aaccttccac tgtccgcctt cttttacaag aatagtctgc   7800
atctggactt caaattccgt tgtctcgtta tg                                 7832
```

```
SEQ ID NO: 53          moltype =   length =
SEQUENCE: 53
000

SEQ ID NO: 54          moltype = DNA   length = 25
FEATURE                Location/Qualifiers
source                 1..25
                       mol_type = other DNA
                       organism = synthetic construct
SEQUENCE: 54
gtttacacac tccctctcat agggt                                           25

SEQ ID NO: 55          moltype = DNA   length = 25
FEATURE                Location/Qualifiers
source                 1..25
                       mol_type = other DNA
                       organism = synthetic construct
SEQUENCE: 55
gtttacacac tccctctcat gaggt                                           25

SEQ ID NO: 56          moltype = DNA   length = 25
FEATURE                Location/Qualifiers
source                 1..25
                       mol_type = other DNA
                       organism = synthetic construct
SEQUENCE: 56
ttttacatac ccctctcat gggat                                            25

SEQ ID NO: 57          moltype = DNA   length = 25
FEATURE                Location/Qualifiers
source                 1..25
                       mol_type = other DNA
                       organism = synthetic construct
SEQUENCE: 57
gtttacacac tccctctcat ggggg                                           25

SEQ ID NO: 58          moltype = DNA   length = 10
FEATURE                Location/Qualifiers
source                 1..10
                       mol_type = other DNA
                       organism = synthetic construct
SEQUENCE: 58
aaaaaaaaaa                                                            10

SEQ ID NO: 59          moltype =   length =
SEQUENCE: 59
000

SEQ ID NO: 60          moltype =   length =
SEQUENCE: 60
000

SEQ ID NO: 61          moltype = RNA   length = 43
FEATURE                Location/Qualifiers
source                 1..43
                       mol_type = other RNA
                       organism = synthetic construct
SEQUENCE: 61
ccgataagta aaacgcatca aagnnnnnnn nnnnnnnnnn nnn                       43

SEQ ID NO: 62          moltype = RNA   length = 70
FEATURE                Location/Qualifiers
```

-continued

```
source                  1..70
                        mol_type = other RNA
                        organism = synthetic construct
SEQUENCE: 62
atttgaaggt atctccgata agtaaaacgc atcaaagnnn nnnnnnnnnn nnnnnnnnnn   60
nnnnnnnnnn                                                          70

SEQ ID NO: 63          moltype = RNA   length = 174
FEATURE                Location/Qualifiers
source                  1..174
                        mol_type = other RNA
                        organism = synthetic construct
SEQUENCE: 63
aagtagtaaa ttacatctgg cgcgtttatt ccattacttt ggagccagtc ccagcgacta   60
tgtcgtatgg acgaagcgct tatttatcgg agatagctcc gaaaatttga aggtatctcc  120
gataagtaaa acgcatcaaa gnnnnnnnnn nnnnnnnnnn nnnnnnnnnn nnnn         174

SEQ ID NO: 64          moltype = RNA   length = 128
FEATURE                Location/Qualifiers
source                  1..128
                        mol_type = other RNA
                        organism = synthetic construct
SEQUENCE: 64
nnnnnnnnnn nnnnnnnnnn ctttgatgcg ttttacttat cgggaaatct ccgataaata   60
agcgcttcgt ccatacgaca tagtcgctgg gactggctcc aaagtaatgg aataaacgcg  120
ccagatgt                                                            128

SEQ ID NO: 65          moltype = RNA   length = 171
FEATURE                Location/Qualifiers
source                  1..171
                        mol_type = other RNA
                        organism = synthetic construct
SEQUENCE: 65
nnnnnnnnnn nnnnnnnnnn nnnnnnnnnn ctttgatgcg ttttacttat cggagatacc   60
ttcaaatgaa aggagctatc tccgataaat aagcgcttcg tccatacgac atagtcgctg  120
ggactggctc caaagtaatg gaataaacgc gccagatgta atttactact t           171

SEQ ID NO: 66          moltype = RNA   length = 65
FEATURE                Location/Qualifiers
source                  1..65
                        mol_type = other RNA
                        organism = synthetic construct
SEQUENCE: 66
ttccattact ttggagccag tcccagcgac tatgtcgtat ggacgaagcg cttatttatc   60
ggaga                                                               65

SEQ ID NO: 67          moltype = RNA   length = 46
FEATURE                Location/Qualifiers
source                  1..46
                        mol_type = other RNA
                        organism = synthetic construct
SEQUENCE: 67
gtcccagcga ctatgtcgta tggacgaagc gcttatttat cggaga                  46

SEQ ID NO: 68          moltype = RNA   length = 21
FEATURE                Location/Qualifiers
source                  1..21
                        mol_type = other RNA
                        organism = synthetic construct
SEQUENCE: 68
gaagcgctta tttatcggag a                                             21

SEQ ID NO: 69          moltype = RNA   length = 46
FEATURE                Location/Qualifiers
source                  1..46
                        mol_type = other RNA
                        organism = synthetic construct
SEQUENCE: 69
tctccgataa ataagaagca tcaaagnnnn nnnnnnnnnn nnnnnn                   46

SEQ ID NO: 70          moltype =    length =
SEQUENCE: 70
000

SEQ ID NO: 71          moltype = AA   length = 949
FEATURE                Location/Qualifiers
source                  1..949
                        mol_type = protein
                        organism = unidentified
```

-continued

```
SEQUENCE: 71
MRDSITAPRY SSALAARIKE FNSAFKLGID LGTKTGGVAL VKDNKVLLAK TFLDYHKQTL  60
EERRIHRRNR RSRLARRKRI ARLRSWILRQ KIYGKQLPDP YKIKKMQLPN GVRKGENWID  120
LVVSGRDLSP EAFVRAITLI FQKRGQRYEE VAKEIEEMSY KEFSTHIKAL TSVTEEEFTA  180
LAAEIERRQD VVDTDKEAER YTQLSELLSK VSESKSESKD RAQRKEDLGK VVNAFCSAHR  240
IEDKDKWCKE LMKLLDRPVR HARFLNKVLI RCNICDRATP KKSRPDVREL LYFDTVRNFL  300
KAGRVEQNPD VISYYKKIYM DAEVIRVKIL NKEKLTDEDK KQKRKLASEL NRYKNKEYVT  360
DAQKKMQEQL KTLLFMKLTG RSRYCMAHLK ERAAGKDVEE GLHGVVQKRH DRNIAQRNHD  420
LRVINLIESL LFDQNKSLSD AIRKNGLMYV TIEAPEPKTK HAKKGAAVVR DPRKLKEKLF  480
DDQNGVCIYT GLQLDKLEIS KYEKDHIFPD SRDGPSIRDN LVLTTKEINS DKGDRTPWEW  540
MHDNPEKWKA FERRVAEFYK KGRINERKRE LLLNKGTEYP GDNPTELARG GARVNNFITE  600
FNDRLKTHGV QELQTIFERN KPIVQVVRGE ETQRLRRQWN ALNQNFIPLK DRAMSFNHAE  660
DAAIAASMPP KFWREQIYRT AWHFGPSGNE RPDFALAELA PQWNDFFMTK GGPIIAVLGK  720
TKYSWKHSII DDTIYKPFSK SAYYVGIYKK PNAITSNAIK VLRPKLLNGE HTMSKNAKYY  780
HQKIGNERFL MKSQKGGSII TVKPHDGPEK VLQISPTYEC AVLTKHDGKI IVKFKPIKPL  840
RDMYARGVIK AMDKELETSL SSMSKHAKYK ELHTHDIIYL PATKKHVDGY FIITKLSAKH  900
GIKALPESMV KVKYTQIGSE NNSEVKLTKP KPEITLDSED ITNIYNFTR  949

SEQ ID NO: 72        moltype = AA   length = 967
FEATURE              Location/Qualifiers
source               1..967
                     mol_type = protein
                     organism = unidentified
SEQUENCE: 72
MLGSSRYLRY NLTSFEGKEP FLIMGYYKEY NKELSSKAQK EFNDQISEFN SYYKLGIDLG  60
DKTGIAIVKG NKIILAKTLI DLHSQKLDKR REARRNRRTR LSRKKRLARL RSWVMRQKVG  120
NQRLPDPYKI MHDNKYWSIY NKSNSANKKN WIDLLIHSNS LSADDFVRGL TIIFRKRGYL  180
APKYLSRLSD KEFEKYIDNL KPPISKYEYD EDLEELSSRV ENGEIEEKKF EGLKNKLDKI  240
DKESKDFQVK QREEVKKELE DLVDLFAKSV DNKIDKARWK RELNNLLDKK VRKIRFDNRF  300
ILKCKIKGCN KNTPKKEKVR DFELKMVLNN ARSDYQISDE DLNSFRNEVI NIFQKKENLK  360
KGELKGVTIE DLRKQLNKTF NKAKIKKGIR EQIRSIVFEK ISGRSKFCKE HLKEFSEKPA  420
PSDRINYGVN SAREQHDFRV LNFIDKKIFK DKLIDPSKLR YITIESPEPE TEKLEKGQIS  480
EKSFETLKEK LAKETGGIDI YTGEKLKKDF EIEHIFPRAR MGPSIRENEV ASNLETNKEK  540
ADRTPWEWFG QDEKRWSEFE KRVNSLYSKK KISERKREIL LNKSNEYPGL NPTELSRIPS  600
TLSDFVESIR KMFVKYGYEE PQTLVQKGKP IIQVVRGRDT QALRWRWHAL DSNIIPEKDR  660
KSSFNHAEDA VIAACMPPYY LRQKIFREEA KIKRKVSNKE KEVTRPDMPT KKIAPNWSEF  720
MKTRNEPVIE VIGKVKPSWK NSIMDQTFYK YLLKPFKDNL IKIPNVKNTY KWIGVNGQTD  780
SLSLPSKVLS ISNKKVDSST VLLVHDKKGG KRNWVPKSIG GLLVVYITPKD GPKRIVQVKP  840
ATQGLLIYRN EDGRVDAVRE FINPVIEMYN NGKLAFVEKE NEEELLKYFN LLEKGQKFER  900
IRRYDMITYN SKFYVVTKIN KNHRVTIQEE SKIKAESDKV KSSSGKEYTR KETEELSLQK  960
LAELISI  967

SEQ ID NO: 73        moltype = RNA   length = 56
FEATURE              Location/Qualifiers
source               1..56
                     mol_type = other RNA
                     organism = synthetic construct
SEQUENCE: 73
nnnnnnnnnn nnnnnnnnnn cttacaatcg acacttaaat aatttgcatg tgtaag  56

SEQ ID NO: 74        moltype = RNA   length = 56
FEATURE              Location/Qualifiers
source               1..56
                     mol_type = other RNA
                     organism = synthetic construct
SEQUENCE: 74
nnnnnnnnnn nnnnnnnnnn ctttcaataa acaaataaat cttagtaata tgtaac  56

SEQ ID NO: 75        moltype = RNA   length = 36
FEATURE              Location/Qualifiers
source               1..36
                     mol_type = other RNA
                     organism = synthetic construct
SEQUENCE: 75
cttacaatcg acacttaaat aatttgcatg tgtaag  36

SEQ ID NO: 76        moltype = RNA   length = 36
FEATURE              Location/Qualifiers
source               1..36
                     mol_type = other RNA
                     organism = synthetic construct
SEQUENCE: 76
ctttcaataa acaaataaat cttagtaata tgtaac  36

SEQ ID NO: 77        moltype = RNA   length = 180
FEATURE              Location/Qualifiers
source               1..180
                     mol_type = other RNA
                     organism = synthetic construct
```

-continued

```
SEQUENCE: 77
ggcatggacc atatccaggt gttgattgta aacacctagc gggggaaatta tatatgtttg   60
taatatcttc actatccaaa gttatctctg gttttggttt ggtaagcttc acttcactat  120
tgttttcact cccaatttga gtatggttgg gggtaaggat gctttcgggg agtgcttta   180

SEQ ID NO: 78            moltype = RNA   length = 85
FEATURE                  Location/Qualifiers
source                   1..85
                         mol_type = other RNA
                         organism = synthetic construct
SEQUENCE: 78
aactggctat tgctaatatt atttgtttat tgaaagaagc ctagacgtta gggttcgcgt   60
gcatgtaggc tccagcaggt acctc                                        85

SEQ ID NO: 79            moltype = RNA   length = 204
FEATURE                  Location/Qualifiers
source                   1..204
                         mol_type = other RNA
                         organism = synthetic construct
SEQUENCE: 79
nnnnnnnnnn nnnnnnnnnn cttacaatcg acacttaaac aggtgttgat tgtaaacacc   60
tagcggggaa attatatatg tttgtaatat cttcactatc caaagttatc tctggttttg  120
gtttggtaag cttcacttca ctattgtttt cactcccaat ttgagtatgg ttggggggtaa  180
ggatgctttc ggggagtgct ttta                                        204

SEQ ID NO: 80            moltype = RNA   length = 109
FEATURE                  Location/Qualifiers
source                   1..109
                         mol_type = other RNA
                         organism = synthetic construct
SEQUENCE: 80
nnnnnnnnnn nnnnnnnnnn ctttcaataa acaaataaaa acttatttgt ttattgaaag   60
aagcctagac gttagggttc gcgtgcatgt aggctccagc aggtacctc              109

SEQ ID NO: 81            moltype = RNA   length = 184
FEATURE                  Location/Qualifiers
source                   1..184
                         mol_type = other RNA
                         organism = synthetic construct
SEQUENCE: 81
cttacaatcg acacttaaac aggtgttgat tgtaaacacc tagcggggaa attatatatg   60
tttgtaatat cttcactatc caaagttatc tctggttttg gtttggtaag cttcacttca  120
ctattgtttt cactcccaat ttgagtatgg ttggggggtaa ggatgctttc ggggagtgct  180
ttta                                                              184

SEQ ID NO: 82            moltype = RNA   length = 89
FEATURE                  Location/Qualifiers
source                   1..89
                         mol_type = other RNA
                         organism = synthetic construct
SEQUENCE: 82
ctttcaataa acaaataaaa acttatttgt ttattgaaag aagcctagac gttagggttc   60
gcgtgcatgt aggctccagc aggtacctc                                    89

SEQ ID NO: 83            moltype = AA   length = 84
FEATURE                  Location/Qualifiers
source                   1..84
                         mol_type = protein
                         organism = synthetic construct
SEQUENCE: 83
MASMISSSAV TTVSRASRGQ SAAMAPFGGL KSMTGFPVRK VNTDITSITS NGGRVKCMQV   60
WPPIGKKKFE TLSYLPPLTR DSRA                                          84

SEQ ID NO: 84            moltype = AA   length = 57
FEATURE                  Location/Qualifiers
source                   1..57
                         mol_type = protein
                         organism = synthetic construct
SEQUENCE: 84
MASMISSSAV TTVSRASRGQ SAAMAPFGGL KSMTGFPVRK VNTDITSITS NGGRVKS       57

SEQ ID NO: 85            moltype = AA   length = 85
FEATURE                  Location/Qualifiers
source                   1..85
                         mol_type = protein
                         organism = synthetic construct
SEQUENCE: 85
MASSMLSSAT MVASPAQATM VAPFNGLKSS AAFPATRKAN NDITSITSNG GRVNCMQVWP   60
PIEKKKFETL SYLPDLTDSG GRVNC                                         85
```

-continued

```
SEQ ID NO: 86              moltype = AA   length = 76
FEATURE                    Location/Qualifiers
source                     1..76
                           mol_type = protein
                           organism = synthetic construct
SEQUENCE: 86
MAQVSRICNG VQNPSLISNL SKSSQRKSPL SVSLKTQQHP RAYPISSSWG LKKSGMTLIG   60
SELRPLKVMS SVSTAC                                                   76

SEQ ID NO: 87              moltype = AA   length = 76
FEATURE                    Location/Qualifiers
source                     1..76
                           mol_type = protein
                           organism = synthetic construct
SEQUENCE: 87
MAQVSRICNG VWNPSLISNL SKSSQRKSPL SVSLKTQQHP RAYPISSSWG LKKSGMTLIG   60
SELRPLKVMS SVSTAC                                                   76

SEQ ID NO: 88              moltype = AA   length = 72
FEATURE                    Location/Qualifiers
source                     1..72
                           mol_type = protein
                           organism = synthetic construct
SEQUENCE: 88
MAQINNMAQG IQTLNPNSNF HKPQVPKSSS FLVFGSKKLK NSANSMLVLK KDSIFMQLFC   60
SFRISASVAT AC                                                       72

SEQ ID NO: 89              moltype = AA   length = 69
FEATURE                    Location/Qualifiers
source                     1..69
                           mol_type = protein
                           organism = synthetic construct
SEQUENCE: 89
MAALVTSQLA TSGTVLSVTD RFRRPGFQGL RPRNPADAAL GMRTVGASAA PKQSRKPHRF   60
DRRCLSMVV                                                           69

SEQ ID NO: 90              moltype = AA   length = 77
FEATURE                    Location/Qualifiers
source                     1..77
                           mol_type = protein
                           organism = synthetic construct
SEQUENCE: 90
MAALTTSQLA TSATGFGIAD RSAPSSLLRH GFQGLKPRSP AGGDATSLSV TTSARATPKQ   60
QRSVQRGSRR FPSVVVC                                                  77

SEQ ID NO: 91              moltype = AA   length = 57
FEATURE                    Location/Qualifiers
source                     1..57
                           mol_type = protein
                           organism = synthetic construct
SEQUENCE: 91
MASSVLSSAA VATRSNVAQA NMVAPFTGLK SAASFPVSRK QNLDITSIAS NGGRVQC      57

SEQ ID NO: 92              moltype = AA   length = 65
FEATURE                    Location/Qualifiers
source                     1..65
                           mol_type = protein
                           organism = synthetic construct
SEQUENCE: 92
MESLAATSVF APSRVAVPAA RALVRAGTVV PTRRTSSTSG TSGVKCSAAV TPQASPVISR   60
SAAAA                                                               65

SEQ ID NO: 93              moltype = AA   length = 72
FEATURE                    Location/Qualifiers
source                     1..72
                           mol_type = protein
                           organism = synthetic construct
SEQUENCE: 93
MGAAATSMQS LKFSNRLVPP SRRLSPVPNN VTCNNLPKSA APVRTVKCCA SSWNSTINGA   60
AATTNGASAA SS                                                       72

SEQ ID NO: 94              moltype = AA   length = 20
FEATURE                    Location/Qualifiers
VARIANT                    4
                           note = X can be K, H, or R
VARIANT                    8
                           note = X can be K, H, or R
VARIANT                    11
```

-continued

```
                        note = X can be K, H, or R
VARIANT                 15
                        note = X can be K, H, or R
VARIANT                 19
                        note = X can be K, H, or R
source                  1..20
                        mol_type = protein
                        organism = synthetic construct
SEQUENCE: 94
GLFXALLXLL XSLWXLLLXA                                            20

SEQ ID NO: 95           moltype = AA  length = 20
FEATURE                 Location/Qualifiers
source                  1..20
                        mol_type = protein
                        organism = synthetic construct
SEQUENCE: 95
GLFHALLHLL HSLWHLLLHA                                            20

SEQ ID NO: 96           moltype = AA  length = 7
FEATURE                 Location/Qualifiers
source                  1..7
                        mol_type = protein
                        organism = synthetic construct
SEQUENCE: 96
PKKKRKV                                                          7

SEQ ID NO: 97           moltype = AA  length = 16
FEATURE                 Location/Qualifiers
source                  1..16
                        mol_type = protein
                        organism = synthetic construct
SEQUENCE: 97
KRPAATKKAG QAKKKK                                                16

SEQ ID NO: 98           moltype = AA  length = 9
FEATURE                 Location/Qualifiers
source                  1..9
                        mol_type = protein
                        organism = synthetic construct
SEQUENCE: 98
PAAKRVKLD                                                        9

SEQ ID NO: 99           moltype = AA  length = 11
FEATURE                 Location/Qualifiers
source                  1..11
                        mol_type = protein
                        organism = synthetic construct
SEQUENCE: 99
RQRRNELKRS P                                                     11

SEQ ID NO: 100          moltype = AA  length = 38
FEATURE                 Location/Qualifiers
source                  1..38
                        mol_type = protein
                        organism = synthetic construct
SEQUENCE: 100
NQSSNFGPMK GGNFGGRSSG PYGGGGQYFA KPRNQGGY                        38

SEQ ID NO: 101          moltype = AA  length = 42
FEATURE                 Location/Qualifiers
source                  1..42
                        mol_type = protein
                        organism = synthetic construct
SEQUENCE: 101
RMRIZFKNKG KDTAELRRRR VEVSVELRKA KKDEQILKRR NV                   42

SEQ ID NO: 102          moltype = AA  length = 8
FEATURE                 Location/Qualifiers
source                  1..8
                        mol_type = protein
                        organism = synthetic construct
SEQUENCE: 102
VSRKRPRP                                                         8

SEQ ID NO: 103          moltype = AA  length = 8
FEATURE                 Location/Qualifiers
source                  1..8
                        mol_type = protein
```

-continued

```
                              organism = synthetic construct
SEQUENCE: 103
PPKKARED                                                                8

SEQ ID NO: 104                moltype = AA   length = 8
FEATURE                       Location/Qualifiers
source                        1..8
                              mol_type = protein
                              organism = synthetic construct
SEQUENCE: 104
PQPKKKPL                                                                8

SEQ ID NO: 105                moltype = AA   length = 12
FEATURE                       Location/Qualifiers
source                        1..12
                              mol_type = protein
                              organism = synthetic construct
SEQUENCE: 105
SALIKKKKM AP                                                           12

SEQ ID NO: 106                moltype = AA   length = 5
FEATURE                       Location/Qualifiers
source                        1..5
                              mol_type = protein
                              organism = synthetic construct
SEQUENCE: 106
DRLRR                                                                   5

SEQ ID NO: 107                moltype = AA   length = 7
FEATURE                       Location/Qualifiers
source                        1..7
                              mol_type = protein
                              organism = synthetic construct
SEQUENCE: 107
PKQKKRK                                                                 7

SEQ ID NO: 108                moltype = AA   length = 10
FEATURE                       Location/Qualifiers
source                        1..10
                              mol_type = protein
                              organism = synthetic construct
SEQUENCE: 108
RKLKKKIKKL                                                             10

SEQ ID NO: 109                moltype = AA   length = 10
FEATURE                       Location/Qualifiers
source                        1..10
                              mol_type = protein
                              organism = synthetic construct
SEQUENCE: 109
REKKKFLKRR                                                             10

SEQ ID NO: 110                moltype = AA   length = 20
FEATURE                       Location/Qualifiers
source                        1..20
                              mol_type = protein
                              organism = synthetic construct
SEQUENCE: 110
KRKGDEVDGV DEVAKKKSKK                                                  20

SEQ ID NO: 111                moltype = AA   length = 17
FEATURE                       Location/Qualifiers
source                        1..17
                              mol_type = protein
                              organism = synthetic construct
SEQUENCE: 111
RKCLQAGMNL EARKTKK                                                     17

SEQ ID NO: 112                moltype = AA   length = 11
FEATURE                       Location/Qualifiers
source                        1..11
                              mol_type = protein
                              organism = synthetic construct
SEQUENCE: 112
YGRKKRRQRR R                                                           11

SEQ ID NO: 113                moltype = AA   length = 12
FEATURE                       Location/Qualifiers
source                        1..12
```

-continued

```
                          mol_type = protein
                          organism = synthetic construct
SEQUENCE: 113
RRQRRTSKLM KR                                                    12

SEQ ID NO: 114          moltype = AA  length = 27
FEATURE                 Location/Qualifiers
source                  1..27
                        mol_type = protein
                        organism = synthetic construct
SEQUENCE: 114
GWTLNSAGYL LGKINLKALA ALAKKIL                                    27

SEQ ID NO: 115          moltype = AA  length = 33
FEATURE                 Location/Qualifiers
source                  1..33
                        mol_type = protein
                        organism = synthetic construct
SEQUENCE: 115
KALAWEAKLA KALAKALAKH LAKALAKALK CEA                             33

SEQ ID NO: 116          moltype = AA  length = 16
FEATURE                 Location/Qualifiers
source                  1..16
                        mol_type = protein
                        organism = synthetic construct
SEQUENCE: 116
RQIKIWFQNR RMKWKK                                                16

SEQ ID NO: 117          moltype = AA  length = 11
FEATURE                 Location/Qualifiers
source                  1..11
                        mol_type = protein
                        organism = synthetic construct
SEQUENCE: 117
YGRKKRRQRR R                                                     11

SEQ ID NO: 118          moltype = AA  length = 9
FEATURE                 Location/Qualifiers
source                  1..9
                        mol_type = protein
                        organism = synthetic construct
SEQUENCE: 118
RKKRRQRRR                                                        9

SEQ ID NO: 119          moltype = AA  length = 11
FEATURE                 Location/Qualifiers
source                  1..11
                        mol_type = protein
                        organism = synthetic construct
SEQUENCE: 119
YGRKKRRQRR R                                                     11

SEQ ID NO: 120          moltype = AA  length = 8
FEATURE                 Location/Qualifiers
source                  1..8
                        mol_type = protein
                        organism = synthetic construct
SEQUENCE: 120
RKKRRQRR                                                         8

SEQ ID NO: 121          moltype = AA  length = 11
FEATURE                 Location/Qualifiers
source                  1..11
                        mol_type = protein
                        organism = synthetic construct
SEQUENCE: 121
YARAAARQAR A                                                     11

SEQ ID NO: 122          moltype = AA  length = 11
FEATURE                 Location/Qualifiers
source                  1..11
                        mol_type = protein
                        organism = synthetic construct
SEQUENCE: 122
THRLPRRRR R                                                      11

SEQ ID NO: 123          moltype = AA  length = 11
FEATURE                 Location/Qualifiers
```

-continued

```
source                  1..11
                        mol_type = protein
                        organism = synthetic construct
SEQUENCE: 123
GGRRARRRR R                                                          11

SEQ ID NO: 124          moltype = AA   length = 5
FEATURE                 Location/Qualifiers
source                  1..5
                        mol_type = protein
                        organism = synthetic construct
SEQUENCE: 124
GSGGS                                                                5

SEQ ID NO: 125          moltype = AA   length = 6
FEATURE                 Location/Qualifiers
source                  1..6
                        mol_type = protein
                        organism = synthetic construct
SEQUENCE: 125
GGSGGS                                                               6

SEQ ID NO: 126          moltype = AA   length = 4
FEATURE                 Location/Qualifiers
source                  1..4
                        mol_type = protein
                        organism = synthetic construct
SEQUENCE: 126
GGGS                                                                 4

SEQ ID NO: 127          moltype = AA   length = 4
FEATURE                 Location/Qualifiers
source                  1..4
                        mol_type = protein
                        organism = synthetic construct
SEQUENCE: 127
GGSG                                                                 4

SEQ ID NO: 128          moltype = AA   length = 5
FEATURE                 Location/Qualifiers
source                  1..5
                        mol_type = protein
                        organism = synthetic construct
SEQUENCE: 128
GGSGG                                                                5

SEQ ID NO: 129          moltype = AA   length = 5
FEATURE                 Location/Qualifiers
source                  1..5
                        mol_type = protein
                        organism = synthetic construct
SEQUENCE: 129
GSGSG                                                                5

SEQ ID NO: 130          moltype = AA   length = 5
FEATURE                 Location/Qualifiers
source                  1..5
                        mol_type = protein
                        organism = synthetic construct
SEQUENCE: 130
GSGGG                                                                5

SEQ ID NO: 131          moltype = AA   length = 5
FEATURE                 Location/Qualifiers
source                  1..5
                        mol_type = protein
                        organism = synthetic construct
SEQUENCE: 131
GGGSG                                                                5

SEQ ID NO: 132          moltype = AA   length = 5
FEATURE                 Location/Qualifiers
source                  1..5
                        mol_type = protein
                        organism = synthetic construct
SEQUENCE: 132
GSSSG                                                                5

SEQ ID NO: 133          moltype = AA   length = 16
```

-continued

```
FEATURE                 Location/Qualifiers
REGION                  1..16
                        note = Drosophila melanogaster
source                  1..16
                        mol_type = protein
                        organism = synthetic construct
SEQUENCE: 133
RQIKIWFQNR RMKWKK                                                            16

SEQ ID NO: 134          moltype = AA   length = 11
FEATURE                 Location/Qualifiers
source                  1..11
                        mol_type = protein
                        organism = synthetic construct
SEQUENCE: 134
YGRKKRRQRR R                                                                 11

SEQ ID NO: 135          moltype = AA   length = 1067
FEATURE                 Location/Qualifiers
REGION                  1..1067
                        note = sequence from metagenomic data - from unidentified
                         Lindow bacteria
source                  1..1067
                        mol_type = protein
                        organism = unidentified
SEQUENCE: 135
VSATRKGQGS GAPISRTEAP QIALMATELE QRLNEFLDSL RLGIDFGEDY GGIALVQANR  60
VLHAETFVDF HQATLKDRRR NRRGRRTRHA RKMRLARLRS WILRQKLPGG QRLPDPYGVM  120
HWPFKTKKGH TIKTGLASRQ DGKRTIIQKC KIGTATPEEF VCSLTLLFQK RGFVWEGSDL  180
CELSDQELAE ELMTVRITEA VAAAIKEEIE RRKKEPEDNK EGEIENLETV LCDAVKRARS  240
PRTPEHRSIV ESDLKDIVDG WTRKNCPQMT DMWKKELSCL LNKHVRPARF ENRIVAGCSW  300
CGKMVPRKSK VRELAYKVVV KNIRVEDFTS RQPLTAQEAE YFSQLWVDKE AKPPARTAIE  360
NKLKKLKASP KMANQLYELL APSEPKGHTN LCQQHLEMAA RGAFMCNRHH AICENNNGDH  420
QTIDSVKEGR KRAGPRNPCR EDRDRRMIRR LEQILFETPG KPGKPSHSIP RLITIEFPKP  480
NTAQTAGCPH CKEKLSLDAR VRWKMARPMK LEASNDSTPF FCPSCAAGIK ITLYKKMRIK  540
EKEIVQKYSP KDTDVLVRKT AAGGLKKLKY DMYLKETDGT CVYCGTSIGS GQIDHIFPQS  600
RGGPNIDYNL ISCCRTCNGN LKKNKSPWEW FGNIDQRWRE FEDRVKKLPA PQRKKAILLS  660
RESAYPENPT ALARVGARTK EFIGRIKQML LANGVKENEI ADNYEKDKIV IQTIDGWMTS  720
RLRGCWRTFP DGTANFPPKN DADKRNHAQD AVLIAACPPH TWRERIFTWK PENPYFSVLQ  780
KIAPRWKDHQ ATMKILGRYF PRWHNQNSDI QFVHQHKTQN GTSYTMRDTV ESIDVGTDKK  840
GGSIERIYSK SFRDFFSRTF KSLGIKMAMN EIPKLKSQWL NERRAAWMKK NPATPVPNQR  900
ERAWEASFPR RLQFDMGYGE DVAEVNPKNG PSRFVRAQPV NDRIEVWTND VRQAQIRTVK  960
NRILFRHIQD NSPQGRTLER IFRRNDMIQL DAVQKRGRKG ITGKSYEAGE YMVVKIEKGG  1020
KFTAVPAHRG KGRENQRQVS QREIAKLCGV SLSPKRRKPS RSTSESG              1067

SEQ ID NO: 136          moltype = AA   length = 990
FEATURE                 Location/Qualifiers
REGION                  1..990
                        note = sequence from metagenomic data - from unidentified
                         Delta proteobacteria
source                  1..990
                        mol_type = protein
                        organism = unidentified
SEQUENCE: 136
VAAASLILQR GGLVALHPRL ERKIKEFLPT YRLGVDLGEA AGGLALIHNN NILHAETFTD  60
FHEATLETKR ALRRGRRTRH AKKMRLARLR SWILRQCIPA HVTGAEIKDS YSRLPDPYRL  120
MKDKKYQTLP GFYEVKGQNP EKSPTWIDKA KAGEVDAEGF VIALTHILQK RGYKYDGKEF  180
SDYDDSRLID FIDSCAMLAE APEMRKALED EIMRREVGEK EKPKLHEAFD NALNRQRERK  240
KALPRQVREK DMEDMVDVFG RRWQLSQEII ANWKSQLTGL LNKVVREARY DNRLKSGCSW  300
CGKKTPRLAK PEIRELAFEA AVGNLRIRER DGRDRPISDE ERNPLRGWFQ RRRENHDYSR  360
ATKNTPIEER APSEDNIRTY LEQIGVKKAW IRKKKGKEKW KFDFAMLPQL DNLINKEARK  420
GRARLCVEHM RMQAEGKTMK DADVDWQSMR KRNAPNPRRE QHDARVLKRI ERLIFNRGKK  480
GTDAWRHGPI AVITLEVPMP VDLERAREKE QVERKPLNLR QRLHAETEGV CIYCGENVHD  540
RTMHLEHIVP QAKGGPDVQM NRIASCPKCN ADRDTGKKDM LPSEWLTGDK WNVFKSRVMS  600
LNLPPLKKQL LLLEPGSKYP NDPTPLARVS ARWRAFAADI MWLFDEYSVP VPTLNYEKDK  660
PHIQVVRGNL TSRLRRDWRW KDHEATVENF PDKRRTDLYN HAQDAAILAA IPPHTWQEQI  720
FSDMAVRPCA KKDEQGNILK NEKEMRPRPG IAALALAPEW ADYERTQKEL KRPMVHTLGK  780
LKATWRRQIM DLSFYQNPTD NDGPLFIRKV DAKTGKRETK EVQKGGLVVQ VPHYDGTSGK  840
RKVQIKPIQS NAIILWHDPS GRKDNLNISI ERPAAIKKFV KHPVDPPIAS DAIILGRIER  900
ASTLWLREGK GTVELKADKK SVRSSVVMPE GIYRVKELGS NGVIVVQENA VSKELANKLG  960
ISDDQFSKVP ERALGKKELA EYFKGNQRSG                                 990

SEQ ID NO: 137          moltype = AA   length = 4
FEATURE                 Location/Qualifiers
source                  1..4
                        mol_type = protein
                        organism = synthetic construct
SEQUENCE: 137
GAAA                                                                        4
```

-continued

```
SEQ ID NO: 138        moltype = RNA  length = 70
FEATURE               Location/Qualifiers
source                1..70
                      mol_type = other RNA
                      organism = synthetic construct
SEQUENCE: 138
ttattccatt actttggagc cagtcccagc gactatgtcg tatggacgaa gcgcttattt   60
atcggagata                                                          70

SEQ ID NO: 139        moltype = RNA  length = 112
FEATURE               Location/Qualifiers
source                1..112
                      mol_type = other RNA
                      organism = synthetic construct
SEQUENCE: 139
ttattccatt actttggagc cagtcccagc gactatgtcg tatggacgaa gcgcttattt   60
atcgggaaac cgataagtaa aacgcatcaa agnnnnnnnn nnnnnnnnnn nn           112

SEQ ID NO: 140        moltype = DNA  length = 50
FEATURE               Location/Qualifiers
source                1..50
                      mol_type = other DNA
                      organism = synthetic construct
SEQUENCE: 140
cgggatttca nnnnnnnnnn nnnnnnnnnn gttcgattat tcggcgtaaa              50

SEQ ID NO: 141        moltype = DNA  length = 50
FEATURE               Location/Qualifiers
source                1..50
                      mol_type = other DNA
                      organism = synthetic construct
SEQUENCE: 141
cgggatttca tattaaatac tcgtattgct gttcgattat tcggcgtaaa              50
```

RNA-GUIDED NUCLEIC ACID MODIFYING ENZYMES AND METHODS OF USE THEREOF

CROSS-REFERENCE

This application is a continuation of U.S. application Ser. No. 16/335,516, filed Mar. 21, 2019, which is a national stage filing under 35 U.S.C. § 371 of PCT/US2017/054081, filed Sep. 28, 2017, which claims the benefit of U.S. Provisional Patent Application No. 62/402,846, filed Sep. 30, 2016, each of which applications is incorporated herein by reference in its entirety.

STATEMENT REGARDING FEDERALLY SPONSORED RESEARCH

This invention was made with government support under DE-AC02-05CH11231 awarded by the Department of Energy and under 1244557 awarded by the National Science Foundation. The government has certain rights in the invention.

INCORPORATION BY REFERENCE OF SEQUENCE LISTING PROVIDED AS A SEQUENCE LISTING XML FILE

A Sequence Listing is provided herewith as a Sequence Listing XML, "BERK-342CON2_SEQ_LIST.XML" created on Oct. 20, 2023 and having a size of 157,583 bytes. The contents of the Sequence Listing XML are incorporated by reference herein in their entirety.

INTRODUCTION

The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

Current CRISPR-Cas technologies are based on systems from cultured bacteria, leaving untapped the vast majority of organisms that have not been isolated. To date, only a few Class 2 CRISPR/Cas systems have been discovered. There is a need in the art for additional Class 2 CRISPR/Cas systems (e.g., Cas protein plus guide RNA combinations).

SUMMARY

The present disclosure provides RNA-guided endonuclease polypeptides, referred to herein as "CasX" polypeptides (also referred to as "CasX proteins"); nucleic acids encoding the CasX polypeptides; and modified host cells comprising the CasX polypeptides and/or nucleic acids encoding same. CasX polypeptides are useful in a variety of applications, which are provided.

The present disclosure provides guide RNAs (referred to herein as "CasX guide RNAs") that bind to and provide sequence specificity to the CasX proteins; nucleic acids encoding the CasX guide RNAs; and modified host cells comprising the CasX guide RNAs and/or nucleic acids encoding same. CasX guide RNAs are useful in a variety of applications, which are provided.

The present disclosure provides archaeal Cas9 polypeptides and nucleic acids encoding same, as well as their associated guide RNAs (archaeal Cas9 guide RNAs) and nucleic acids encoding same.

BRIEF DESCRIPTION OF THE DRAWINGS

FIGS. 1A-1B depict three naturally occurring CasX protein sequences.

FIG. 2 depicts an alignment of the two identified naturally occurring CasX protein sequences (SEQ ID NOs:2 and 1, respectively).

FIGS. 4A-4C depict experiments performed to demonstrate plasmid interference by CasX expressed in *Escherichia coli*.

FIGS. 6A-6C depict experiments performed to determine that CasX is a dual-guided CRISPR-Cas effector complex (FIG. 6C: top DNA-SEQ ID NO:140; bottom RNA-SEQ ID NO:139).

FIG. 7 presents a schematic of CasX RNA guided DNA interference (top DNA-SEQ ID NO:141; RNA-SEQ ID NOs:62 and 138, respectively).

FIG. 8 presents a schematic of experimental design for one embodiment to demonstrate editing in human cells using CasX.

FIG. 9 presents data showing recombinant expression and purification of CasX.

FIG. 10 presents data using various different tracrRNA sequences (different sequence lengths) for cleavage activity.

FIG. 11 presents data related to CasX functioning at room temperature versus 37° C.

FIG. 13 presents example archaeal Cas9 proteins (ARMAN-1 and ARMAN-4, SEQ ID NOs: 71 and 72, respectively). Catalytic residues that correspond to D10 and H840 of *S. pyogenes* are bold and underlined.

FIG. 15 presents example dual guide (top panel)(top RNA-SEQ ID NO: 74, bottom RNA-SEQ ID NO: 78) and single guide (bottom panel)(SEQ ID NO: 80) formats that can be used with an archaeal Cas9 protein (e.g., ARMAN-4 Cas9).

FIG. 16 presents two newly identified non-archaeal Cas9 proteins.

Figure 17B:
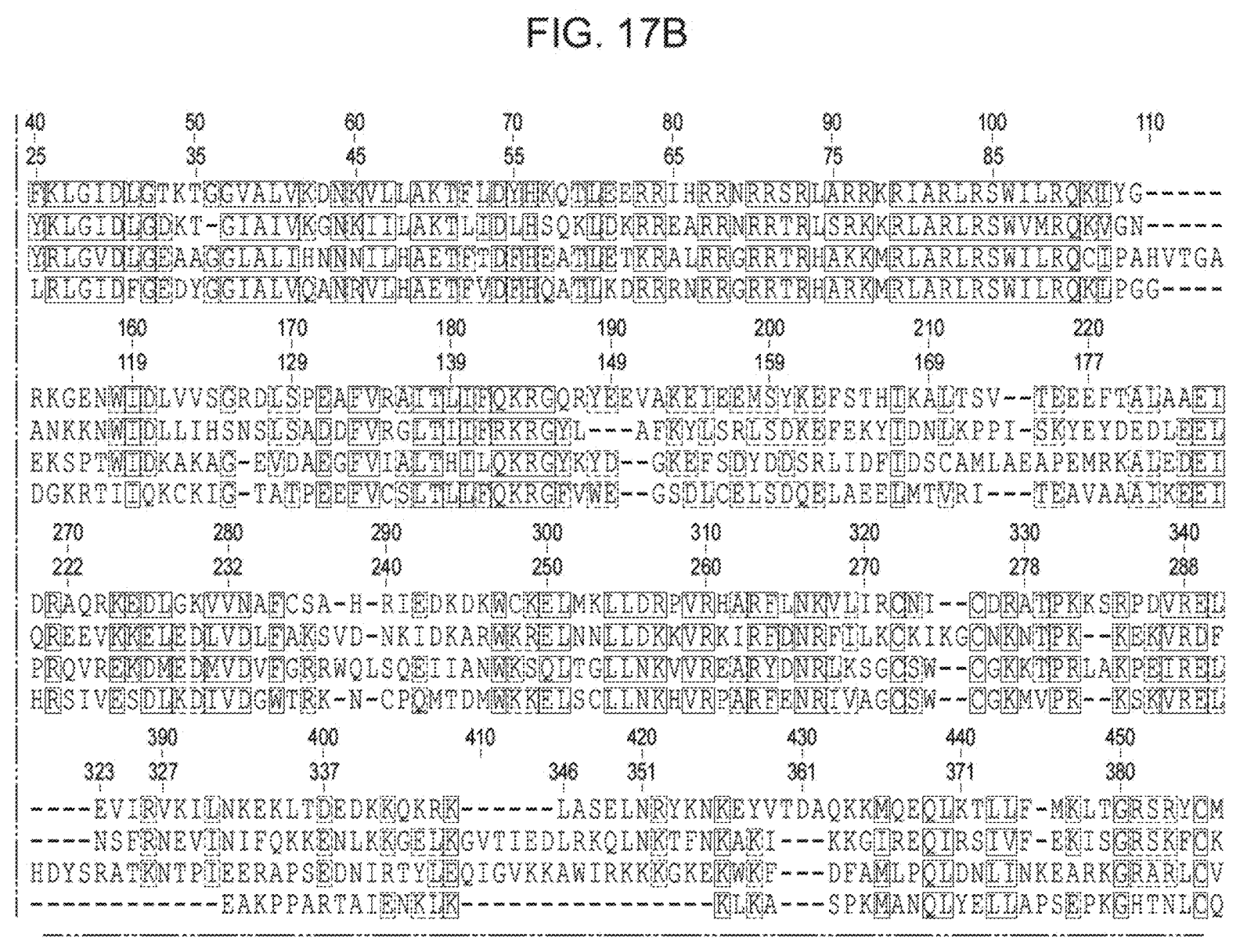
Figure 17D:
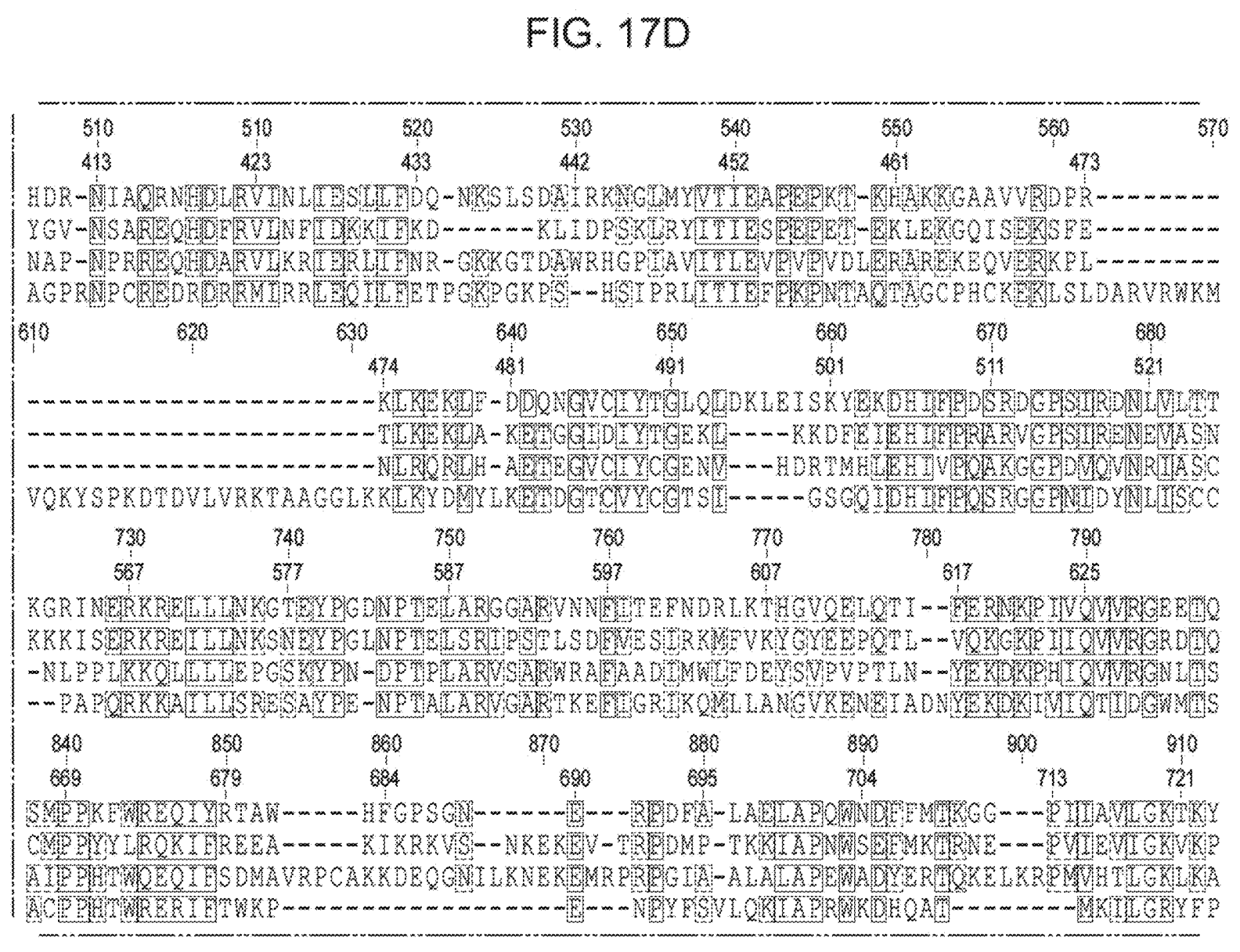
Figure 17F:
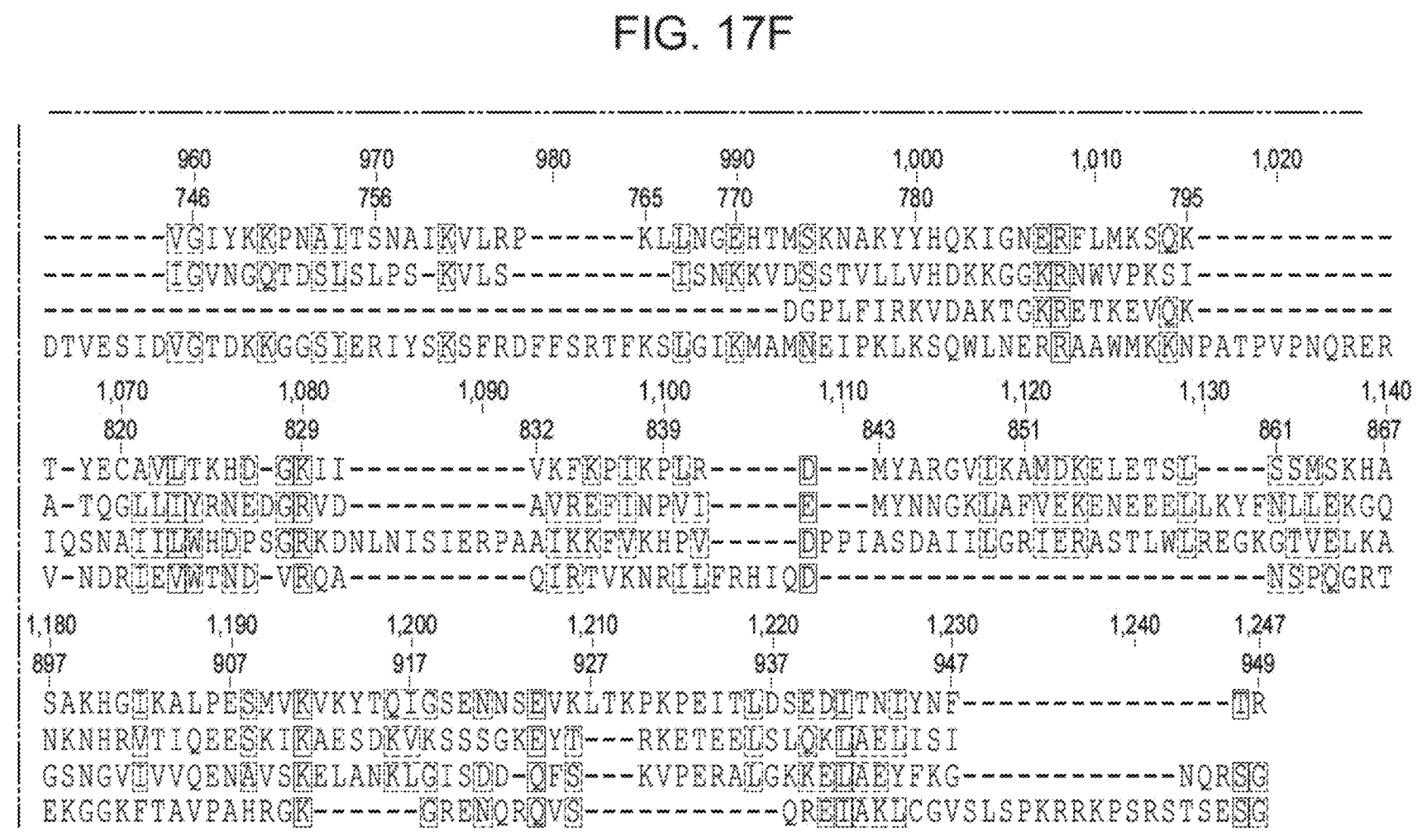

FIGS. 17A-17F presents (i) an alignment of two newly identified non-archaeal Cas9 proteins with ARMAN-1 and ARMAN-4 Cas9 proteins; and (ii) an alignment of Cas9 proteins from ARMAN-1 and ARMAN-4, as well as two closely related Cas9 proteins from uncultivated bacteria, to the *Actinomyces naeslundii* Cas9, whose structure has been solved (SEQ ID NOs:71, 72, 136 and 135, respectively).

FIG. 18A, Ratio of major lineages with and without isolated representatives in all bacteria and archaea, based on data of Hug et al.[32]. The results highlight the massive scale of as yet little investigated biology in these domains. Archaeal Cas9 and the novel CRISPR-CasY were found exclusively in lineages with no isolated representatives. FIG. 18A, Locus organization of the newly discovered CRISPR-Cas systems.

FIG. 19A, CRISPR arrays reconstructed from 15 different AMD samples. White boxes indicate repeats and colored diamonds indicate spacers (identical spacers are similarly colored; unique spacers are in black). The conserved region of the array is highlighted (on the right). The diversity of recently acquired spacers (on the left) indicates the system is active. An analysis that also includes CRISPR fragments from the read data is presented in FIG. 25. FIG. 19B, A single putative viral contig reconstructed from AMD metagenomic data contains 56 protospacers (red vertical bars) from the ARMAN-1 CRISPR arrays. FIG. 19C, Sequence analysis revealed a conserved 'NGG' PAM motif downstream of the protospacers on the non-target strand.

FIGS. 20A-20D present data showing that CasX mediates programmable DNA interference in *E. coli*. FIG. 20A, Diagram of CasX plasmid interference assays. *E. coli* expressing a minimal CasX locus is transformed with a plasmid containing a spacer matching the sequence in the CRISPR array (target) or plasmid containing a non-matching spacer (non-target). After being transformed, cultures are plated and colony forming units (cfu) quantified. FIG. 20B, Serial dilution of *E. coli* expressing the Planctomycetes CasX locus targeting spacer 1 (sX.1) and transformed with the specified target (sX1, CasX spacer 1; sX2, CasX spacer 2; NT, non-target). FIG. 20C, Plasmid interference by Deltaproteobacteria CasX. Experiments were conducted in triplicate and mean±s.d. is shown. FIG. 20D, PAM depletion assays for the Planctomycetes CasX locus expressed in *E. coli*. PAM sequences depleted greater than 30-fold compared to a control library were used to generate the WebLogo.

FIG. 21A, Mapping of environmental RNA sequences (metatranscriptomic data) to the CasX CRISPR locus diagramed below (red arrow, putative tracrRNA; white boxes, repeat sequences; green diamonds, spacer sequences). Inset shows detailed view of the first repeat and spacer. FIG. 21B, Diagram of CasX double-stranded DNA interference. The site of RNA processing is indicated by black arrows. FIG. 21C, Results of. plasmid interference assays with the putative tracrRNA knocked out of the CasX locus and CasX coexpressed with a crRNA alone, a truncated sgRNA or a full length sgRNA (T, target; NT, non-target). Experiments were conducted in triplicate and mean±s.d. is shown.

FIG. 22A, Diagrams of CasY loci and neighboring proteins. FIG. 22B, WebLogo of 5' PAM sequences depleted greater than 3-fold by CasY relative to a control library. FIG. 22C, Plasmid interference by *E. coli* expressing CasY.1 and transformed with targets containing the indicated PAM. Experiments were conducted in triplicate and mean±s.d is shown.

FIG. 23A, Simplified phylogenetic tree of the universal Cas1 protein. CRISPR types of known systems are noted on the wedges and branches; the newly described systems are in bold. Detailed Cas1 phylogeny is presented in Supplementary Data 2.

FIGS. 24A-24D show that archaeal Cas9 from ARMAN-4 is found on numerous contigs with a degenerate CRISPR array. Cas9 from ARMAN-4 is highlighted in dark red on 16 different contigs. Proteins with putative domains or functions are labeled whereas hypothetical proteins are unlabeled. Fifteen of the contigs contain two degenerate direct repeats (one bp mismatch) and a single, conserved spacer. The remaining contig contains only one direct repeat. Unlike ARMAN-1, no additional Cas proteins are found adjacent to Cas9 in ARMAN-4.

Figure 25E:
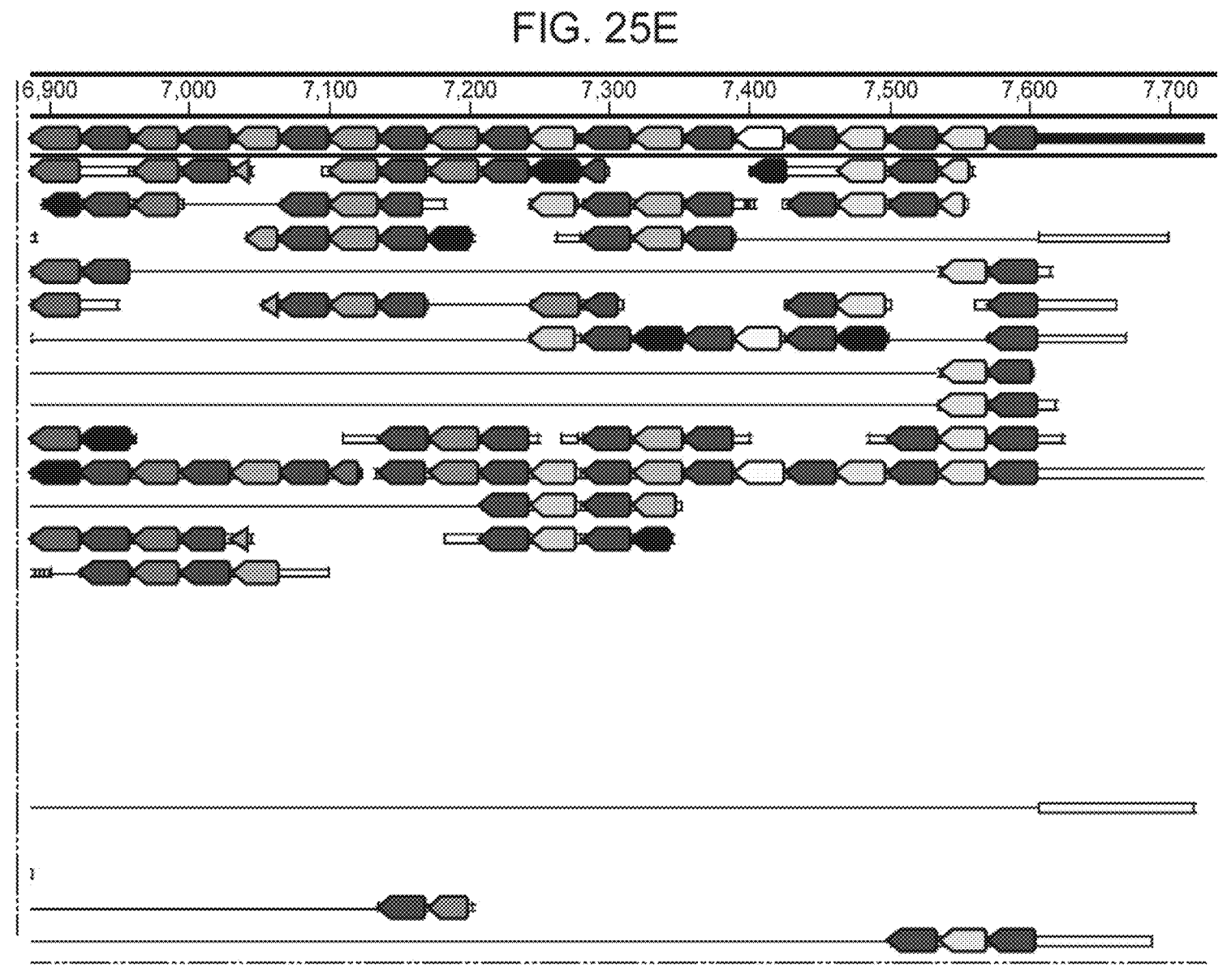

FIGS. 25A-25F present a full reconstruction of ARMAN-1 CRISPR arrays. Reconstruction of CRISPR arrays, that include reference assembled sequences, as well as array segments reconstructed from the short DNA reads. Green arrows indicate repeats and colored arrows indicate CRISPR spacers (identical spacers are colored the same whereas unique spacers are colored in black). In CRISPR systems, spacers are typically added unidirectionally, so the high variety of spacers on the left side is attributed to recent acquisition.

FIG. 26A, Protospacers (red arrows) from ARMAN-1 map to the genome of ARMAN-2, a nanoarchaeon from the same environment. Six protospacers map uniquely to a portion of the genome flanked by two long-terminal repeats (LTRs), and two additional protospacers match perfectly within the LTRs (blue and green). This region is likely a transposon, suggesting the CRISPR-Cas system of ARMAN-1 plays a role in suppressing mobilization of this element. FIG. 26B, Protospacers also map to a Thermoplasmatales archaeon (I-plasma), another member of the Richmond Mine ecosystem that is found in the same samples as ARMAN organisms. The protospacers cluster within a region of the genome encoding short, hypothetical proteins, suggesting this might also represent a mobile element.

FIG. 27A, The CRISPR repeat and tracrRNA anti-repeat are depicted in black whereas the spacer-derived sequence is shown as a series of green N's. No clear termination signal can be predicted from the locus, so three different tracrRNA lengths were tested based on their secondary structure—69, 104, and 179 in red, blue, and pink, respectively (top SEQ ID NO:73; bottom SEQ ID NO:77). FIG. 27B, Engineered single-guide RNA (SEQ ID NO:79) corresponding to dual-guide in FIG. 27A. FIG. 27C, Dual-guide for ARMAN-4 Cas9 with two different hairpins on 3' end of tracrRNA (75 and 122) (top SEQ ID NO:74; bottom SEQ ID NO:78). FIG. 27D, Engineered single-guide RNA (SEQ ID NO:80) corresponding to dual-guide in FIG. 27C. FIG. 27E, Conditions tested in *E. coli* in vivo targeting assay.

FIG. 28A, ARMAN-1 (AR1) and ARMAN-4 (AR4) Cas9 were expressed and purified under

5

Figures 28A, 28B:
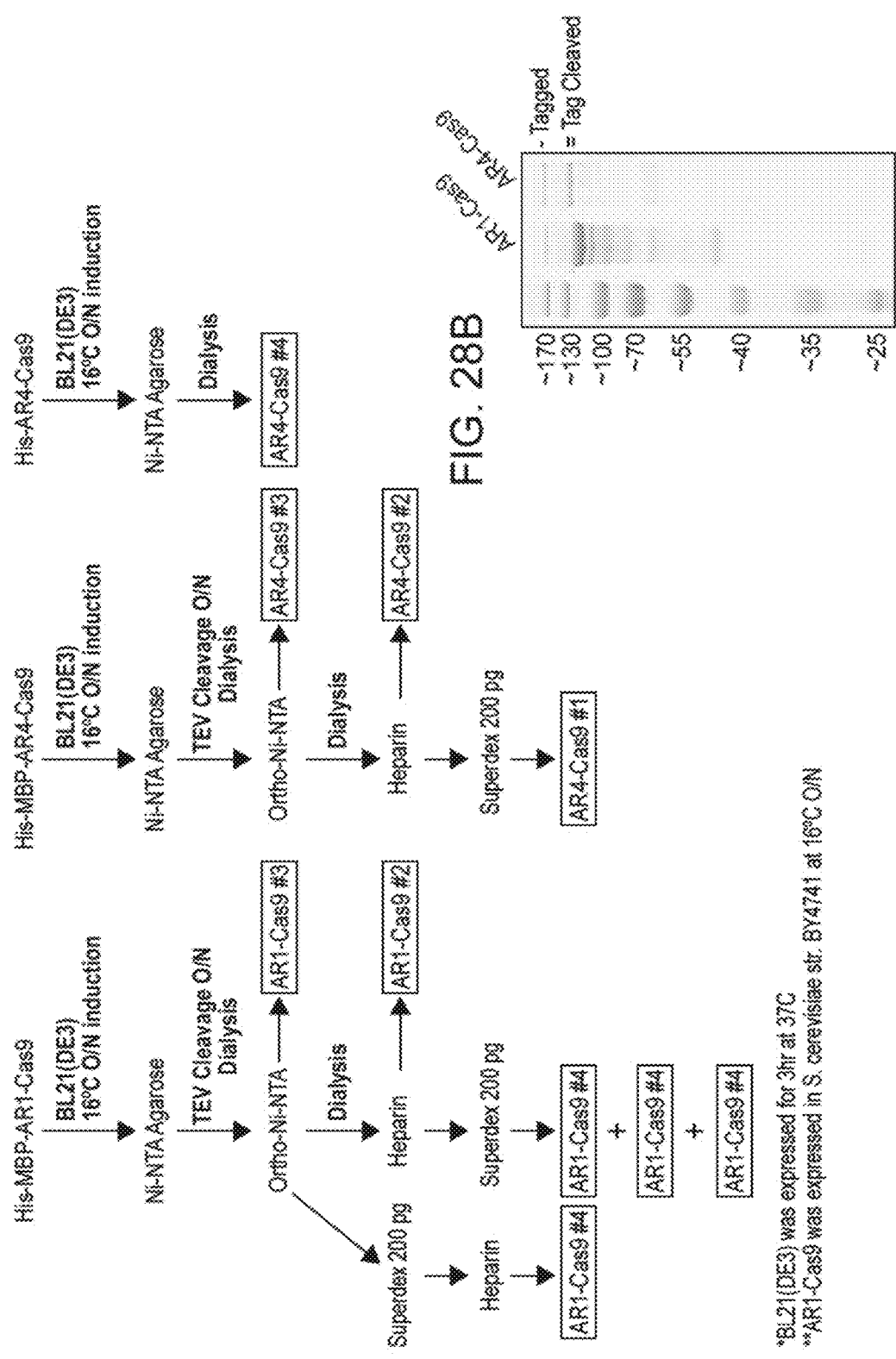
FIGS. 28A-28B present purification schema for in vitro biochemistry studies.

6 a variety of conditions as outlined in the Supplementary Materials. Proteins outlined in blue boxes were tested for cleavage activity in vitro. FIG. 28B, Fractions of AR1-Cas9 and AR4-Cas9 purifications were separated on a 10% SDS-PAGE gel.

Figure 29:
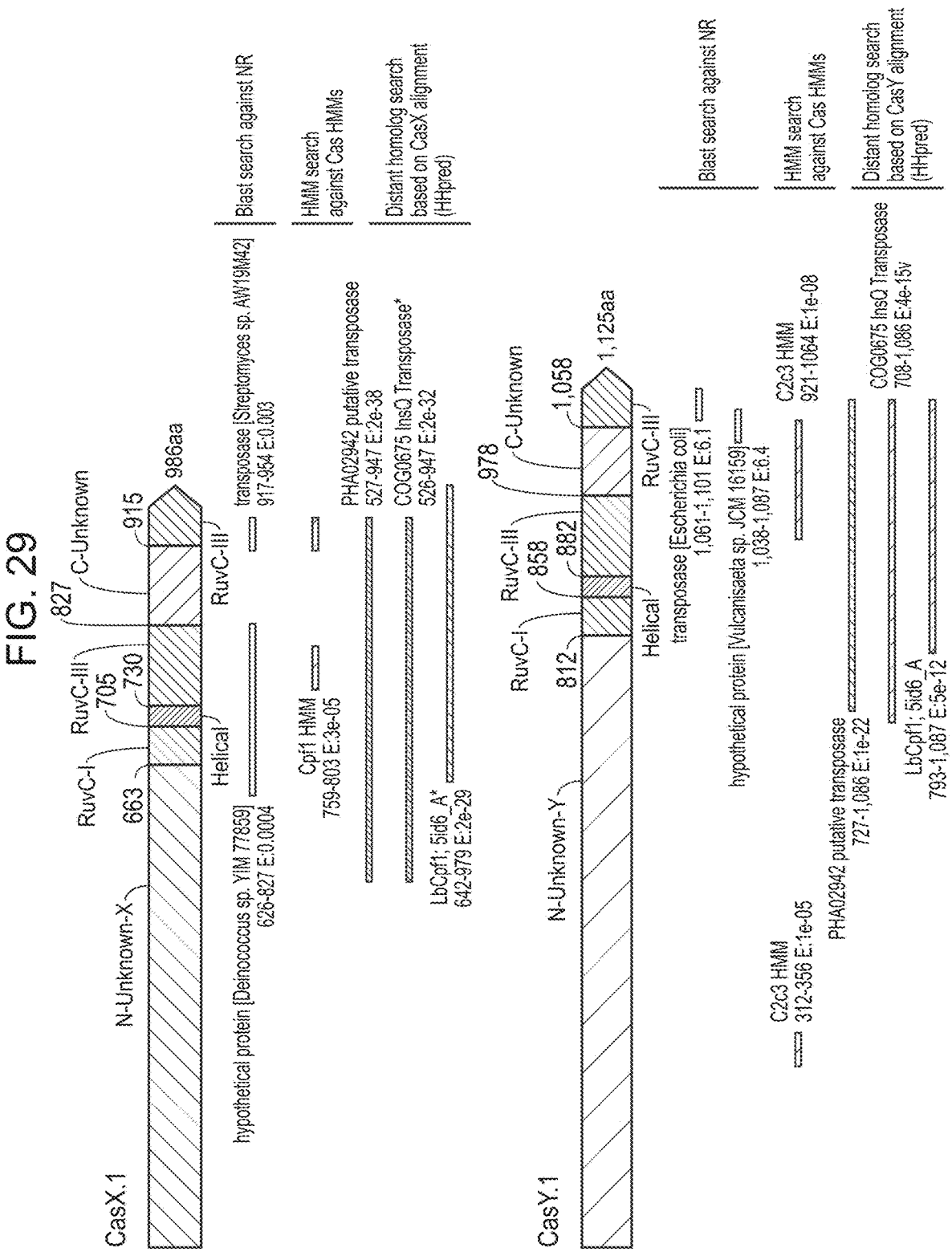

FIG. 29 presents newly identified CRISPR-Cas systems compared to known proteins. Similarity of CasX and CasY to known proteins based on the following searches: (1) Blast search against the non-redundant (NR) protein database of NCBI, (2) Hidden markov model (HMM) search against an HMM database of all known proteins and (3) distant homology search using HHpred[30].

Figure 20C:
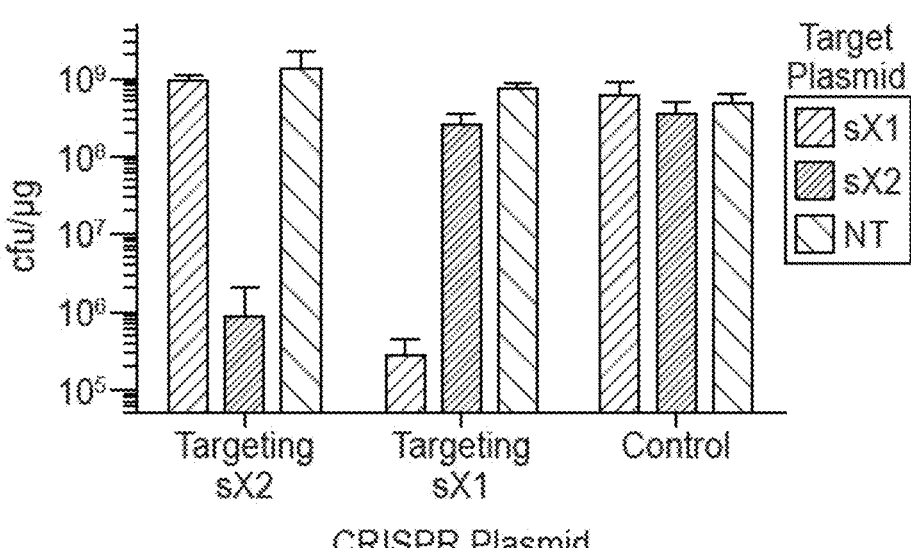
Figures 30A, 30B:
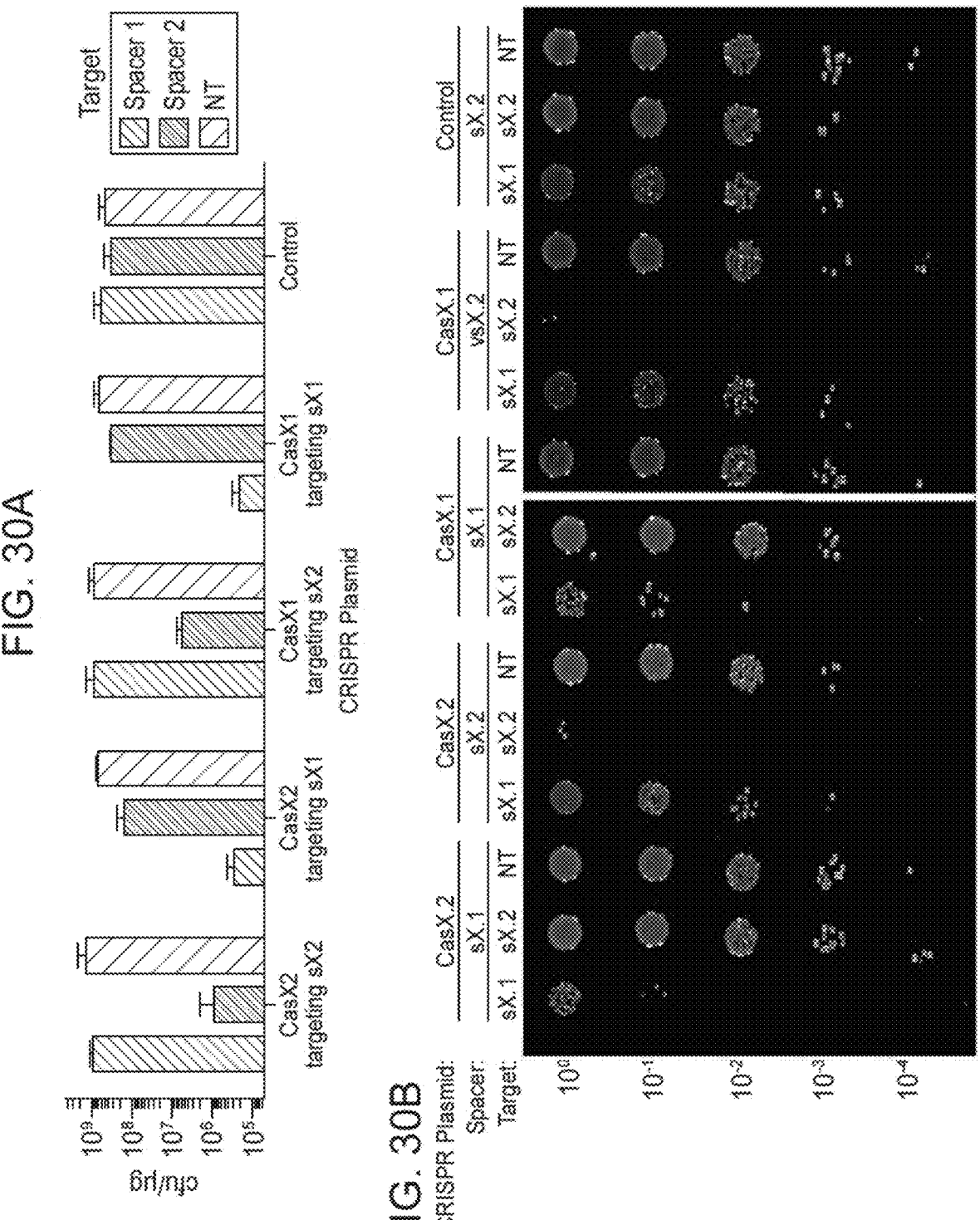
Figure 30C:
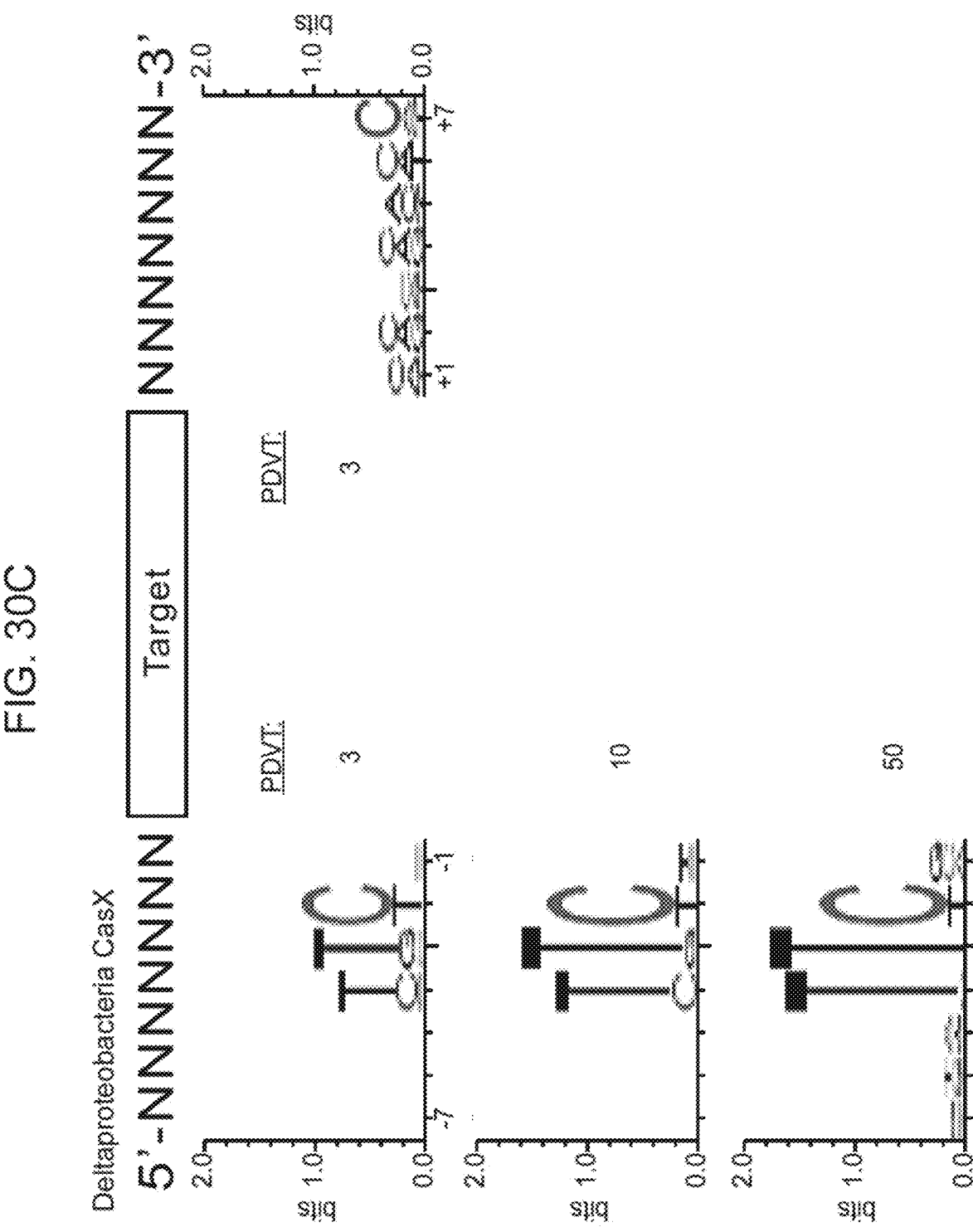
Figure 30D:
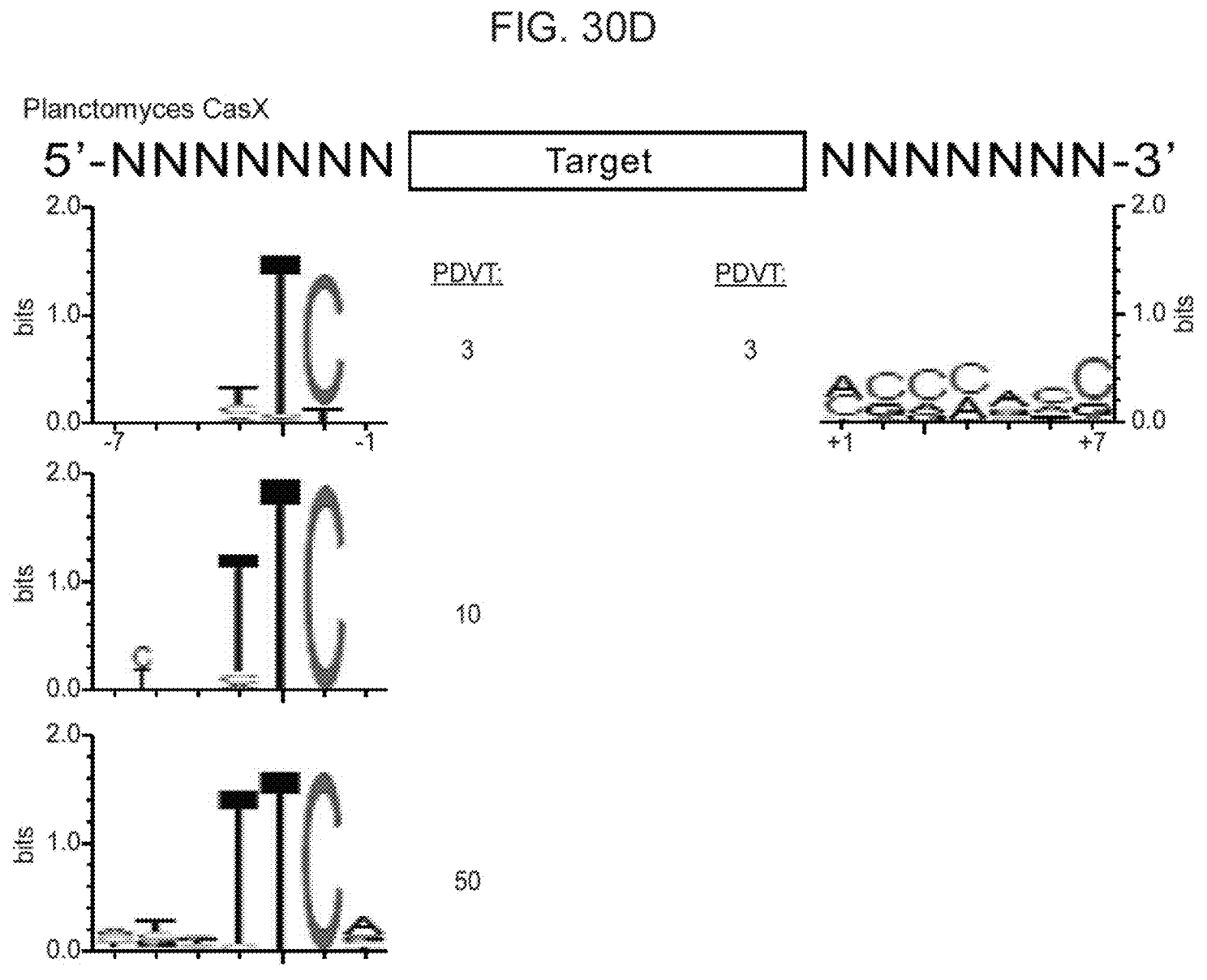
Figure 30E:
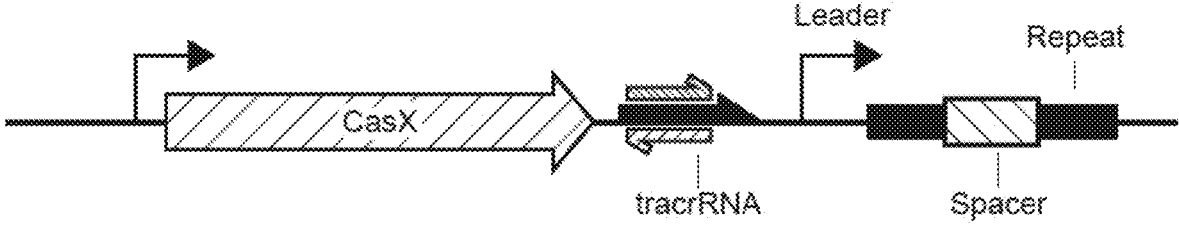
Figure 30F:
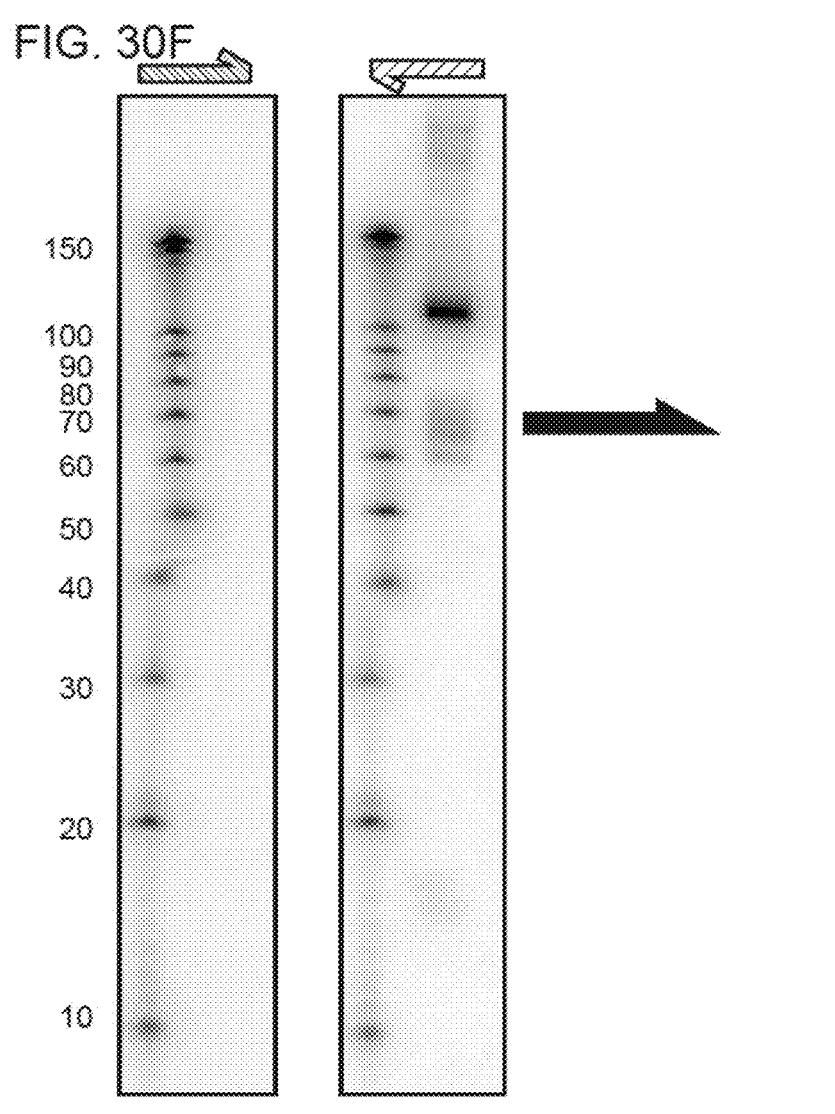

FIGS. 30A-30F present data related to programed DNA interference by CasX. a, Plasmid interference assays for CasX2 (Planctomycetes) and CasX1 (Deltaproteobacteria), continued from FIG. 20C (sX1, CasX spacer 1; sX2, CasX spacer 2; NT, non-target). Experiments were conducted in triplicate and mean±s.d. is shown. FIG. 30B, Serial dilution of *E. coli* expressing a CasX locus and transformed with the specified target, continued from FIG. 20B-20C. FIG. 30C, PAM depletion assays for the Deltaproteobacteria CasX and FIG. 30D, Planctomycetes CasX expressed in *E. coli*. PAM sequences depleted greater than the indicated PAM depletion value threshold (PDVT) compared to a control library were used to generate the WebLogo. FIG. 30E, Diagram depicting the location of Northern blot probes for CasX.1. FIG. 30F, Northern blots for CasX.1 tracrRNA in total RNA extracted from *E. coli* expressing the CasX.1 locus.

Figure 31:
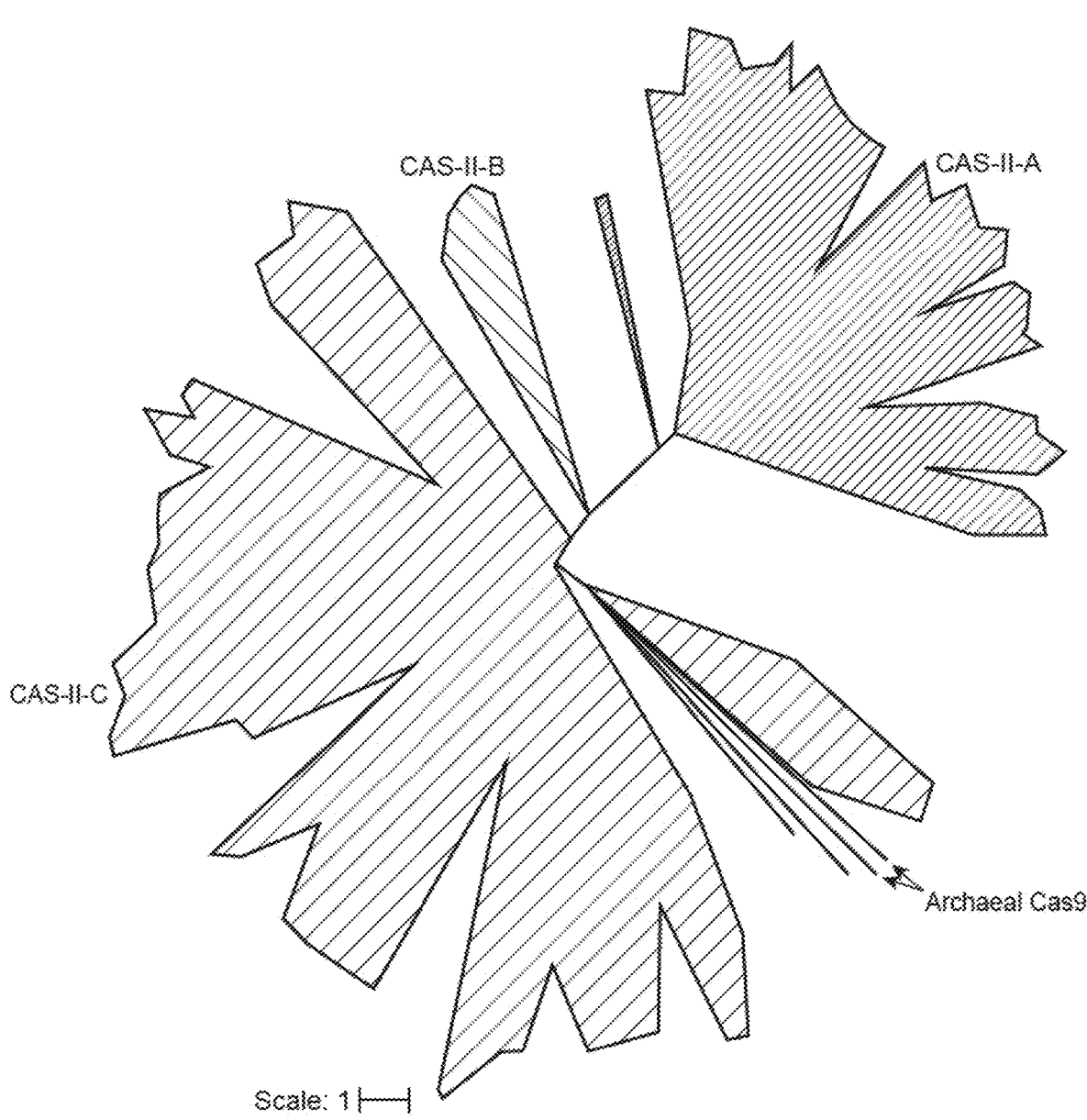

FIG. 31 presents an evolutionary tree of Cas9 homologs. Maximum-likelihood phylogenic tree of Cas9 proteins, showing the previously described systems colored based on their type: II-A in blue, II-B in green and II-C in purple. The Archaeal Cas9, cluster with type II-C CRISPR-Cas systems, together with two newly described bacterial Cas9 from uncultivated bacteria.

FIG. 32 presents a table of cleavage conditions assayed for Cas9 from ARMAN-1 and ARMAN-4.

DEFINITIONS

"Heterologous," as used herein, means a nucleotide or polypeptide sequence that is not found in the native nucleic acid or protein, respectively. For example, relative to a CasX polypeptide, a heterologous polypeptide comprises an amino acid sequence from a protein other than the CasX polypeptide. In some cases, a portion of a CasX protein from one species is fused to a portion of a CasX protein from a different species. The CasX sequence from each species could therefor be considered to be heterologous relative to one another. As another example, a CasX protein (e.g., a dCasX protein) can be fused to an active domain from a non-CasX protein (e.g., a histone deacetylase), and the sequence of the active domain could be considered a heterologous polypeptide (it is heterologous to the CasX protein).

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The terms "polynucleotide" and "nucleic acid" should be understood to include, as applicable to the embodiment being described, single-stranded (such as sense or antisense) and double-stranded polynucleotides.

The terms "polypeptide," "peptide," and "protein", are used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "naturally-occurring" as used herein as applied to a nucleic acid, a protein, a cell, or an organism, refers to a nucleic acid, cell, protein, or organism that is found in nature.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant" polypeptide refers to a polypeptide which is not naturally occurring, e.g., is made by the artificial combination of two otherwise separated segments of amino sequence through human intervention. Thus, e.g., a polypeptide that comprises a heterologous amino acid sequence is recombinant.

By "construct" or "vector" is meant a recombinant nucleic acid, generally recombinant DNA, which has been generated for the purpose of the expression and/or propagation of a specific nucleotide sequence(s), or is to be used in the construction of other recombinant nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (e.g., DNA exogenous to the cell) into the cell. Genetic change ("modification") can be accomplished either by incorporation of the new nucleic acid into the genome of the host cell, or by transient or stable maintenance of the new nucleic acid as an episomal element. Where the cell is a eukaryotic cell, a permanent genetic change is generally achieved by introduction of new DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell of a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to an individual organism, e.g., a mammal, including, but not limited to, murines, simians, humans, mammalian farm animals, mammalian sport animals, and mammalian pets.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a CasX polypeptide" includes a plurality of such polypeptides and reference to "the guide RNA" includes reference to one or more guide RNAs and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides RNA-guided endonuclease polypeptides, referred to herein as "CasX" polypeptides (also referred to as "CasX proteins"); nucleic acids encoding the CasX polypeptides; and modified host cells comprising the CasX polypeptides and/or nucleic acids encoding same. CasX polypeptides are useful in a variety of applications, which are provided.

The present disclosure provides guide RNAs (referred to herein as "CasX guide RNAs") that bind to and provide sequence specificity to the CasX proteins; nucleic acids encoding the CasX guide RNAs; and modified host cells comprising the CasX guide RNAs and/or nucleic acids encoding same. CasX guide RNAs are useful in a variety of applications, which are provided.

The present disclosure provides archaeal Cas9 polypeptides and nucleic acids encoding same, as well as their associated guide RNAs (archaeal Cas9 guide RNAs) and nucleic acids encoding same.

Compositions

CRISPR/CasX Proteins and Guide RNAs

A CRISPR/Cas endonuclease (e.g., a CasX protein) interacts with (binds to) a corresponding guide RNA (e.g., a CasX guide RNA) to form a ribonucleoprotein (RNP) complex that is targeted to a particular site in a target nucleic acid via base pairing between the guide RNA and a target sequence within the target nucleic acid molecule. A guide RNA includes a nucleotide sequence (a guide sequence) that is complementary to a sequence (the target site) of a target nucleic acid. Thus, a CasX protein forms a complex with a CasX guide RNA and the guide RNA provides sequence specificity to the RNP complex via the guide sequence. The CasX protein of the complex provides the site-specific activity. In other words, the CasX protein is guided to a target site (e.g., stabilized at a target site) within a target nucleic acid sequence (e.g. a chromosomal sequence or an extrachromosomal sequence, e.g., an episomal sequence, a minicircle sequence, a mitochondrial sequence, a chloroplast sequence, etc.) by virtue of its association with the guide RNA.

The present disclosure provides compositions comprising a CasX polypeptide (and/or a nucleic acid encoding the CasX polypeptide) (e.g., where the CasX polypeptide can be a naturally existing protein, a nickase CasX protein, a dCasX protein, a chimeric CasX protein, etc.). The present disclosure provides compositions comprising a CasX guide RNA (and/or a nucleic acid encoding the CasX guide RNA) (e.g., where the CasX guide RNA can be in dual or single guide format). The present disclosure provides compositions comprising (a) a CasX polypeptide (and/or a nucleic acid encoding the CasX polypeptide) (e.g., where the CasX polypeptide can be a naturally existing protein, a nickase CasX protein, a dCasX protein, a chimeric CasX protein, etc.) and (b) a CasX guide RNA (and/or a nucleic acid encoding the CasX guide RNA) (e.g., where the CasX guide RNA can be in dual or single guide format). The present disclosure provides a nucleic acid/protein complex (RNP complex)

comprising: (a) a CasX polypeptide of the present disclosure (e.g., where the CasX polypeptide can be a naturally existing protein, a nickase CasX protein, a dCasX protein, a chimeric CasX protein, etc.); and (b) a CasX guide RNA (e.g., where the CasX guide RNA can be in dual or single guide format).

CasX Protein

A CasX polypeptide (this term is used interchangeably with the term "CasX protein") can bind and/or modify (e.g., cleave, nick, methylate, demethylate, etc.) a target nucleic acid and/or a polypeptide associated with target nucleic acid (e.g., methylation or acetylation of a histone tail) (e.g., in some cases the CasX protein includes a fusion partner with an activity, and in some cases the CasX protein provides nuclease activity). In some cases, the CasX protein is a naturally-occurring protein (e.g., naturally occurs in prokaryotic cells). In other cases, the CasX protein is not a naturally-occurring polypeptide (e.g., the CasX protein is a variant CasX protein, a chimeric protein, and the like).

Assays to determine whether given protein interacts with a CasX guide RNA can be any convenient binding assay that tests for binding between a protein and a nucleic acid. Suitable binding assays (e.g., gel shift assays) will be known to one of ordinary skill in the art (e.g., assays that include adding a CasX guide RNA and a protein to a target nucleic acid). Assays to determine whether a protein has an activity (e.g., to determine if the protein has nuclease activity that cleaves a target nucleic acid and/or some heterologous activity) can be any convenient assay (e.g., any convenient nucleic acid cleavage assay that tests for nucleic acid cleavage). Suitable assays (e.g., cleavage assays) will be known to one of ordinary skill in the art.

A naturally occurring CasX protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring guide RNA includes a tracrRNA hybridized to a crRNA, where the crRNA includes a guide sequence that hybridizes to a target sequence in the target DNA.

Figure 2:
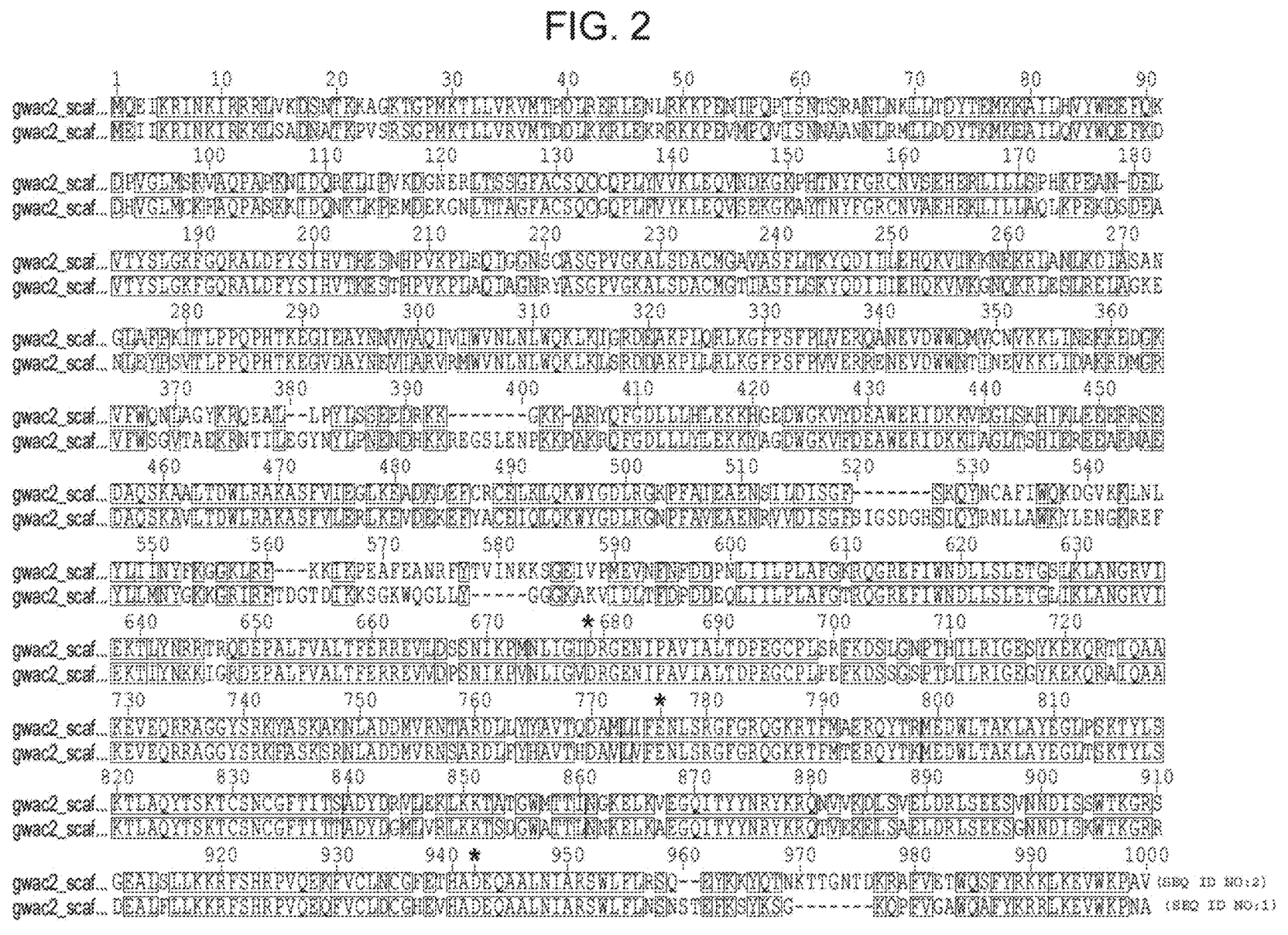

In some embodiments, the CasX protein of the subject methods and/or compositions is (or is derived from) a naturally occurring (wild type) protein. Examples of naturally occurring CasX proteins are depicted in FIGS. 1A-1B and are set forth as SEQ ID NOs: 1-3. An alignment of two naturally occurring CasX proteins is presented in FIG. 2 ('gwa2' is CasX1 and 'gwc2' is CasX2). A partial DNA scaffold of the CRISPR locus assembled from sequencing data (from a Deltaproteobacter (gwa2 scaffold) and from a Planctomycetes (gwc2 scaffold)) is set forth as SEQ ID NOs: 51 and 52, respectively. It is important to note that this newly discovered protein (CasX) is short compared to previously identified CRISPR-Cas endonucleases, and thus use of this protein as an alternative provides the advantage that the nucleotide sequence encoding the protein is relatively short. This is useful, for example, in cases where a nucleic acid encoding the CasX protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications. It is also noted herein that bacteria harboring CasX CRISPR loci were present in environmental samples that were collected at low temperature (e.g., 10-17° C.). Thus, CasX is expected to be able to function well at low temperatures (e.g., 10-14° C., 10-17° C., 10-20° C.) (e.g., better than other Cas endonucleases discovered to date).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 1. In some cases, a CasX protein includes an amino acid sequence having the CasX protein sequence set forth as SEQ ID NO: 1. In some cases, a CasX protein includes an amino acid sequence having the CasX protein sequence set forth as SEQ ID NO: 1, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 2. In some cases, a CasX protein includes an amino acid sequence having the CasX protein sequence set forth as SEQ ID NO: 2. In some cases, a CasX protein includes an amino acid sequence having the CasX protein sequence set forth as SEQ ID NO: 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the CasX protein sequence set forth as SEQ ID NO: 3. In some cases, a CasX protein includes an amino acid sequence having the CasX protein sequence set forth as SEQ ID NO: 3. In some cases, a CasX protein includes an amino acid sequence having the CasX protein sequence set forth as SEQ ID NO: 3, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with any one of the CasX protein sequences set forth as SEQ ID NOs: 1 and 2. In some cases, a CasX protein includes an amino acid sequence having the CasX protein sequence set forth in any one of SEQ ID NOs: 1 and 2. In some cases, a CasX protein includes an amino acid sequence having the CasX protein sequence set forth in any one of SEQ ID NOs: 1 and 2, with the exception that the sequence includes an amino acid substitution (e.g., 1, 2, or 3 amino acid substitutions) that reduces the naturally occurring catalytic activity of the protein (e.g., such as at amino acid positions described below).

In some cases, a CasX protein includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with any one of the CasX protein sequences set forth as SEQ ID NOs: 1-3. In some cases, a CasX protein includes an amino acid sequence having the CasX protein sequence set forth in any one of SEQ ID NOs: 1-3. In some cases, a CasX protein includes an amino acid sequence having the CasX protein sequence set forth in any one of SEQ ID NOs: 1-3, with the exception that the sequence includes an amino acid substitution (e.g., 1, 2, or 3 amino acid substitutions) that reduces the naturally occurring catalytic activity of the protein (e.g., such as at amino acid positions described below).

CasX Protein Domains

Figure 3A:
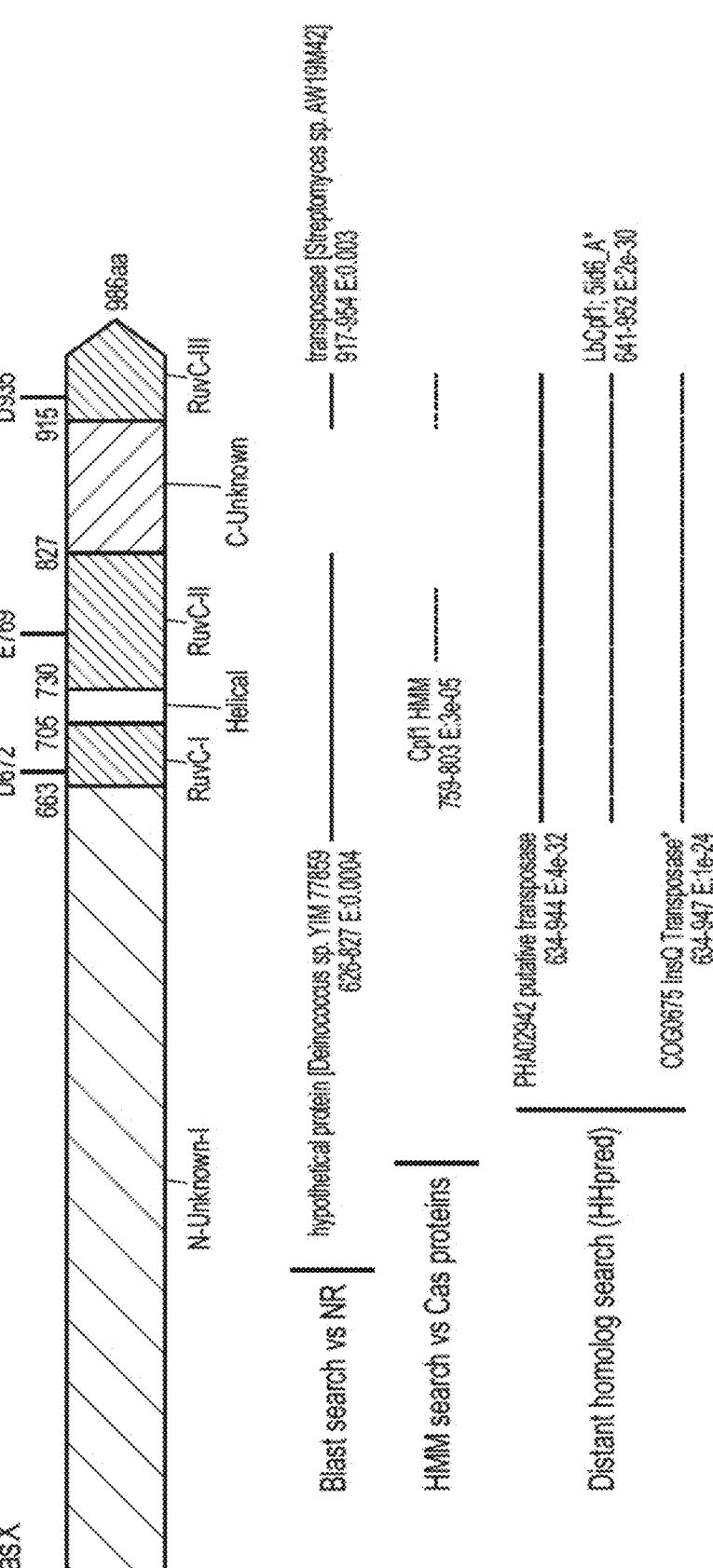
FIGS. 3A-3B depict a schematic domain representation for CasX. Also shown are results from various searches attempting to identify homologs of CasX. Also depicted are portions of the CasX-containing CRISPR loci there were identified from two different species.
Figure 3B:
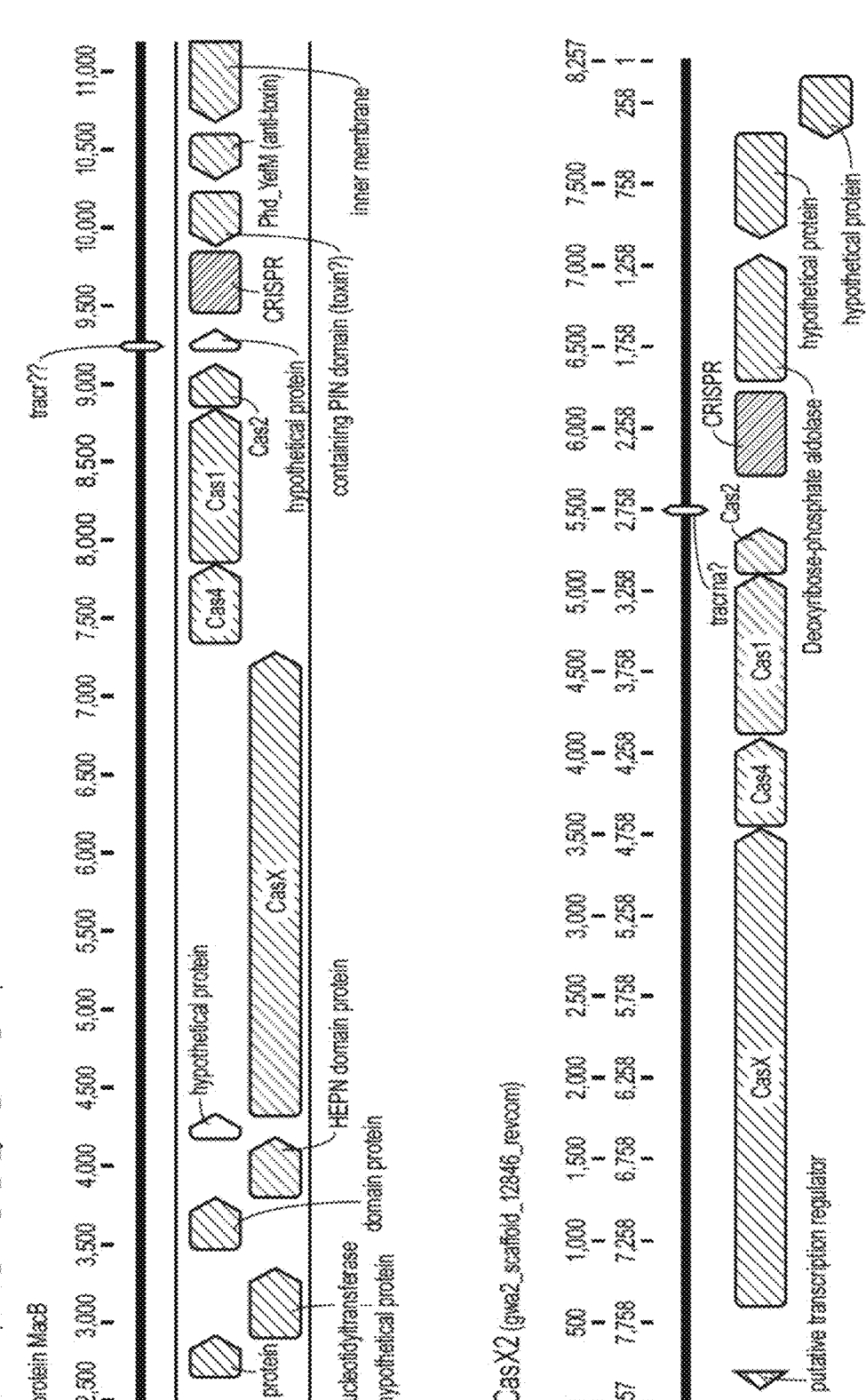

The domains of a CasX protein are depicted in FIGS. 3A-3B. As can be seen in the schematic representation of FIGS. 3A-3B (amino acids are numbered based on the CasX1 protein (SEQ ID NO: 1)), a CasX protein includes an N-terminal domain roughly 650 amino acids in length (e.g., 663 for CasX1 and 650 for CasX2), and a C-terminal domain that includes 3 partial RuvC domains (RuvC-I, RuvC-II, and RuvC-III, also referred to herein as subdomains) that are not contiguous with respect to the primary amino acid sequence of the CasX protein, but form a RuvC domain once the protein is produced and folds. Thus, in some cases, a CasX protein (of the subject compositions and/or methods) includes an amino acid sequence with an N-terminal domain (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids). In some cases, a CasX protein (of the subject compositions and/or methods) includes an amino acid sequence having a length (e.g., not including any fused heterologous sequence such as an NLS and/or a domain with a catalytic activity) in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids) that is N-terminal to a split Ruv C domain (e.g., 3 partial RuvC domains—RuvC-I, RuvC-II, and RuvC-III).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 1. In some cases, a CasX protein includes an amino acid sequence having amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 2. In some cases, a CasX protein includes an amino acid sequence of SEQ ID NO: 2 corresponding to amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of the CasX protein sequence set forth as SEQ ID NO: 3. In some cases, a CasX protein includes an amino acid sequence of SEQ ID NO: 3 corresponding to amino acids 1-663 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2. In some cases, a CasX protein includes an amino acid sequence corresponding to amino acids 1-663 of the CasX protein sequence set forth as SEQ ID NO: 1.

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes a split Ruv C domain (e.g., 3 partial RuvC domains—RuvC-I, RuvC-II, and RuvC-III).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3. In some cases, a CasX protein includes an amino acid sequence corresponding to amino acids 1-663 of the CasX protein sequence set forth as SEQ ID NO: 1.

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes a split Ruv C domain (e.g., 3 partial RuvC domains—RuvC-I, RuvC-II, and RuvC-III). In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes a split Ruv C domain (e.g., 3 partial RuvC domains—RuvC-I, RuvC-II, and RuvC-III).

In some embodiments, the split RuvC domain of a CasX protein (of the subject compositions and/or methods) includes a region between the RuvC-II and RuvC-III subdomains that is larger than the RuvC-III subdomain. For example, in some cases, the ratio of the length of the region between the RuvC-II and RuvC-III subdomains over the length of the RuvC-III subdomain is 1.1 or greater (e.g., 1.2). In some cases, the ratio of the length of the region between the RuvC-II and RuvC-III subdomains over the length of the RuvC-III subdomain is greater than 1.). In some cases, the ratio of the length of the region between the RuvC-II and RuvC-III subdomains over the length of the RuvC-III subdomain is greater than land between 1 and 1.3 (e.g., 1 and 1.2).

In some embodiments (for a CasX protein of the subject compositions and/or methods), the ratio of the length of the RuvC-II subdomain over the length of the RuvC-III subdomain is 2 or less (e.g., 1.8 or less, 1.7 or less, 1.6 or less, 1.5 or less, or 1.4 or less). For example, in some cases, the ratio of the length of the RuvC-II subdomain over the length of the RuvC-III subdomain is 1.5 or less (e.g., 1.4 or less). In some embodiments, the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4).

In some cases (for a CasX protein of the subject compositions and/or methods), the ratio of the length of the region between the RuvC-II and RuvC-III subdomains over the length of the RuvC-III subdomain is greater than 1. In some cases, the ratio of the length of the region between the RuvC-II and RuvC-III subdomains over the length of the RuvC-III subdomain is greater than 1and between 1 and 1.3 (e.g., 1 and 1.2).

In some cases (for a CasX protein of the subject compositions and/or methods), the region between the RuvC-II and RuvC-III subdomains is at least 73 amino acids in length (e.g., at least 75, 77, 80, 85, or 87 amino acids in length). For example, in some cases, the region between the RuvC-II and RuvC-III subdomains is at least 78 amino acids in length (e.g., at least 80, 85, or 87 amino acids in length). In some cases, the region between the RuvC-II and RuvC-III subdomains is at least 85 amino acids in length. In some cases, the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids). In some cases, the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains— RuvC-I, RuvC-II, and RuvC-III where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III sub-domain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1 and 2; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III sub-domain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III sub-domain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III sub-domain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

For example, in some cases, a CasX protein includes a first amino acid sequence having 50% or more sequence identity (e.g., 60% or more, 70% or more, 80% or more, 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 80% or more sequence identity (e.g., 85% or more, 90% or more, 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than land between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes a first amino acid sequence having 90% or more sequence identity (e.g., 95% or more, 97% or more, 98% or more, 99% or more, or 100% sequence identity) with the N-terminal domain (e.g., the domain depicted as amino acids 1-663 for CasX1 in FIG. 3A) of any one of the CasX protein sequences set forth as SEQ ID NOs: 1-3; and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than land between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than l and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein includes an amino acid sequence corresponding to amino acids 1-663 of the CasX protein sequence set forth as SEQ ID NO: 1 (e.g., amino acids 1-650 of the CasX protein sequence set forth as SEQ ID NO: 2); and a second amino acid sequence, C-terminal to the first amino acid sequence, that includes 3 partial RuvC domains—RuvC-I, RuvC-II, and RuvC-III—where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than l and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than l and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence with an N-terminal domain (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence (C-terminal to the first) having a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than l and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than l and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes a first amino acid sequence having a length (e.g., not including any fused heterologous sequence such as an NLS and/or a domain with a catalytic activity) in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids) that is N-terminal to a split Ruv C domain with 3 partial RuvC domains—RuvC-I, RuvC-II, and RuvC-III, where: (i) the ratio of the length of the region between the RuvC-II and RuvC-III subdomains over the length of the RuvC-III subdomain is 1.1 or greater (e.g., 1.2); (ii) the ratio of the length of the region between the RuvC-II and RuvC-III subdomains over the length of the RuvC-III subdomain is greater than 1; (iii) the ratio of the length of the region between the RuvC-II and RuvC-III subdomains over the length of the RuvC-III subdomain is greater than 1 and between 1 and 1.3 (e.g., 1 and 1.2); (iv) the ratio of the length of the RuvC-II subdomain over the length of the RuvC-III subdomain is 2 or less (e.g., 1.8 or less, 1.7 or less, 1.6 or less, 1.5 or less, or 1.4 or less); (v) the ratio of the length of the RuvC-II subdomain over the length of the RuvC-III subdomain is 1.5 or less (e.g., 1.4 or less); (vi) the ratio of the length of the RuvC-II subdomain over the length of the RuvC-III subdomain is in a range of from 1 to 2 (e.g., from 1.1 to 2, 1.2 to 2, 1 to 1.8, 1.1 to 1.8, 1.2 to 1.8, 1 to 1.6, 1.1 to 1.6, 1.2 to 1.6, 1 to 14, 1.1 to 1.4, or 1.2 to 1.4); (vii) the ratio of the length of the region between the RuvC-II and RuvC-III subdomains over the length of the RuvC-III subdomain is greater than 1; (viii) the ratio of the length of the region between the RuvC-II and RuvC-III subdomains over the length of the RuvC-III subdomain is greater than 1 and between 1 and 1.3 (e.g., 1 and 1.2); (ix) the region between the RuvC-II and RuvC-III subdomains is at least 73 amino acids in length (e.g., at least 75, 77, 80, 85, or 87 amino acids in length); (x) the region between the RuvC-II and RuvC-III subdomains is at least 78 amino acids in length (e.g., at least 80, 85, or 87 amino acids in length); (xi) the region between the RuvC-II and RuvC-III subdomains is at least 85 amino acids in length; (x) the region between the RuvC-II and RuvC-III subdomains has a length in a range of from 75-100 amino acids (e.g., a range of from 75-95, 75-90, 75-88, 78-100, 78-95, 78-90, 78-88, 80-100, 80-95, 80-90, 80-88, 83-100, 83-95, 83-90, 83-88, 85-100, 85-95, 85-90, or 85-88 amino acids); or (xi) the region between the RuvC-II and RuvC-III subdomains has a length in a range of from 80-95 amino acids (e.g., a range of from 80-90, 80-88, 83-95, 83-90, 83-88, 85-95, 85-90, or 85-88 amino acids).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 1. In some cases, a CasX protein includes an amino acid sequence having amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 2. In some cases, a CasX protein includes an amino acid sequence of SEQ ID NO: 2 corresponding to amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO: 3. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of the CasX protein sequence set forth as SEQ ID NO:

3. In some cases, a CasX protein includes an amino acid sequence of SEQ ID NO: 3 corresponding to amino acids 664-986 of the CasX protein sequence set forth as SEQ ID NO: 1.

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2 (e.g., amino acids 651-978 for the CasX protein sequence set forth as SEQ ID NO: 2). For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes an amino acid sequence corresponding to amino acids 664-986 of the CasX protein sequence set forth as SEQ ID NO: 1 (e.g., amino acids 651-978 of the CasX protein sequence set forth as SEQ ID NO: 2).

In some cases, a CasX protein (of the subject compositions and/or methods) includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2 (e.g., amino acids 651-978 for the CasX protein sequence set forth as SEQ ID NO: 2). For example, in some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-

680, 600-680, 640-680, 650-680, 500-670, 550-670, 600-670, 640-670, or 650-670 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1 and 2. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having an amino acid sequence corresponding to amino acids 664-986 of the CasX protein sequence set forth as SEQ ID NO: 1 (e.g., amino acids 651-978 of the CasX protein sequence set forth as SEQ ID NO: 2).

In some cases, a CasX protein (of the subject compositions and/or methods) includes an amino acid sequence having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3 (e.g., amino acids 651-978 for the CasX protein sequence set forth as SEQ ID NO: 2). For example, in some cases, a CasX protein includes an amino acid sequence having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes an amino acid sequence corresponding to amino acids 664-986 of the CasX protein sequence set forth as SEQ ID NO: 1 (e.g., amino acids 651-978 of the CasX protein sequence set forth as SEQ ID NO: 2).

In some cases, a CasX protein (of the subject compositions and/or methods) includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 20% or more sequence identity (e.g., 30% or more, 40% or more, 50% or more, 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3 (e.g., amino acids 651-978 for the CasX protein sequence set forth as SEQ ID NO: 2). For example, in some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 50% or more sequence identity (e.g., 60% or more, 70% or more, 80% or more, 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 80% or more sequence identity (e.g., 85% or more, 90% or more, 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having 90% or more sequence identity (e.g., 95% or more, 97% or more, 98% or more, 99% or more, or 100% sequence identity) with the C-terminal domain (e.g., the domain depicted as amino acids 664-986 for CasX1 in FIG. 3A) of any one of the CasX protein sequences set forth as SEQ ID NOs: 1-3. In some cases, a CasX protein includes a first amino acid sequence (an N-terminal domain) (e.g., not including any fused heterologous sequence such as an NLS and/or a domain with a catalytic activity) having a length in a range of from 500-750 amino acids (e.g, from 550-750, 600-750, 640-750, 650-750, 500-700, 550-700, 600-700, 640-700, 650-700, 500-680, 550-680, 600-680, 640-680, 650-680, 500-670, 550-670, 600-670, 640-670, or 650-670 amino acids); and a second amino acid sequence, positioned C-terminal to the first amino acid sequence, having an amino acid sequence corresponding to amino acids 664-986 of the CasX protein sequence set forth as SEQ ID NO: 1 (e.g., amino acids 651-978 of the CasX protein sequence set forth as SEQ ID NO: 2).

CasX Variants

A variant CasX protein has an amino acid sequence that is different by at least one amino acid (e.g., has a deletion, insertion, substitution, fusion) when compared to the amino acid sequence of the corresponding wild type CasX protein. A CasX protein that cleaves one strand but not the other of a double stranded target nucleic acid is referred to herein as a "nickase" (e.g., a "nickase CasX"). A CasX protein that has substantially no nuclease activity is referred to herein as a dead CasX protein ("dCasX") (with the caveat that nuclease activity can be provided by a heterologous polypeptide—a fusion partner—in the case of a chimeric CasX protein, which is described in more detail below). For any of the CasX variant proteins described herein (e.g., nickase CasX, dCasX, chimeric CasX), the CasX variant can include a CasX protein sequence with the same parameters described above (e.g., domains that are present, percent identity, and the like).

Variants—Catalytic Activity

In some cases, the CasX protein is a variant CasX protein, e.g., mutated relative to the naturally occurring catalytically active sequence, and exhibits reduced cleavage activity (e.g., exhibits 90%, or less, 80% or less, 70% or less, 60% or less, 50% or less, 40% or less, or 30% or less cleavage activity) when compared to the corresponding naturally occurring sequence. In some cases, such a variant CasX protein is a catalytically 'dead' protein (has substantially no cleavage activity) and can be referred to as a 'dCasX.' In some cases, the variant CasX protein is a nickase (cleaves only one strand of a double stranded target nucleic acid, e.g., a double stranded target DNA). As described in more detail herein, in some cases, a CasX protein (in some case a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein).

Conserved catalytic residues of CasX include D672, E769, D935 when numbered according to CasX1 (SEQ ID NO: 1) and 659D, 756E, and 922D when numbered according to CasX2 (SEQ ID NO: 2) (these residues are underlined in FIGS. 1A-1B). (Note, in the alignment of FIG. 2, the numbering does not track with either CasX protein but instead tracks with the alignment itself. The conserved residues noted above in this paragraph are marked in the FIG., CasX2 is the top sequence ('gwc2') and CasX1 is the bottom sequence ('gwa2')).

Thus, in some cases, the CasX protein has reduced activity and one or more of the above described amino acids (or one or more corresponding amino acids of any CasX protein) are mutated (e.g., substituted with an alanine). In some cases, the variant CasX protein is a catalytically 'dead' protein (is catalytically inactive) and is referred to as 'dCasX.' A dCasX protein can be fused to a fusion partner that provides an activity, and in some cases, the dCasX (e.g., one without a fusion partner that provides catalytic activity—but which can have an NLS when expressed in a eukaryotic cell) can bind to target DNA and can block RNA polymerase from translating from a target DNA. In some cases, the variant CasX protein is a nickase (cleaves only one strand of a double stranded target nucleic acid, e.g., a double stranded target DNA).

Variants—Chimeric CasX (i.e., Fusion Proteins)

As noted above, in some cases, a CasX protein (in some cases a CasX protein with wild type cleavage activity and in some cases a variant CasX with reduced cleavage activity, e.g., a dCasX or a nickase CasX) is fused (conjugated) to a heterologous polypeptide that has an activity of interest (e.g., a catalytic activity of interest) to form a fusion protein (a chimeric CasX protein). A heterologous polypeptide to which a CasX protein can be fused is referred to herein as a 'fusion partner.'

In some cases the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a chimeric CasX protein includes a heterologous polypeptide that has enzymatic activity that modifies a target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, a chimeric CasX protein includes a heterologous polypeptide that has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used in increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1, and the like; histone lysine demethylases such as JHDM2a/b, UTX, JMJD3, and the like; histone acetyltransferases such as GCN5, PCAF, CBP, p300, TAF1, TIP60/PLIP, MOZ/MYST3, MORF/MYST4, SRC1, ACTR, P160, CLOCK, and the like; and DNA demethylases such as Ten-Eleven Translocation (TET) dioxygenase 1 (TET1CD), TET1, DME, DML1, DML2, ROS1, and the like.

Examples of proteins (or fragments thereof) that can be used in decrease transcription include but are not limited to: transcriptional repressors such as the Krüppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY, and the like; histone lysine deacetylases such as HDAC1, HDAC2, HDAC3, HDAC8, HDAC4, HDAC5, HDAC7, HDAC9, SIRT1, SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like; and periphery recruitment elements such as Lamin A, Lamin B, and the like.

In some cases the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants), and the like); demethylase activity such as that provided by a demethylase (e.g., Ten-Eleven Translocation (TET) dioxygenase 1 (TET1CD), TET1, DME, DML1, DML2, ROS1, and the like), DNA repair activity, DNA damage activity, deamination activity such as that provided by a deaminase (e.g., a cytosine deaminase enzyme such as rat APOBEC1), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyl-transferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

An additional examples of a suitable fusion partners are dihydrofolate reductase (DHFR) destabilization domain (e.g., to generate a chemically controllable chimeric CasX protein), and a chloroplast transit peptide. Suitable chloroplast transit peptides include, but are not limited to:

```
                                        (SEQ ID NO: 83)
MASMISSSAVTTVSRASRGQSAAMAPFGGLKSMTGFPVRKVNTDITSITSN

GGRVKCMQVWPPIGKKKFETLSYLPPLTRDSRA;
```

```
                                        (SEQ ID NO: 84)
MASMISSSAVTTVSRASRGQSAAMAPFGGLKSMTGFPVRKVNTDITSITSN

GGRVKS;
```

```
                                        (SEQ ID NO: 85)
MASSMLSSATMVASPAQATMVAPFNGLKSSAAFPATRKANNDITSITSNGG

RVNCMQVWPPIEKKKFETLSYLPDLTDSGGRVNC;
```

```
                                        (SEQ ID NO: 86)
MAQVSRICNGVQNPSLISNLSKSSQRKSPLSVSLKTQQHPRAYPISSSWGL

KKSGMTLIGSELRPLKVMSSVSTAC;
```

```
                                        (SEQ ID NO: 87)
MAQVSRICNGVWNPSLISNLSKSSQRKSPLSVSLKTQQHPRAYPISSSWGL

KKSGMTLIGSELRPLKVMSSVSTAC;
```

-continued

```
                                        (SEQ ID NO: 88)
MAQINNMAQGIQTLNPNSNFHKPQVPKSSSFLVFGSKKLKNSANSMLVLKK

DSIFMQLFCSFRISASVATAC;
```

```
                                        (SEQ ID NO: 89)
MAALVTSQLATSGTVLSVTDRFRRPGFQGLRPRNPADAALGMRTVGASAAP

KQSRKPHRFDRRCLSMVV;
```

```
                                        (SEQ ID NO: 90)
MAALTTSQLATSATGFGIADRSAPSSLLRHGFQGLKPRSPAGGDATSLSVT

TSARATPKQQRSVQRGSRRFPSVVVC;
```

```
                                        (SEQ ID NO: 91)
MASSVLSSAAVATRSNVAQANMVAPFTGLKSAASFPVSRKQNLDITSIASN

GGRVQC;
```

```
                                        (SEQ ID NO: 92)
MESLAATSVFAPSRVAVPAARALVRAGTVVPTRRTSSTSGTSGVKCSAAVT

PQASPVISRSAAAA;
and
```

```
                                        (SEQ ID NO: 93)
MGAAATSMQSLKFSNRLVPPSRRLSPVPNNVTCNNLPKSAAPVRTVKCCAS

SWNSTINGAAAATTNGASAASS.
```

In some case, a CasX fusion polypeptide of the present disclosure comprises: a) a CasX polypeptide of the present disclosure; and b) a chloroplast transit peptide. Thus, for example, a CRISPR-CasX complex can be targeted to the chloroplast. In some cases, this targeting may be achieved by the presence of an N-terminal extension, called a chloroplast transit peptide (CTP) or plastid transit peptide. Chromosomal transgenes from bacterial sources must have a sequence encoding a CTP sequence fused to a sequence encoding an expressed polypeptide if the expressed polypeptide is to be compartmentalized in the plant plastid (e.g. chloroplast). Accordingly, localization of an exogenous polypeptide to a chloroplast is often 1 accomplished by means of operably linking a polynucleotide sequence encoding a CTP sequence to the 5' region of a polynucleotide encoding the exogenous polypeptide. The CTP is removed in a processing step during translocation into the plastid. Processing efficiency may, however, be affected by the amino acid sequence of the CTP and nearby sequences at the NH 2 terminus of the peptide. Other options for targeting to the chloroplast which have been described are the maize cab-m7 signal sequence (U.S. Pat. No. 7,022,896, WO 97/41228) a pea glutathione reductase signal sequence (WO 97/41228) and the CTP described in US2009029861.

In some cases, a CasX fusion polypeptide of the present disclosure can comprise: a) a CasX polypeptide of the present disclosure; and b) an endosomal escape peptide. In some cases, an endosomal escape polypeptide comprises the amino acid sequence GLFXALLXLLXSLWXLLLXA (SEQ ID NO:94), wherein each X is independently selected from lysine, histidine, and arginine. In some cases, an endosomal escape polypeptide comprises the amino acid sequence GLFHALLHLLHSLWHLLLHA (SEQ ID NO:95).

For examples of some of the above fusion partners (and more) used in the context of fusions with Cas9, Zinc Finger, and/or TALE proteins (for site specific target nucleic modi-fication, modulation of transcription, and/or target protein modification, e.g., histone modification), see, e.g.: Nomura et al, J Am Chem Soc. 2007 Jul. 18; 129(28):8676-7; Rivenbark et al., Epigenetics. 2012 April; 7(4):350-60; Nucleic Acids Res. 2016 Jul. 8; 44(12):5615-28; Gilbert et. al., Cell. 2013 Jul. 18; 154(2):442-51; Kearns et al., Nat Methods. 2015 May; 12(5):401-3; Mendenhall et. al., Nat Biotechnol. 2013 December; 31(12):1133-6; Hilton et. al., Nat Biotechnol. 2015 May; 33(5):510-7; Gordley et. al., Proc Natl Acad Sci USA. 2009 Mar. 31; 106(13):5053-8; Akopian et. al., Proc Natl Acad Sci USA. 2003 Jul. 22; 100(15):8688-91; Tan et., al., J Virol. 2006 February; 80(4): 1939-48; Tan et. al., Proc Natl Acad Sci USA. 2003 Oct. 14; 100(21):11997-2002; Papworth et. al., Proc Natl Acad Sci USA. 2003 Feb. 18; 100(4):1621-6; Sanjana et. al., Nat Protoc. 2012 Jan. 5; 7(1):171-92; Beerli et. al., Proc Natl Acad Sci USA. 1998 Dec. 8; 95(25):14628-33; Snowden et. al., Curr Biol. 2002 Dec. 23; 12(24):2159-66; Xu et. al., Xu et. al., Cell Discov. 2016 May 3; 2:16009; Komor et al., Nature. 2016 Apr. 20; 533(7603):420-4; Chaikind et. al., Nucleic Acids Res. 2016 Aug. 11; Choudhury at. al., Onco-target. 2016 Jun. 23; Du et. al., Cold Spring Harb Protoc. 2016 Jan. 4; Pham et. al., Methods Mol Biol. 2016; 1358: 43-57; Balboa et al., Stem Cell Reports. 2015 Sep. 8; 5(3):448-59; Hara et. al., Sci Rep. 2015 Jun. 9; 5:11221; Piatek et. al., Plant Biotechnol J. 2015 May; 13(4):578-89; Hu et al., Nucleic Acids Res. 2014 April; 42(7):4375-90; Cheng et. al., Cell Res. 2013 October; 23(10):1163-71; cheng et. al., Cell Res. 2013 October; 23(10):1163-71; and Maeder et. al., Nat Methods. 2013 October; 10(10):977-9.

Additional suitable heterologous polypeptide include, but are not limited to, a polypeptide that directly and/or indirectly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). Non-limiting examples of heterologous polypeptides to accomplish increased or decreased transcription include transcription activator and transcription repressor domains. In some such cases, a chimeric CasX polypeptide is targeted by the guide nucleic acid (guide RNA) to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of heterologous polypeptides for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or in some cases can include a fragment of the protein (e.g., a functional domain).

The heterologous polypeptide of a subject chimeric CasX polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; Endonucleases (for example RNase III, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP Si, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising Endonucleases; proteins and protein domains capable of stimulating RNA cleavage; Exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as heterologous polypeptides for a chimeric CasX polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.).

Examples of various additional suitable heterologous polypeptide (or fragments thereof) for a subject chimeric CasX polypeptide include, but are not limited to those described in the following applications (which publications are related to other CRISPR endonucleases such as Cas9, but the described fusion partners can also be used with CasX instead): PCT patent applications: WO2010075303, WO2012068627, and WO2013155555, and can be found, for example, in U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a CasX fusion polypeptide does not include a NLS so that the protein is not targeted to the nucleus (which can be advantageous, e.g., when the target nucleic acid is an RNA that is present in the cyosol). In some embodiments, the heterologous polypeptide can provide a tag (i.e., the heterologous polypeptide is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like).

In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) a nuclear localization signal (NLS) (e.g, in some cases 2 or more, 3 or more, 4 or more, or 5 or more NLSs). Thus, in some cases, a CasX polypeptide includes one or more NLSs (e.g., 2 or more, 3 or more, 4 or more, or 5 or more NLSs). In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus.

In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases a CasX protein (e.g., a wild type CasX protein, a variant CasX protein, a chimeric CasX protein, a dCasX protein, a chimeric CasX protein where the CasX portion has reduced nuclease activity—such as a dCasX protein fused to a fusion partner, and the like) includes (is fused to) between 2 and 5 NLSs (e.g., 2-4, or 2-3 NLSs).

Non-limiting examples of NLSs include an NLS sequence derived from: the NLS of the SV40 virus large T-antigen, having the amino acid sequence PKKKRKV (SEQ ID NO: 96); the NLS from nucleoplasmin (e.g., the nucleoplasmin bipartite NLS with the sequence KRPAATKKAGQAKKKK (SEQ ID NO: 97)); the c-myc NLS having the amino acid sequence PAAKRVKLD (SEQ ID NO: 98) or RQRR-NELKRSP (SEQ ID NO: 99); the hRNPA1 M9 NLS having the sequence NQSSNFGPMKGGNFGGRSSGPYGG-GGQYFAKPRNQGGY (SEQ ID NO: 100); the sequence RMRIZFKNKGKDTAELRRRRVEVSVELRKAKKD-EQILKRRNV (SEQ ID NO: 101) of the IBB domain from importin-alpha; the sequences VSRKRPRP (SEQ ID NO: 102) and PPKKARED (SEQ ID NO: 103) of the myoma T protein; the sequence PQPKKKPL (SEQ ID NO: 104) of human p53; the sequence SALIKKKKKMAP (SEQ ID NO: 105) of mouse c-abl IV; the sequences DRLRR (SEQ ID NO: 106) and PKQKKRK (SEQ ID NO: 107) of the influenza virus NS1; the sequence RKLKKKIKKL (SEQ ID NO: 108) of the Hepatitis virus delta antigen; the sequence REKKKFLKRR (SEQ ID NO: 109) of the mouse Mx1 protein; the sequence KRKGDEVDGVDEVAKKKSKK (SEQ ID NO: 110) of the human poly(ADP-ribose) poly-merase; and the sequence RKCLQAGMNLEARKTKK (SEQ ID NO: 111) of the steroid hormone receptors (human) glucocorticoid. In general, NLS (or multiple NLSs) are of sufficient strength to drive accumulation of the CasX protein in a detectable amount in the nucleus of a eukaryotic cell. Detection of accumulation in the nucleus may be performed by any suitable technique. For example, a detectable marker may be fused to the CasX protein such that location within a cell may be visualized. Cell nuclei may also be isolated from cells, the contents of which may then be analyzed by any suitable process for detecting protein, such as immuno-histochemistry, Western blot, or enzyme activity assay. Accumulation in the nucleus may also be determined indi-rectly.

In some cases, a CasX fusion polypeptide includes a "Protein Transduction Domain" or PTD (also known as a CPP—cell penetrating peptide), which refers to a polypep-tide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a mem-brane, for example going from extracellular space to intra-cellular space, or cytosol to within an organelle. In some embodiments, a PTD is covalently linked to the amino terminus a polypeptide (e.g., linked to a wild type CasX to generate a fusino protein, or linked to a variant CasX protein such as a dCasX, nickase CasX, or chimeric CasX protein to generate a fusion protein). In some embodiments, a PTD is covalently linked to the carboxyl terminus of a polypeptide (e.g., linked to a wild type CasX to generate a fusino protein, or linked to a variant CasX protein such as a dCasX, nickase CasX, or chimeric CasX protein to generate a fusion pro-tein). In some cases, the PTD is inserted internally in the CasX fusion polypeptide (i.e., is not at the N- or C-terminus of the CasX fusion polypeptide) at a suitable insertion site. In some cases, a subject CasX fusion polypeptide includes (is conjugated to, is fused to) one or more PTDs (e.g., two or more, three or more, four or more PTDs). In some cases a PTD includes a nuclear localization signal (NLS) (e.g, in some cases 2 or more, 3 or more, 4 or more, or 5 or more NLSs). Thus, in some cases, a CasX fusion polypeptide includes one or more NLSs (e.g., 2 or more, 3 or more, 4 or more, or 5 or more NLSs). In some embodiments, a PTD is covalently linked to a nucleic acid (e.g., a CasX guide nucleic acid, a polynucleotide encoding a CasX guide nucleic acid, a polynucleotide encoding a CasX fusion polypeptide, a donor polynucleotide, etc.). Examples of PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); an Drosophila Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:113); Transportan GWTLNSAGYLLGKINL-KALAALAKKIL (SEQ ID NO:114); KALAWEAKLAKA-LAKALAKHLAKALAKALKCEA (SEQ ID NO:115); and RQIKIWFQNRRMKWKK (SEQ ID NO:116). Exemplary PTDs include but are not limited to, YGRKKRRQRRR (SEQ ID NO:117), RKKRRQRRR (SEQ ID NO:118); an arginine homopolymer of from 3 arginine residues to 50 arginine residues; Exemplary PTD domain amino acid sequences include, but are not limited to, any of the follow-ing: YGRKKRRQRRR (SEQ ID NO:119); RKKRRQRR (SEQ ID NO:120); YARAAARQARA (SEQ ID NO:121); THRLPRRRRRR (SEQ ID NO:122); and GGR-RARRRRRR (SEQ ID NO:123). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleav-age of the linker, the polyanion is released, locally unmask-ing the polyarginine and its inherent adhesiveness, thus "activating" the ACPP to traverse the membrane.

Linkers (e.g., for Fusion Partners)

In some embodiments, a subject CasX protein can fused to a fusion partner via a linker polypeptide (e.g., one or more linker polypeptides). The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers can be produced by using synthetic, linker-encoding oligonucleotides to couple the proteins, or can be encoded by a nucleic acid sequence encoding the fusion protein. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commer-cially available and are considered suitable for use.

Examples of linker polypeptides include glycine poly-mers $(G)_n$, glycine-serine polymers (including, for example, $(GS)_n$, $GSGGS_n$ (SEQ ID NO: 124), $GGSGGS_n$ (SEQ ID NO: 125), and $GGGS_n$ (SEQ ID NO: 126), where n is an integer of at least one), glycine-alanine polymers, alanine-serine polymers. Exemplary linkers can comprise amino acid sequences including, but not limited to, GGSG (SEQ ID NO: 127), GGSGG (SEQ ID NO: 128), GSGSG (SEQ ID NO: 129), GSGGG (SEQ ID NO: 130), GGGSG (SEQ ID NO: 131), GSSSG (SEQ ID NO: 132), and the like. The ordinarily skilled artisan will recognize that design of a peptide conjugated to any desired element can include linkers that are all or partially flexible, such that the linker can include a flexible linker as well as one or more portions that confer less flexible structure.

Detectable Labels

In some cases, a CasX polypeptide of the present disclo-sure comprises a detectable label. Suitable detectable labels and/or moieties that can provide a detectable signal can include, but are not limited to, an enzyme, a radioisotope, a member of a specific binding pair; a fluorophore; a fluorescent protein; a quantum dot; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Protospacer Adjacent Motif (PAM)

A CasX protein binds to target DNA at a target sequence defined by the region of complementarity between the DNA-targeting RNA and the target DNA. As is the case for many CRISPR endonucleases, site-specific binding (and/or cleavage) of a double stranded target DNA occurs at locations determined by both (i) base-pairing complementarity between the guide RNA and the target DNA; and (ii) a short motif [referred to as the protospacer adjacent motif (PAM)] in the target DNA.

In some embodiments, the PAM for a CasX protein is immediately 5' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). In some embodiments (e.g., when CasX1 as described herein is used), the PAM sequence of the non-complementary strand is 5'-TCN-3' (and in some cases TTCN), where N is any DNA nucleotide. As an example, see FIG. 6C, and FIG. 7, in which the PAM (TCN) (on the non-complementary strand) is TCA (and in the FIG. PAM shown is TTCA), and the PAM is 5' of the target sequence.

In some cases, different CasX proteins (i.e., CasX proteins from various species) may be advantageous to use in the various provided methods in order to capitalize on various enzymatic characteristics of the different CasX proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). CasX proteins from different species may require different PAM sequences in the target DNA. Thus, for a particular CasX protein of choice, the PAM sequence requirement may be different than the 5'-TCN-3' sequence described above. Various methods (including in silico and/or wet lab methods) for identification of the appropriate PAM sequence are known in the art and are routine, and any convenient method can be used. The TCN PAM sequence described herein was identified using a PAM depletion assay (e.g., see FIGS. 5A-5C of the working examples below).

CasX Guide RNA

A nucleic acid molecule that binds to a CasX protein, forming a ribonucleoprotein complex (RNP), and targets the complex to a specific location within a target nucleic acid (e.g., a target DNA) is referred to herein as a "CasX guide RNA" or simply as a "guide RNA." It is to be understood that in some cases, a hybrid DNA/RNA can be made such that a CasX guide RNA includes DNA bases in addition to RNA bases, but the term "CasX guide RNA" is still used to encompass such a molecule herein.

A CasX guide RNA can be said to include two segments, a targeting segment and a protein-binding segment. The targeting segment of a CasX guide RNA includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) a CasX polypeptide. The protein-binding segment of a subject CasX guide RNA includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the CasX guide RNA (the guide sequence of the CasX guide RNA) and the target nucleic acid.

A CasX guide RNA and a CasX protein, e.g., a fusion CasX polypeptide, form a complex (e.g., bind via non-covalent interactions). The CasX guide RNA provides target specificity to the complex by including a targeting segment, which includes a guide sequence (a nucleotide sequence that is complementary to a sequence of a target nucleic acid). The CasX protein of the complex provides the site-specific activity (e.g., cleavage activity provided by the CasX protein and/or an activity provided by the fusion partner in the case of a chimeric CasX protein). In other words, the CasX protein is guided to a target nucleic acid sequence (e.g. a target sequence) by virtue of its association with the CasX guide RNA.

The "guide sequence" also referred to as the "targeting sequence" of a CasX guide RNA can be modified so that the CasX guide RNA can target a CasX protein (e.g., a naturally occurring CasX protein, a fusion CasX polypeptide (chimeric CasX), and the like) to any desired sequence of any desired target nucleic acid, with the exception (e.g., as described herein) that the PAM sequence can be taken into account. Thus, for example, a CasX guide RNA can have a guide sequence with complementarity to (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

Figures 6C, 7:
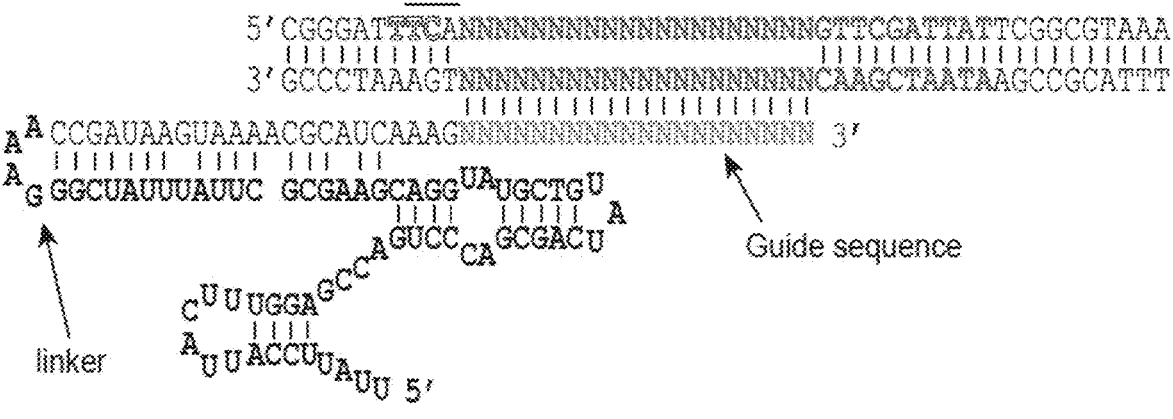

A subject CasX guide RNA can also be said to include an "activator" and a "targeter" (e.g., an "activator-RNA" and a "targeter-RNA," respectively). When the "activator" and a "targeter" are two separate molecules the guide RNA is referred to herein as a "dual guide RNA", a "dgRNA," a "double-molecule guide RNA", or a "two-molecule guide RNA." (e.g., a "CasX dual guide RNA"). In some embodiments, the activator and targeter are covalently linked to one another (e.g., via intervening nucleotides) and the guide RNA is referred to herein as a "single guide RNA", an "sgRNA," a "single-molecule guide RNA," or a "one-molecule guide RNA" (e.g., a "CasX single guide RNA"). Thus, a subject CasX single guide RNA comprises a targeter (e.g., targeter-RNA) and an activator (e.g., activator-RNA) that are linked to one another (e.g., by intervening nucleotides), and hybridize to one another to form the double stranded RNA duplex (dsRNA duplex) of the protein-binding segment of the guide RNA, thus resulting in a stem-loop structure (FIG. 6C). Thus, the targeter and the activator each have a duplex-forming segment, where the duplex forming segment of the targeter and the duplex-forming segment of the activator have complementarity with one another and hybridize to one another.

In some embodiments, the linker of a CasX single guide RNA is a stretch of nucleotides (depicted as GAAA in FIG. 6C). In some cases, the targeter and activator of a CasX single guide RNA are linked to one another by intervening nucleotides and the linker can have a length of from 3 to 20 nucleotides (nt) (e.g., from 3 to 15, 3 to 12, 3 to 10, 3 to 8, 3 to 6, 3 to 5, 3 to 4, 4 to 20, 4 to 15, 4 to 12, 4 to 10, 4 to 8, 4 to 6, or 4 to 5 nt). In some embodiments, the linker of a CasX single guide RNA can have a length of from 3 to 100 nucleotides (nt) (e.g., from 3 to 80, 3 to 50, 3 to 30, 3 to 25, 3 to 20, 3 to 15, 3 to 12, 3 to 10, 3 to 8, 3 to 6, 3 to 5, 3 to 4, 4 to 100, 4 to 80, 4 to 50, 4 to 30, 4 to 25, 4 to 20, 4 to 15, 4 to 12, 4 to 10, 4 to 8, 4 to 6, or 4 to 5 nt). In some embodiments, the linker of a CasX single guide RNA can have a length of from 3 to 10 nucleotides (nt) (e.g., from 3 to 9, 3 to 8, 3 to 7, 3 to 6, 3 to 5, 3 to 4, 4 to 10, 4 to 9, 4 to 8, 4 to 7, 4 to 6, or 4 to 5 nt).

Guide Sequence of a CasX Guide RNA

The targeting segment of a subject CasX guide RNA includes a guide sequence (i.e., a targeting sequence), which is a nucleotide sequence that is complementary to a sequence (a target site) in a target nucleic acid. In other words, the targeting segment of a CasX guide RNA can interact with a target nucleic acid (e.g., double stranded DNA (dsDNA), single stranded DNA (ssDNA), single stranded RNA (ssRNA), or double stranded RNA (dsRNA)) in a sequence-specific manner via hybridization (i.e., base pairing). The guide sequence of a CasX guide RNA can be modified (e.g., by genetic engineering)/designed to hybridize to any desired target sequence (e.g., while taking the PAM into account, e.g., when targeting a dsDNA target) within a target nucleic acid (e.g., a eukaryotic target nucleic acid such as genomic DNA).

In some embodiments, the percent complementarity between the guide sequence and the target site of the target nucleic acid is 60% or more (e.g., 65% or more, 70% or more, 75% or more, 80% or more, 85% or more, 90% or more, 95% or more, 97% or more, 98% or more, 99% or more, or 100%). In some cases, the percent complementarity between the guide sequence and the target site of the target nucleic acid is 80% or more (e.g., 85% or more, 90% or more, 95% or more, 97% or more, 98% or more, 99% or more, or 100%). In some cases, the percent complementarity between the guide sequence and the target site of the target nucleic acid is 90% or more (e.g., 95% or more, 97% or more, 98% or more, 99% or more, or 100%). In some cases, the percent complementarity between the guide sequence and the target site of the target nucleic acid is 100%. In some cases, the percent complementarity between the guide sequence and the target site of the target nucleic acid is 100% over the seven contiguous 3'-most nucleotides of the target site of the target nucleic acid.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 19 or more (e.g., 20 or more, 21 or more, 22 or more) contiguous nucleotides. In some cases, the percent complementarity between the guide sequence and the target site of the target nucleic acid is 100% over 19 or more (e.g., 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 19-25 contiguous nucleotides. In some cases, the percent complementarity between the guide sequence and the target site of the target nucleic acid is 90% or more (e.g., 95% or more, 97% or more, 98% or more, 99% or more, or 100%) over 19-25 contiguous nucleotides. In some cases, the percent complementarity between the guide sequence and the target site of the target nucleic acid is 100% over 19-25 contiguous nucleotides.

In some cases, the guide sequence has a length in a range of from 19-30 nucleotides (nt) (e.g., from 19-25, 19-22, 19-20, 20-30, 20-25, or 20-22 nt). In some cases, the guide sequence has a length in a range of from 19-25 nucleotides (nt) (e.g., from 19-22, 19-20, 20-25, 20-25, or 20-22 nt). In some cases, the guide sequence has a length of 19 or more nt (e.g., 20 or more, 21 or more, or 22 or more nt; 19 nt, 20 nt, 21 nt, 22 nt, 23 nt, 24 nt, 25 nt, etc.). In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Protein-Binding Segment of a CasX Guide RNA

The protein-binding segment of a subject CasX guide RNA interacts with a CasX protein. The CasX guide RNA guides the bound CasX protein to a specific nucleotide sequence within target nucleic acid via the above mentioned guide sequence. The protein-binding segment of a CasX guide RNA comprises two stretches of nucleotides (the duplex-forming segment of the activator and the duplex-forming segment of the targeter) that are complementary to one another and hybridize to form a double stranded RNA duplex (dsRNA duplex). Thus, the protein-binding segment includes a dsRNA duplex.

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge (e.g., see FIG. 6C, and FIG. 7). The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some embodiments, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject CasX guide RNA (in dual guide or single guide RNA format) can include one or more (1, 2, 3, 4, 5, etc) mutations relative to a naturally occurring duplex region. For example, in some cases a base pair can be maintained while the nucleotides contributing to the base pair from each segment (targeter and activator) can be different. In some cases, the duplex region of a subject CasX guide RNA includes more paired bases, less paired bases, a smaller bulge, a larger bulge, fewer bulges, more bulges, or any convenient combination thereof, as compared to a naturally occurring duplex region (of a naturally occurring CasX guide RNA).

In some cases, the activator (e.g., activator-RNA) of a subject CasX guide RNA (in dual or single guide RNA format) includes at least two internal RNA duplexes (i.e., two internal hairpins in addition to the activator/targeter dsRNA). The internal RNA duplexes (hairpins) of the activator can be positioned 5' of the activator/targeter dsRNA duplex (e.g., see FIG. 6C, and FIG. 7, both of which include an activator with 2 internal hairpins positioned 5' of the activator/targeter dsRNA duplex). In some cases, the activator includes one hairpin positioned 5' of the activator/targeter dsRNA duplex. In some cases, the activator includes two hairpins positioned 5' of the activator/targeter dsRNA duplex. In some cases, the activator includes three hairpins positioned 5' of the activator/targeter dsRNA duplex. In some cases, the activator includes two or more hairpins (e.g., 3 or more or 4 or more hairpins) positioned 5' of the activator/targeter dsRNA duplex. In some cases, the activator includes 2 to 5 hairpins (e.g., 2 to 4, or 2 to 3 hairpins) positioned 5' of the activator/targeter dsRNA duplex.

In some cases, the activator-RNA (e.g., in dual or single guide RNA format) comprises at least 2 nucleotides (nt) (e.g., at least 3 or at least 4 nt) 5' of the 5'-most hairpin stem, e.g., as depicted in the tracrRNA of FIGS. 6A-6C and FIG. 7. In some cases, the activator-RNA (e.g., in dual or single guide RNA format) comprises at least 4 nt 5' of the 5'-most hairpin stem, e.g., as depicted in the tracrRNA of FIGS. 6A-6C and FIG. 7.

In some cases, the activator-RNA (e.g., in dual or single guide format) has a length of 65 nucleotides (nt) or more (e.g., 66 or more, 67 or more, 68 or more, 69 or more, 70 or more, or 75 or more nt). In some cases, the activator-RNA (e.g., in dual or single guide format) has a length of 66 nt or more (e.g., 67 or more, 68 or more, 69 or more, 70 or more, or 75 or more nt). In some cases, the activator-RNA (e.g., in dual or single guide format) has a length of 67 nt or more (e.g., 68 or more, 69 or more, 70 or more, or 75 or more nt).

In some cases, the activator-RNA (e.g., in dual or single guide format) includes 45 or more nucleotides (nt) (e.g., 46 or more, 47 or more, 48 or more, 49 or more, 50 or more, 51 or more, 52 or more, 53 or more, 54 or more, or 55 or more nt) 5' of the dsRNA duplex formed between the activator and the targeter (the activator/targeter dsRNA duplex). In some cases, the activator is truncated at the 5' end relative to a naturally occurring CasX activator. In some cases, the activator is extended at the 5' end relative to a naturally occurring CasX activator.

Examples of various Cas9 guide RNAs can be found in the art, and in some cases variations similar to those introduced into Cas9 guide RNAs can also be introduced into CasX guide RNAs of the present disclosure. For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4): 910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013

December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

The term "activator" or "activator RNA" is used herein to mean a tracrRNA-like molecule (tracrRNA: "trans-acting CRISPR RNA") of a CasX dual guide RNA (and therefore of a CasX single guide RNA when the "activator" and the "targeter" are linked together by, e.g., intervening nucleotides). Thus, for example, a CasX guide RNA (dgRNA or sgRNA) comprises an activator sequence (e.g., a tracrRNA sequence). A tracr molecule (a tracrRNA) is a naturally existing molecule that hybridizes with a CRISPR RNA molecule (a crRNA) to form a CasX dual guide RNA. The term "activator" is used herein to encompass naturally existing tracrRNAs, but also to encompass tracrRNAs with modifications (e.g., truncations, extensions, sequence variations, base modifications, backbone modifications, linkage modifications, etc.) where the activator retains at least one function of a tracrRNA (e.g., contributes to the dsRNA duplex to which CasX protein binds). In some cases the activator provides one or more stem loops that can interact with CasX protein. An activator can be referred to as having a tracr sequence (tracrRNA sequence) and in some cases is a tracrRNA, but the term "activator" is not limited to naturally existing tracrRNAs.

In some cases (e.g., in some cases where the guide RNA is in single guide format), the activator-RNA is truncated (shorter) relative to the corresponding wild type tracrRNA. In some cases (e.g., in some cases where the guide RNA is in single guide format) the activator-RNA is not truncated (shorter) relative to the corresponding wild type tracrRNA. In some cases (e.g., in some cases where the guide RNA is in single guide format) the activator-RNA has a length that is greater than 50 nt (e.g., greater than 55 nt, greater than 60 nt, greater than 65 nt, greater than 70 nt, greater than 75 nt, greater than 80 nt). In some cases (e.g., in some cases where the guide RNA is in single guide format) the activator-RNA has a length that is greater than 80 nt. In some cases (e.g., in some cases where the guide RNA is in single guide format) the activator-RNA has a length in a range of from 51 to 90 nt (e.g., from 51-85, 51-84, 55-90, 55-85, 55-84, 60-90, 60-85, 60-84, 65-90, 65-85, 65-84, 70-90, 70-85, 70-84, 75-90, 75-85, 75-84, 80-90, 80-85, or 80-84 nt). In some cases (e.g., in some cases where the guide RNA is in single guide format) the activator-RNA has a length in a range of from 80-90 nt.

The term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together, e.g., by intervening nucleotides). Thus, for example, a CasX guide RNA (dgRNA or sgRNA) comprises a guide sequences and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, the duplex-forming segment of a targeter (described in more detail herein), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

As noted above, a targeter comprises both the guide sequence of the CasX guide RNA and a stretch (a "duplex-forming segment") of nucleotides that forms one half of the dsRNA duplex of the protein-binding segment of the CasX guide RNA. A corresponding tracrRNA-like molecule (activator) comprises a stretch of nucleotides (a duplex-forming segment) that forms the other half of the dsRNA duplex of the protein-binding segment of the CasX guide RNA. In other words, a stretch of nucleotides of the targeter is complementary to and hybridizes with a stretch of nucleotides of the activator to form the dsRNA duplex of the protein-binding segment of a CasX guide RNA. As such, each targeter can be said to have a corresponding activator (which has a region that hybridizes with the targeter). The targeter molecule additionally provides the guide sequence. Thus, a targeter and an activator (as a corresponding pair) hybridize to form a CasX guide RNA. The particular sequence of a given naturally existing crRNA or tracrRNA molecule can be characteristic of the species in which the RNA molecules are found. Examples of suitable activators and targeters are provided herein.

Example Guide RNA sequences

The guide RNAs depicted in FIGS. 6A-6C (dual guide format) and FIG. 7 (dual guide format) are from the natural locus for CasX1. For the sequences discussed in the paragraphs below, and for the sequences described and tested in the working examples below, the tracrRNA and crRNA sequences were from the CasX1 locus. The same parameters and sets of possible targeter-RNAs and activator-RNAs are expected and can be derived from comparing the sequences for the CasX1 locus with those of the CasX2 locus. For example, CasX1 tracrRNA sequences:

```
                                            (SEQ ID NO: 25)
UUAUUCCAUUACUUUGGAGCCAGUCCCAGCGACUAUGUCGUAUGGACGAAG

CGCUUAUUUAUCGGAGA
and (SEQ ID NO: 23)
UUAUUCCAUUACUUUGGAGCCAGUCCCAGCGACUAUGUCGUAUGGACGAAG

CGCUUAUUUAUCGG
``` can be compared to the CasX2 tracrRNA sequences:

```
                                        (SEQ ID NO: 26)
UUAUCUCAUUACUUUGAGAGCCAUCACCAGCGACUAUGUCGUAUGGGUAAA

GCGCUUAUUUAUCGGAGA
and
                                        (SEQ ID NO: 27)
UUAUCUCAUUACUUUGAGAGCCAUCACCAGCGACUAUGUCGUAUGGGUAAA

GCGCUUAUUUAUCGG.
```

For the CasX3 locus, tracr is likely within these 230 nt (complementary region is underlined):

```
                                        (SEQ ID NO: 28)
UAAAUUUUUUGAGCCCUAUCUCCGCGAGGAAGACAGGGCUCUUUUCAUGAG

AGGAAGCUUUUAUACCCGACCGGUAAUCCGGUCGGGGGAUUGGCCGUUGAA

ACGAUUUUAAAGCGGCCAAUGGGCCCCUCUAUAUGGAUACUACUUAUAUAA

GGAGCUUGGGGAAGAAGAUAGCUUAAUCCCGCUAUCUUGUCAAGGGGUUGG

GGGAGUAUCAGUAUCCGGCAGGCGCC.
```

Likewise, the CasX1 crRNA sequence CCGAUA-AGUAAAACGCAU-CAAAGNNNNNNNNNNNNNNNNNNNNNN (SEQ ID NO: 11 without the Ns, SEQ ID NO: 61 with the Ns) can be compared to the CasX2 crRNA sequence UCUCCG AUAAAUAAGAAGCAUCAAAGNNNNNNNNN NNN NNNNNNNN (SEQ ID NO: 13 without the Ns, SEQ ID NO: 69 with the Ns).

crRNA repeats from the CasX3 locus are GTTTA-CACACTCCCTCTCATAGGGT (SEQ ID NO: 54), GTT-TACACACTCCCTCTCATGAGGT (SEQ ID NO: 55), TTTTACATACCCCCTCTCATGGGAT (SEQ ID NO: 56), and GTTTACACACTCCCTCTCATGGGGG (SEQ ID NO: 57). Therefore crRNA sequences (e.g., from the CasX3 locus) can include GUUUACACACUCCCUCUCAUAGG-GUNNNNNNNNNNNNNNNNNNNNNN (SEQ ID NO: 14 without the Ns, SEQ ID NO: 31 with the Ns), GUUUA-CACACUCCCUCUCAUGAGGUNNNNNNNNNNNNNNN NNNNNNN (SEQ ID NO: 15 without the Ns, SEQ ID NO: 32 with the Ns), UUUUACAUACCCCCUCUCAUGG-GAUNNNNNNNNNNNNNNNNNNNNNN (SEQ ID NO: 16 without the Ns, SEQ ID NO: 33 with the Ns), and/or GUUUACACACUCCCUCUCAUGGGGGNNNNNNNN NNNNNNNNNNNNN (SEQ ID NO: 17 without the Ns, SEQ ID NO: 34 with the Ns).

Example Targeter-RNA (e.g., crRNA) Sequences

In some cases, the targeter-RNA (e.g., in dual or single guide RNA format) comprises (e.g., in addition to a guide sequence) the crRNA sequence CCGAUAAGUAAAACG-CAUCAAAG (SEQ ID NO: 11) (e.g., see the sgRNA of FIG. 6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence CCGAUAAGUAAAACGCAUCAAAG (SEQ ID NO: 11).

In some cases, the targeter-RNA comprises (e.g., in addition to a guide sequence) the crRNA sequence AUUUGAAGGUAUCUCCGAUAAGUAAAACGCAU-CAAAG (SEQ ID NO: 12). In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence AUUUGAAGGUAUCUCCGAUAAGU AAAACGCAUCAAAG (SEQ ID NO: 12).

In some cases, the targeter-RNA (e.g., in dual or single guide RNA format) comprises (e.g., in addition to a guide sequence) the crRNA sequence UCUCCGAUAAA UAAGAAGCAUCAAAG (SEQ ID NO: 13). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence

```
                                        (SEQ ID NO: 13)
     UCUCCGAUAAAUAAGAAGCAUCAAAG
```

In some cases, the targeter-RNA (e.g., in dual or single guide RNA format) comprises (e.g., in addition to a guide sequence) the crRNA sequence GUUUACACACUCCCU-CUCAUAGGGU (SEQ ID NO: 14). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence

```
                                        (SEQ ID NO: 14)
     GUUUACACACUCCCUCUCAUAGGGU
```

In some cases, the targeter-RNA (e.g., in dual or single guide RNA format) comprises (e.g., in addition to a guide sequence) the crRNA sequence GUUUACACACUCCCU-CUCAUGAGGU (SEQ ID NO: 15). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence

```
                                        (SEQ ID NO: 15)
     GUUUACACACUCCCUCUCAUGAGGU
```

In some cases, the targeter-RNA (e.g., in dual or single guide RNA format) comprises (e.g., in addition to a guide sequence) the crRNA sequence UUUUACAUACCCCCU-CUCAUGGGAU (SEQ ID NO: 16). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence

```
                                        (SEQ ID NO: 16)
     UUUUACAUACCCCCUCUCAUGGGAU
```

In some cases, the targeter-RNA (e.g., in dual or single guide RNA format) comprises (e.g., in addition to a guide sequence) the crRNA sequence GUUUACACACUCCCU-CUCAUGGGGG (SEQ ID NO: 17). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence

```
                                        (SEQ ID NO: 17)
     GUUUACACACUCCCUCUCAUGGGGG
```

In some cases, the targeter-RNA (e.g., in dual or single guide RNA format) comprises (e.g., in addition to a guide sequence) the crRNA sequence set forth in any one of SEQ ID NOs: 11 and 13. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11 and 13.

In some cases, the targeter-RNA comprises (e.g., in addition to a guide sequence) the crRNA sequence set forth in any one of SEQ ID NOs: 11-13. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-13.

In some cases, the targeter-RNA comprises (e.g., in addition to a guide sequence) the crRNA sequence set forth in any one of SEQ ID NOs: 14-17. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 14-17.

In some cases, the targeter-RNA comprises (e.g., in addition to a guide sequence) the crRNA sequence set forth in any one of SEQ ID NOs: 11-17. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 11-17.

Example Activator-RNA (e.g., tracrRNA) Sequences

In some cases, the activator-RNA (e.g., in dual or single guide RNA format) comprises the tracrRNA sequence ACAUCUGGCGCGUUUAUUCCAUUACUUUG-GAGCCAGUCCCAGCGACUAUGUCGUAUGGAC GAAGCGCUUAUUUAUCGGAGA (SEQ ID NO: 21). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 21)
ACAUCUGGCGCGUUUAUUCCAUUACUUUGGAGCCAGUCCCAGCGACUAUGU

CGUAUGGACGAAGCGCUUAUUUAUCGGAGA.
```

In some cases, the activator-RNA (e.g., in dual or single guide RNA format) comprises the tracrRNA sequence ACAUCUGGCGCGUUUAUUCCAUUACUUUG-GAGCCAGUCCCAGCGACUAUGUCGUAUGGAC GAAGCGCUUAUUUAUCGG (SEQ ID NO: 22). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 22)
ACAUCUGGCGCGUUUAUUCCAUUACUUUGGAGCCAGUCCCAGCGACUAUGU

CGUAUGGACGAAGCGCUUAUUUAUCGG.
```

In some cases, the activator-RNA (e.g., in dual or single guide RNA format) comprises the tracrRNA sequence UUAUUCCAUUACUUUGGAGCCAGUCCCAGCGAC-UAUGUCGUAUGGACGAAGCGCUUAUU UAUCGG (SEQ ID NO: 23) (e.g., see the sgRNA of FIG. 6). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 23)
UUAUUCCAUUACUUUGGAGCCAGUCCCAGCGACUAUGUCGUAUGGACGAAG

CGCUUAUUUAUCGG.
```

In some cases, the activator-RNA (e.g., in dual or single guide RNA format) comprises the tracrRNA sequence AAGUAGUAAAUUACAUCUGGCGCGUUUAUUC-CAUUACUUUGGAGCCAGUCCCAGCGACU AUGU-CGUAUGGACGAAGCGCUUAUUUAUCGGAGA (SEQ ID NO: 24) (e.g., see the sgRNA of 6). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 24)
AAGUAGUAAAUUACAUCUGGCGCGUUUAUUCCAUUACUUUGGAGCCAGUCC

CAGCGACUAUGUCGUAUGGACGAAGCGCUUAUUUAUCGGAGA.
```

In some cases, the activator-RNA (e.g., in dual or single guide RNA format) comprises the tracrRNA sequence UUAUUCCAUUACUUUGGAGCCAGUCCCAGCGAC-UAUGUCGUAUGGACGAAGCGCUUAUU UAUCG-GAGA (SEQ ID NO: 25) (e.g., see the sgRNA of FIGS. 6A-6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 25)
UUAUUCCAUUACUUUGGAGCCAGUCCCAGCGACUAUGUCGUAUGGACGAAG

CGCUUAUUUAUCGGAGA.
```

In some cases, the activator-RNA (e.g., in dual or single guide RNA format) comprises the tracrRNA sequence UUAUCUCAUUACUUUGAGAGCCAU-CACCAGCGACUAUGUCGUAUGGGUAAAGCGC-UUAU UUAUCGGAGA (SEQ ID NO: 26). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                     (SEQ ID NO: 26)
UUAUCUCAUUACUUUGAGAGCCAUCACCAGCGACUAUGUCGUAUGGGUAAA

GCGCUUAUUUAUCGGAGA.
```

In some cases, the activator-RNA (e.g., in dual or single guide RNA format) comprises the tracrRNA sequence UUAUCUCAUUACUUUGAGAGCCAUCACCAGCGA CUAUGUCGUAUGGGUAAAGCGCUUAU UUAUCGG (SEQ ID NO: 27). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 27)
UUAUCUCAUUACUUUGAGAGCCAUCACCAGCGACUAUGUCGUAUGGGUAAA

GCGCUUAUUUAUCGG.
```

In some cases, the activator-RNA (e.g., in dual or single guide RNA format) comprises a tracrRNA sequence from within the following sequence: UAAAUUUUUUGAGCC-CUAUCUCCGCGAGGAAGACAGGGCUCUUUUCA UGAGAGGAAGCU UUUUAUACCCGACCGGUAAU CCGGUCGGGGGAUUGGCCGUUGAAACGAUUUU AAAGCGGC CAAUGGGCCCCUCUAUAUGGAUAC-UACUUAUAUAAGGAGCUUGGGGAAGAAGAUA GCUU AAUCCCGCUAUCUUGUCAAGGGGUUGGGG-GAGUAUCAGUAUCCGGCAGGCGCC (SEQ ID NO: 28). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the a tracrRNA sequence from within:

```
                                      (SEQ ID NO: 28)
UAAAUUUUUUGAGCCCUAUCUCCGCGAGGAAGACAGGGCUCUUUUCAUGA

GAGGAAGCUUUUUAUACCCGACCGGUAAUCCGGUCGGGGGAUUGGCCGUUG

AAACGAUUUUAAAGCGGCCAAUGGGCCCCUCUAUAUGGAUACUACUUAUA

UAAGGAGCUUGGGGAAGAAGAUAGCUUAAUCCCGCUAUCUUGUCAAGGGG

UUGGGGGAGUAUCAGUAUCCGGCAGGCGCC.
```

In some cases, the activator-RNA (e.g., in dual or single guide RNA format) comprises the tracrRNA sequence set forth in any one of SEQ ID NOs: 21-27. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 21-27.

In some cases, the activator-RNA (e.g., in dual or single guide RNA format) comprises the tracrRNA sequence set forth in any one of SEQ ID NOs: 21-27. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 21-28.

In some cases, a CasX single guide RNA comprises the sequence UUAUUCCAUUACUUUGGAGCCAGU-CCCAGCGACUAUGUCGUAUGGACGAAGCGC-UUAUU UAUCGGgaaaCCGAUAAGUAAAACGCAU-CAAAG (SEQ ID NO: 41). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 41)
UUAUUCCAUUACUUUGGAGCCAGUCCCAGCGACUAUGUCGUAUGGACGAAG

CGCUUAUUUAUCGGgaaaCCGAUAAGUAAAACGCAUCAAAG.
```

In some cases, a CasX single guide RNA comprises the sequence ACAUCUGGCGCGUUUAUUCCAUUAC-UUUGGAGCCAGUCCCAGCGACUAUGU-CGUAUGGAC GAAGCGCUUAUUUAUCG-GAGAgaaaCCGAUAAGUAAAACGCAUCAAAG (SEQ ID NO: 42). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 42)
ACAUCUGGCGCGUUUAUUCCAUUACUUUGGAGCCAGUCCCAGCGACUAUG

UCGUAUGGACGAAGCGCUUAUUUAUCGGAGAgaaaCCGAUAAGUAAAACG

CAUCAAAG.
```

In some cases, a CasX single guide RNA comprises the sequence UUAUCUCAUUACUUUGAGAGCCAU-CACCAGCGACUAUGUCGUAUGGGUAAAGCGC-UUAU UUAUCGGgaaaUCUCCGAUAAAUAAGAA GCAUCAAAG (SEQ ID NO: 43). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 43)
UUAUCUCAUUACUUUGAGAGCCAUCACCAGCGACUAUGUCGUAUGGGUAA

AGCGCUUAUUUAUCGGgaaaUCUCCGAUAAAUAAGAAGCAUCAAAG.
```

In some cases, a CasX single guide RNA comprises the sequence set forth in any one of SEQ ID NOs: 41-43. In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 41-43.

CasX Systems

The present disclosure provides a CasX system. A CasX system of the present disclosure can comprise: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; 1) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r).

Nucleic Acids

The present disclosure provides one ore more nucleic acids comprising one or more of: a donor polynucleotide sequence, a nucleotide sequence encoding a CasX polypeptide (e.g., a wild type CasX protein, a nickase CasX protein, a dCasX protein, chimeric CasX protein, and the like), a CasX guide RNA, and a nucleotide sequence encoding a CasX guide RNA (which can include two separate nucleotide sequences in the case of dual guide RNA format or which can include a singe nucleotide sequence in the case of single guide RNA format). The present disclosure provides a nucleic acid comprising a nucleotide sequence encoding a CasX fusion polypeptide. The present disclosure provides a recombinant expression vector that comprises a nucleotide sequence encoding a CasX polypeptide. The present disclosure provides a recombinant expression vector that comprises a nucleotide sequence encoding a CasX fusion polypeptide. The present disclosure provides a recombinant expression vector that comprises: a) a nucleotide sequence encoding a CasX polypeptide; and b) a nucleotide sequence encoding a CasX guide RNA(s). The present disclosure provides a recombinant expression vector that comprises: a) a nucleotide sequence encoding a CasX fusion polypeptide; and b) a nucleotide sequence encoding a CasX guide RNA(s). In some cases, the nucleotide sequence encoding the CasX protein and/or the nucleotide sequence encoding the CasX guide RNA is operably linked to a promoter that is operable in a cell type of choice (e.g., a prokaryotic cell, a eukaryotic cell, a plant cell, an animal cell, a mammalian cell, a primate cell, a rodent cell, a human cell, etc.).

In some cases, a nucleotide sequence encoding a CasX polypeptide of the present disclosure is codon optimized. This type of optimization can entail a mutation of a CasX-encoding nucleotide sequence to mimic the codon preferences of the intended host organism or cell while encoding the same protein. Thus, the codons can be changed, but the encoded protein remains unchanged. For example, if the intended target cell was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX-encoding nucleotide sequence could be generated. As another non-limiting example, if the intended host cell were an insect cell, then an insect codon-optimized CasX-encoding nucleotide sequence could be generated.

The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (iii) a nucleotide sequence encoding a CasX protein (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence of a donor template nucleic acid (where the donor template comprises a nucleotide sequence having homology to a target sequence of a target nucleic acid (e.g., a target genome)); and (ii) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell). The present disclosure provides one or more recombinant expression vectors that include (in different recombinant expression vectors in some cases, and in the same recombinant expression vector in some cases): (i) a nucleotide sequence that encodes a CasX guide RNA that hybridizes to a target sequence of the target locus of the targeted genome (e.g., a single or dual guide RNA) (e.g., operably linked to a promoter that is operable in a target cell such as a eukaryotic cell); and (ii) a nucleotide sequence encoding a CasX protein (e.g., operably linked to a promoter that is operable in a target cell such as a eukaryotic cell).

Suitable expression vectors include viral expression vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (AAV) (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, a recombinant expression vector of the present disclosure is a recombinant adeno-associated virus (AAV) vector. In some cases, a recombinant expression vector of the present disclosure is a recombinant lentivirus vector. In some cases, a recombinant expression vector of the present disclosure is a recombinant retroviral vector.

Depending on the host/vector system utilized, any of a number of suitable transcription and translation control elements, including constitutive and inducible promoters, transcription enhancer elements, transcription terminators, etc. may be used in the expression vector.

In some embodiments, a nucleotide sequence encoding a CasX guide RNA is operably linked to a control element, e.g., a transcriptional control element, such as a promoter. In some embodiments, a nucleotide sequence encoding a CasX protein or a CasX fusion polypeptide is operably linked to a control element, e.g., a transcriptional control element, such as a promoter.

The transcriptional control element can be a promoter. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., hematopoietic stem cells (e.g., mobilized peripheral blood (mPB) CD34(+) cell, bone marrow (BM) CD34(+) cell, etc.).

Non-limiting examples of eukaryotic promoters (promoters functional in a eukaryotic cell) include EF1α, those from cytomegalovirus (CMV) immediate early, herpes simplex virus (HSV) thymidine kinase, early and late SV40, long terminal repeats (LTRs) from retrovirus, and mouse metal-lothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, fluorescent protein, etc.) that can be fused to the CasX protein, thus resulting in a chimeric CasX polypeptide.

In some embodiments, a nucleotide sequence encoding a CasX guide RNA and/or a CasX fusion polypeptide is operably linked to an inducible promoter. In some embodiments, a nucleotide sequence encoding a CasX guide RNA and/or a CasX fusion protein is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

In some cases, a nucleotide sequence encoding a CasX guide RNA is operably linked to (under the control of) a promoter operable in a eukaryotic cell (e.g., a U6 promoter, an enhanced U6 promoter, an H1 promoter, and the like). As would be understood by one of ordinary skill in the art, when expressing an RNA (e.g., a guide RNA) from a nucleic acid (e.g., an expression vector) using a U6 promoter (e.g., in a eukaryotic cell), or another PolIII promoter, the RNA may need to be mutated if there are several Ts in a row (coding for Us in the RNA). This is because a string of Ts (e.g., 5 Ts) in DNA can act as a terminator for polymerase III (PolIII). Thus, in order to ensure transcription of a guide RNA (e.g., the activator portion and/or targeter portion, in dual guide or single guide format) in a eukaryotic cell it may sometimes be necessary to modify the sequence encoding the guide RNA to eliminate runs of Ts. In some cases, a nucleotide sequence encoding a CasX protein (e.g., a wild type CasX protein, a nickase CasX protein, a dCasX protein, a chimeric CasX protein and the like) is operably linked to a promoter operable in a eukaryotic cell (e.g., a CMV promoter, an EF1α promoter, an estrogen receptor-regulated promoter, and the like).

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; estrogen and/or an estrogen analog; IPTG; etc.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Methods of introducing a nucleic acid (e.g., a nucleic acid comprising a donor polynucleotide sequence, one or more nucleic acids encoding a CasX protein and/or a CasX guide RNA, and the like) into a host cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct microinjection, nanoparticle-mediated nucleic acid delivery, and the like.

Introducing the recombinant expression vector into cells can occur in any culture media and under any culture conditions that promote the survival of the cells. Introducing the recombinant expression vector into a target cell can be carried out in vivo or ex vivo. Introducing the recombinant expression vector into a target cell can be carried out in vitro.

In some embodiments, a CasX protein can be provided as RNA. The RNA can be provided by direct chemical synthesis or may be transcribed in vitro from a DNA (e.g., encoding the CasX protein). Once synthesized, the RNA may be introduced into a cell by any of the well-known techniques for introducing nucleic acids into cells (e.g., microinjection, electroporation, transfection, etc.).

Nucleic acids may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008) PNAS 105(50):19821-19826.

Vectors may be provided directly to a target host cell. In other words, the cells are contacted with vectors comprising the subject nucleic acids (e.g., recombinant expression vectors having the donor template sequence and encoding the CasX guide RNA; recombinant expression vectors encoding the CasX protein; etc.) such that the vectors are taken up by the cells. Methods for contacting cells with nucleic acid vectors that are plasmids, include electroporation, calcium chloride transfection, microinjection, and lipofection are well known in the art. For viral vector delivery, cells can be contacted with viral particles comprising the subject viral expression vectors.

Retroviruses, for example, lentiviruses, are suitable for use in methods of the present disclosure. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art. Nucleic acids can also introduced by direct micro-injection (e.g., injection of RNA).

Vectors used for providing the nucleic acids encoding CasX guide RNA and/or a CasX polypeptide to a target host cell can include suitable promoters for driving the expression, that is, transcriptional activation, of the nucleic acid of interest. In other words, in some cases, the nucleic acid of interest will be operably linked to a promoter. This may include ubiquitously acting promoters, for example, the CMV-3-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a nucleic acid encoding a CasX guide RNA and/or a CasX protein to a cell may include nucleic acid sequences that encode for selectable markers in the target cells, so as to identify cells that have taken up the CasX guide RNA and/or CasX protein.

A nucleic acid comprising a nucleotide sequence encoding a CasX polypeptide, or a CasX fusion polypeptide, is in some cases an RNA. Thus, a CasX fusion protein can be introduced into cells as RNA. Methods of introducing RNA into cells are known in the art and may include, for example, direct injection, transfection, or any other method used for the introduction of DNA. A CasX protein may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endosomolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a CasX polypeptide of the present disclosure may be fused to a polypeptide permeant domain to promote uptake by the cell. A number of permeant domains are known in the art and may be used in the non-integrating polypeptides of the present disclosure, including peptides, peptidomimetics, and non-peptide carriers. For example, a permeant peptide may be derived from the third alpha helix of *Drosophila melanogaster* transcription factor Antennapaedia, referred to as penetratin, which comprises the amino acid sequence RQIKIWFQNRRMKWKK (SEQ ID NO: 133). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A CasX polypeptide of the present disclosure may be produced in vitro or by eukaryotic cells or by prokaryotic cells, and it may be further processed by unfolding, e.g. heat denaturation, dithiothreitol reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also suitable for inclusion in embodiments of the present disclosure are nucleic acids (e.g., encoding a CasX guide RNA, encoding a CasX fusion protein, etc.) and proteins (e.g., a CasX fusion protein derived from a wild type protein or a variant protein) that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues.

A CasX polypeptide of the present disclosure may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

A CasX polypeptide of the present disclosure may also be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein. Thus, in some cases, a CasX polypeptide, or a CasX fusion polypeptide, of the present disclosure is at least 80% pure, at least 85% pure, at least 90% pure, at least 95% pure, at least 98% pure, or at least 99% pure (e.g., free of contaminants, non-CasX proteins or other macromolecules, etc.).

To induce cleavage or any desired modification to a target nucleic acid (e.g., genomic DNA), or any desired modification to a polypeptide associated with target nucleic acid, the CasX guide RNA and/or the CasX polypeptide of the present disclosure and/or the donor template sequence, whether they be introduced as nucleic acids or polypeptides, are provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different CasX guide RNAs that are complementary to different sequences within the same or different target nucleic acid), the complexes may be provided simultaneously (e.g. as two poly-peptides and/or nucleic acids), or delivered simultaneously. Alternatively, they may be provided consecutively, e.g. the targeting complex being provided first, followed by the second targeting complex, etc. or vice versa.

To improve the delivery of a DNA vector into a target cell, the DNA can be protected from damage and its entry into the cell facilitated, for example, by using lipoplexes and poly-plexes. Thus, in some cases, a nucleic acid of the present disclosure (e.g., a recombinant expression vector of the present disclosure) can be covered with lipids in an orga-nized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are called polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the den-drimer-nucleic acid complex can be taken up into a cell by endocytosis.

In some cases, a nucleic acid of the disclosure (e.g., an expression vector) includes an insertion site for a guide sequence of interest. For example, a nucleic acid can include an insertion site for a guide sequence of interest, where the insertion site is immediately adjacent to a nucleotide sequence encoding the portion of a CasX guide RNA that does not change when the guide sequence is changed to hybridized to a desired target sequence (e.g., sequences that contribute to the CasX binding aspect of the guide RNA, e.g, the sequences that contribute to the dsRNA duplex(es) of the CasX guide RNA—this portion of the guide RNA can also be referred to as the 'scaffold' or 'constant region' of the guide RNA). Thus, in some cases, a subject nucleic acid (e.g., an expression vector) includes a nucleotide sequence encoding a CasX guide RNA, except that the portion encod-ing the guide sequence portion of the guide RNA is an insertion sequence (an insertion site). An insertion site is any nucleotide sequence used for the insertion of a the desired sequence. "Insertion sites" for use with various technologies are known to those of ordinary skill in the art and any convenient insertion site can be used. An insertion site can be for any method for manipulating nucleic acid sequences. For example, in some cases the insertion site is a multiple cloning site (MCS) (e.g., a site including one or more restriction enzyme recognition sequences), a site for ligation independent cloning, a site for recombination based cloning (e.g., recombination based on att sites), a nucleotide sequence recognized by a CRISPR/Cas (e.g. Cas9) based technology, and the like.

An insertion site can be any desirable length, and can depend on the type of insertion site (e.g., can depend on whether (and how many) the site includes one or more restriction enzyme recognition sequences, whether the site includes a target site for a CRISPR/Cas protein, etc.). In some cases, an insertion site of a subject nucleic acid is 3 or more nucleotides (nt) in length (e.g., 5 or more, 8 or more, 10 or more, 15 or more, 17 or more, 18 or more, 19 or more, 20 or more or 25 or more, or 30 or more nt in length). In some cases, the length of an insertion site of a subject nucleic acid has a length in a range of from 2 to 50 nucleotides (nt) (e.g., from 2 to 40 nt, from 2 to 30 nt, from 2 to 25 nt, from 2 to 20 nt, from 5 to 50 nt, from 5 to 40 nt, from 5 to 30 nt, from 5 to 25 nt, from 5 to 20 nt, from 10 to 50 nt, from 10 to 40 nt, from 10 to 30 nt, from 10 to 25 nt, from 10 to 20 nt, from 17 to 50 nt, from 17 to 40 nt, from 17 to 30 nt, from 17 to 25 nt). In some cases, the length of an insertion site of a subject nucleic acid has a length in a range of from 5 to 40 nt.

Nucleic Acid Modifications

In some embodiments, a subject nucleic acid (e.g., a CasX guide RNA) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group cova-lently linked to the sugar portion of the nucleoside. For those nucleosides that include a pentofuranosyl sugar, the phos-phate group can be linked to the 2', the 3', or the 5' hydroxyl moiety of the sugar. In forming oligonucleotides, the phos-phate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The nor-mal linkage or backbone of RNA and DNA is a 3' to 5' phosphodiester linkage.

Suitable nucleic acid modifications include, but are not limited to: 2'Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid has one or more nucleotides that are 2'-O-Methyl modified nucleotides. In some embodiments, a subject nucleic acid (e.g., a dsRNA, a siNA, etc.) has one or more 2' Fluoro modified nucleotides. In some embodiments, a subject nucleic acid (e.g., a dsRNA, a siNA, etc.) has one or more LNA bases. In some embodiments, a subject nucleic acid (e.g., a dsRNA, a siNA, etc.) has one or more nucleotides that are linked by a phosphorothioate bond (i.e., the subject nucleic acid has one or more phosphorothioate linkages). In some embodiments, a subject nucleic acid (e.g., a dsRNA, a siNA, etc.) has a 5' cap (e.g., a 7-methylguanylate cap (m7G)). In some embodiments, a subject nucleic acid (e.g., a dsRNA, a siNA, etc.) has a combination of modified nucleotides. For example, a subject nucleic acid (e.g., a dsRNA, a siNA, etc.) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids (e.g., a CasX guide RNA) containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —$CH_2$—NHO—$CH_2$—, —$CH_2$—$N(CH_3)$—O—$CH_2$— (known as a methylene (methylimino) or MMI backbone), —$CH_2$—O—$N(CH_3)$—$CH_2$—, —$CH_2$—$N(CH_3)$—$N(CH_3)$—$CH_2$— and —O—$N$ ($CH_3$)—$CH_2$—$CH_2$— (wherein the native phosphodiester internucleotide linkage is represented as —O—P($=$O) (OH)—O—$CH_2$—). MMI type internucleoside linkages are disclosed in the above referenced U.S. Pat. No. 5,489,677, the disclosure of which is incorporated herein by reference in its entirety. Suitable amide internucleoside linkages are disclosed in U.S. Pat. No. 5,602,240, the disclosure of which is incorporated herein by reference in its entirety.

Also suitable are nucleic acids having morpholino backbone structures as described in, e.g., U.S. Pat. No. 5,034, 506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262, the disclosures of which are incorporated herein by reference in their entirety.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, *Biochemistry*, 2002, 41(14), 4503-4510). Morpholino-based polynucleotides are disclosed in U.S. Pat. No. 5,034,506, the disclosure of which is incorporated herein by reference in its entirety. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602, the disclosure of which is incorporated herein by reference in its entirety). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., *Chem. Commun.,* 1998, 4, 455-456, the disclosure of which is incorporated herein by reference in its entirety). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., *Proc. Natl. Acad. Sci. U.S.A.,* 2000, 97, 5633-5638, the disclosure of which is incorporated herein by reference in its entirety).

The synthesis and preparation of the LNA monomers adenine, cytosine, guanine, 5-methylcytosine, thymine and uracil, along with their oligomerization, and nucleic acid recognition properties have been described (e.g., Koshkin et al., *Tetrahedron,* 1998, 54, 3607-3630, the disclosure of which is incorporated herein by reference in its entirety). LNAs and preparation thereof are also described in WO 98/39352 and WO 99/14226, as well as U.S. applications 20120165514, 20100216983, 20090041809, 20060117410, 20040014959, 20020094555, and 20020086998, the disclosures of which are incorporated herein by reference in their entirety.

Modified Sugar Moieties

A subject nucleic acid can also include one or more substituted sugar moieties. Suitable polynucleotides comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C.sub.1 to C$_{10}$ alkyl or C$_2$ to C$_{10}$ alkenyl and alkynyl. Particularly suitable are O ((CH$_2$)$_n$O)$_m$CH$_3$, O(CH$_2$)$_n$OCH$_3$, O(CH$_2$)$_n$NH$_2$, O(CH$_2$) $_n$ CH$_3$, O(CH$_2$)$_n$ONH$_2$, and O(CH$_2$)$_n$ON((CH$_2$)$_n$CH$_3$)$_2$, where n and m are from 1 to about 10. Other suitable polynucleotides comprise a sugar substituent group selected from: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta,* 1995, 78, 486-504, the disclosure of which is incorporated herein by reference in its entirety) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—OCH$_2$CH$_2$CH$_2$NH$_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. A suitable 2'-arabino modification is 2'-F Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering, pages* 858-859, Kroschwitz, J. I., ed. John Wiley & Sons, 1990, those disclosed by Englisch et al., *Angewandte Chemie, International Edition,* 1991, 30, 613, and those disclosed by Sanghvi, Y. S., *Chapter* 15, *Antisense Research and Applications,* pages 289-302, Crooke, S. T. and Lebleu, B., ed., CRC Press, 1993; the disclosures of which are incorporated herein by reference in their entirety. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., *Antisense Research and Applications,* CRC Press, Boca Raton, 1993, pp. 276-278; the disclosure of which is incorporated herein by reference in its entirety) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937).

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle (e.g., the nucleus). In some embodiments, a PTD is covalently linked to the 3' end of an exogenous polynucleotide. In some embodiments, a PTD is covalently linked to the 5' end of an exogenous polynucleotide. Exemplary PTDs include but are not limited to a minimal undecapeptide protein transduction domain (corresponding to residues 47-57 of HIV-1 TAT comprising YGRKKRRQRRR; SEQ ID NO:112); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR SEQ ID NO:113); Transportan GWTLNSAGYLLGKINLKALAALAKKIL SEQ ID NO:114); KALAWEAKLAKALAKA-LAKHLAKALAKALKCEA SEQ ID NO:115); and RQIKIWFQNRRMKWKK SEQ ID NO:116). Exemplary PTDs include but are not limited to, YGRKKRRQRRR SEQ ID NO:117), RKKRRQRRR SEQ ID NO:118); an arginine homopolymer of from 3 arginine residues to 50 arginine residues; Exemplary PTD domain amino acid sequences include, but are not limited to, any of the following: YGRKKRRQRRR SEQ ID NO:119); RKKRRQRR SEQ ID NO:120); YARAAARQARA SEQ ID NO:121); THRL-PRRRRRR SEQ ID NO:122); and GGRRARRRRRR SEQ ID NO:123). In some embodiments, the PTD is an activatable CPP (ACPP) (Aguilera et al. (2009) *Integr Biol* (*Camb*) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Introducing Components into a Target Cell

A CasX guide RNA (or a nucleic acid comprising a nucleotide sequence encoding same) and/or a CasX polypeptide of the present disclosure (or a nucleic acid comprising a nucleotide sequence encoding same) and/or a CasX fusion polypeptide of the present disclosure (or a nucleic acid that includes a nucleotide sequence encoding a CasX fusion polypeptide of the present disclosure) and/or a donor polynucleotide (donor template) can be introduced into a host cell by any of a variety of well-known methods.

Any of a variety of compounds and methods can be used to deliver to a target cell a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). As a non-limiting example, a CasX system of the present disclosure can be combined with a lipid. As another non-limiting example, a CasX system of the present disclosure can be combined with a particle, or formulated into a particle.

Methods of introducing a nucleic acid into a host cell are known in the art, and any convenient method can be used to introduce a subject nucleic acid (e.g., an expression construct/vector) into a target cell (e.g., prokaryotic cell, eukaryotic cell, plant cell, animal cell, mammalian cell, human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

In some cases, a CasX polypeptide of the present disclosure is provided as a nucleic acid (e.g., an mRNA, a DNA, a plasmid, an expression vector, a viral vector, etc.) that encodes the CasX polypeptide. In some cases, the CasX polypeptide of the present disclosure is provided directly as a protein (e.g., without an associated guide RNA or with an associate guide RNA, i.e., as a ribonucleoprotein complex). A CasX polypeptide of the present disclosure can be introduced into a cell (provided to the cell) by any convenient method; such methods are known to those of ordinary skill in the art. As an illustrative example, a CasX polypeptide of the present disclosure can be injected directly into a cell (e.g., with or without a CasX guide RNA or nucleic acid encoding a CasX guide RNA, and with or without a donor polynucleotide). As another example, a preformed complex of a CasX polypeptide of the present disclosure and a CasX guide RNA (an RNP) can be introduced into a cell (e.g, eukaryotic cell) (e.g., via injection, via nucleofection; via a protein transduction domain (PTD) conjugated to one or more components, e.g., conjugated to the CasX protein, conjugated to a guide RNA, conjugated to a CasX polypeptide of the present disclosure and a guide RNA; etc.).

In some cases, a CasX fusion polypeptide (e.g., dCasX fused to a fusion partner, nickase CasX fused to a fusion partner, etc.) of the present disclosure is provided as a nucleic acid (e.g., an mRNA, a DNA, a plasmid, an expression vector, a viral vector, etc.) that encodes the CasX fusion polypeptide. In some cases, the CasX fusion polypeptide of the present disclosure is provided directly as a protein (e.g., without an associated guide RNA or with an associate guide RNA, i.e., as a ribonucleoprotein complex). A CasX fusion polypeptide of the present disclosure can be introduced into a cell (provided to the cell) by any convenient method; such methods are known to those of ordinary skill in the art. As an illustrative example, a CasX fusion polypeptide of the present disclosure can be injected directly into a cell (e.g., with or without nucleic acid encoding a CasX guide RNA and with or without a donor polynucleotide). As another example, a preformed complex of a CasX fusion polypep-tide of the present disclosure and a CasX guide RNA (an RNP) can be introduced into a cell (e.g., via injection, via nucleofection; via a protein transduction domain (PTD) conjugated to one or more components, e.g., conjugated to the CasX fusion protein, conjugated to a guide RNA, conjugated to a CasX fusion polypeptide of the present disclosure and a guide RNA; etc.).

In some cases, a nucleic acid (e.g., a CasX guide RNA; a nucleic acid comprising a nucleotide sequence encoding a CasX polypeptide of the present disclosure; etc.) is delivered to a cell (e.g., a target host cell) and/or a polypeptide (e.g., a CasX polypeptide; a CasX fusion polypeptide) in a par-ticle, or associated with a particle. In some cases, a CasX system of the present disclosure is delivered to a cell in a particle, or associated with a particle. The terms "particle" and nanoparticle" can be used interchangeable, as appropri-ate. A recombinant expression vector comprising a nucleo-tide sequence encoding a CasX polypeptide of the present disclosure and/or a CasX guide RNA, an mRNA comprising a nucleotide sequence encoding a CasX polypeptide of the present disclosure, and guide RNA may be delivered simul-taneously using particles or lipid envelopes; for instance, a CasX polypeptide and a CasX guide RNA, e.g., as a com-plex (e.g., a ribonucleoprotein (RNP) complex), can be delivered via a particle, e.g., a delivery particle comprising lipid or lipidoid and hydrophilic polymer, e.g., a cationic lipid and a hydrophilic polymer, for instance wherein the cationic lipid comprises 1,2-dioleoyl-3-trimethylammo-nium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cho-lesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5). For example, a particle can be formed using a multistep process in which a CasX polypeptide and a CasX guideRNA are mixed together, e.g., at a 1:1 molar ratio, e.g., at room temperature, e.g., for 30 minutes, e.g., in sterile, nuclease free 1× phosphate-buffered saline (PBS); and separately, DOTAP, DMPC, PEG, and cholesterol as applicable for the formulation are dissolved in alcohol, e.g., 100% ethanol; and, the two solutions are mixed together to form particles containing the complexes).

A CasX polypeptide of the present disclosure (or an mRNA comprising a nucleotide sequence encoding a CasX polypeptide of the present disclosure; or a recombinant expression vector comprising a nucleotide sequence encod-ing a CasX polypeptide of the present disclosure) and/or CasX guide RNA (or a nucleic acid such as one or more expression vectors encoding the CasX guide RNA) may be delivered simultaneously using particles or lipid envelopes. For example, a biodegradable core-shell structured nanopar-ticle with a poly (β-amino ester) (PBAE) core enveloped by a phospholipid bilayer shell can be used. In some cases, particles/nanoparticles based on self assembling bioadhesive polymers are used; such particles/nanoparticles may be applied to oral delivery of peptides, intravenous delivery of peptides and nasal delivery of peptides, e.g., to the brain. Other embodiments, such as oral absorption and ocular delivery of hydrophobic drugs are also contemplated. A molecular envelope technology, which involves an engi-neered polymer envelope which is protected and delivered to the site of the disease, can be used. Doses of about 5 mg/kg can be used, with single or multiple doses, depending on various factors, e.g., the target tissue.

Lipidoid compounds (e.g., as described in US patent application 20110293703) are also useful in the administra-tion of polynucleotides, and can be used to deliver a CasX polypeptide of the present disclosure, a CasX fusion poly-peptide of the present disclosure, an RNP of the present disclosure, a nucleic acid of the present disclosure, or a CasX system of the present disclosure (e.g., where a CasX system comprises: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX poly-peptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encod-ing a CasX fusion polypeptide of the present disclosure and a nucleotide sequence encoding a CasX guide RNA; 1) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector com-prising a nucleotide sequence encoding a CasX polypeptide of the present disclosure, and a second recombinant expres-sion vector comprising a nucleotide sequence encoding a CasX guide RNA; n) a first recombinant expression vector comprising a nucleotide sequence encoding a CasX poly-peptide of the present disclosure, and a second recombinant expression vector comprising a nucleotide sequence encod-ing a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector com-prising a nucleotide sequence encoding a CasX fusion polypeptide of the present disclosure, and a second recom-binant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r). In one aspect, the aminoalcohol lipidoid compounds are combined with an agent to be delivered to a cell or a subject to form microparticles, nanoparticles, liposomes, or micelles. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

A poly(beta-amino alcohol) (PBAA) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. US Patent Publication No. 20130302401 relates to a class of poly(beta-amino alcohols) (PBAAs) that has been prepared using combinatorial polymerization.

Sugar-based particles may be used, for example GalNAc, as described with reference to WO2014118272 (incorporated herein by reference) and Nair, J K et al., 2014, Journal of the American Chemical Society 136 (49), 16958-16961) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell.

In some cases, lipid nanoparticles (LNPs) are used to deliver a CasX polypeptide of the present disclosure, a CasX fusion polypeptide of the present disclosure, an RNP of the present disclosure, a nucleic acid of the present disclosure, or a CasX system of the present disclosure, to a target cell. Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1, 3]-dioxolane (DLinKC2-DMA). Preparation of LNPs and is described in, e.g., Rosin et al. (2011) Molecular Therapy 19:1286-2200). The cationic lipids 1,2-dilineoyl-3-dimethylammonium-propane (DLinDAP), 1,2-dilinoleyloxy-3-N, N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(.omega.-methoxy-poly(ethylene glycol)2000) carbamoyl]-1,2-dimyristyloxlpropyl-3-amine (PEG-CDOMG) may be used. A nucleic acid (e.g., a CasX guide RNA; a nucleic acid of the present disclosure; etc.) may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). In some cases, 0.2% SP-DiOC18 is incorporated.

Spherical Nucleic Acid (SNA™) constructs and other nanoparticles (particularly gold nanoparticles) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. See, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19): 7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG).

In general, a "nanoparticle" refers to any particle having a diameter of less than 1000 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 500 nm or less, e.g., from 25 nm to 35 nm, from 35 nm to 50 nm, from 50 nm to 75 nm, from 75 nm to 100 nm, from 100 nm to 150 nm, from 150 nm to 200 nm, from 200 nm to 300 nm, from 300 nm to 400 nm, or from 400 nm to 500 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 25 nm to 200 nm. In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of 100 nm or less In some cases, nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell have a diameter of from 35 nm to 60 nm.

Nanoparticles suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., coreshell nanoparticles). Nanoparticles made of semiconducting material may also be labeled quantum dots if they are small enough (typically below 10 nm) that quantization of electronic energy levels occurs. Such nanoscale particles are used in biomedical applications as drug carriers or imaging agents and may be adapted for similar purposes in the present disclosure.

Semi-solid and soft nanoparticles are also suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell. A prototype nanoparticle of semi-solid nature is the liposome.

In some cases, an exosome is used to deliver a CasX polypeptide of the present disclosure, a CasX fusion poly-peptide of the present disclosure, an RNP of the present disclosure, a nucleic acid of the present disclosure, or a CasX system of the present disclosure, to a target cell. Exosomes are endogenous nano-vesicles that transport RNAs and proteins, and which can deliver RNA to the brain and other target organs.

In some cases, a liposome is used to deliver a CasX polypeptide of the present disclosure, a CasX fusion poly-peptide of the present disclosure, an RNP of the present disclosure, a nucleic acid of the present disclosure, or a CasX system of the present disclosure, to a target cell. Liposomes are spherical vesicle structures composed of a uni- or multilamellar lipid bilayer surrounding internal aque-ous compartments and a relatively impermeable outer lipo-philic phospholipid bilayer. Liposomes can be made from several different types of lipids; however, phospholipids are most commonly used to generate liposomes. Although lipo-some formation is spontaneous when a lipid film is mixed with an aqueous solution, it can also be expedited by applying force in the form of shaking by using a homog-enizer, sonicator, or an extrusion apparatus. Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. A liposome for-mulation may be mainly comprised of natural phospholipids and lipids such as 1,2-distearoryl-sn-glycero-3-phosphatidyl choline (DSPC), sphingomyelin, egg phosphatidylcholines and monosialoganglioside.

A stable nucleic-acid-lipid particle (SNALP) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. The SNALP formulation may contain the lipids 3-N-[(methoxypoly(ethylene glycol) 2000) carbamoyl]-1,2-dimyristyloxy-propylamine (PEG-C-DMA), 1,2-dilinoley-loxy-N,N-dimethyl-3-aminopropane (DLinDMA), 1,2-dis-tearoyl-sn-glycero-3-phosphocholine (DSPC) and cholesterol, in a 2:40:10:48 molar percent ratio. The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulting SNALP liposomes can be about 80-100 nm in size. A SNALP may comprise synthetic cholesterol (Sigma-Aldrich, St Louis, Mo., USA), dipalmi-toylphosphatidylcholine (Avanti Polar Lipids, Alabaster, Ala., USA), 3-N-[(w-methoxy poly(ethylene glycol)2000) carbamoyl]-1,2-dimyrestyloxypropylamine, and cationic 1,2-dilinoleyloxy-3-N,Ndimethylaminopropane. A SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA).

Other cationic lipids, such as amino lipid 2,2-dilinoleyl-4-dimethylaminoethyl-[1,3]-dioxolane (DLin-KC2-DMA)

can be used to deliver a CasX polypeptide of the present disclosure, a CasX fusion polypeptide of the present disclo-sure, an RNP of the present disclosure, a nucleic acid of the present disclosure, or a CasX system of the present disclo-sure, to a target cell. A preformed vesicle with the following lipid composition may be contemplated: amino lipid, dis-tearoylphosphatidylcholine (DSPC), cholesterol and (R)-2, 3-bis(octadecyloxy) propyl-1-(methoxy poly(ethylene gly-col)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11.+−0.0.04 (n=56), the particles may be extruded up to three times through 80 nm mem-branes prior to adding the guide RNA. Particles containing the highly potent amino lipid 16 may be used, in which the molar ratio of the four lipid components 16, DSPC, choles-terol and PEG-lipid (50/10/38.5/1.5) which may be further optimized to enhance in vivo activity.

Lipids may be formulated with a CasX system of the present disclosure or component(s) thereof or nucleic acids encoding the same to form lipid nanoparticles (LNPs). Suitable lipids include, but are not limited to, DLin-KC2-DMA4, C12-200 and colipids disteroylphosphatidyl cho-line, cholesterol, and PEG-DMG may be formulated with a CasX system, or component thereof, of the present disclo-sure, using a spontaneous vesicle formation procedure. The component molar ratio may be about 50/10/38.5/1.5 (DLin-KC2-DMA or C12-200/disteroylphosphatidyl choline/cho-lesterol/PEG-DMG).

A CasX system of the present disclosure, or a component thereof, may be delivered encapsulated in PLGA micro-spheres such as that further described in US published applications 20130252281 and 20130245107 and 20130244279.

Supercharged proteins can be used to deliver a CasX polypeptide of the present disclosure, a CasX fusion poly-peptide of the present disclosure, an RNP of the present disclosure, a nucleic acid of the present disclosure, or a CasX system of the present disclosure, to a target cell. Supercharged proteins are a class of engineered or naturally occurring proteins with unusually high positive or negative net theoretical charge. Both supernegatively and superposi-tively charged proteins exhibit the ability to withstand thermally or chemically induced aggregation. Superposi-tively charged proteins are also able to penetrate mammalian cells. Associating cargo with these proteins, such as plasmid DNA, RNA, or other proteins, can facilitate the functional delivery of these macromolecules into mammalian cells both in vitro and in vivo.

Cell Penetrating Peptides (CPPs) can be used to deliver a CasX polypeptide of the present disclosure, a CasX fusion polypeptide of the present disclosure, an RNP of the present disclosure, a nucleic acid of the present disclosure, or a CasX system of the present disclosure, to a target cell. CPPs typically have an amino acid composition that either con-tains a high relative abundance of positively charged amino acids such as lysine or arginine or has sequences that contain an alternating pattern of polar/charged amino acids and non-polar, hydrophobic amino acids.

An implantable device can be used to deliver a CasX polypeptide of the present disclosure, a CasX fusion poly-peptide of the present disclosure, an RNP of the present disclosure, a nucleic acid of the present disclosure (e.g., a CasX guide RNA, a nucleic acid encoding a CasX guide RNA, a nucleic acid encoding CasX polypeptide, a donor template, and the like), or a CasX system of the present disclosure, to a target cell (e.g., a target cell in vivo, where the target cell is a target cell in circulation, a target cell in a tissue, a target cell in an organ, etc.). An implantable device suitable for use in delivering a CasX polypeptide of the present disclosure, a CasX fusion polypeptide of the present disclosure, an RNP of the present disclosure, a nucleic acid of the present disclosure, or a CasX system of the present disclosure, to a target cell (e.g., a target cell in vivo, where the target cell is a target cell in circulation, a target cell in a tissue, a target cell in an organ, etc.) can include a container (e.g., a reservoir, a matrix, etc.) that comprises the CasX polypeptide, the CasX fusion polypeptide, the RNP, or the CasX system (or component thereof, e.g., a nucleic acid of the present disclosure).

A suitable implantable device can comprise a polymeric substrate, such as a matrix for example, that is used as the device body, and in some cases additional scaffolding materials, such as metals or additional polymers, and materials to enhance visibility and imaging. An implantable delivery device can be advantageous in providing release locally and over a prolonged period, where the polypeptide and/or nucleic acid to be delivered is released directly to a target site, e.g., the extracellular matrix (ECM), the vasculature surrounding a tumor, a diseased tissue, etc. Suitable implantable delivery devices include devices suitable for use in delivering to a cavity such as the abdominal cavity and/or any other type of administration in which the drug delivery system is not anchored or attached, comprising a biostable and/or degradable and/or bioabsorbable polymeric substrate, which may for example optionally be a matrix. In some cases, a suitable implantable drug delivery device comprises degradable polymers, wherein the main release mechanism is bulk erosion. In some cases, a suitable implantable drug delivery device comprises non degradable, or slowly degraded polymers, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the can be maintained effectively constant during a significant period of the total releasing period, and therefore the diffusion rate is effectively constant (termed "zero mode" diffusion). By the term "constant" it is meant a diffusion rate that is maintained above the lower threshold of therapeutic effectiveness, but which may still optionally feature an initial burst and/or may fluctuate, for example increasing and decreasing to a certain degree. The diffusion rate can be so maintained for a prolonged period, and it can be considered constant to a certain level to optimize the therapeutically effective period, for example the effective silencing period.

In some cases, the implantable delivery system is designed to shield the nucleotide based therapeutic agent from degradation, whether chemical in nature or due to attack from enzymes and other factors in the body of the subject.

The site for implantation of the device, or target site, can be selected for maximum therapeutic efficacy. For example, a delivery device can be implanted within or in the proximity of a tumor environment, or the blood supply associated with a tumor. The target location can be, e.g.: 1) the brain at degenerative sites like in Parkinson or Alzheimer disease at the basal ganglia, white and gray matter; 2) the spine, as in the case of amyotrophic lateral sclerosis (ALS); 3) uterine cervix; 4) active and chronic inflammatory joints; 5) dermis as in the case of psoriasis; 7) sympathetic and sensoric nervous sites for analgesic effect; 7) a bone; 8) a site of acute or chronic infection; 9) Intra vaginal; 10) Inner ear-auditory system, labyrinth of the inner ear, vestibular system; 11) Intra tracheal; 12) Intra-cardiac; coronary, epicardiac; 13) urinary tract or bladder; 14) biliary system; 15) parenchymal tissue including and not limited to the kidney, liver, spleen; 16) lymph nodes; 17) salivary glands; 18) dental gums; 19) Intra-articular (into joints); 20) Intra-ocular; 21) Brain tissue; 22) Brain ventricles; 23) Cavities, including abdominal cavity (for example but without limitation, for ovary cancer); 24) Intra esophageal; and 25) Intra rectal; and 26) into the vasculature.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as stereotactic methods into the brain tissue, laparoscopy, including implantation with a laparoscope into joints, abdominal organs, the bladder wall and body cavities.

Modified Host Cells

The present disclosure provides a modified cell comprising a CasX polypeptide of the present disclosure and/or a nucleic acid comprising a nucleotide sequence encoding a CasX polypeptide of the present disclosure. The present disclosure provides a modified cell comprising a CasX polypeptide of the present disclosure, where the modified cell is a cell that does not normally comprise a CasX polypeptide of the present disclosure. The present disclosure provides a modified cell (e.g., a genetically modified cell) comprising nucleic acid comprising a nucleotide sequence encoding a CasX polypeptide of the present disclosure. The present disclosure provides a genetically modified cell that is genetically modified with an mRNA comprising a nucleotide sequence encoding a CasX polypeptide of the present disclosure. The present disclosure provides a genetically modified cell that is genetically modified with a recombinant expression vector comprising a nucleotide sequence encoding a CasX polypeptide of the present disclosure. The present disclosure provides a genetically modified cell that is genetically modified with a recombinant expression vector comprising: a) a nucleotide sequence encoding a CasX polypeptide of the present disclosure; and b) a nucleotide sequence encoding a CasX guide RNA of the present disclosure. The present disclosure provides a genetically modified cell that is genetically modified with a recombinant expression vector comprising: a) a nucleotide sequence encoding a CasX polypeptide of the present disclosure; b) a nucleotide sequence encoding a CasX guide RNA of the present disclosure; and c) a nucleotide sequence encoding a donor template.

A cell that serves as a recipient for a CasX polypeptide of the present disclosure and/or a nucleic acid comprising a nucleotide sequence encoding a CasX polypeptide of the present disclosure and/or a CasX guide RNA of the present disclosure, can be any of a variety of cells, including, e.g., in vitro cells; in vivo cells; ex vivo cells; primary cells; cancer cells; animal cells; plant cells; algal cells; fungal cells; etc. A cell that serves as a recipient for a CasX polypeptide of the present disclosure and/or a nucleic acid comprising a nucleotide sequence encoding a CasX polypeptide of the present disclosure and/or a CasX guide RNA of the present disclosure is referred to as a "host cell" or a "target cell." A host cell or a target cell can be a recipient of a CasX system of the present disclosure. A host cell or a target cell can be a recipient of a CasX RNP of the present disclosure. A host cell or a target cell can be a recipient of a single component of a CasX system of the present disclosure.

Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera, or Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Kits

The present disclosure provides a kit comprising a CasX system of the present disclosure, or a component of a CasX system of the present disclosure.

A kit of the present disclosure can comprise: a) a CasX polypeptide of the present disclosure and a CasX guide RNA; b) a CasX polypeptide of the present disclosure, a CasX guide RNA, and a donor template nucleic acid; c) a CasX fusion polypeptide of the present disclosure and a CasX guide RNA; d) a CasX fusion polypeptide of the present disclosure, a CasX guide RNA, and a donor template nucleic acid; e) an mRNA encoding a CasX polypeptide of the present disclosure; and a CasX guide RNA; f) an mRNA encoding a CasX polypeptide of the present disclosure, a CasX guide RNA, and a donor template nucleic acid; g) an mRNA encoding a CasX fusion polypeptide of the present disclosure; and a CasX guide RNA; h) an mRNA encoding a CasX fusion polypeptide of the present disclosure, a CasX guide RNA, and a donor template nucleic acid; i) a recombinant expression vector comprising a nucleotide sequence encoding a CasX polypeptide of the present disclosure and a nucleotide sequence encoding a CasX guide RNA; j) a recombinant expression vector comprising a nucleotide sequence encoding a CasX polypeptide of the present disclosure, a nucleotide sequence encoding a CasX guide RNA, and a nucleotide sequence encoding a donor template nucleic acid; k) a recombinant expression vector comprising a nucleotide sequence encoding a CasX fusion polypeptide of the present disclosure and a nucleotide sequence encoding a CasX guide RNA; l) a recombinant expression vector comprising a nucleotide sequence encoding a CasX fusion polypeptide of the present disclosure, a nucleotide sequence encoding a CasX guide RNA, and a nucleotide sequence encoding a donor template nucleic acid; m) a first recombinant expression vector comprising a nucleotide sequence encoding a CasX polypeptide of the present disclosure, and a second recombinant expression vector comprising a nucleotide sequence encoding a CasX guide RNA; n) a first recombinant expression vector comprising a nucleotide sequence encoding a CasX polypeptide of the present disclosure, and a second recombinant expression vector comprising a nucleotide sequence encoding a CasX guide RNA; and a donor template nucleic acid; o) a first recombinant expression vector comprising a nucleotide sequence encoding a CasX fusion polypeptide of the present disclosure, and a second recombinant expression vector comprising a nucleotide sequence encoding a CasX guide RNA; p) a first recombinant expression vector comprising a nucleotide sequence encoding a CasX fusion polypeptide of the present disclosure, and a second recombinant expression vector comprising a nucleotide sequence encoding a CasX guide RNA; and a donor template nucleic acid; q) a recombinant expression vector comprising a nucleotide sequence encoding a CasX polypeptide of the present disclosure, a nucleotide sequence encoding a first CasX guide RNA, and a nucleotide sequence encoding a second CasX guide RNA; or r) a recombinant expression vector comprising a nucleotide sequence encoding a CasX fusion polypeptide of the present disclosure, a nucleotide sequence encoding a first CasX guide RNA, and a nucleotide sequence encoding a second CasX guide RNA; or some variation of one of (a) through (r).

A kit of the present disclosure can comprise: a) a component, as described above, of a CasX system of the present disclosure, or can comprise a CasX system of the present disclosure; and b) one or more additional reagents, e.g., i) a buffer; ii) a protease inhibitor; iii) a nuclease inhibitor; iv) a reagent required to develop or visualize a detectable label; v) a positive and/or negative control target DNA; vi) a positive and/or negative control CasX guide RNA; and the like. A kit of the present disclosure can comprise: a) a component, as described above, of a CasX system of the present disclosure, or can comprise a CasX system of the present disclosure; and b) a therapeutic agent.

A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; and b) a nucleotide sequence encoding the CasX-binding portion of a CasX guide RNA. A kit of the present disclosure can comprise a recombinant expression vector comprising: a) an insertion site for inserting a nucleic acid comprising a nucleotide sequence encoding a portion of a CasX guide RNA that hybridizes to a target nucleotide sequence in a target nucleic acid; b) a nucleotide sequence encoding the CasX-binding portion of a CasX guide RNA; and c) a nucleotide sequence encoding a CasX polypeptide of the present disclosure.

Utility

A CasX polypeptide of the present disclosure, or a CasX fusion polypeptide of the present disclosure, finds use in a variety of methods (e.g., in combination with a CasX guide RNA and in some cases further in combination with a donor template). For example, a CasX polypeptide of the present disclosure can be used to (i) modify (e.g., cleave, e.g., nick; methylate; etc.) target nucleic acid (DNA or RNA; single stranded or double stranded); (ii) modulate transcription of a target nucleic acid; (iii) label a target nucleic acid; (iv) bind a target nucleic acid (e.g., for purposes of isolation, labeling, imaging, tracking, etc.); (v) modify a polypeptide (e.g., a histone) associated with a target nucleic acid; and the like. Thus, the present disclosure provides a method of modifying a target nucleic acid. In some cases, a method of the present disclosure for modifying a target nucleic acid comprises contacting the target nucleic acid with: a) a CasX polypeptide of the present disclosure; and b) one or more (e.g., two) CasX guide RNAs. In some cases, a method of the present disclosure for modifying a target nucleic acid comprises contacting the target nucleic acid with: a) a CasX polypeptide of the present disclosure; b) a CasX guide RNA; and c) a donor nucleic acid (e.g, a donor template). In some cases, the contacting step is carried out in a cell in vitro. In some cases, the contacting step is carried out in a cell in vivo. In some cases, the contacting step is carried out in a cell ex vivo.

Because a method that uses a CasX polypeptide includes binding of the CasX polypeptide to a particular region in a target nucleic acid (by virtue of being targeted there by an associated CasX guide RNA), the methods are generally referred to herein as methods of binding (e.g., a method of binding a target nucleic acid). However, it is to be understood that in some cases, while a method of binding may result in nothing more than binding of the target nucleic acid, in other cases, the method can have different final results (e.g., the method can result in modification of the target nucleic acid, e.g., cleavage/methylation/etc., modulation of transcription from the target nucleic acid; modulation of translation of the target nucleic acid; genome editing; modulation of a protein associated with the target nucleic acid; isolation of the target nucleic acid; etc.).

For examples of suitable methods, see, for example, Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et al., Genome Res. 2013 Oct. 31; Chen et al., Nucleic Acids Res. 2013 Nov. 1; 41(20):e19; Cheng et al., Cell Res. 2013 October; 23(10):1163-71; Cho et al., Genetics. 2013 November; 195(3):1177-80; DiCarlo et al., Nucleic Acids Res. 2013 April; 41(7):4336-43; Dickinson et al., Nat Methods. 2013 October; 10(10):1028-34; Ebina et al., Sci Rep. 2013; 3:2510; Fujii et al, Nucleic Acids Res. 2013 Nov. 1; 41(20):e187; Hu et al., Cell Res. 2013 November; 23(11):1322-5; Jiang et al., Nucleic Acids Res. 2013 Nov. 1; 41(20):e188; Larson et al., Nat Protoc. 2013 November; 8(11):2180-96; Mali et. at., Nat Methods. 2013 October; 10(10):957-63; Nakayama et al., Genesis. 2013 December; 51(12):835-43; Ran et al., Nat Protoc. 2013 November; 8(11):2281-308; Ran et al., Cell. 2013 Sep. 12; 154(6):1380-9; Upadhyay et al., G3 (Bethesda). 2013 Dec. 9; 3(12):2233-8; Walsh et al., Proc Natl Acad Sci USA. 2013 Sep. 24; 110(39):15514-5; Xie et al., Mol Plant. 2013 Oct. 9; Yang et al., Cell. 2013 Sep. 12; 154(6):1370-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; each of which is hereby incorporated by reference in its entirety.

For example, the present disclosure provides (but is not limited to) methods of cleaving a target nucleic acid; methods of editing a target nucleic acid; methods of modulating transcription from a target nucleic acid; methods of isolating a target nucleic acid, methods of binding a target nucleic acid, methods of imaging a target nucleic acid, methods of modifying a target nucleic acid, and the like.

As used herein, the terms/phrases "contact a target nucleic acid" and "contacting a target nucleic acid", for example, with a CasX polypeptide or with a CasX fusion polypeptide, etc., encompass all methods for contacting the target nucleic acid. For example, a CasX polypeptide can be provided to a cell as protein, RNA (encoding the CasX polypeptide), or DNA (encoding the CasX polypeptide); while a CasX guide RNA can be provided as a guide RNA or as a nucleic acid encoding the guide RNA. As such, when, for example, performing a method in a cell (e.g., inside of a cell in vitro, inside of a cell in vivo, inside of a cell ex vivo), a method that includes contacting the target nucleic acid encompasses the introduction into the cell of any or all of the components in their active/final state (e.g., in the form of a protein(s) for CasX polypeptide; in the form of a protein for a CasX fusion polypeptide; in the form of an RNA in some cases for the guide RNA), and also encompasses the introduction into the cell of one or more nucleic acids encoding one or more of the components (e.g., nucleic acid(s) comprising nucleotide sequence(s) encoding a CasX polypeptide or a CasX fusion polypeptide, nucleic acid(s) comprising nucleotide sequence(s) encoding guide RNA(s), nucleic acid comprising a nucleotide sequence encoding a donor template, and the like). Because the methods can also be performed in vitro outside of a cell, a method that includes contacting a target nucleic acid, (unless otherwise specified) encompasses contacting outside of a cell in vitro, inside of a cell in vitro, inside of a cell in vivo, inside of a cell ex vivo, etc.

In some cases, a method of the present disclosure for modifying a target nucleic acid comprises contacting a target nucleic acid with a CasX polypeptide of the present disclosure, or with a CasX fusion polypeptide of the present disclosure. In some cases, a method of the present disclosure for modifying a target nucleic acid comprises contacting a target nucleic acid with a CasX polypeptide and a CasX guide RNA. In some cases, a method of the present disclosure for modifying a target nucleic acid comprises contacting a target nucleic acid with a CasX polypeptide, a first CasX guide RNA, and a second CasX guide RNA In some cases, a method of the present disclosure for modifying a target nucleic acid comprises contacting a target nucleic acid with a CasX polypeptide of the present disclosure and a CasX guide RNA and a donor DNA template.

Target Nucleic Acids and Target Cells of Interest

A CasX polypeptide of the present disclosure, or a CasX fusion polypeptide of the present disclosure, when bound to a CasX guide RNA, can bind to a target nucleic acid, and in some cases, can bind to and modify a target nucleic acid. A target nucleic acid can be any nucleic acid (e.g., DNA, RNA), can be double stranded or single stranded, can be any type of nucleic acid (e.g., a chromosome (genomic DNA), derived from a chromosome, chromosomal DNA, plasmid, viral, extracellular, intracellular, mitochondrial, chloroplast, linear, circular, etc.) and can be from any organism (e.g., as long as the CasX guide RNA comprises a nucleotide sequence that hybridizes to a target sequence in a target nucleic acid, such that the target nucleic acid can be targeted).

A target nucleic acid can be DNA or RNA. A target nucleic acid can be double stranded (e.g., dsDNA, dsRNA) or single stranded (e.g., ssRNA, ssDNA). In some cases, a target nucleic acid is single stranded. In some cases, a target nucleic acid is a single stranded RNA (ssRNA). In some cases, a target ssRNA (e.g., a target cell ssRNA, a viral ssRNA, etc.) is selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA). As noted above, in some cases, a target nucleic acid is single stranded.

A target nucleic acid can be located anywhere, for example, outside of a cell in vitro, inside of a cell in vitro, inside of a cell in vivo, inside of a cell ex vivo. Suitable target cells (which can comprise target nucleic acids such as genomic DNA) include, but are not limited to: a bacterial cell; an archaeal cell; a cell of a single-cell eukaryotic organism; a plant cell; an algal cell, e.g., *Botryococcus braunii, Chlamydomonas reinhardtii, Nannochloropsis gaditana, Chlorella pyrenoidosa, Sargassum patens, C. agardh*, and the like; a fungal cell (e.g., a yeast cell); an animal cell; a cell from an invertebrate animal (e.g. fruit fly, a cnidarian, an echinoderm, a nematode, etc.); a cell of an insect (e.g., a mosquito; a bee; an agricultural pest; etc.); a cell of an arachnid (e.g., a spider; a tick; etc.); a cell from a vertebrate animal (e.g., a fish, an amphibian, a reptile, a bird, a mammal); a cell from a mammal (e.g., a cell from a rodent; a cell from a human; a cell of a non-human mammal; a cell of a rodent (e.g., a mouse, a rat); a cell of a lagomorph (e.g., a rabbit); a cell of an ungulate (e.g., a cow, a horse, a camel, a llama, a vicuna, a sheep, a goat, etc.); a cell of a marine mammal (e.g., a whale, a seal, an elephant seal, a dolphin, a sea lion; etc.) and the like. Any type of cell may be of interest (e.g. a stem cell, e.g. an embryonic stem (ES) cell, an induced pluripotent stem (iPS) cell, a germ cell (e.g., an oocyte, a sperm, an oogonia, a spermatogonia, etc.), an adult stem cell, a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.).

Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines are maintained for fewer than 10 passages in vitro. Target cells can be unicellular organisms and/or can be grown in culture. If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. can be conveniently harvested by biopsy.

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA, to cleave or otherwise modify target DNA, to generically modify a target cell, and the like). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens, C. agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.). In some cases, a subject CasX protein (and/or nucleic acid encoding the protein such as DNA and/or RNA), and/or CasX guide RNA (and/or a DNA encoding the guide RNA), and/or donor template, and/or RNP can be introduced into an individual (i.e., the target cell can be in vivo) (e.g., a mammal, a rat, a mouse, a pig, a primate, a non-human primate, a human, etc.). In some case, such an administration can be for the purpose of treating and/or preventing a disease, e.g., by editing the genome of targeted cells.

Plant cells include cells of a monocotyledon, and cells of a dicotyledon. The cells can be root cells, leaf cells, cells of the xylem, cells of the phloem, cells of the cambium, apical meristem cells, parenchyma cells, collenchyma cells, sclerenchyma cells, and the like. Plant cells include cells of agricultural crops such as wheat, corn, rice, sorghum, millet, soybean, etc. Plant cells include cells of agricultural fruit and nut plants, e.g., plant that produce apricots, oranges, lemons, apples, plums, pears, almonds, etc.

Additional examples of target cells are listed above in the section titled "Modified cells." Non-limiting examples of cells (target cells) include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, cannabis, tobacco, flowering plants, conifers, gymnosperms, angiosperms, ferns, clubmosses, hornworts, liverworts, mosses, dicotyledons, monocotyledons, etc.), an algal cell, (e.g., *Botryococcus braunii, Chlamydomonas reinhardtii, Nannochloropsis gaditana, Chlorella pyrenoidosa, Sargassum patens, C. agardh*, and the like), seaweeds (e.g. kelp) a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., an ungulate (e.g., a pig, a cow, a goat, a sheep); a rodent (e.g., a rat, a mouse); a non-human primate; a human; a feline (e.g., a cat); a canine (e.g., a dog); etc.), and the like. In some cases, the cell is a cell that does not originate from a natural organism (e.g., the cell can be a synthetically made cell; also referred to as an artificial cell).

A cell can be an in vitro cell (e.g., established cultured cell line). A cell can be an ex vivo cell (cultured cell from an individual). A cell can be and in vivo cell (e.g., a cell in an individual). A cell can be an isolated cell. A cell can be a cell inside of an organism. A cell can be an organism. A cell can be a cell in a cell culture (e.g., in vitro cell culture). A cell can be one of a collection of cells. A cell can be a prokaryotic cell or derived from a prokaryotic cell. A cell can be a bacterial cell or can be derived from a bacterial cell. A cell can be an archaeal cell or derived from an archaeal cell. A cell can be a eukaryotic cell or derived from a eukaryotic cell. A cell can be a plant cell or derived from a plant cell. A cell can be an animal cell or derived from an animal cell. A cell can be an invertebrate cell or derived from an invertebrate cell. A cell can be a vertebrate cell or derived from a vertebrate cell. A cell can be a mammalian cell or derived from a mammalian cell. A cell can be a rodent cell or derived from a rodent cell. A cell can be a human cell or derived from a human cell. A cell can be a microbe cell or derived from a microbe cell. A cell can be a fungi cell or derived from a fungi cell. A cell can be an insect cell. A cell can be an arthropod cell. A cell can be a protozoan cell. A cell can be a helminth cell.

Suitable cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Suitable cells include human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

In some cases, the cell is an immune cell, a neuron, an epithelial cell, and endothelial cell, or a stem cell. In some cases, the immune cell is a T cell, a B cell, a monocyte, a natural killer cell, a dendritic cell, or a macrophage. In some cases, the immune cell is a cytotoxic T cell. In some cases, the immune cell is a helper T cell. In some cases, the immune cell is a regulatory T cell (Treg).

In some cases, the cell is a stem cell. Stem cells include adult stem cells. Adult stem cells are also referred to as somatic stem cells.

Adult stem cells are resident in differentiated tissue, but retain the properties of self-renewal and ability to give rise to multiple cell types, usually cell types typical of the tissue in which the stem cells are found. Numerous examples of somatic stem cells are known to those of skill in the art, including muscle stem cells; hematopoietic stem cells; epithelial stem cells; neural stem cells; mesenchymal stem cells; mammary stem cells; intestinal stem cells; mesodermal stem cells; endothelial stem cells; olfactory stem cells; neural crest stem cells; and the like.

Stem cells of interest include mammalian stem cells, where the term "mammalian" refers to any animal classified as a mammal, including humans; non-human primates; domestic and farm animals; and zoo, laboratory, sports, or pet animals, such as dogs, horses, cats, cows, mice, rats, rabbits, etc. In some cases, the stem cell is a human stem cell. In some cases, the stem cell is a rodent (e.g., a mouse; a rat) stem cell. In some cases, the stem cell is a non-human primate stem cell.

Stem cells can express one or more stem cell markers, e.g., SOX9, KRT19, KRT7, LGR5, CA9, FXYD2, CDH6, CLDN18, TSPAN8, BPIFB1, OLFM4, CDH17, and PPARGC1A.

In some embodiments, the stem cell is a hematopoietic stem cell (HSC). HSCs are mesoderm-derived cells that can be isolated from bone marrow, blood, cord blood, fetal liver and yolk sac. HSCs are characterized as CD34+ and CD3−. HSCs can repopulate the erythroid, neutrophil-macrophage, megakaryocyte and lymphoid hematopoietic cell lineages in vivo. In vitro, HSCs can be induced to undergo at least some self-renewing cell divisions and can be induced to differentiate to the same lineages as is seen in vivo. As such, HSCs can be induced to differentiate into one or more of erythroid cells, megakaryocytes, neutrophils, macrophages, and lymphoid cells.

In other embodiments, the stem cell is a neural stem cell (NSC). Neural stem cells (NSCs) are capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, e.g., cells committed to become one or more types of neurons and glial cells respectively. Methods of obtaining NSCs are known in the art.

In other embodiments, the stem cell is a mesenchymal stem cell (MSC). MSCs originally derived from the embryonal mesoderm and isolated from adult bone marrow, can differentiate to form muscle, bone, cartilage, fat, marrow stroma, and tendon. Methods of isolating MSC are known in the art; and any known method can be used to obtain MSC. See, e.g., U.S. Pat. No. 5,736,396, which describes isolation of human MSC.

A cell is in some cases a plant cell. A plant cell can be a cell of a monocotyledon. A cell can be a cell of a dicotyledon.

In some cases, the cell is a plant cell. For example, the cell can be a cell of a major agricultural plant, e.g., Barley, Beans (Dry Edible), Canola, Corn, Cotton (Pima), Cotton (Upland), Flaxseed, Hay (Alfalfa), Hay (Non-Alfalfa), Oats, Peanuts, Rice, Sorghum, Soybeans, Sugarbeets, Sugarcane, Sunflowers (Oil), Sunflowers (Non-Oil), Sweet Potatoes, Tobacco (Burley), Tobacco (Flue-cured), Tomatoes, Wheat (Durum), Wheat (Spring), Wheat (Winter), and the like. As another example, the cell is a cell of a vegetable crops which include but are not limited to, e.g., alfalfa sprouts, aloe leaves, arrow root, arrowhead, artichokes, asparagus, bamboo shoots, banana flowers, bean sprouts, beans, beet tops, beets, bittermelon, bok choy, broccoli, broccoli rabe (rappini), brussels sprouts, cabbage, cabbage sprouts, cactus leaf (nopales), calabaza, cardoon, carrots, cauliflower, celery, chayote, chinese artichoke (crosnes), chinese cabbage, chinese celery, chinese chives, choy sum, chrysanthemum leaves (tung ho), collard greens, corn stalks, corn-sweet, cucumbers, daikon, dandelion greens, dasheen, dau mue (pea tips), donqua (winter melon), eggplant, endive, escarole, fiddle head ferns, field cress, frisee, gai choy (chinese mustard), gailon, galanga (siam, thai ginger), garlic, ginger root, gobo, greens, hanover salad greens, huauzontle, jerusalem artichokes, jicama, kale greens, kohlrabi, lamb's quarters (quilete), lettuce (bibb), lettuce (boston), lettuce (boston red), lettuce (green leaf), lettuce (iceberg), lettuce (lolla rossa), lettuce (oak leaf—green), lettuce (oak leaf—red), lettuce (processed), lettuce (red leaf), lettuce (romaine), lettuce (ruby romaine), lettuce (russian red mustard), linkok, lo bok, long beans, lotus root, mache, maguey (agave) leaves, malanga, mesculin mix, mizuna, moap (smooth luffa), moo, moqua (fuzzy squash), mushrooms, mustard, nagaimo, okra, ong choy, onions green, opo (long squash), ornamental corn, ornamental gourds, parsley, parsnips, peas, peppers (bell type), peppers, pumpkins, radicchio, radish sprouts, radishes, rape greens, rape greens, rhubarb, romaine (baby red), rutabagas, salicornia (sea bean), sinqua (angled/ridged luffa), spinach, squash, straw bales, sugarcane, sweet potatoes, swiss chard, tamarindo, taro, taro leaf, taro shoots, tatsoi, tepeguaje (guaje), tindora, tomatillos, tomatoes, tomatoes (cherry), tomatoes (grape type), tomatoes (plum type), tumeric, turnip tops greens, turnips, water chestnuts, yampi, yams (names), yu choy, yuca (cassava), and the like.

A cell is in some cases an arthropod cell. For example, the cell can be a cell of a sub-order, a family, a sub-family, a group, a sub-group, or a species of, e.g., *Chelicerata, Myriapodia, Hexipodia, Arachnida, Insecta, Archaeognatha, Thysanura, Palaeoptera, Ephemeroptera, Odonata, Anisoptera, Zygoptera, Neoptera, Exopterygota, Plecoptera, Embioptera, Orthoptera, Zoraptera, Dermaptera, Dictyoptera, Notoptera, Grylloblattidae, Mantophasmatidae, Phasmatodea, Blattaria, Isoptera, Mantodea, Parapneuroptera, Psocoptera, Thysanoptera, Phthiraptera, Hemiptera, Endopterygota or Holometabola, Hymenoptera, Coleoptera, Strepsiptera, Raphidioptera, Megaloptera, Neuroptera, Mecoptera, Siphonaptera, Diptera, Trichoptera,* or *Lepidoptera.*

A cell is in some cases an insect cell. For example, in some cases, the cell is a cell of a mosquito, a grasshopper, a true bug, a fly, a flea, a bee, a wasp, an ant, a louse, a moth, or a beetle.

Introducing Components into a Target Cell

A Cas9 guide RNA (or a nucleic acid comprising a nucleotide sequence encoding same), and/or a Cas9 fusion polypeptide (or a nucleic acid comprising a nucleotide sequence encoding same) and/or a donor polynucleotide can be introduced into a host cell by any of a variety of well-known methods.

Methods of introducing a nucleic acid into a cell are known in the art, and any convenient method can be used to introduce a nucleic acid (e.g., an expression construct) into a target cell (e.g., eukaryotic cell, human cell, stem cell, progenitor cell, and the like). Suitable methods are described in more detail elsewhere herein and include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like. Any or all of the components can be introduced into a cell as a composition (e.g., including any convenient combination of: a CasX polypeptide, a CasX guide RNA, a donor polynucleotide, etc.) using known methods, e.g., such as nucleofection.

Donor Polynucleotide (Donor Template)

Guided by a CasX dual or single guide RNA, a CasX protein in some cases generates site-specific double strand breaks (DSBs) or single strand breaks (SSBs) (e.g., when the CasX protein is a nickase variant) within double-stranded DNA (dsDNA) target nucleic acids, which are repaired either by non-homologous end joining (NHEJ) or homology-directed recombination (HDR).

In some cases, contacting a target DNA (with a CasX protein and a CasX guide RNA) occurs under conditions that are permissive for nonhomologous end joining or homology-directed repair. Thus, in some cases, a subject method includes contacting the target DNA with a donor polynucleotide (e.g., by introducing the donor polynucleotide into a cell), wherein the donor polynucleotide, a portion of the donor polynucleotide, a copy of the donor polynucleotide, or a portion of a copy of the donor polynucleotide integrates into the target DNA. In some cases, the method does not comprise contacting a cell with a donor polynucleotide, and the target DNA is modified such that nucleotides within the target DNA are deleted.

In some cases, CasX guide RNA (or DNA encoding same) and a CasX protein (or a nucleic acid encoding same, such as an RNA or a DNA, e.g, one or more expression vectors) are coadministered (e.g., contacted with a target nucleic acid, administered to cells, etc.) with a donor polynucleotide sequence that includes at least a segment with homology to the target DNA sequence, the subject methods may be used to add, i.e. insert or replace, nucleic acid material to a target DNA sequence (e.g. to "knock in" a nucleic acid, e.g., one that encodes for a protein, an siRNA, an miRNA, etc.), to add a tag (e.g., 6×His, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation, remove a disease causing mutation by introducing a correct sequence), and the like. As such, a complex comprising a CasX guide RNA and CasX protein is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

In applications in which it is desirable to insert a polynucleotide sequence into he genome where a target sequence is cleaved, a donor polynucleotide (a nucleic acid comprising a donor sequence) can also be provided to the cell. By a "donor sequence" or "donor polynucleotide" or "donor template" it is meant a nucleic acid sequence to be inserted at the site cleaved by the CasX protein (e.g., after dsDNA cleavage, after nicking a target DNA, after dual nicking a target DNA, and the like). The donor polynucleotide can contain sufficient homology to a genomic sequence at the target site, e.g. 70%, 80%, 85%, 90%, 95%, or 100% homology with the nucleotide sequences flanking the target site, e.g. within about 50 bases or less of the target site, e.g. within about 30 bases, within about 15 bases, within about 10 bases, within about 5 bases, or immediately flanking the target site, to support homology-directed repair between it and the genomic sequence to which it bears homology. Approximately 25, 50, 100, or 200 nucleotides, or more than 200 nucleotides, of sequence homology between a donor and a genomic sequence (or any integral value between 10 and 200 nucleotides, or more) can support homology-directed repair. Donor polynucleotides can be of any length, e.g. 10 nucleotides or more, 50 nucleotides or more, 100 nucleotides or more, 250 nucleotides or more, 500 nucleotides or more, 1000 nucleotides or more, 5000 nucleotides or more, etc.

The donor sequence is typically not identical to the genomic sequence that it replaces. Rather, the donor sequence may contain at least one or more single base changes, insertions, deletions, inversions or rearrangements with respect to the genomic sequence, so long as sufficient homology is present to support homology-directed repair (e.g., for gene correction, e.g., to convert a disease-causing base pair to a non disease-causing base pair). In some embodiments, the donor sequence comprises a non-homologous sequence flanked by two regions of homology, such that homology-directed repair between the target DNA region and the two flanking sequences results in insertion of the non-homologous sequence at the target region. Donor sequences may also comprise a vector backbone containing sequences that are not homologous to the DNA region of interest and that are not intended for insertion into the DNA region of interest. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

The donor sequence may comprise certain sequence differences as compared to the genomic sequence, e.g. restriction sites, nucleotide polymorphisms, selectable markers (e.g., drug resistance genes, fluorescent proteins, enzymes etc.), etc., which may be used to assess for successful insertion of the donor sequence at the cleavage site or in some cases may be used for other purposes (e.g., to signify expression at the targeted genomic locus). In some cases, if located in a coding region, such nucleotide sequence differences will not change the amino acid sequence, or will make silent amino acid changes (i.e., changes which do not affect the structure or function of the protein). Alternatively, these sequences differences may include flanking recombination sequences such as FLPs, loxP sequences, or the like, that can be activated at a later time for removal of the marker sequence.

In some cases, the donor sequence is provided to the cell as single-stranded DNA. In some cases, the donor sequence is provided to the cell as double-stranded DNA. It may be introduced into a cell in linear or circular form. If introduced in linear form, the ends of the donor sequence may be protected (e.g., from exonucleolytic degradation) by any convenient method and such methods are known to those of skill in the art. For example, one or more dideoxynucleotide residues can be added to the 3' terminus of a linear molecule and/or self-complementary oligonucleotides can be ligated to one or both ends. See, for example, Chang et al. (1987) Proc. Natl. Acad Sci USA 84:4959-4963; Nehls et al. (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. As an alternative to protecting the termini of a linear donor sequence, additional lengths of sequence may be included outside of the regions of homology that can be degraded without impacting recombination. A donor sequence can be introduced into a cell as part of a vector molecule having additional sequences such as, for example, replication origins, promoters and genes encoding antibiotic resistance. Moreover, donor sequences can be introduced as naked nucleic acid, as nucleic acid complexed with an agent such as a liposome or poloxamer, or can be delivered by viruses (e.g., adenovirus, AAV), as described elsewhere herein for nucleic acids encoding a CasX guide RNA and/or a CasX fusion polypeptide and/or donor polynucleotide.

Transgenic, Non-Human Organisms

As described above, in some cases, a nucleic acid (e.g., a recombinant expression vector) of the present disclosure (e.g., a nucleic acid comprising a nucleotide sequence encoding a CasX polypeptide of the present disclosure; a nucleic acid comprising a nucleotide sequence encoding a CasX fusion polypeptide of the present disclosure; etc.), is used as a transgene to generate a transgenic non-human organism that produces a CasX polypeptide, or a CasX fusion polypeptide, of the present disclosure. The present disclosure provides a transgenic-non-human organism comprising a nucleotide sequence encoding a CasX polypeptide, or a CasX fusion polypeptide, of the present disclosure.

Transgenic, Non-Human Animals

The present disclosure provides a transgenic non-human animal, which animal comprises a transgene comprising a nucleic acid comprising a nucleotide sequence encoding a CasX polypeptide or a CasX fusion polypeptide. In some embodiments, the genome of the transgenic non-human animal comprises a nucleotide sequence encoding a CasX polypeptide, or a CasX fusion polypeptide, of the present disclosure. In some cases, the transgenic non-human animal is homozygous for the genetic modification. In some cases, the transgenic non-human animal is heterozygous for the genetic modification. In some embodiments, the transgenic non-human animal is a vertebrate, for example, a fish (e.g., salmon, trout, zebra fish, gold fish, puffer fish, cave fish, etc.), an amphibian (frog, newt, salamander, etc.), a bird (e.g., chicken, turkey, etc.), a reptile (e.g., snake, lizard, etc.), a non-human mammal (e.g., an ungulate, e.g., a pig, a cow, a goat, a sheep, etc.; a lagomorph (e.g., a rabbit); a rodent (e.g., a rat, a mouse); a non-human primate; etc.), etc. In some cases, the transgenic non-human animal is an invertebrate. In some cases, the transgenic non-human animal is an insect (e.g., a mosquito; an agricultural pest; etc.). In some cases, the transgenic non-human animal is an arachnid.

Nucleotide sequences encoding a CasX polypeptide, or a CasX fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc.

Transgenic Plants

As described above, in some cases, a nucleic acid (e.g., a recombinant expression vector) of the present disclosure (e.g., a nucleic acid comprising a nucleotide sequence encoding a CasX polypeptide of the present disclosure; a nucleic acid comprising a nucleotide sequence encoding a CasX fusion polypeptide of the present disclosure; etc.), is used as a transgene to generate a transgenic plant that produces a CasX polypeptide, or a CasX fusion polypeptide, of the present disclosure. The present disclosure provides a transgenic plant comprising a nucleotide sequence encoding a CasX polypeptide, or a CasX fusion polypeptide, of the present disclosure. In some embodiments, the genome of the transgenic plant comprises a subject nucleic acid. In some embodiments, the transgenic plant is homozygous for the genetic modification. In some embodiments, the transgenic plant is heterozygous for the genetic modification.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, Agrobacterium-mediated transformation and the like. The choice of method is generally dependent on the type of cell being transformed and the circumstances under which the transformation is taking place (i.e. in vitro, ex vivo, or in vivo).

Transformation methods based upon the soil bacterium Agrobacterium tumefaciens are particularly useful for introducing an exogenous nucleic acid molecule into a vascular plant. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An Agrobacterium-based vector is a modified form of a Ti plasmid, in which the tumor inducing functions are replaced by the nucleic acid sequence of interest to be introduced into the plant host.

Agrobacterium-mediated transformation generally employs cointegrate vectors or binary vector systems, in which the components of the Ti plasmid are divided between a helper vector, which resides permanently in the Agrobacterium host and carries the virulence genes, and a shuttle vector, which contains the gene of interest bounded by T-DNA sequences. A variety of binary vectors is well known in the art and are commercially available, for example, from Clontech (Palo Alto, Calif.). Methods of coculturing Agrobacterium with cultured plant cells or wounded tissue such as leaf tissue, root explants, hypocotyledons, stem pieces or tubers, for example, also are well known in the art. See, e.g., Glick and Thompson, (eds.), Methods in Plant Molecular Biology and Biotechnology, Boca Raton, Fla.: CRC Press (1993).

Microprojectile-mediated transformation also can be used to produce a subject transgenic plant. This method, first described by Klein et al. (Nature 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A nucleic acid of the present disclosure (e.g., a nucleic acid (e.g., a recombinant expression vector) comprising a nucleotide sequence encoding a CasX polypeptide, or a CasX fusion polypeptide, of the present disclosure) may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of Agrobacterium tumefaciens, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-9 and 4462) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for Agrobacterium-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576, 198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice.

The present disclosure provides transformed plant cells, tissues, plants and products that contain the transformed plant cells. A feature of the subject transformed cells, and tissues and products that include the same is the presence of a subject nucleic acid integrated into the genome, and production by plant cells of a CasX polypeptide, or a CasX fusion polypeptide, of the present disclosure. Recombinant plant cells of the present invention are useful as populations of recombinant cells, or as a tissue, seed, whole plant, stem, fruit, leaf, root, flower, stem, tuber, grain, animal feed, a field of plants, and the like.

Nucleotide sequences encoding a CasX polypeptide, or a CasX fusion polypeptide, of the present disclosure can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters, inducible promoters, spatially restricted and/or temporally restricted promoters, etc.

Archaeal Cas9 Polypeptides and Guide RNAs

The inventors have discovered a type II CRISPR/Cas locus in archaeal cells for the first time. It was previously thought that archaeal cells include only type I and/or type III CRISPR/cas systems, but not type II systems, and Cas9 is the signature protein of type II CRISPR systems. In other words, prior to this disclosure the art has taught that organisms that belong to the archaea do not include Cas9 proteins. Provided are methods and compositions that include an archaeal Cas9 protein (or a nucleic acid encoding same) (e.g., an ARMAN-1 Cas9 protein, an ARMAN-4 Cas9 protein, variants thereof, and the like), and/or an archaeal Cas9 guide RNA (dual or single guide RNA format) (or DNA encoding same, e.g., one or more expression vectors), and/or a donor template.

The term ARMAN refers to "archaeal Richmond Mine acidophilic nanoorganisms", see, e.g., Baker et. al., Proc Natl Acad Sci USA. 2010 May 11; 107(19): 8806-8811; Baker et. al., Science. 2006 Dec. 22; 314(5807):1933-5. ARMAN-1 can also be referred to as "Candidatus Micrarchaeum acidiphilum ARMAN-1"; while ARMAN-4 can also be referred to as "Candidatus Parvarchaeum acidiphilum ARMAN-4." ARMAN-2 and ARMAN-5 have also been identified and can be referred to as "Candidatus Micrarchaeum acidiphilum ARMAN-2" while ARMAN-5 can be referred to as "Candidatus Parvarchaeum acidiphilum ARMAN-5." Thus, the term "Candidatus Micrarchaeum acidiphilum" is a generic term encompassing at least Candidatus Micrarchaeum acidiphilum ARMAN-1 and Candidatus Micrarchaeum acidiphilum ARMAN-2, while the term "Candidatus Parvarchaeum acidiphilum" is a generic term encompassing at least Candidatus Parvarchaeum acidiphilum ARMAN-4 and Candidatus Parvarchaeum acidiphilum ARMAN-5. Thus, provided are methods and compositions that include an archaeal Cas9 protein (or a nucleic acid encoding same) (e.g., a Candidatus Micrarchaeum acidiphilum Cas9 protein, a Candidatus Parvarchaeum acidiphilum Cas9 protein, an ARMAN-1 Cas9 protein, an ARMAN-4

Cas9 protein, variants thereof, and the like), and/or an archaeal Cas9 guide RNA (dual or single guide RNA format) (or DNA encoding same, e.g., one or more expression vectors), and/or a donor template.

In any of the embodiments described herein (e.g., including all described compositions and methods, e.g., nucleic acids, methods of binding, methods of imaging, methods of modifying, genome editing, etc.), instead of a CasX protein, an archaeal Cas9 protein (e.g., an ARMAN-1 Cas9 protein, an ARMAN-4 Cas9 protein, and the like) can be used. In other words, an archaeal Cas9 protein (e.g., an ARMAN-1 Cas9 protein, an ARMAN-4 Cas9 protein, and the like) can substitute for a CasX protein. In such cases, where appropriate, the corresponding guide RNA (an archael Cas9 guide RNA, e.g., in either dual or single guide format) should be used instead of a CasX guide RNA. Examples of archaeal Cas9 proteins and archael Cas9 guide RNAs are illustrated in FIG. 13 (ARMAN-1 and ARMAN-4 Cas9 proteins), FIGS. 14A-14B (ARMAN-1 Cas9 guide RNAs), and FIG. 15 (ARMAN-4 Cas9 guide RNAs). Note that the orientation of the guide sequence of an archaeal Cas9 guide RNA relative to the rest of the guide RNA (e.g., relative to the duplex-forming segment of the targeter) is the opposite of a CasX guide RNA (e.g., compare the Ns of FIG. 6 and FIG. 7 where the guide sequence is at the 3' end for a CasX guide RNA to the Ns of FIGS. 14 A-14B and FIG. 15 where the guide sequence is at the 5' end for an archaeal Cas9 guide RNA); while the location of a PAM on a target dsDNA is also opposite for archael Cas9 proteins compared to CasX proteins (see below for more details).

Archaeal Cas9 Protein

Non-archaeal Cas9 proteins (i.e., Cas9 proteins from bacteria, but not from archaea) are known in the art, and a subject archaeal Cas9 protein has similar domain structure. However, the overall sequence of archaeal Cas9 proteins are highly divergent and share very little overall sequence homology.

A naturally occurring archaeal Cas9 protein functions as an endonuclease that catalyzes a double strand break at a specific sequence in a targeted double stranded DNA (dsDNA). The sequence specificity is provided by the associated guide RNA, which hybridizes to a target sequence within the target DNA. The naturally occurring guide RNA includes a tracrRNA hybridized to a crRNA, where the crRNA includes a guide sequence that hybridizes to a target sequence in the target DNA.

In some embodiments, the archaeal Cas9 protein of the subject methods and/or compositions is (or is derived from) a naturally occurring (wild type) protein. Examples of naturally occurring archaeal Cas9 proteins are depicted in FIG. 13 and are set forth as SEQ ID NOs: 71 and 72. It is important to note that the newly discovered archaeal Cas9 proteins (e.g., see FIG. 13) are short compared to previously identified CRISPR-Cas endonucleases (e.g., they are among the smallest known Cas9 proteins), and thus use of archaeal Cas9 proteins as an alternative provides the advantage that the nucleotide sequence encoding the protein is relatively short. This is useful, for example, in cases where a nucleic acid encoding the CasX protein is desirable, e.g., in situations that employ a viral vector (e.g., an AAV vector), for delivery to a cell such as a eukaryotic cell (e.g., mammalian cell, human cell, mouse cell, in vitro, ex vivo, in vivo) for research and/or clinical applications.

Figure 12A:
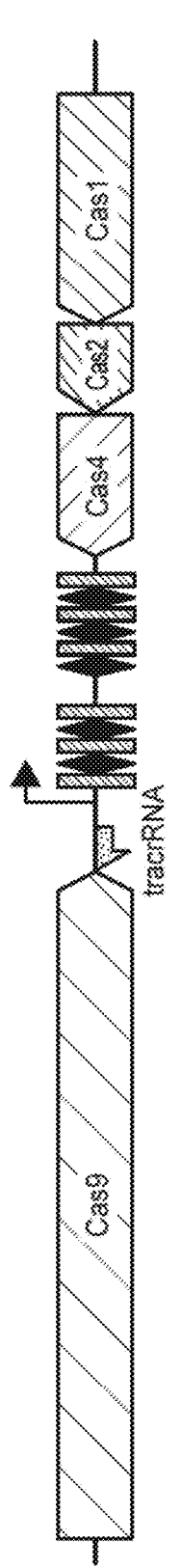
FIGS. 12A-12E present a information related to an archaeal Cas9 CRISPR system (the ARMAN-1 type II CRISPR-cas system).
Figure 12B:
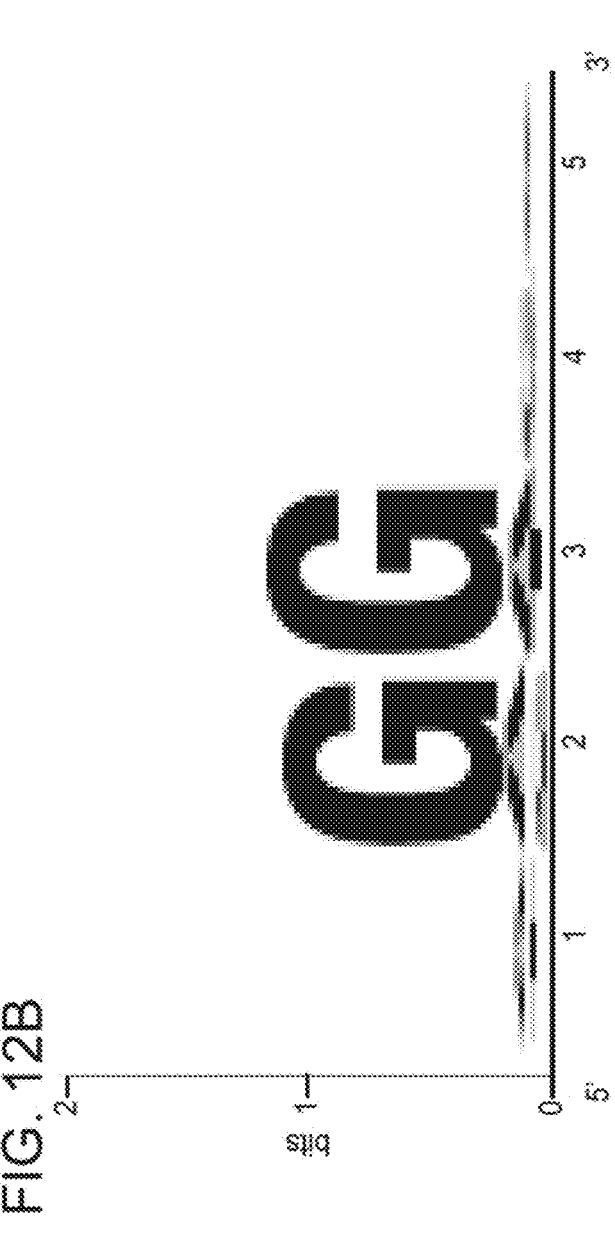
Figure 12C:
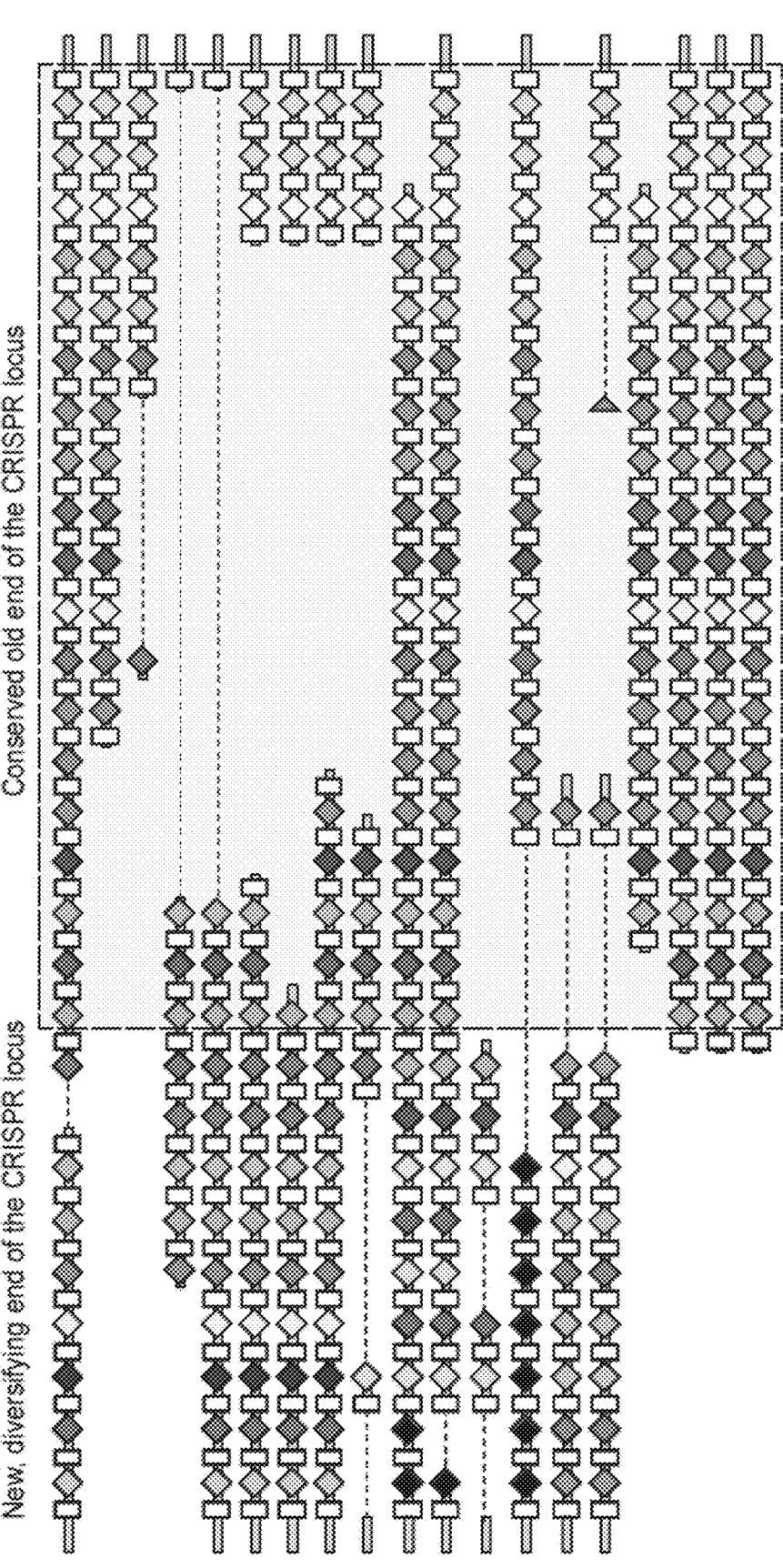
Figures 12D, 12E:
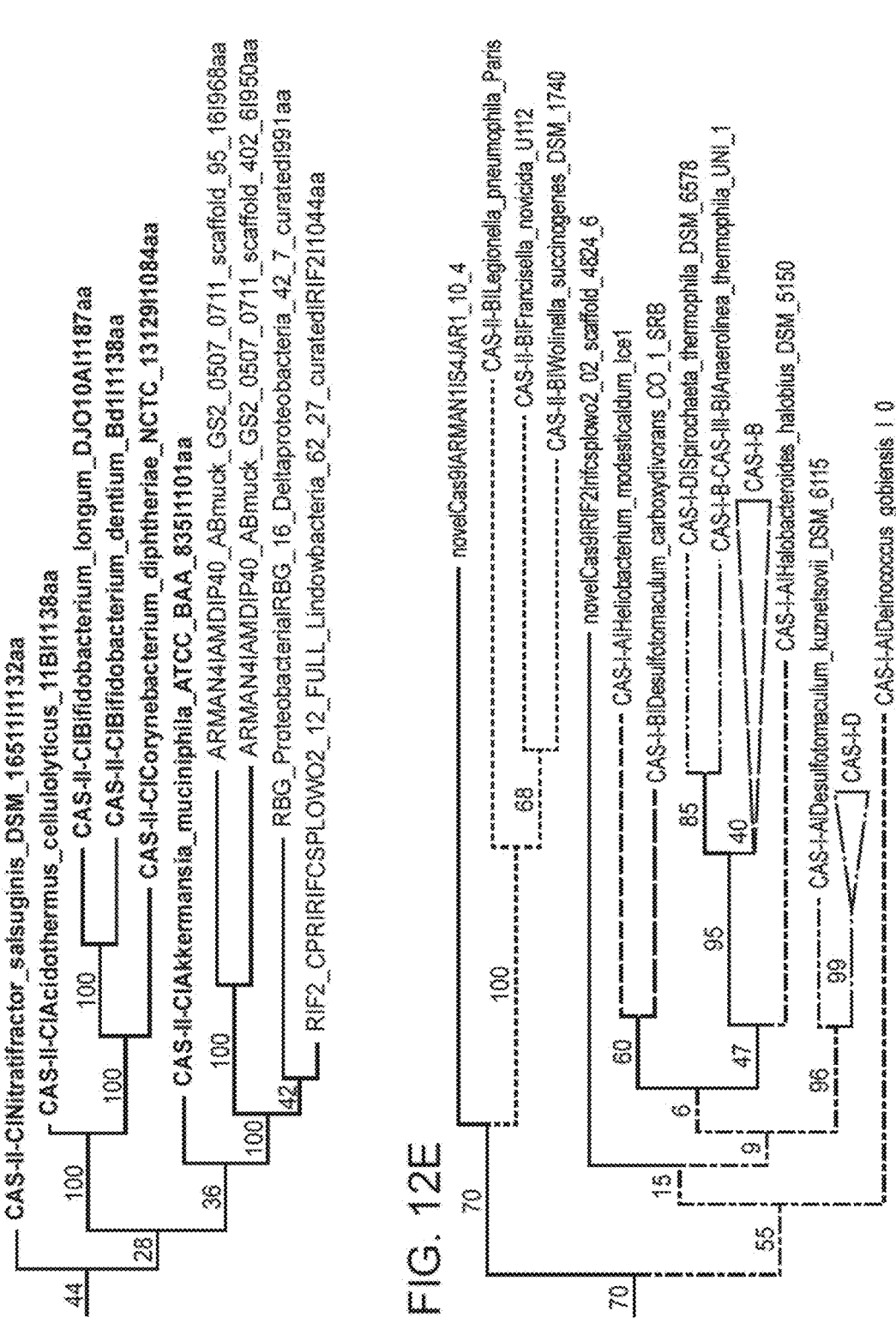

Two additional Cas9 proteins (see FIG. 16) were identified by the inventors that are non-archaeal Cas9 proteins, but cluster with archaeal Cas9s on phylogeny trees, and thus are related in sequence to archaeal Cas9s (e.g, Deltaproteobacteria Cas9 of FIG. 16 appears in the tree of FIG. 12D as RBG_ProteobacterialRBG_16_Deltaproteobacteria_42_7_curatedl991aa; while Lindowbacteria Cas9 of FIG. 16 appears in the tree of FIG. 12D as RIF2_ CPRIRIFC-SPLOWO2_12_ FULL_Lindowbacteria_62_27_ curatedl-RIF2I1044aa). An alignment of the sequences of FIG. 16 to ARMAN-1 Cas9 and ARMAN-4 Cas9 is provided in FIGS. 17A-17F.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes an amino acid sequence having 95% or more sequence identity (e.g., 98% or more, 99% or more, or 100% sequence identity) with the amino acid sequence set forth as SEQ ID NO: 71 (ARMAN-1). In some cases, a subject Cas9 protein (e.g., archaeal Cas9 protein) includes the amino acid sequence set forth as SEQ ID NO: 71. In some cases, a subject Cas9 protein (e.g., archaeal Cas9 protein) is a Candidatus Micrarchaeum acidiphilum Cas9 protein. In some cases, a subject Cas9 protein (e.g., archaeal Cas9 protein) is an ARMAN-1 Cas9 protein.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes an amino acid sequence having 95% or more sequence identity (e.g., 98% or more, 99% or more, or 100% sequence identity) with the amino acid sequence set forth as SEQ ID NO: 72 (ARMAN-4). In some cases, a subject Cas9 protein (e.g., archaeal Cas9 protein) includes the amino acid sequence set forth as SEQ ID NO: 72. In some cases, a subject Cas9 protein (e.g., archaeal Cas9 protein) is a Candidatus Parvarchaeum acidiphilum Cas9 protein. In some cases, a subject Cas9 protein (e.g., archaeal Cas9 protein) is an ARMAN-4 Cas9 protein.

In some cases, a subject Cas9 protein (e.g., archaeal Cas9 protein) includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes an amino acid sequence having 80% or more sequence identity (e.g., 90% or more, 95% or more, 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes an amino acid sequence having 95% or more sequence identity (e.g., 98% or more, 99% or more, or 100% sequence identity) with the amino acid sequence set forth in any one of SEQ ID NOs: 71 and 72 (ARMAN-1 AND ARMAN-4, respectively). In some cases, a subject Cas9 protein (e.g., archaeal Cas9 protein) includes the amino acid sequence set forth in any one of SEQ ID NOs: 71 and 72. In some cases, a subject Cas9 protein (e.g., archaeal Cas9 protein) is a Candidatus Micrarchaeum acidiphilum Cas9 protein (e.g., an ARMAN-1 Cas9 protein) or a Candidatus Parvarchaeum acidiphilum Cas9 protein (e.g., an ARMAN-4 Cas9 protein).

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 135. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth as SEQ ID NO: 135. In some cases, a subject Cas9 protein includes an amino acid sequence having 80% or more sequence identity (e.g., 90% or more, 95% or more, 98% or more, 99% or more, or 100% sequence identity) with the amino acid sequence set forth as SEQ ID NO: 135. In some cases, a subject Cas9 protein includes an amino acid sequence having 95% or more sequence identity (e.g., 98% or more, 99% or more, or 100% sequence identity) with the amino acid sequence set forth as SEQ ID NO: 135. In some cases, a subject Cas9 protein includes the amino acid sequence set forth as SEQ ID NO: 135.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth as SEQ ID NO: 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth as SEQ ID NO: 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth as SEQ ID NO: 136. In some cases, a subject Cas9 protein includes an amino acid sequence having 95% or more sequence identity (e.g., 98% or more, 99% or more, or 100% sequence identity) with the amino acid sequence set forth as SEQ ID NO: 136. In some cases, a subject Cas9 protein includes the amino acid sequence set forth as SEQ ID NO: 136.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth in any one of SEQ ID NOs: 135 and 136. In some cases, a subject Cas9 protein includes an amino acid sequence having 95% or more sequence identity (e.g., 98% or more, 99% or more, or 100% sequence identity) with the amino acid sequence in any one of SEQ ID NOs: 135 and 136. In some cases, a subject Cas9 protein includes the amino acid sequence set forth in any one of SEQ ID NOs: 135 and 136.

In some cases, a subject Cas9 protein includes an amino acid sequence having 50% or more sequence identity (e.g., 60% or more, 70% or more, 80% or more, 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 70% or more sequence identity (e.g., 80% or more, 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 80% or more sequence identity (e.g., 90% or more, 95% or more, 98% or more, 99% or more, or 100% sequence identity) with the amino acid sequence set forth in any one of SEQ ID NOs: 71, 72, 135, and 136. In some cases, a subject Cas9 protein includes an amino acid sequence having 95% or more sequence identity (e.g., 98% or more, 99% or more, or 100% sequence identity) with the amino acid sequence in any one of SEQ ID NOs: 71, 72, 135, and 136. In some cases, a subject Cas9 protein includes the amino acid sequence set forth in any one of SEQ ID NOs: 71, 72, 135, and 136.

Variants (Including Nickases, dCas9, and Chimeric Cas9 Proteins)

Please refer to the section on variants of CasX proteins for nomenclature and uses, etc., for variants that can be used (e.g., swap in archaeal Cas9 proteins for CasX proteins, swap in either of the two newly identified non-archaeal Cas9 proteins for CasX proteins, etc.). Any of the above parameters for a subject Cas9 protein (e.g., archaeal Cas9 protein) can be swapped in, e.g., including the % identity parameters above, ARMAN-1 Cas9 protein, ARMAN-4 Cas9 protein, Candidatus Micrarchaeum acidiphilum Cas9 protein, Candidatus Parvarchaeum acidiphilum Cas9 protein, and the like).

Catalytic residues of Cas9 proteins (e.g., archaeal Cas9 proteins) are readily identifiable despite the extremely low overall sequence identity with non-archaeal Cas9 proteins. For example, D30 (RuvC domain) and H506 (HNH domain) of the archaeal Cas9 set forth as SEQ ID NO: 71 (ARMAN-1) correspond to D10 and H840 of *S. pyogenes* Cas9, respectively; while D58 (RuvC domain) and H514 (HNH domain) of the archaeal Cas9 set forth as SEQ ID NO: 72 (ARMAN-4) correspond to D10 and H840 of *S. pyogenes* Cas9, respectively. These residues are bold and underlined in FIG. 13.

A Cas9 nickase (e.g., archaeal Cas9 nickase) can be generated by removing the catalytic activity (e.g., by mutating a catalytic residue) of either the RuvC domain (e.g., by mutating D30 of ARMAN-1 Cas9; D58 of ARMAN-4 Cas9 protein) or the HNH domain (e.g., by mutating H506 of ARMAN-1 Cas9; H514 of ARMAN-4 Cas9 protein) (e.g., each domain cleaves one strand of a target double stranded DNA). A dead version of a Cas9 protein (e.g., archaeal Cas9 protein) (e.g., dCas9, archaeal dCas9) can be generated by removing the catalytic activity (e.g., by mutating catalytic residues) of both the RuvC domain and the HNH domain.

All of the same fusion proteins can be used, except that archaeal Cas9 (or one of the newly identified non-archaeal Cas9s) can be swapped in for CasX. Non-limiting examples include: archaeal Cas9 or dCas9 or nickase Cas9 with an NLS(s), archaeal Cas9 or dCas9 or nickase Cas9 with a fusion partner that has catalytic activity and/or transcription repression or activation activity (e.g., to modify a target DNA, to modify a protein such as a histone associated with a target DNA, to modulate transcription from a target DNA, and the like), archaeal Cas9 or dCas9 or nickase Cas9 with a detectable label, and the like. The list of fusion partners that can be used for an archaeal Cas9 is the same as the list that can be used for a CasX protein (discussed in more detail herein).

Protospacer Adjacent Motif (PAM) for Archaeal Cas9 Protein

The PAM for an archaeal Cas9 protein is immediately 3' of the target sequence of the non-complementary strand of the target DNA (the complementary strand hybridizes to the guide sequence of the guide RNA while the non-complementary strand does not directly hybridize with the guide RNA and is the reverse complement of the non-complementary strand). Thus, the PAM for an archaeal Cas9 protein is on the opposite side of the target sequence compared to a PAM for a CasX protein (e.g., see FIG. 6C, and FIG. 7, which shows the 5' orientation of a PAM for a CasX protein). In some embodiments (e.g., when an archaeal Cas9 protein as described herein is used), the PAM sequence of the non-complementary strand is 5'-NGG-3', where N is any DNA nucleotide.

In some cases, different archaeal Cas9 proteins (i.e., archaeal Cas9 proteins from various archaeal species, variants of archaeal Cas9 proteins where the PAM preferences have changed) may be advantageous to use in the various provided methods in order to capitalize on various enzymatic characteristics of the different archaeal Cas9 proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.; to take advantage of a short total sequence; and the like). Archaeal Cas9 proteins from different species (or variant thereof) may prefer different PAM sequences in the target DNA. Thus, for a particular archaeal Cas9 protein of choice, the PAM sequence preference may be different than the 5'-NGG-3' sequence described above. Various methods (including in silico and/or wet lab methods) for identification of the appropriate PAM sequence are known in the art and are routine, and any convenient method can be used. The NGG PAM sequence described herein was identified using in silico sequence analysis techniques (e.g., see FIG. 12B of the working examples below).

Archaeal Cas9 Guide RNA

Non-archaeal Cas9 guide RNAs (i.e., Cas9 guide RNAs from bacteria, but not from archaea) are known in the art, and a subject archaeal Cas9 guide RNA has similar structure as non-archaeal Cas9 guide RNAs. Note that for an archaeal Cas9 guide RNA, the guide sequence is located 5' of the duplex-forming segment of the targeter RNA, while it is located 3' of the duplex-forming segment in a CasX guide RNA (e.g., compare FIGS. 14A-14B and FIG. 15, which depict example archaeal Cas9 guide RNAs, to FIG. 6C, and FIG. 7, which depict example CasX guide RNAs).

In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form one or more stem loops (e.g., 2 or more, 3 or more, 1, 2, or 3). In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of an archaeal Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of an archaeal Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences.

Although a number of different alternative sequences can be used, example archaeal Cas9 guide RNA sequences can include one or more of the sequences set forth in SEQ ID NOs: 75-76 (example crRNA sequences minus the guide sequence), 77-78 (example tracrRNA sequences), and 81-82 (example single guide RNA sequences minus the guide sequence).

In some cases, the dsRNA duplex region formed between the activator and targeter (i.e., the activator/targeter dsRNA duplex) (e.g., in dual or single guide RNA format) includes a range of from 8-25 base pairs (bp) (e.g., from 8-22, 8-18, 8-15, 8-12, 12-25, 12-22, 12-18, 12-15, 13-25, 13-22, 13-18, 13-15, 14-25, 14-22, 14-18, 14-15, 15-25, 15-22, 15-18, 17-25, 17-22, or 17-18 bp, e.g., 15 bp, 16 bp, 17 bp, 18 bp, 19 bp, 20 bp, 21 bp, etc.). In some cases, the duplex region (e.g., in dual or single guide RNA format) includes 8 or more bp (e.g., 10 or more, 12 or more, 15 or more, or 17 or more bp). In some cases, not all nucleotides of the duplex region are paired, and therefore the duplex forming region can include a bulge (e.g., see FIG. 6C, and FIG. 7). The term "bulge" herein is used to mean a stretch of nucleotides (which can be one nucleotide) that do not contribute to a double stranded duplex, but which are surround 5' and 3' by nucleotides that do contribute, and as such a bulge is considered part of the duplex region. In some cases, the dsRNA duplex formed between the activator and targeter (i.e., the activator/targeter dsRNA duplex) includes 1 or more bulges (e.g., 2 or more, 3 or more, 4 or more bulges). In some cases, the dsRNA duplex formed between the activator and targeter (i.e., the activator/targeter dsRNA duplex) includes 2 or more bulges (e.g., 3 or more, 4 or more bulges). In some cases, the dsRNA duplex formed between the activator and targeter (i.e., the activator/targeter dsRNA duplex) includes 1-5 bulges (e.g., 1-4, 1-3, 2-5, 2-4, or 2-3 bulges).

Thus, in some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 70%-100% complementarity (e.g., 75%-100%, 80%-10%, 85%-100%, 90%-100%, 95%-100% complementarity) with one another. In some cases, the duplex-forming segments of the activator and targeter have 85%-100% complementarity (e.g., 90%-100%, 95%-100% complementarity) with one another. In some cases, the duplex-forming segments of the activator and targeter have 70%-95% complementarity (e.g., 75%-95%, 80%-95%, 85%-95%, 90%-95% complementarity) with one another.

In other words, in some embodiments, the dsRNA duplex formed between the activator and targeter (i.e., the activator/targeter dsRNA duplex) includes two stretches of nucleotides that have 70%-100% complementarity (e.g., 75%-100%, 80%-10%, 85%-100%, 90%-100%, 95%-100% complementarity) with one another. In some cases, the activator/targeter dsRNA duplex includes two stretches of nucleotides that have 85%-100% complementarity (e.g., 90%-100%, 95%-100% complementarity) with one another. In some cases, the activator/targeter dsRNA duplex includes two stretches of nucleotides that have 70%-95% complementarity (e.g., 75%-95%, 80%-95%, 85%-95%, 90%-95% complementarity) with one another.

The duplex region of a subject archaeal Cas9 guide RNA (in dual guide or single guide RNA format) can include one or more (1, 2, 3, 4, 5, etc) mutations relative to a naturally occurring duplex region. For example, in some cases a base pair can be maintained while the nucleotides contributing to the base pair from each segment (targeter and activator) can be different. In some cases, the duplex region of a subject archaeal Cas9 guide RNA includes more paired bases, less paired bases, a smaller bulge, a larger bulge, fewer bulges, more bulges, or any convenient combination thereof, as compared to a naturally occurring duplex region (of a naturally occurring archaeal Cas9 guide RNA).

Example Sequences for an Archaeal Cas9 Guide RNA

In some cases, the targeter-RNA (e.g., in dual or single guide RNA format) comprises the crRNA sequence CUUA-CAAUCGACACUUAAAUAAUUUGCAUGUGUAAG (SEQ ID NO: 75) (e.g., see the sgRNA of 6C). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, or 100% identity) with the crRNA sequence CUUACAAUCGACA-CUUAAAUAAUUUGCAUGUGUAAG (SEQ ID NO: 75). In some cases, the targeter-RNA (e.g., in dual or single guide RNA format) comprises the crRNA sequence CUUA-CAAUCGACACUUAAAUAAUUUGCAUGUGUAAG (SEQ ID NO: 75).

In some cases, the targeter-RNA comprises the crRNA sequence CCUUUCAAUAAACAAAUAAAUCUU-AGUAAUAUGUAAC (SEQ ID NO: 76). In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence CUUU-CAAUAAACAAAUAAAUCUUAGUAAUAUGUAAC (SEQ ID NO: 76). In some cases, the targeter-RNA (e.g., in dual or single guide RNA format) comprises the crRNA sequence CUUUCAAUAAACAAAUAAAUCUU-AGUAAUAUGUAAC (SEQ ID NO: 76).

In some cases, the targeter-RNA comprises the crRNA sequence set forth in any one of SEQ ID NOs: 75-76. In some cases, the targeter-RNA comprises a nucleotide sequence having 80% or more identity (e.g., 85% or more, 90% or more, 93% or more, 95% or more, 97% or more, 98% or more, or 100% identity) with the crRNA sequence set forth in any one of SEQ ID NOs: 75-76.

In some cases, the activator-RNA (e.g., in dual or single guide RNA format) comprises the tracrRNA sequence GGCAUGGACCAUAUCCAGGUGUUGAUU-GUAAACACCUAGCGGGGAAAUUAUAUAUGUUU GUAAUAUCUUCACUAUCCAAAGUUAUCUCUG-GUUUUGGUUUGGUAAGCUUCACUUCACU AUU-GUUUUCACUCCCAAUUUGAGUAUGGUUGGGG-GUAAGGAUGCUUUCGGGGAGUGCUU UUA (SEQ ID NO: 77). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 77)
GGCAUGGACCAUAUCCAGGUGUUGAUUGUAAACACCUAGCGGGGAAAUUA

UAUAUGUUUGUAAUAUCUUCACUAUCCAAAGUUAUCUCUGGUUUUGGUUU

GGUAAGCUUCACUUCACUAUUGUUUUCACUCCCAAUUUGAGUAUGGUUGG

GGGUAAGGAUGCUUUCGGGGAGUGCUUUUA.
```

In some cases, the activator-RNA (e.g., in dual or single guide RNA format) comprises the tracrRNA sequence AACUGGCUAUUGCUAAUAUUAUUUGUUUAUU GAAAGAAGCCUAGACGUUAGGGUUCGCG UGCAUGUAGGCUCCAGCAGGUACCUC (SEQ ID NO: 78). In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 78)
AACUGGCUAUUGCUAAUAUUAUUUGUUUAUUGAAAGAAGCCUAGACGUUA

GGGUUCGCGUGCAUGUAGGCUCCAGCAGGUACCUC.
```

In some cases, the activator-RNA (e.g., in dual or single guide RNA format) comprises the tracrRNA sequence set forth in any one of SEQ ID NOs: 77-78. In some cases, the targeter-RNA (e.g., in dual or single guide RNA format) comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 77-78.

In some cases, an archaeal Cas9 single guide RNA comprises the sequence CUUACAAUCGACACUU aaacAGGUGUUGAUUGUAAACACCUAGCGGGGA AAUUAUAUAUGU UUGUAAUAUCUUCACUAUC-CAAAGUUAUCUCUGGUUUUGGUUUGGUAAGCUU-CACUUCA CUAUUGUUUUCACUCCCAAUUUGAGU AUGGUUGGGGGGUAAGGAUGCUUUCGGGGAGUGC UUUUA (SEQ ID NO: 81). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 81)
CUUACAAUCGACACUUaaacAGGUGUUGAUUGUAAACACCUAGCGGGGAA

AUUAUAUAUGUUUGUAAUAUCUUCACUAUCCAAAGUUAUCUCUGGUUUUG

GUUUGGUAAGCUUCACUUCACUAUUGUUUUCACUCCCAAUUUGAGUAUGG

UUGGGGGUAAGGAUGCUUUCGGGGAGUGCUUUUA.
```

In some cases, an archaeal Cas9 single guide RNA comprises the sequence CUUUCAAUAA ACAA AUAAAaaacUUAUUUGUUUAUUGAAAGAAGCCUA-GACGUUAGGGUUC GCGUGCAUGUAGGCUCCA GCAGGUACCUC (SEQ ID NO: 82). In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence

```
                                      (SEQ ID NO: 82)
CUUUCAAUAAACAAAUAAAaaacUUAUUUGUUUAUUGAAAGAAGCCUAGAC

GUUAGGGUUCGCGUGCAUGUAGGCUCCAGCAGGUACCUC.
```

In some cases, an archaeal Cas9 single guide RNA comprises the sequence set forth in any one of SEQ ID NOs: 81-82. In some cases, the targeter-RNA comprises a nucleotide sequence having 80% or more identity (e.g., 85% or more, 90% or more, 93% or more, 95% or more, 97% or more, 98% or more, 99% or more, or 100% identity) with the tracrRNA sequence set forth in any one of SEQ ID NOs: 81-82.

Guide Sequence of an Archaeal Cas9 Guide RNA

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 90% or more (e.g., 95% or more, 97% or more, 98% or more, 99% or more, or 100%) over 17 or more (e.g., 18 or more, 19 or more, 20 or more, 21 or more, 22 or more) contiguous nucleotides. In some cases, the percent complementarity between the guide sequence and the target site of the target nucleic acid is 100% over 17 or more (e.g., 18 or more, 19 or more, 20 or more, 21 or more, 22 or more) contiguous nucleotides.

In some cases, the percent complementarity between the guide sequence and the target site of the target nucleic acid is 60% or more (e.g., 70% or more, 75% or more, 80% or more, 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 80% or more (e.g., 85% or more, 90% or more, 95% or more, 97% or more, 98% or more, 99% or more, or 100%) over 17-25 contiguous nucleotides. In some cases, the percent complementarity between the guide sequence and the target site of the target nucleic acid is 90% or more (e.g., 95% or more, 97% or more, 98% or more, 99% or more, or 100%) over 17-25 contiguous nucleotides. In some cases, the percent complementarity between the guide sequence and the target site of the target nucleic acid is 100% over 17-25 contiguous nucleotides.

In some cases, the guide sequence has a length in a range of from 17-30 nucleotides (nt) (e.g., from 17-25, 17-22, 17-20, 19-30, 19-25, 19-22, 19-20, 20-30, 20-25, or 20-22 nt). In some cases, the guide sequence has a length in a range of from 17-25 nucleotides (nt) (e.g., from 17-22, 17-20, 19-25, 19-22, 19-20, 20-25, 20-25, or 20-22 nt). In some cases, the guide sequence has a length of 17 or more nt (e.g., 18 or more, 19 or more, 20 or more, 21 or more, or 22 or more nt; 17 nt, 18 nt, 19 nt, 20 nt, 21 nt, 22 nt, 23 nt, 24 nt, 25 nt, etc.). In some cases the guide sequence has a length of 17 nt. In some cases the guide sequence has a length of 18 nt. In some cases the guide sequence has a length of 19 nt. In some cases the guide sequence has a length of 20 nt. In some cases the guide sequence has a length of 21 nt. In some cases the guide sequence has a length of 22 nt. In some cases the guide sequence has a length of 23 nt.

Examples of various Cas proteins and Cas9 guide RNAs (albeit non-archeal Cas9 proteins and guide RNAs) can be found in the art, and in some cases variations similar to those introduced into non-archeal Cas9 proteins and guide RNAs can also be introduced into archeal Cas9 proteins and guide RNAs of the present disclosure, including, for example, high fidelity versions of Cas9. For example, mutations that can be introduced into previously known Cas9 proteins in order to generate a high fidelity Cas9 can also be introduced into archaeal Cas9 proteins for a same or similar purpose (e.g., a sequence and/or structural alignment can be performed to determine the appropriate amino acids to mutate in a subject archaeal Cas9 protein—e.g., amino acids N497, R661, Q695, and Q926 of a S. pyogenes Cas9 protein, which is not an archaeal Cas9 protein) (e.g., see Kleinstiver et al. (2016) Nature 529:490). For example, see Jinek et al., Science. 2012 Aug. 17; 337(6096):816-21; Chylinski et al., RNA Biol. 2013 May; 10(5):726-37; Ma et al., Biomed Res Int. 2013; 2013:270805; Hou et al., Proc Natl Acad Sci USA. 2013 Sep. 24; 110(39):15644-9; Jinek et al., Elife. 2013; 2:e00471; Pattanayak et al., Nat Biotechnol. 2013 September; 31(9):839-43; Qi et al, Cell. 2013 Feb. 28; 152(5):1173-83; Wang et al., Cell. 2013 May 9; 153(4):910-8; Auer et. al., Genome Res. 2013 Oct. 31; Chen et. al., Nucleic Acids Res. 2013 Nov. 1; 41(20):e19; Cheng et. al., Cell Res. 2013 October; 23(10):1163-71; Cho et. al., Genetics. 2013 November; 195(3):1177-80; DiCarlo et al., Nucleic Acids Res. 2013 April; 41(7):4336-43; Dickinson et. al., Nat Methods. 2013 October; 10(10):1028-34; Ebina et. al., Sci Rep. 2013; 3:2510; Fujii et. al, Nucleic Acids Res. 2013 Nov. 1; 41(20):e187; Hu et. al., Cell Res. 2013 November; 23(11):1322-5; Jiang et. al., Nucleic Acids Res. 2013 Nov. 1; 41(20):e188; Larson et. al., Nat Protoc. 2013 November; 8(11):2180-96; Mali et. at., Nat Methods. 2013 October; 10(10):957-63; Nakayama et. al., Genesis. 2013 December; 51(12):835-43; Ran et. al., Nat Protoc. 2013 November; 8(11):2281-308; Ran et. al., Cell. 2013 Sep. 12; 154(6):1380-9; Upadhyay et. al., G3 (Bethesda). 2013 Dec. 9; 3(12):2233-8; Walsh et. al., Proc Natl Acad Sci USA. 2013 Sep. 24; 110(39):15514-5; Xie et. al., Mol Plant. 2013 Oct. 9; Yang et. al., Cell. 2013 Sep. 12; 154(6):1370-9; Briner et al., Mol Cell. 2014 Oct. 23; 56(2):333-9; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 20140068797; 20140170753; 20140179006; 20140179770; 20140186843; 20140186919; 20140186958; 20140189896; 20140227787; 20140234972; 20140242664; 20140242699; 20140242700; 20140242702; 20140248702; 20140256046; 20140273037; 20140273226; 20140273230; 20140273231; 20140273232; 20140273233; 20140273234; 20140273235; 20140287938; 20140295556; 20140295557; 20140298547; 20140304853; 20140309487; 20140310828; 20140310830; 20140315985; 20140335063; 20140335620; 20140342456; 20140342457; 20140342458; 20140349400; 20140349405; 20140356867; 20140356956; 20140356958; 20140356959; 20140357523; 20140357530; 20140364333; and 20140377868; all of which are hereby incorporated by reference in their entirety.

Examples of Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure, (SET A—related to CasX) numbered 1-131; and (SET B—related to archaeal Cas9) numbered 1-133 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

Set A

Related to CasX

1. A composition comprising:

a) a CasX polypeptide, or a nucleic acid molecule encoding the CasX polypeptide; and b) a CasX guide RNA, or one or more DNA molecules encoding the CasX guide RNA.

2. The composition of 1, wherein the CasX polypeptide comprises an amino acid sequence having 50% or more identity to the amino acid sequence set forth in SEQ ID NO:1 or SEQ ID NO:2 or SEQ ID NO:3.

3. The composition of 1 or 2, wherein the CasX guide RNA is a single guide RNA.

4. The composition of 1 or 2, wherein the CasX guide RNA is a dual-guide RNA.

5. The composition of any one of 1-4, wherein the composition comprises a lipid.

6. The composition of any one of 1-4, wherein a) and b) are within a liposome.

7. The composition of any one of 1-4, wherein a) and b) are within a particle.

8. The composition of any one of 1-7, comprising one or more of: a buffer, a nuclease inhibitor, and a protease inhibitor.

9. The composition of any one of 1-8, wherein the CasX polypeptide comprises an amino acid sequence having 85% or more identity to the amino acid sequence set forth in SEQ ID NO:1 or SEQ ID NO:2 or SEQ ID NO:3.

10. The composition of any one of 1-9, wherein the CasX polypeptide is a nickase that can cleave only one strand of a double-stranded target nucleic acid molecule.

11. The composition of any one of 1-9, wherein the CasX polypeptide is a catalytically inactive CasX Polypeptide (dCasX).

12. The composition of 10 or 11, wherein the CasX polypeptide comprises one or more mutations at a position corresponding to those selected from: D672, E769, and D935 of SEQ ID NO: 1.

13. The composition of any one of 1-12, further comprising a DNA donor template.

14. A CasX single guide RNA molecule, comprising:

a) a targeter sequence comprising a guide sequence that hybridizes to a target nucleic acid, and a duplex-forming segment; and b) an activator sequence that hybridizes with the duplex-forming segment of the targeter sequence to form a double stranded RNA (dsRNA) duplex that can bind a CasX polypeptide.

15. The CasX single guide RNA molecule of 14, wherein the guide sequence has a length of from 19 to 30 nucleotides.

16. A DNA molecule comprising a nucleotide sequence encoding the CasX single guide RNA molecule of 14 or 15.

17. The DNA molecule of 16, wherein the nucleotide sequence encoding the CasX single guide RNA is operably linked to a promoter.

18. The DNA molecule of 17, wherein the promoter is functional in a eukaryotic cell.

19. The DNA molecule of 18, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

20. The DNA molecule of any one of 17-19, wherein the promoter is one or more of: a constitutive promoter, an inducible promoter, a cell type-specific promoter, and a tissue-specific promoter.

21. The DNA molecule of any one of 16-20, wherein the DNA molecule is a recombinant expression vector.

22. The DNA molecule of 21, wherein the recombinant expression vector is a recombinant adenoassociated viral vector, a recombinant retroviral vector, or a recombinant lentiviral vector.

23. The DNA molecule of 17, wherein the promoter is functional in a prokaryotic cell.

24. A CasX fusion polypeptide comprising: a CasX polypeptide fused to a heterologous polypeptide.

25. The CasX fusion polypeptide of 24, wherein the CasX polypeptide comprises an amino acid sequence having 50% or more identity to the amino acid sequence set forth in SEQ ID NO:1 or SEQ ID NO:2 or SEQ ID NO:3.

26. The CasX fusion polypeptide of 24, wherein the CasX polypeptide comprises an amino acid sequence having 85% or more identity to the amino acid sequence set forth in SEQ ID NO:1 or SEQ ID NO:2 or SEQ ID NO:3.

27. The CasX fusion polypeptide of any one of 24-27, wherein the CasX polypeptide is a nickase that can cleave only one strand of a double-stranded target nucleic acid molecule.

28. The CasX fusion polypeptide of any one of 24-27, wherein the CasX polypeptide is a catalytically inactive CasX Polypeptide (dCasX).

29. The CasX fusion polypeptide of 27 or 28, wherein the CasX polypeptide comprises one or more mutations at a position corresponding to those selected from: D672, E769, and D935 of SEQ ID NO: 1.

30. The CasX fusion polypeptide of any one of 24-29, wherein the heterologous polypeptide is fused to the N-terminus and/or the C-terminus of the CasX polypeptide.

31. The CasX fusion polypeptide of any one of 24-30, comprising an NLS.

32. The CasX fusion polypeptide of any one of 24-31, wherein the heterologous polypeptide is a targeting polypeptide that provides for binding to a cell surface moiety on a target cell or target cell type.

33. The CasX fusion polypeptide of any one of 24-31, wherein the heterologous polypeptide exhibits an enzymatic activity that modifies target DNA.

34. The CasX fusion polypeptide of 33, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

35. The CasX fusion polypeptide of 34, wherein the heterologous polypeptide exhibits an one or more enzymatic activities selected from: nuclease activity, methyltransferase activity, demethylase activity, deamination activity, depurination activity, integrase activity, transposase activity, and recombinase activity.

36. The CasX fusion polypeptide of any one of 24-31, wherein the heterologous polypeptide exhibits an enzymatic activity that modifies a target polypeptide associated with a target nucleic acid.

37. The CasX fusion polypeptide of 36, wherein the heterologous polypeptide exhibits histone modification activity.

38. The CasX fusion polypeptide of 36 or 37, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

39. The CasX fusion polypeptide of 38, wherein the heterologous polypeptide exhibits an one or more enzymatic activities selected from: methyltransferase activity, demethylase activity, acetyltransferase activity, and deacetylase activity.

40. The CasX fusion polypeptide of any one of 24-31, wherein the heterologous polypeptide is an endosomal escape polypeptide.

41. The CasX fusion polypeptide of 40, wherein the endosomal escape polypeptide comprises an amino acid sequence selected from: GLFXALLXLLXSLWXLLLXA (SEQ ID NO:94), and GLFHALLHLLHSLWHLLLHA (SEQ ID NO:95), wherein each X is independently selected from lysine, histidine, and arginine.

42. The CasX fusion polypeptide of any one of 24-31, wherein the heterologous polypeptide is a chloroplast transit peptide.

43. The CasX fusion polypeptide of 42, wherein the chloroplast transit peptide comprises an amino acid sequence selected from

```
                                    (SEQ ID NO: 83)
MASMISSSAVTTVSRASRGQSAAMAPFGGLKSMTGFPVRKVNTDITSITS

NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS

NGGRVKS;

(SEQ ID NO: 85)
MASSMLSSATMVASPAQATMVAPFNGLKSSAAFPATRKANNDITSITSNG

GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG

LKKSGMTLIGSELRPLKVMSSVSTAC;

(SEQ ID NO: 87)
MAQVSRICNGVWNPSLISNLSKSSQRKSPLSVSLKTQQHPRAYPISSSWG

LKKSGMTLIGSELRPLKVMSSVSTAC;

(SEQ ID NO: 88)
MAQINNMAQGIQTLNPNSNFHKPQVPKSSSFLVFGSKKLKNSANSMLVLK

KDSIFMQLFCSFRISASVATAC;

(SEQ ID NO: 89)
MAALVTSQLATSGTVLSVTDRFRRPGFQGLRPRNPADAALGMRTVGASAA

PKQSRKPHRFDRRCLSMVV;

(SEQ ID NO: 90)
MAALTTSQLATSATGFGIADRSAPSSLLRHGFQGLKPRSPAGGDATSLSV

TTSARATPKQQRSVQRGSRRFPSVVVC;

(SEQ ID NO: 91)
MASSVLSSAAVATRSNVAQANMVAPFTGLKSAASFPVSRKQNLDITSIAS

NGGRVQC;
```

-continued
```
                                    (SEQ ID NO: 92)
MESLAATSVFAPSRVAVPAARALVRAGTVVPTRRTSSTSGTSGVKCSAAV TPQASPVISRSAAAA;
and (SEQ ID NO: 93)
MGAAATSMQSLKFSNRLVPPSRRLSPVPNNVTCNNLPKSAAPVRTVKCCA

SSWNSTINGAAATTNGASAASS.
```

44. The CasX fusion polypeptide of any one of 24-31, wherein the heterologous polypeptide is protein that increases or decreases transcription.

45. The CasX fusion polypeptide of 44, wherein the heterologous polypeptide is a transcriptional repressor domain.

46. The CasX fusion polypeptide of 44, wherein the heterologous polypeptide is a transcriptional activation domain.

47. The CasX fusion polypeptide of any one of 24-31, wherein the heterologous polypeptide is a protein biding domain.

48. A nucleic acid molecule encoding the CasX fusion polypeptide of any one of 24-47.

49. The nucleic acid molecule of 48, wherein the nucleotide sequence encoding the CasX fusion polypeptide is operably linked to a promoter.

50. The nucleic acid molecule of 49, wherein the promoter is functional in a eukaryotic cell.

51. The nucleic acid molecule of 50, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

52. The nucleic acid molecule of any one of 49-51, wherein the promoter is one or more of: a constitutive promoter, an inducible promoter, a cell type-specific promoter, and a tissue-specific promoter.

53. The nucleic acid molecule of any one of 48-52, wherein the DNA molecule is a recombinant expression vector.

54. The nucleic acid molecule of 53, wherein the recombinant expression vector is a recombinant adenoassociated viral vector, a recombinant retroviral vector, or a recombinant lentiviral vector.

55. The nucleic acid molecule of 49, wherein the promoter is functional in a prokaryotic cell.

56. The nucleic acid molecule of 48, wherein the nucleic acid molecule is an mRNA.

57. One or more nucleic molecules encoding:
(a) a CasX guide RNA comprising an activator RNA and a targeter RNA; and
(b) a CasX polypeptide.

58. The one or more nucleic acid molecules of 57, wherein the CasX polypeptide comprises an amino acid sequence having 50% or more identity to the amino acid sequence set forth in SEQ ID NO:1 or SEQ ID NO:2 or SEQ ID NO:3.

59. The one or more nucleic acid molecules of 57, wherein the CasX polypeptide comprises an amino acid sequence having 85% or more identity to the amino acid sequence set forth in SEQ ID NO:1 or SEQ ID NO:2 or SEQ ID NO:3.

60. The one or more nucleic acid molecules of any one of 57-59, wherein the CasX guide RNA is a single guide RNA.

61. The one or more nucleic acid molecules of any one of 57-59, wherein the CasX guide RNA is a dual-guide RNA.

62. The one or more nucleic acid molecules of 61, wherein said one or more nucleic acid molecules comprises a first nucleotide sequence encoding the activator and a second nucleotide sequence encoding the targeter, and wherein said first and second nucleotide sequences are present on different DNA molecules.

63. The one or more nucleic acid molecules of any one of 57-62, wherein said one or more nucleic acid molecules comprises a nucleotide sequence encoding the CasX polypeptide that is operably linked to a promoter.

64. The one or more nucleic acid molecules of 63, wherein the promoter is functional in a eukaryotic cell.

65. The one or more nucleic acid molecules of 64, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

66. The one or more nucleic acid molecules of any one of 63-65, wherein the promoter is one or more of: a constitutive promoter, an inducible promoter, a cell type-specific promoter, and a tissue-specific promoter.

67. The one or more nucleic acid molecules of any one of 57-66, wherein the one or more nucleic acid molecules is one or more recombinant expression vectors.

68. The one or more nucleic acid molecules of 67, wherein the one or more recombinant expression vectors are selected from: one or more adenoassociated viral vectors, one or more recombinant retroviral vectors, or one or more recombinant lentiviral vectors.

69. The one or more nucleic acid molecules of 63, wherein the promoter is functional in a prokaryotic cell.

70. A eukaryotic cell comprising one or more of:
a) a Casx polypeptide, or a nucleic acid molecule encoding the Casx polypeptide,
b) a CasX fusion polypeptide, or a nucleic acid molecule encoding the CasX fusion polypeptide, and
c) a CasX guide RNA, or a nucleic acid molecule encoding the CasX guide RNA.

71. The eukaryotic cell of 70, comprising the nucleic acid molecule encoding the Casx polypeptide, wherein said nucleic acid molecule is integrated into the genomic DNA of the cell.

72. The eukaryotic cell of 70 or 71, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

73. A cell comprising a CasX fusion polypeptide, or a nucleic acid molecule encoding the CasX fusion polypeptide.

74. The cell of 73, wherein the cell is a prokaryotic cell.

75. The cell of 73 or 74, comprising the nucleic acid molecule encoding the CasX fusion polypeptide, wherein said nucleic acid molecule is integrated into the genomic DNA of the cell.

76. A method of modifying a target nucleic acid, the method comprising contacting the target nucleic acid with:
a) a CasX polypeptide; and
b) a CasX guide RNA comprising a guide sequence that hybridizes to a target sequence of the target nucleic acid, wherein said contacting results in modification of the target nucleic acid by the CasX polypeptide.

77. The method of 76, wherein said modification is cleavage of the target nucleic acid.

78. The method of 76 or 77, wherein the target nucleic acid is selected from: double stranded DNA, single stranded DNA, RNA, genomic DNA, and extrachromosomal DNA.

79. The method of any of 76-78, wherein said contacting takes place in vitro outside of a cell.

80. The method of any of 76-78, wherein said contacting takes place inside of a cell in culture.

81. The method of any of 76-78, wherein said contacting takes place inside of a cell in vivo.

82. The method of 80 or 81, wherein the cell is a eukaryotic cell.

83. The method of 82, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

84. The method of 80 or 81, wherein the cell is a prokaryotic cell.

85. The method of any one of 76-84, wherein said contacting results in genome editing.

86. The method of any one of 76-85, wherein said contacting comprises: introducing into a cell: (a) the CasX polypeptide, or a nucleic acid molecule encoding the CasX polypeptide, and (b) the Casx guide RNA, or a nucleic acid molecule encoding the CasX guide RNA.

87. The method of 86, wherein said contacting further comprises: introducing a DNA donor template into the cell.

88. The method of any one of 76-87, wherein the CasX guide RNA is a single guide RNA.

89. The method of any one of 76-87, wherein the CasX guide RNA is a dual guide RNA.

90. A method of modulating transcription from a target DNA, modifying a target nucleic acid, or modifying a protein associated with a target nucleic acid, the method comprising contacting the target nucleic acid with:
a) a CasX fusion polypeptide comprising a CasX polypeptide fused to a heterologous polypeptide; and
b) a CasX guide RNA comprising a guide sequence that hybridizes to a target sequence of the target nucleic acid.

91. The method of 90, wherein the CasX guide RNA is a single guide RNA.

92. The method of 90, wherein the CasX guide RNA is a dual guide RNA.

93. The method of any of 90-92, wherein said modification is not cleavage of the target nucleic acid.

94. The method of any of 90-93, wherein the target nucleic acid is selected from: double stranded DNA, single stranded DNA, RNA, genomic DNA, and extrachromosomal DNA.

95. The method of any of 90-94, wherein said contacting takes place in vitro outside of a cell.

96. The method of any of 90-94, wherein said contacting takes place inside of a cell in culture.

97. The method of any of 90-94, wherein said contacting takes place inside of a cell in vivo.

98. The method of 96 or 97, wherein the cell is a eukaryotic cell.

99. The method of 98, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

100. The method of 96 or 97, wherein the cell is a prokaryotic cell.

101. The method of any one of 90-100, wherein said contacting comprises: introducing into a cell: (a) the CasX fusion polypeptide, or a nucleic acid molecule encoding the CasX fusion polypeptide, and (b) the Casx guide RNA, or a nucleic acid molecule encoding the CasX guide RNA.

102. The method of any one of 90-101, wherein the CasX polypeptide is a catalytically inactive CasX Polypeptide (dCasX).

103. The method of any one of 90-102, wherein the CasX polypeptide comprises one or more mutations at a position corresponding to those selected from: D672, E769, and D935 of SEQ ID NO: 1.

104. The method of any one of 90-103, wherein the heterologous polypeptide exhibits an enzymatic activity that modifies target DNA.

105. The method of 104, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

106. The method of 105, wherein the heterologous polypeptide exhibits an one or more enzymatic activities selected from: nuclease activity, methyltransferase activity, demethylase activity, deamination activity, depurination activity, integrase activity, transposase activity, and recombinase activity.

107. The method of any one of 90-103, wherein the heterologous polypeptide exhibits an enzymatic activity that modifies a target polypeptide associated with a target nucleic acid.

108. The method of 107, wherein the heterologous polypeptide exhibits histone modification activity.

109. The method of 107 or 108, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

110. The method of 109, wherein the heterologous polypeptide exhibits an one or more enzymatic activities selected from: methyltransferase activity, demethylase activity, acetyltransferase activity, and deacetylase activity.

111. The method of any one of 90-103, wherein the heterologous polypeptide is protein that increases or decreases transcription.

112. The method of 111, wherein the heterologous polypeptide is a transcriptional repressor domain.

113. The method of 111, wherein the heterologous polypeptide is a transcriptional activation domain.

114. The method of any one of 90-103, wherein the heterologous polypeptide is a protein biding domain.

115. A transgenic, multicellular, non-human organism whose genome comprises a transgene comprising a nucleotide sequence encoding one or more of:
    a) a Casx polypeptide,
    b) a CasX fusion polypeptide, and
    c) a CasX guide RNA.

116. The transgenic, multicellular, non-human organism of 115, wherein the CasX polypeptide comprises an amino acid sequence having 50% or more amino acid sequence identity to the amino acid sequence set forth in SEQ ID NO:1 or SEQ ID NO:2 or SEQ ID NO:3.

117. The transgenic, multicellular, non-human organism of 115, wherein the CasX polypeptide comprises an amino acid sequence having 85% or more amino acid sequence identity to the amino acid sequence set forth in SEQ ID NO:1 or SEQ ID NO:2 or SEQ ID NO:3.

118. The transgenic, multicellular, non-human organism of any one of 115-117, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

119. A system comprising:
    a) a CasX polypeptide and a CasX single guide RNA;
    b) a CasX polypeptide, a CasX guide RNA, and a DNA donor template;
    c) a CasX fusion polypeptide and a CasX guide RNA;
    d) a CasX fusion polypeptide, a CasX guide RNA, and a DNA donor template;
    e) an mRNA encoding a CasX polypeptide, and a CasX single guide RNA;
    f) an mRNA encoding a CasX polypeptide; a CasX guide RNA, and a DNA donor template;
    g) an mRNA encoding a CasX fusion polypeptide, and a CasX guide RNA;
    h) an mRNA encoding a CasX fusion polypeptide, a CasX guide RNA, and a DNA donor template;
    i) one or more recombinant expression vectors comprising: i) a nucleotide sequence encoding a CasX polypeptide; and ii) a nucleotide sequence encoding a CasX guide RNA;
    j) one or more recombinant expression vectors comprising: i) a nucleotide sequence encoding a CasX polypeptide; ii) a nucleotide sequence encoding a CasX guide RNA; and iii) a DNA donor template;
    k) one or more recombinant expression vectors comprising: i) a nucleotide sequence encoding a CasX fusion polypeptide; and ii) a nucleotide sequence encoding a CasX guide RNA; and
    l) one or more recombinant expression vectors comprising: i) a nucleotide sequence encoding a CasX fusion polypeptide; ii) a nucleotide sequence encoding a CasX guide RNA; and a DNA donor template.

120. The CasX system of 119, wherein the CasX polypeptide comprises an amino acid sequence having 50% or more amino acid sequence identity to the amino acid sequence set forth in SEQ ID NO:1 or SEQ ID NO:2 or SEQ ID NO:3.

121. The CasX system of 119, wherein the CasX polypeptide comprises an amino acid sequence having 85% or more amino acid sequence identity to the amino acid sequence set forth in SEQ ID NO:1 or SEQ ID NO:2 or SEQ ID NO:3.

122. The CasX system of any of 119-121, wherein the donor template nucleic acid has a length of from 8 nucleotides to 1000 nucleotides.

123. The CasX system of any of 119-121, wherein the donor template nucleic acid has a length of from 25 nucleotides to 500 nucleotides.

124. A kit comprising the CasX system of any one of 119-123.

125. The kit of 124, wherein the components of the kit are in the same container.

126. The kit of 124, wherein the components of the kit are in separate containers.

127. A sterile container comprising the CasX system of any one of 119-126.

128. The sterile container of 127, wherein the container is a syringe.

129. An implantable device comprising the CasX system of any one of 119-126.

130. The implantable device of 129, wherein the CasX system is within a matrix.

131. The implantable device of 129, wherein the CasX system is in a reservoir.

Set B

Related to Archaeal Cas9

1. A composition comprising:
   a) a archaeal Cas9 polypeptide, or a nucleic acid molecule encoding the archaeal Cas9 polypeptide; and
   b) a archaeal Cas9 guide RNA, or one or more DNA molecules encoding the archaeal Cas9 guide RNA.

2. The composition of 1, wherein the archaeal Cas9 polypeptide comprises an amino acid sequence having 50% or more identity to the amino acid sequence set forth in SEQ ID NO:71 or SEQ ID NO:72.

3. The composition of 1 or 2, wherein the archaeal Cas9 guide RNA is a single guide RNA.

4. The composition of 1 or 2, wherein the archaeal Cas9 guide RNA is a dual-guide RNA.

5. The composition of any one of 1-4, wherein the composition comprises a lipid.

6. The composition of any one of 1-4, wherein a) and b) are within a liposome.

7. The composition of any one of 1-4, wherein a) and b) are within a particle.

8. The composition of any one of 1-7, comprising one or more of: a buffer, a nuclease inhibitor, and a protease inhibitor.

9. The composition of any one of 1-8, wherein the archaeal Cas9 polypeptide comprises an amino acid sequence having 85% or more identity to the amino acid sequence set forth in SEQ ID NO:71 or SEQ ID NO:72.

10. The composition of any one of 1-9, wherein the archaeal Cas9 polypeptide is a nickase that can cleave only one strand of a double-stranded target nucleic acid molecule.

11. The composition of any one of 1-9, wherein the archaeal Cas9 polypeptide is a catalytically inactive archaeal Cas9 polypeptide (dead archaeal Cas9).

12. The composition of 10 or 11, wherein the archaeal Cas9 polypeptide comprises one or more mutations at a position corresponding to those selected from: D672, E769, and D935 of SEQ ID NO:71.

13. The composition of any one of 1-12, further comprising a DNA donor template.

14. A archaeal Cas9 single guide RNA molecule, comprising:
   a) a targeter sequence comprising a guide sequence that hybridizes to a target nucleic acid, and a duplex-forming segment; and
   b) an activator sequence that hybridizes with the duplex-forming segment of the targeter sequence to form a double stranded RNA (dsRNA) duplex that can bind a archaeal Cas9 polypeptide.

15. The archaeal Cas9 single guide RNA molecule of 14, wherein the guide sequence has a length of from 19 to 30 nucleotides.

16. A DNA molecule comprising a nucleotide sequence encoding the archaeal Cas9 single guide RNA molecule of 14 or 15.

17. The DNA molecule of 16, wherein the nucleotide sequence encoding the archaeal Cas9 single guide RNA is operably linked to a promoter.

18. The DNA molecule of 17, wherein the promoter is functional in a eukaryotic cell.

19. The DNA molecule of 18, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

20. The DNA molecule of any one of 17-19, wherein the promoter is one or more of: a constitutive promoter, an inducible promoter, a cell type-specific promoter, and a tissue-specific promoter.

21. The DNA molecule of any one of 16-20, wherein the DNA molecule is a recombinant expression vector.

22. The DNA molecule of 21, wherein the recombinant expression vector is a recombinant adenoassociated viral vector, a recombinant retroviral vector, or a recombinant lentiviral vector.

23. The DNA molecule of 17, wherein the promoter is functional in a prokaryotic cell.

24. An archaeal Cas9 fusion polypeptide comprising: a archaeal Cas9 polypeptide fused to a heterologous polypeptide.

25. The archaeal Cas9 fusion polypeptide of 24, wherein the archaeal Cas9 polypeptide comprises an amino acid sequence having 50% or more identity to the amino acid sequence set forth in SEQ ID NO:71 or SEQ ID NO:72.

26. The archaeal Cas9 fusion polypeptide of 24, wherein the archaeal Cas9 polypeptide comprises an amino acid sequence having 85% or more identity to the amino acid sequence set forth in SEQ ID NO:71 or SEQ ID NO:72.

27. The archaeal Cas9 fusion polypeptide of any one of 24-27, wherein the archaeal Cas9 polypeptide is a nickase that can cleave only one strand of a double-stranded target nucleic acid molecule.

28. The archaeal Cas9 fusion polypeptide of any one of 24-27, wherein the archaeal Cas9 polypeptide is a catalytically inactive archaeal Cas9 Polypeptide (dead archaeal Cas9).

29. The archaeal Cas9 fusion polypeptide of 27 or 28, wherein the archaeal Cas9 polypeptide comprises one or more mutations at a position corresponding to those selected from: D672, E769, and D935 of SEQ ID NO:71.

30. The archaeal Cas9 fusion polypeptide of any one of 24-29, wherein the heterologous polypeptide is fused to the N-terminus and/or the C-terminus of the archaeal Cas9 polypeptide.

31. The archaeal Cas9 fusion polypeptide of any one of 24-30, comprising an NLS.

32. The archaeal Cas9 fusion polypeptide of any one of 24-31, wherein the heterologous polypeptide is a targeting polypeptide that provides for binding to a cell surface moiety on a target cell or target cell type.

33. The archaeal Cas9 fusion polypeptide of any one of 24-31, wherein the heterologous polypeptide exhibits an enzymatic activity that modifies target DNA.

34. The archaeal Cas9 fusion polypeptide of 33, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

35. The archaeal Cas9 fusion polypeptide of 34, wherein the heterologous polypeptide exhibits an one or more enzymatic activities selected from: nuclease activity, methyltransferase activity, demethylase activity, deamination activity, depurination activity, integrase activity, transposase activity, and recombinase activity.

36. The archaeal Cas9 fusion polypeptide of any one of 24-31, wherein the heterologous polypeptide exhibits an enzymatic activity that modifies a target polypeptide associated with a target nucleic acid.

37. The archaeal Cas9 fusion polypeptide of 36, wherein the heterologous polypeptide exhibits histone modification activity.

38. The archaeal Cas9 fusion polypeptide of 36 or 37, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

39. The archaeal Cas9 fusion polypeptide of 38, wherein the heterologous polypeptide exhibits an one or more enzymatic activities selected from: methyltransferase activity, demethylase activity, acetyltransferase activity, and deacetylase activity.

40. The archaeal Cas9 fusion polypeptide of any one of 24-31, wherein the heterologous polypeptide is an endosomal escape polypeptide.

41. The archaeal Cas9 fusion polypeptide of 40, wherein the endosomal escape polypeptide comprises an amino acid sequence selected from: GLFXALLXLLXSLWXLLLXA (SEQ ID NO:94), and GLFHALLHLLHSLWHLLLHA (SEQ ID NO:95), wherein each X is independently selected from lysine, histidine, and arginine.

42. The archaeal Cas9 fusion polypeptide of any one of 24-31, wherein the heterologous polypeptide is a chloroplast transit peptide.

43. The archaeal Cas9 fusion polypeptide of 42, wherein the chloroplast transit peptide comprises an amino acid sequence selected from

```
                                    (SEQ ID NO: 83)
MASMISSSAVTTVSRASRGQSAAMAPFGGLKSMTGFPVRKVNTDITSITS

NGGRVKCMQVWPPIGKKKFETLSYLPPLTRDSRA;

(SEQ ID NO: 84)
MASMISSSAVTTVSRASRGQSAAMAPFGGLKSMTGFPVRKVNTDITSITS

NGGRVKS;

(SEQ ID NO: 85)
MASSMLSSATMVASPAQATMVAPFNGLKSSAAFPATRKANNDITSITSNG

GRVNCMQVWPPIEKKKFETLSYLPDLTDSGGRVNC;

(SEQ ID NO: 86)
MAQVSRICNGVQNPSLISNLSKSSQRKSPLSVSLKTQQHPRAYPISSSWG

LKKSGMTLIGSELRPLKVMSSVSTAC;

(SEQ ID NO: 87)
MAQVSRICNGVWNPSLISNLSKSSQRKSPLSVSLKTQQHPRAYPISSSWG

LKKSGMTLIGSELRPLKVMSSVSTAC;

(SEQ ID NO: 88)
MAQINNMAQGIQTLNPNSNFHKPQVPKSSSFLVFGSKKLKNSANSMLVLK

KDSIFMQLFCSFRISASVATAC;

(SEQ ID NO: 89)
MAALVTSQLATSGTVLSVTDRFRRPGFQGLRPRNPADAALGMRTVGASAA

PKQSRKPHRFDRRCLSMVV;
```

-continued

```
                                    (SEQ ID NO: 90)
MAALTTSQLATSATGFGIADRSAPSSLLRHGFQGLKPRSPAGGDATSLSV

TTSARATPKQQRSVQRGSRRFPSVVVC;

(SEQ ID NO: 91)
MASSVLSSAAVATRSNVAQANMVAPFTGLKSAASFPVSRKQNLDITSIAS

NGGRVQC;

(SEQ ID NO: 92)
MESLAATSVFAPSRVAVPAARALVRAGTVVPTRRTSSTSGTSGVKCSAAV

TPQASPVISRSAAAA;
and (SEQ ID NO: 93)
MGAAATSMQSLKFSNRLVPPSRRLSPVPNNVTCNNLPKSAAPVRTVKCCA

SSWNSTINGAAATTNGASAASS.
```

44. The archaeal Cas9 fusion polypeptide of any one of 24-31, wherein the heterologous polypeptide is protein that increases or decreases transcription.

45. The archaeal Cas9 fusion polypeptide of 44, wherein the heterologous polypeptide is a transcriptional repressor domain.

46. The archaeal Cas9 fusion polypeptide of 44, wherein the heterologous polypeptide is a transcriptional activation domain.

47. The archaeal Cas9 fusion polypeptide of any one of 24-31, wherein the heterologous polypeptide is a protein biding domain.

48. A nucleic acid molecule encoding the archaeal Cas9 fusion polypeptide of any one of 24-47.

49. The nucleic acid molecule of 48, wherein the nucleotide sequence encoding the archaeal Cas9 fusion polypeptide is operably linked to a promoter.

50. The nucleic acid molecule of 49, wherein the promoter is functional in a eukaryotic cell.

51. The nucleic acid molecule of 50, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

52. The nucleic acid molecule of any one of 49-51, wherein the promoter is one or more of: a constitutive promoter, an inducible promoter, a cell type-specific promoter, and a tissue-specific promoter.

53. The nucleic acid molecule of any one of 48-52, wherein the DNA molecule is a recombinant expression vector.

54. The nucleic acid molecule of 53, wherein the recombinant expression vector is a recombinant adenoassociated viral vector, a recombinant retroviral vector, or a recombinant lentiviral vector.

55. The nucleic acid molecule of 49, wherein the promoter is functional in a prokaryotic cell.

56. The nucleic acid molecule of 48, wherein the nucleic acid molecule is an mRNA.

57. One or more nucleic molecules encoding:
(a) a archaeal Cas9 guide RNA comprising an activator RNA and a targeter RNA; and
(b) a archaeal Cas9 polypeptide.

58. The one or more nucleic acid molecules of 57, wherein the archaeal Cas9 polypeptide comprises an amino acid sequence having 50% or more identity to the amino acid sequence set forth in SEQ ID NO:71 or SEQ ID NO:72.

59. The one or more nucleic acid molecules of 57, wherein the archaeal Cas9 polypeptide comprises an amino acid sequence having 85% or more identity to the amino acid sequence set forth in SEQ ID NO:71 or SEQ ID NO:72.

60. The one or more nucleic acid molecules of any one of 57-59, wherein the archaeal Cas9 guide RNA is a single guide RNA.

61. The one or more nucleic acid molecules of any one of 57-59, wherein the archaeal Cas9 guide RNA is a dual-guide RNA.

62. The one or more nucleic acid molecules of 61, wherein said one or more nucleic acid molecules comprises a first nucleotide sequence encoding the activator and a second nucleotide sequence encoding the targeter, and wherein said first and second nucleotide sequences are present on different DNA molecules.

63. The one or more nucleic acid molecules of any one of 57-62, wherein said one or more nucleic acid molecules comprises a nucleotide sequence encoding the archaeal Cas9 polypeptide that is operably linked to a promoter.

64. The one or more nucleic acid molecules of 63, wherein the promoter is functional in a eukaryotic cell.

65. The one or more nucleic acid molecules of 64, wherein the promoter is functional in one or more of: a plant cell, a fungal cell, an animal cell, cell of an invertebrate, a fly cell, a cell of a vertebrate, a mammalian cell, a primate cell, a non-human primate cell, and a human cell.

66. The one or more nucleic acid molecules of any one of 63-65, wherein the promoter is one or more of: a constitutive promoter, an inducible promoter, a cell type-specific promoter, and a tissue-specific promoter.

67. The one or more nucleic acid molecules of any one of 57-66, wherein the one or more nucleic acid molecules is one or more recombinant expression vectors.

68. The one or more nucleic acid molecules of 67, wherein the one or more recombinant expression vectors are selected from: one or more adenoassociated viral vectors, one or more recombinant retroviral vectors, or one or more recombinant lentiviral vectors.

69. The one or more nucleic acid molecules of 63, wherein the promoter is functional in a prokaryotic cell.

70. A eukaryotic cell comprising one or more of:
a) a archaeal Cas9 polypeptide, or a nucleic acid molecule encoding the archaeal Cas9 polypeptide,
b) a archaeal Cas9 fusion polypeptide, or a nucleic acid molecule encoding the archaeal Cas9 fusion polypeptide, and
c) a archaeal Cas9 guide RNA, or a nucleic acid molecule encoding the archaeal Cas9 guide RNA.

71. The eukaryotic cell of 70, comprising the nucleic acid molecule encoding the archaeal Cas9 polypeptide, wherein said nucleic acid molecule is integrated into the genomic DNA of the cell.

72. The eukaryotic cell of 70 or 71, wherein the eukaryotic cell is a plant cell, a mammalian cell, an insect cell, an arachnid cell, a fungal cell, a bird cell, a reptile cell, an amphibian cell, an invertebrate cell, a mouse cell, a rat cell, a primate cell, a non-human primate cell, or a human cell.

73. A cell comprising a archaeal Cas9 fusion polypeptide, or a nucleic acid molecule encoding the archaeal Cas9 fusion polypeptide.

74. The cell of 73, wherein the cell is a prokaryotic cell.

75. The cell of 73 or 74, comprising the nucleic acid molecule encoding the archaeal Cas9 fusion polypeptide, wherein said nucleic acid molecule is integrated into the genomic DNA of the cell.

76. A method of modifying a target nucleic acid, the method comprising contacting the target nucleic acid with:
a) a archaeal Cas9 polypeptide; and
b) a archaeal Cas9 guide RNA comprising a guide sequence that hybridizes to a target sequence of the target nucleic acid, wherein said contacting results in modification of the target nucleic acid by the archaeal Cas9 polypeptide.

77. The method of 76, wherein said modification is cleavage of the target nucleic acid.

78. The method of 76 or 77, wherein the target nucleic acid is selected from: double stranded DNA, single stranded DNA, RNA, genomic DNA, and extrachromosomal DNA.

79. The method of any of 76-78, wherein said contacting takes place in vitro outside of a cell.

80. The method of any of 76-78, wherein said contacting takes place inside of a cell in culture.

81. The method of any of 76-78, wherein said contacting takes place inside of a cell in vivo.

82. The method of 80 or 81, wherein the cell is a eukaryotic cell.

83. The method of 82, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

84. The method of 80 or 81, wherein the cell is a prokaryotic cell.

85. The method of any one of 76-84, wherein said contacting results in genome editing.

86. The method of any one of 76-85, wherein said contacting comprises: introducing into a cell: (a) the archaeal Cas9 polypeptide, or a nucleic acid molecule encoding the archaeal Cas9 polypeptide, and (b) the archaeal Cas9 guide RNA, or a nucleic acid molecule encoding the archaeal Cas9 guide RNA.

87. The method of 86, wherein said contacting further comprises: introducing a DNA donor template into the cell.

88. The method of any one of 76-87, wherein the archaeal Cas9 guide RNA is a single guide RNA.

89. The method of any one of 76-87, wherein the archaeal Cas9 guide RNA is a dual guide RNA.

90. A method of modulating transcription from a target DNA, modifying a target nucleic acid, or modifying a protein associated with a target nucleic acid, the method comprising contacting the target nucleic acid with:
a) a archaeal Cas9 fusion polypeptide comprising a archaeal Cas9 polypeptide fused to a heterologous polypeptide; and
b) a archaeal Cas9 guide RNA comprising a guide sequence that hybridizes to a target sequence of the target nucleic acid.

91. The method of 90, wherein the archaeal Cas9 guide RNA is a single guide RNA.

92. The method of 90, wherein the archaeal Cas9 guide RNA is a dual guide RNA.

93. The method of any of 90-92, wherein said modification is not cleavage of the target nucleic acid.

94. The method of any of 90-93, wherein the target nucleic acid is selected from: double stranded DNA, single stranded DNA, RNA, genomic DNA, and extrachromosomal DNA.

95. The method of any of 90-94, wherein said contacting takes place in vitro outside of a cell.

96. The method of any of 90-94, wherein said contacting takes place inside of a cell in culture.

97. The method of any of 90-94, wherein said contacting takes place inside of a cell in vivo.

98. The method of 96 or 97, wherein the cell is a eukaryotic cell.

99. The method of 98, wherein the cell is selected from: a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

100. The method of 96 or 97, wherein the cell is a prokaryotic cell.

101. The method of any one of 90-100, wherein said contacting comprises: introducing into a cell: (a) the archaeal Cas9 fusion polypeptide, or a nucleic acid molecule encoding the archaeal Cas9 fusion polypeptide, and (b) the archaeal Cas9 guide RNA, or a nucleic acid molecule encoding the archaeal Cas9 guide RNA.

102. The method of any one of 90-101, wherein the archaeal Cas9 polypeptide is a catalytically inactive archaeal Cas9 Polypeptide (dead archaeal Cas9).

103. The method of any one of 90-102, wherein the archaeal Cas9 polypeptide comprises one or more mutations at a position corresponding to those selected from: D672, E769, and D935 of SEQ ID NO:71.

104. The method of any one of 90-103, wherein the heterologous polypeptide exhibits an enzymatic activity that modifies target DNA.

105. The method of 104, wherein the heterologous polypeptide exhibits an one or more enzymatic activities selected from: nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity and glycosylase activity.

106. The method of 105, wherein the heterologous polypeptide exhibits an one or more enzymatic activities selected from: nuclease activity, methyltransferase activity, demethylase activity, deamination activity, depurination activity, integrase activity, transposase activity, and recombinase activity.

107. The method of any one of 90-103, wherein the heterologous polypeptide exhibits an enzymatic activity that modifies a target polypeptide associated with a target nucleic acid.

108. The method of 107, wherein the heterologous polypeptide exhibits histone modification activity.

109. The method of 107 or 108, wherein the heterologous polypeptide exhibits an one or more enzymatic activities selected from: methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, glycosylation activity (e.g., from O-GlcNAc transferase) and deglycosylation activity.

110. The method of 109, wherein the heterologous polypeptide exhibits an one or more enzymatic activities selected from: methyltransferase activity, demethylase activity, acetyltransferase activity, and deacetylase activity.

111. The method of any one of 90-103, wherein the heterologous polypeptide is protein that increases or decreases transcription.

112. The method of 111, wherein the heterologous polypeptide is a transcriptional repressor domain.

113. The method of 111, wherein the heterologous polypeptide is a transcriptional activation domain.

114. The method of any one of 90-103, wherein the heterologous polypeptide is a protein biding domain.

115. A transgenic, multicellular, non-human organism whose genome comprises a transgene comprising a nucleotide sequence encoding one or more of:
   a) a archaeal Cas9 polypeptide,
   b) a archaeal Cas9 fusion polypeptide, and
   c) a archaeal Cas9 guide RNA.

116. The transgenic, multicellular, non-human organism of 115, wherein the archaeal Cas9 polypeptide comprises an amino acid sequence having 50% or more amino acid sequence identity to the amino acid sequence set forth in SEQ ID NO:71 or SEQ ID NO:72.

117. The transgenic, multicellular, non-human organism of 115, wherein the archaeal Cas9 polypeptide comprises an amino acid sequence having 85% or more amino acid sequence identity to the amino acid sequence set forth in SEQ ID NO:71 or SEQ ID NO:72.

118. The transgenic, multicellular, non-human organism of any one of 115-117, wherein the organism is a plant, a monocotyledon plant, a dicotyledon plant, an invertebrate animal, an insect, an arthropod, an arachnid, a parasite, a worm, a cnidarian, a vertebrate animal, a fish, a reptile, an amphibian, an ungulate, a bird, a pig, a horse, a sheep, a rodent, a mouse, a rat, or a non-human primate.

119. A system comprising:
   a) a archaeal Cas9 polypeptide and a archaeal Cas9 single guide RNA;
   b) a archaeal Cas9 polypeptide, a archaeal Cas9 guide RNA, and a DNA donor template;
   c) a archaeal Cas9 fusion polypeptide and a archaeal Cas9 guide RNA;
   d) a archaeal Cas9 fusion polypeptide, a archaeal Cas9 guide RNA, and a DNA donor template;
   e) an mRNA encoding a archaeal Cas9 polypeptide, and a archaeal Cas9 single guide RNA;
   f) an mRNA encoding a archaeal Cas9 polypeptide; a archaeal Cas9 guide RNA, and a DNA donor template;
   g) an mRNA encoding a archaeal Cas9 fusion polypeptide, and a archaeal Cas9 guide RNA;
   h) an mRNA encoding a archaeal Cas9 fusion polypeptide, a archaeal Cas9 guide RNA, and a DNA donor template;
   i) one or more recombinant expression vectors comprising: i) a nucleotide sequence encoding a archaeal Cas9 polypeptide; and ii) a nucleotide sequence encoding a archaeal Cas9 guide RNA;
   j) one or more recombinant expression vectors comprising: i) a nucleotide sequence encoding a archaeal Cas9 polypeptide; ii) a nucleotide sequence encoding a archaeal Cas9 guide RNA; and iii) a DNA donor template;
   k) one or more recombinant expression vectors comprising: i) a nucleotide sequence encoding a archaeal Cas9 fusion polypeptide; and ii) a nucleotide sequence encoding a archaeal Cas9 guide RNA; and
   l) one or more recombinant expression vectors comprising: i) a nucleotide sequence encoding a archaeal Cas9 fusion polypeptide; ii) a nucleotide sequence encoding a archaeal Cas9 guide RNA; and a DNA donor template.

120. The archaeal Cas9 system of 119, wherein the archaeal Cas9 polypeptide comprises an amino acid sequence having 50% or more amino acid sequence identity to the amino acid sequence set forth in SEQ ID NO:71 or SEQ ID NO:72.

121. The archaeal Cas9 system of 119, wherein the archaeal Cas9 polypeptide comprises an amino acid sequence having 85% or more amino acid sequence identity to the amino acid sequence set forth in SEQ ID NO:71 or SEQ ID NO:72.

122. The archaeal Cas9 system of any of 119-121, wherein the donor template nucleic acid has a length of from 8 nucleotides to 1000 nucleotides.

123. The archaeal Cas9 system of any of 119-121, wherein the donor template nucleic acid has a length of from 25 nucleotides to 500 nucleotides.

124. A kit comprising the archaeal Cas9 system of any one of 119-123.

125. The kit of 124, wherein the components of the kit are in the same container.

126. The kit of 124, wherein the components of the kit are in separate containers.

127. A sterile container comprising the archaeal Cas9 system of any one of 119-126.

128. The sterile container of 127, wherein the container is a syringe.

129. An implantable device comprising the archaeal Cas9 system of any one of 119-126.

130. The implantable device of 129, wherein the archaeal Cas9 system is within a matrix.

131. The implantable device of 129, wherein the archaeal Cas9 system is in a reservoir.

132. Any one of aspects 1-131 (Set B), wherein the archaeal Cas9 protein is an ARMAN-1 Cas9 protein or an ARMAN-4 Cas9 protein.

133. Any one of aspects 1-131 (Set B), wherein the archaeal Cas9 protein is a Candidatus Micrarchaeum acidiphilum Cas9 protein or a Candidatus Parvarchaeum acidiphilum Cas9 protein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

The work described herein includes an analysis of metagenomic samples of microbial communities from groundwater, sediments, and acid mine drainage. New Class 2 CRISPR-Cas systems were identified that are not represented among cultured organisms.

FIGS. 3A-3B. CasX domains and similarity searches. FIG. 3A Schematic domain representation for CasX inferred from distant homolog alignments with AcCpf1, using HHpred. Conserved catalytic residues are marked by red bars above the proteins. CasX contains a RuvC split domain in the C-terminal region (RuvC-I, RuvC-II, and RuvC-III), and a large novel N-terminal domain. Below the schematic are displayed top hits based on the following searches: (1) BLAST search against all the proteins in NCBI (NR database, including model and environmental proteins). (2) Profile hidden markov model (HMM) search based on models built using all the Cas proteins described in Makarova et al. Nat Rev Microbiol. 2015 November; 13(11):722-36, and Shmakov et al. Mol Cell. 2015 Nov. 5; 60(3):385-97). (3) Distant homolog search based on HHpred. Hits are color-coded based on their significance, and the hit range and E-value is provided. Notably, CasX had only local hits. The 620 N-terminal amino acid of CasX had no hit in any of the search schemes. Combined, these finding indicate CasX is a new Cas protein. FIG. 3B Two different CasX-containing CRISPR loci scaffolds were constructed from sequence data, the top is from a Deltaproteobacter (CasX1) and the bottom is from a Planctomycetes (CasX2). The corresponding DNA sequence is set forth as SEQ ID NOs: 51 and 52, respectively.

Example 2

Figure 4A:
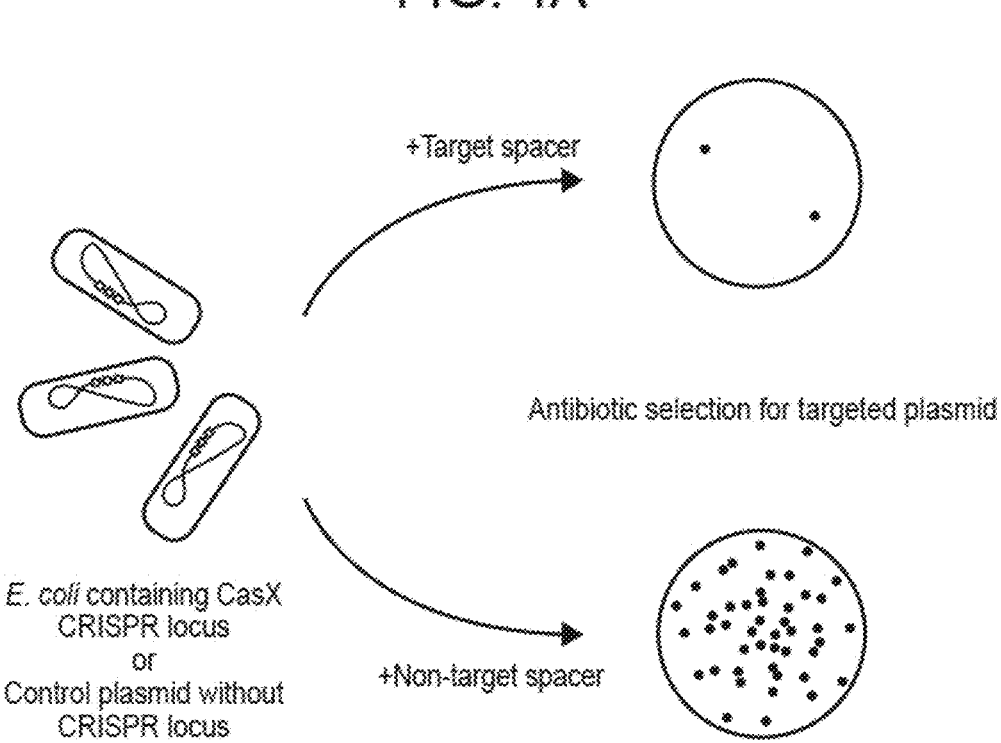
Figure 4B:
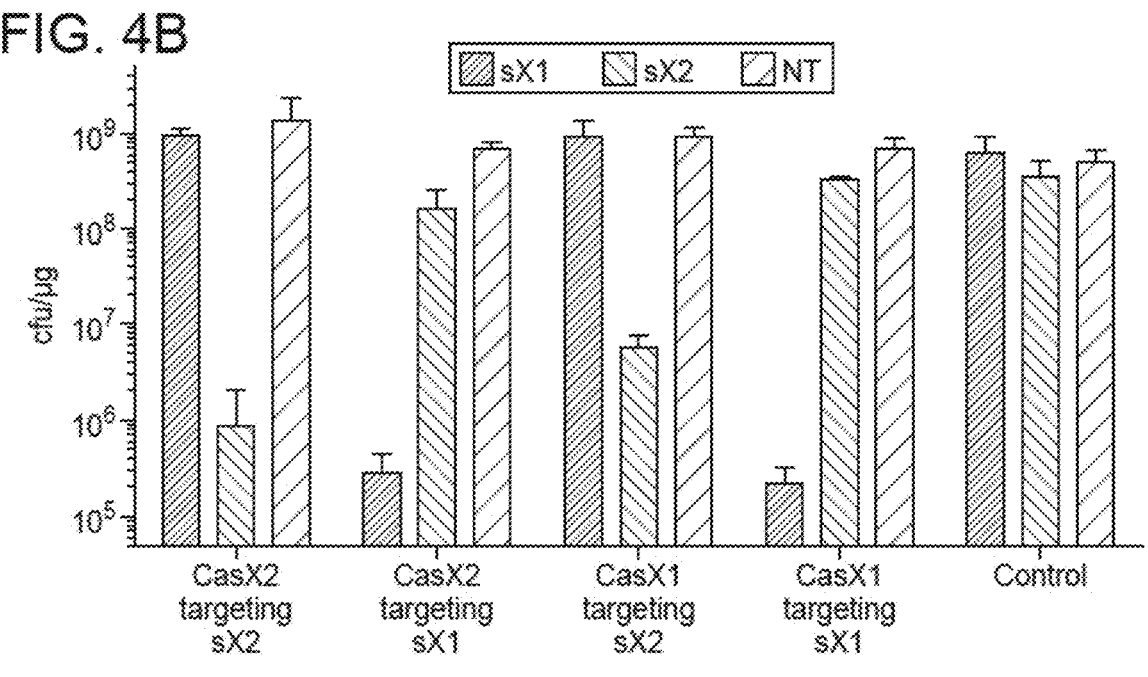

FIGS. 4A-4C. Plasmid Interference by CasX expressed in *E. coli*. Experimental design of CasX plasmid interference. Competent *E. coli* cells expressing the minimal interference CasX locus (acquisition proteins removed) were prepared. These cells were transformed with a plasmid containing a match to the spacer in the CasX CRISPR locus (target) or not (non-target) and plated on media containing antibiotic selection for the CRISPR and target plasmid. Successful plasmid interference results in reduced number of transformed colonies for the target plasmid. FIG. 4B cfu/ug of transformed plasmid containing spacer from CasX1 (sX1), spacer from CasX2 (sX2) or a non-target plasmid containing a random 30 nt sequence. FIG. 4C serial dilution was performed of transformants from FIG. 4B on media containing antibiotic selection for both the CRISPR and target plasmid.

Figure 5A:
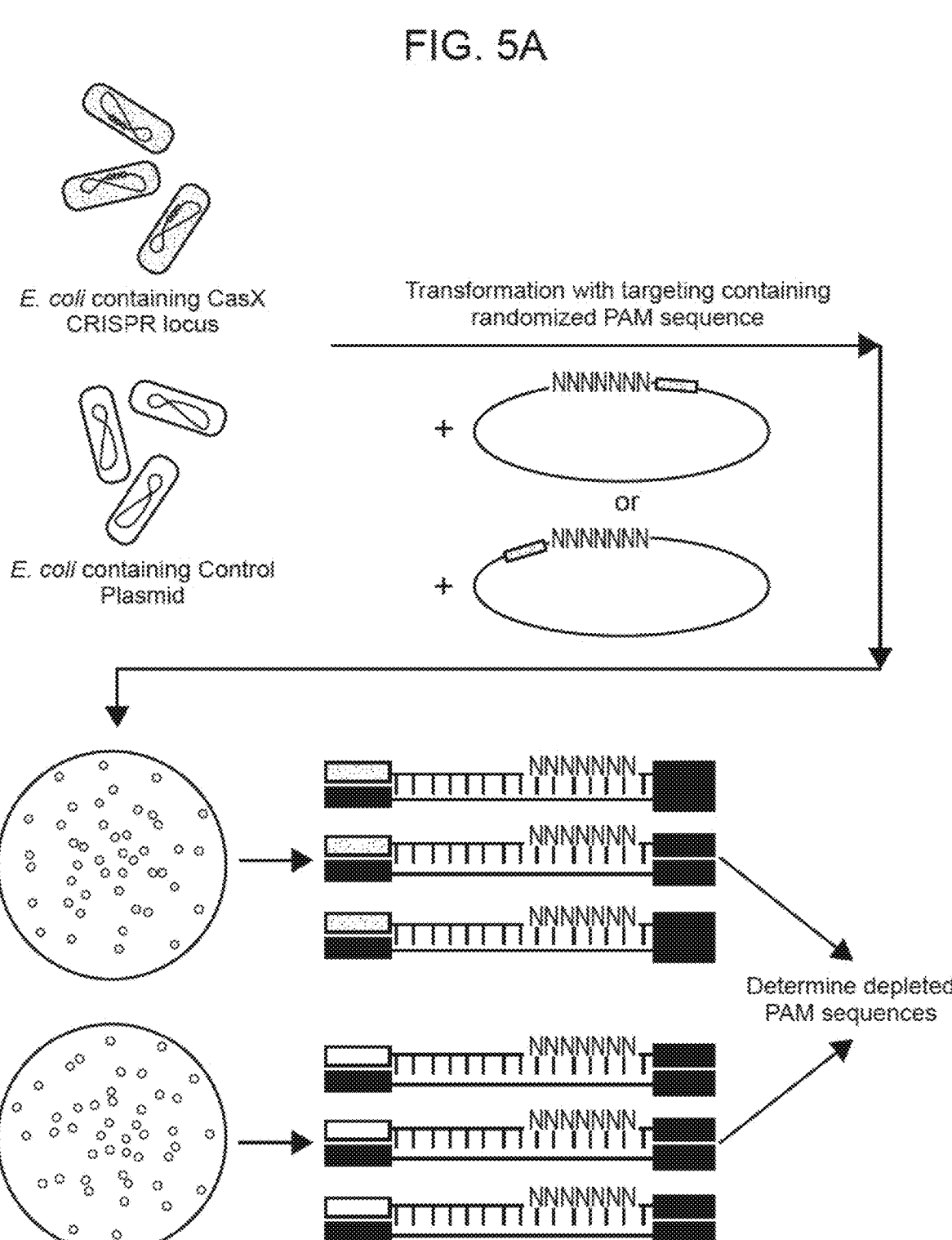
FIGS. 5A-5C depict experiments performed (PAM dependent plasmid interference by CasX) to determine a PAM sequence for CasX.
Figures 5B, 5C:
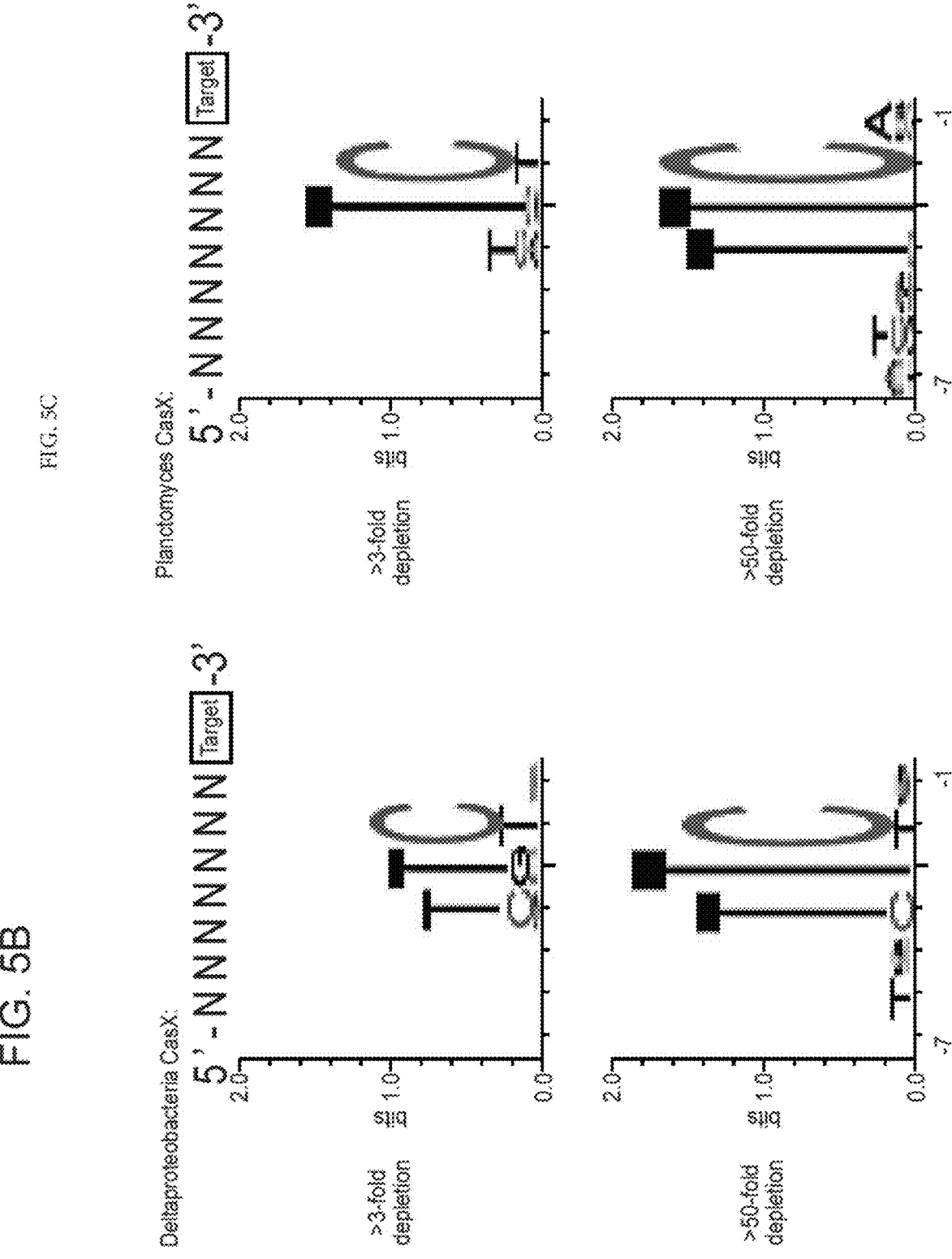

FIGS. 5A-5B PAM dependent plasmid interference by CasX. PAM depletion assays were conducted with CasX. *E. coli* containing the CasX CRISPR locus were transformed with a plasmid library with 7 nucleotides randomized 5' or 3' of the target sequence. The target plasmid was selected for and transformants were pooled. The randomized region was amplified and prepared for deep sequencing. Depleted sequences were identified and used to generate a PAM logo. FIG. 5B PAM logo generated for deltaproteobacteria CasX showed a strong preference for sequences containing a 5'-TTCN-3' flanking sequence 5' of the target. A 3' PAM was not detected. c, PAM logo generated for planctomyces CasX showed a strong preference for sequences containing a 5'-TTCN-3' flanking sequence 5' of the target with lower stringency at the first T. A 3' PAM was not detected.

FIGS. 6A-6C. CasX is a dual-guided CRISPR-Cas effector complex. FIG. 6A CRISPR locus for tracrRNA knockout experiments and sgRNA tests. FIG. 6B colony forming units (cfu) per g of transformed plasmid containing a target or non-target sequence. Deletion of the tracrRNA resulted in ablation of plasmid interference. Expression of a synthetic sgRNA in place of the tracrRNA and CRISPR array resulted in robust plasmid interference by CasX. FIG. 6C diagram of sgRNA design (derived from tracrRNA and crRNA sequences for CasX1). The tracrRNA (green) was joined to the crRNA (repeat, black; spacer, red) by a tetraloop (GAAA; SEQ ID NO:137).

FIG. 7. Schematic of CasX RNA guided DNA interference. CasX binds to a tracrRNA (green) and the crRNA (black, repeat; red, spacer). Base pairing of the guide RNA to the target sequence (blue) containing the correct protospacer adjacent motif (yellow) results in double stranded cleavage of the target DNA. The depicted sequences are derived from tracrRNA and crRNA sequences for CasX1.

Example 3

FIG. 8. Experimental design for editing human cells using CasX. HEK293 cells expressing a destabilized GFP is treated with CasX using either lipofection of plasmid expressing CasX and its guide RNA or nucleofection of CasX preassembled with its guide RNA. Successful genome cleavage will result in indels in the GFP locus causing a loss of fluorescence signal, which can be detected by flow cytometry and/or surveyor assay (e.g., T7E1 assay).

Example 4

FIG. 9. Recombinant expression and purification of CasX. CasX was fused to a maltose binding protein and was expressed in *E. coli*. The lysate was purified over Ni-NTA resin, treated with TEV, purified over a heparin column and size exclusion column. The fractions from the size exclusion column are shown with a molecular weight marker for reference. The calculated size of CasX was ~110 kDa.

Example 5

FIG. 10. Test of various tracrRNA sequences. The tracrRNA sequences tested were as follows (refer to FIG. 7 for a schematic of CasX dual guide RNA):

```
tracrRNA T1:
                              (SEQ ID NO: 24)
AAGUAGUAAAUUACAUCUGGCGCGUUUAUUCCAUUACUUUGGAGCCAGUC

CCAGCGACUAUGUCGUAUGGACGAAGCGCUUAUUUAUCGGAGA tracrRNA T2:
                              (SEQ ID NO: 21)
ACAUCUGGCGCGUUUAUUCCAUUACUUUGGAGCCAGUCCCAGCGACUAUG

UCGUAUGGACGAAGCGCUUAUUUAUCGGAGA tracrRNA T3:
                              (SEQ ID NO: 66)
UUCCAUUACUUUGGAGCCAGUCCCAGCGACUAUGUCGUAUGGACGAAGCG

CUUAUUUAUCGGAGA tracrRNA T4:
                              (SEQ ID NO: 67)
GUCCCAGCGACUAUGUCGUAUGGACGAAGCGCUUAUUUAUCGGAGA tracrRNA T5:
                              (SEQ ID NO: 68)
GAAGCGCUUAUUUAUCGGAGA
```

In addition, the following crRNA sequences were tested for function:

```
crRNA 1 (Processed version of crRNA-was active in
both sgRNA and dual guide format):
                              (SEQ ID NO: 61)
CCGAUAAGUAAAACGCAUCAAAGNNNNNNNNNNNNNNNNNNNNNNNN crRNA 2 (was active in dual guide format):
                              (SEQ ID NO: 62)
AUUUGAAGGUAUCUCCGAUAAGUAAAACGCAUCAAAGNNNNNNNNNNNNNN

NNNNNNNNNNNNNNNNNNNNNNN
```

In addition, the following sgRNA sequences were tested for function (refer to 6 and 7 for a schematic representation of CasX guide RNA):

```
sgRNA1 (was active, sense, processed):
                              (SEQ ID NO: 42)
ACAUCUGGCGCGUUUAUUCCAUUACUUUGGAGCCAGUCCCAGCGACUAU GUCGUAUGGACGAAGCGCUUAUUUAUCGGAGAgaaaCCGAUAAGUAAAA

CGCAUCAAAGNNNNNNNNNNNNNNNNNNNNNNNN sgRNA2 (was inactive, sense, preprocessing, the
underlined sequences are different relative to
sgRNA1):
                              (SEQ ID NO: 63)
AAGUAGUAAAUUACAUCUGGCGCGUUUAUUCCAUUACUUUGGAGCCAGU

CCCAGCGACUAUGUCGUAUGGACGAAGCGCUUAUUUAUCGGAGAUAGCU

CCgaaaAUUUGAAGGUAUCUCCGAUAAGUAAAACGCAUCAAAGNNNNNNN

NNNNNNNNNNNNNNNNNNNNNNNNNNN sgRNA3 (was inactive, antisense, processed):
                              (SEQ ID NO: 64)
NNNNNNNNNNNNNNNNNNNNNNNCUUUGAUGCGUUUUACUUAUCGGgaaaUC

UCCGAUAAAUAAGCGCUUCGUCCAUACGACAUAGUCGCUGGGACUGGCU

CCAAAGUAAUGGAAUAAACGCGCCAGAUGU sgRNA4 (was inactive):
                              (SEQ ID NO: 65)
NNNNNNNNNNNNNNNNNNNNNNNNNNNNNNNNNNNNCUUUGAUGCGUUUUACUUA UCGGAGAUACCUUCAAAUgaaaGGAGCUAUCUCCGAUAAAUAAGCGCUU

CGUCCAUACGACAUAGUCGCUGGGACUGGCUCCAAAGUAAUGGAAUAAA

CGCGCCAGAUGUAAUUUACUACUU
```

Example 6

FIG. 11. The CasX system (CasX protein and guide RNA) was tested for function in bacterial cells at room temperature and at 37° C. Colony forming units (cfu) per g of transformed plasmid were assayed for plasmids containing a target or non-target sequence. The assay was performed at either room temperature or 37° C. The data show that the CasX system functioned to a similar extent at either room temperature or 37° C.

Example 7—Archaeal Cas9

FIGS. 12A-12E. ARMAN-1 type II CRISPR-cas system. FIG. 12A, ARMAN-1 CRISPR-Cas locus outline. FIG. 12B Strong preference to NGG 3' PAM was inferred from analysis of 240 protospacers. FIG. 12C Reconstruction of CRISPR arrays in ARMAN-1 genomes sampled from Richmond Mine ecosystem. Green arrows indicate repeats and colored arrows indicate CRISPR spacers (identical spacers are colored the same whereas unique spacers are colored in black). The contigs (grey bars) are aligned based on the order of the spacers on the metagenomic contigs. The grey background indicates the conserved and presumably old region of the array. In CRISPR systems, spacers are typically added unidirectionally so the high variety of spacers in the left side of the locus indicates that the left side is where recent acquisition has occurred. The presence of a diversity of recently acquired spacers as well as the preservation of repeat and spacer sequences in genome fragments assembled from datasets collected from different sites and at different times indicated that the system is active. FIG. 12D Phylogeny of the ARMAN-1 Cas9 clustered it together with the ARMAN-4 Cas9 and two new bacterial Cas9s first reported here (black). These Cas9s seem to be evolutionary related to Type II-C systems, even though the loci contain Cas4, typically found in Type II-B systems. FIG. 12E Phylogeny of the ARMAN-1 Cas1 clustered it with a different set of Type II-B. Combined, the phylogenetic trees in FIGS. 12D-12E suggest the ARMAN-1 Type II system might be the result of recombination of Type II-B and II-C CRSIPR-Cas systems.

Figure 14A:
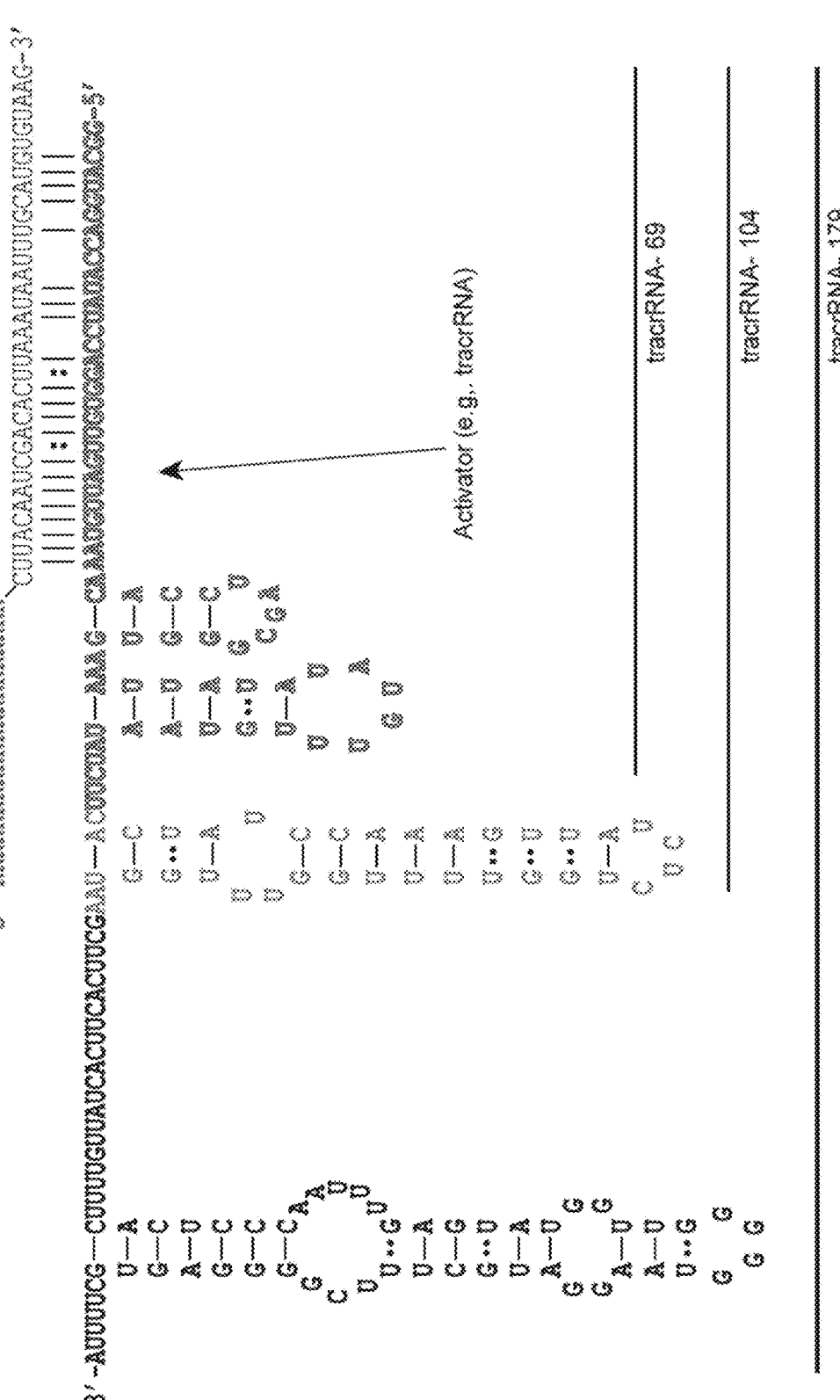
FIGS. 14A-14B present example dual guide (top panel) (top RNA-SEQ ID NO: 73, bottom RNA-SEQ ID NO: 77) and single guide (bottom panel)(SEQ ID NO: 79) formats that can be used with an archaeal Cas9 protein (e.g., ARMAN-1 Cas9).
Figure 14B:
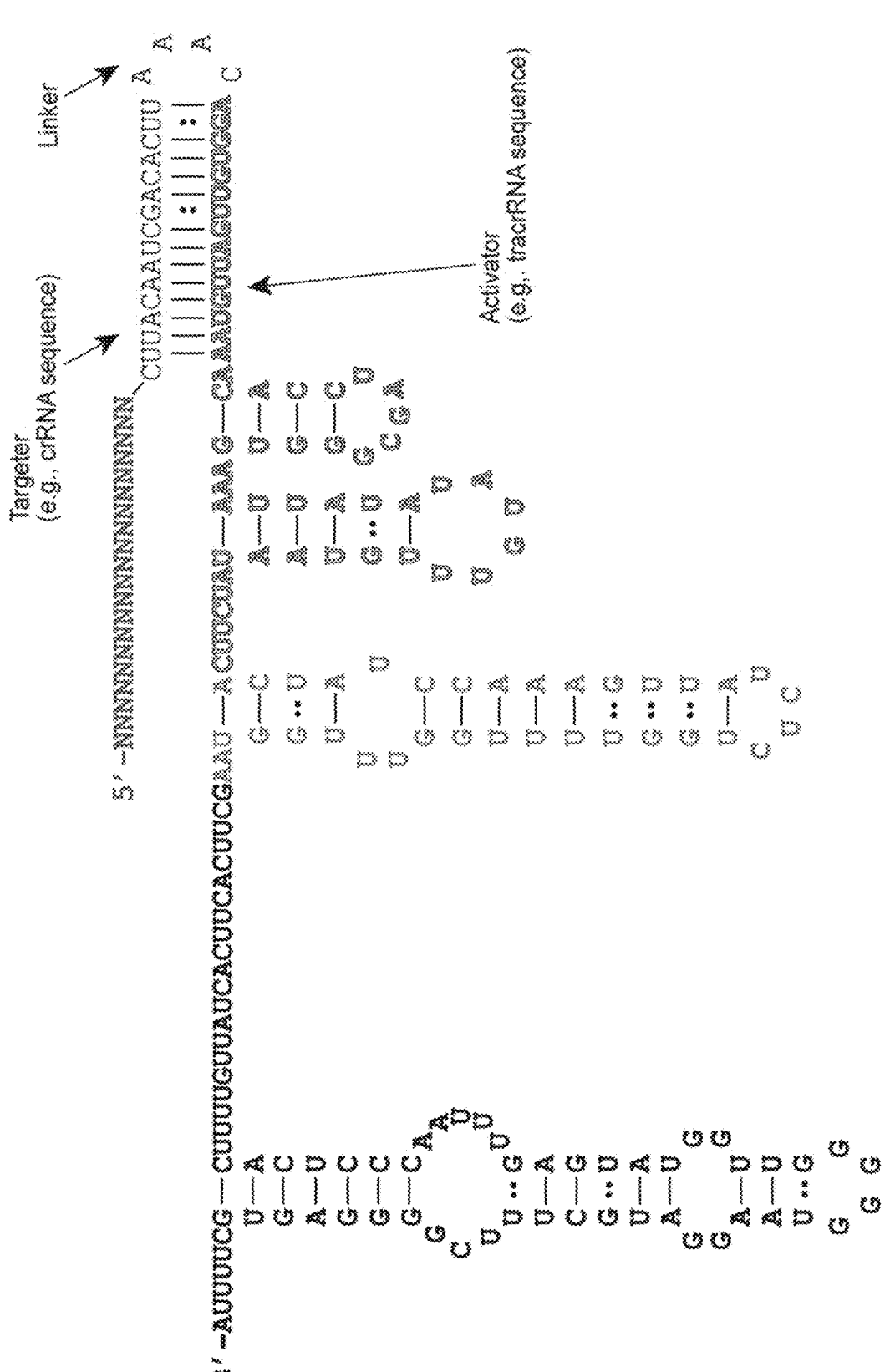

FIGS. 14A-14B. (TOP panel) Predicted secondary structures of crRNA:tracrRNA dual-guide RNA for ARMAN-1 Cas9. Secondary structure and base-pairing between the crRNA (top strand) and predicted tracrRNA sequences of varying lengths (bottom strand) are depicted. The "crRNA" represents the direct repeat sequence from ARMAN-1 while the $N_{20}$ in green is a user-defined sequence (guide sequence). TracrRNA-69 is shown in red while tracrRNA-104 and tracrRNA-179 are extended by the blue and pink sequences, respectively. (BOTTOM panel) Predicted structures of an example single-guide RNA for ARMAN-1 Cas9. Secondary structures of sgRNA is depicted. The "Targeter" represent a partial direct repeat (truncated) and the engineered tetraloop (linker), connecting the targeter to the activator (also truncated). The $N_{20}$ in green is a user-defined sequence (guide sequence). SgRNA including tracrRNA-69, tracrRNA-104, and tracrRNA-179 are depicted.

FIG. 15. (TOP panel) Predicted secondary structures of crRNA:tracrRNA dual-guide RNA for ARMAN-4 Cas9. Secondary structure and base-pairing between the crRNA (top strand) and predicted tracrRNA sequences (bottom strand) are depicted. The "crRNA" represents the direct repeat sequence from ARMAN-4 while the $N_{20}$ in green is a user-defined sequence (guide sequence). (BOTTOM panel) Predicted structure of an example single-guide RNA for ARMAN-4 Cas9. Secondary structures of sgRNA is depicted. The "Targeter" represent a partial direct repeat (truncated) and the engineered tetraloop (linker), connecting the targeter to the activator (also truncated). The $N_{20}$ in green is a user-defined sequence (guide sequence).

Example 8: New CRISPR-Cas Systems from Uncultivated Microbes

CRISPR-Cas adaptive immune systems have revolutionized genome engineering by providing programmable enzymes capable of site-specific DNA cleavage. However, current CRISPR-Cas technologies are based solely on systems from cultured bacteria, leaving untapped the vast majority of enzymes from organisms that have not been isolated. The data provided herein show, using cultivation-independent genome-resolved metagenomics, identification of new CRISPR-Cas systems, including the first reported Cas9 in the archaeal domain of life. This divergent Cas9 enzyme was found in little-studied nanoarchaea as part of an active CRISPR-Cas system. In bacteria, two previously unknown systems were discovered, CRISPR-CasX and CRISPR-CasY, which are among the most streamlined systems yet identified. Notably, all required functional components were identified by metagenomics, which allowed validation of robust RNA-guided DNA interference activity in *E. coli*. The data herein show that interrogation of environmental microbial communities combined with experiments in living cells allows access to an unprecedented diversity of genomes whose content will expand the repertoire of microbe-based biotechnologies.

Results

Figures 18A, 18B:
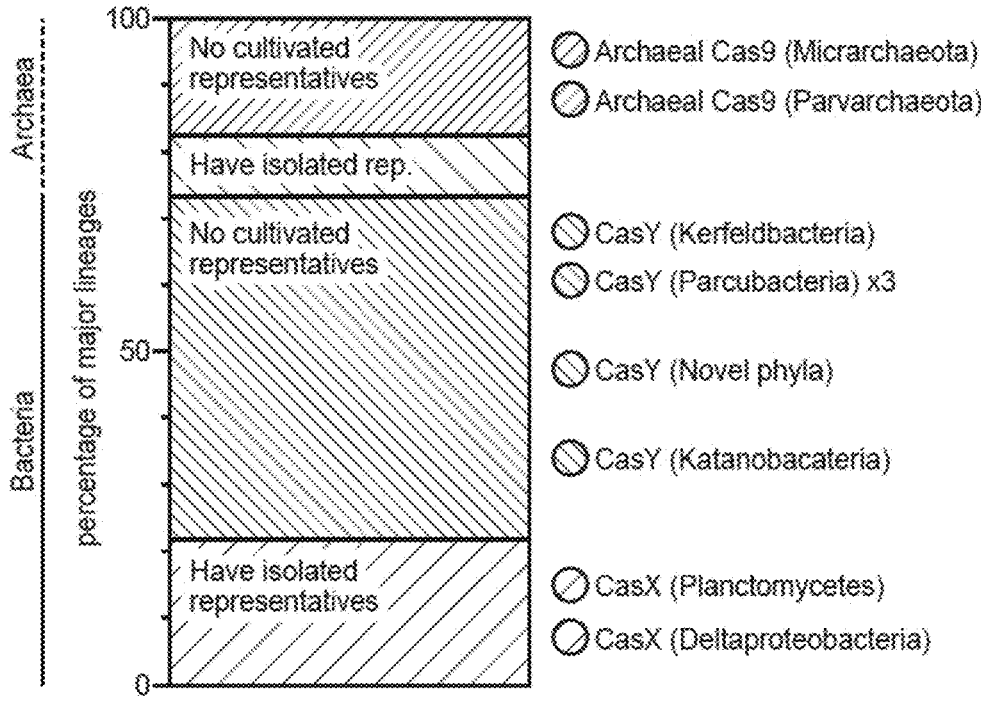
FIGS. 18A-18B present novel identified CRISPR-Cas systems from uncultivated organisms.

Terabase-scale metagenomic datasets from groundwater, sediment, and acid mine drainage microbial communities were analyzed, seeking class 2 CRISPR-Cas systems that are not represented among cultured organisms. The first Cas9 proteins in domain Archaea were identified and two new CRISPR-Cas systems were discovered, CRISPR-CasX and CRISPR-CasY, in uncultivated bacteria (FIGS. 18A-18B). Notably, both the archaeal Cas9 and CasY were encoded exclusively in the genomes of organisms from lineages with no known isolated representatives.

First Identification of Archaeal Cas9

One of the hallmarks of CRISPR-Cas9 was its presumed presence only in the bacterial domain. It was therefore surprising to discover Cas9 proteins encoded in genomes of the nanoarchaea ARMAN-1 (Candidatus Micrarchaeum acidiphilum ARMAN-1) and ARMAN-4 (Candidatus Parvarchaeum acidiphilum ARMAN-4) in acid-mine drainage (AMD) metagenomic datasets. These findings expand the occurrence of Cas9-containing CRISPR systems to another domain of life.

The ARMAN-4 cas9 gene was found in 16 different samples in the same genomic context, but with no other adjacent cas genes (despite being centrally located in several DNA sequence contigs >25 kbp), and with only one adjacent CRISPR repeat-spacer unit (FIGS. 24A-24D). The lack of a typical CRISPR array and cas1, which encodes the universal CRISPR integrase, points to a system with no capacity to acquire new spacers. No target could be identified for the spacer sequence, but given the conservation of the locus in samples collected over several years, its function in a "single-target" CRISPR-Cas system cannot be ruled out at this time.

Conversely, the CRISPR-Cas locus in ARMAN-1, recovered from 15 different samples, includes large CRISPR arrays adjacent to cas1, cas2, cas4 and cas9 genes. Numerous alternative ARMAN-1 CRISPR arrays with a largely conserved end (likely comprised of the oldest spacers) and a variable region into which many distinct spacers have been incorporated were reconstructed (FIG. 19A and FIGS. 25A-25F). Based on this hypervariability in spacer content, these data show that the ARMAN-1 CRISPR-Cas9 system is active in the sampled populations.

Figure 19A:
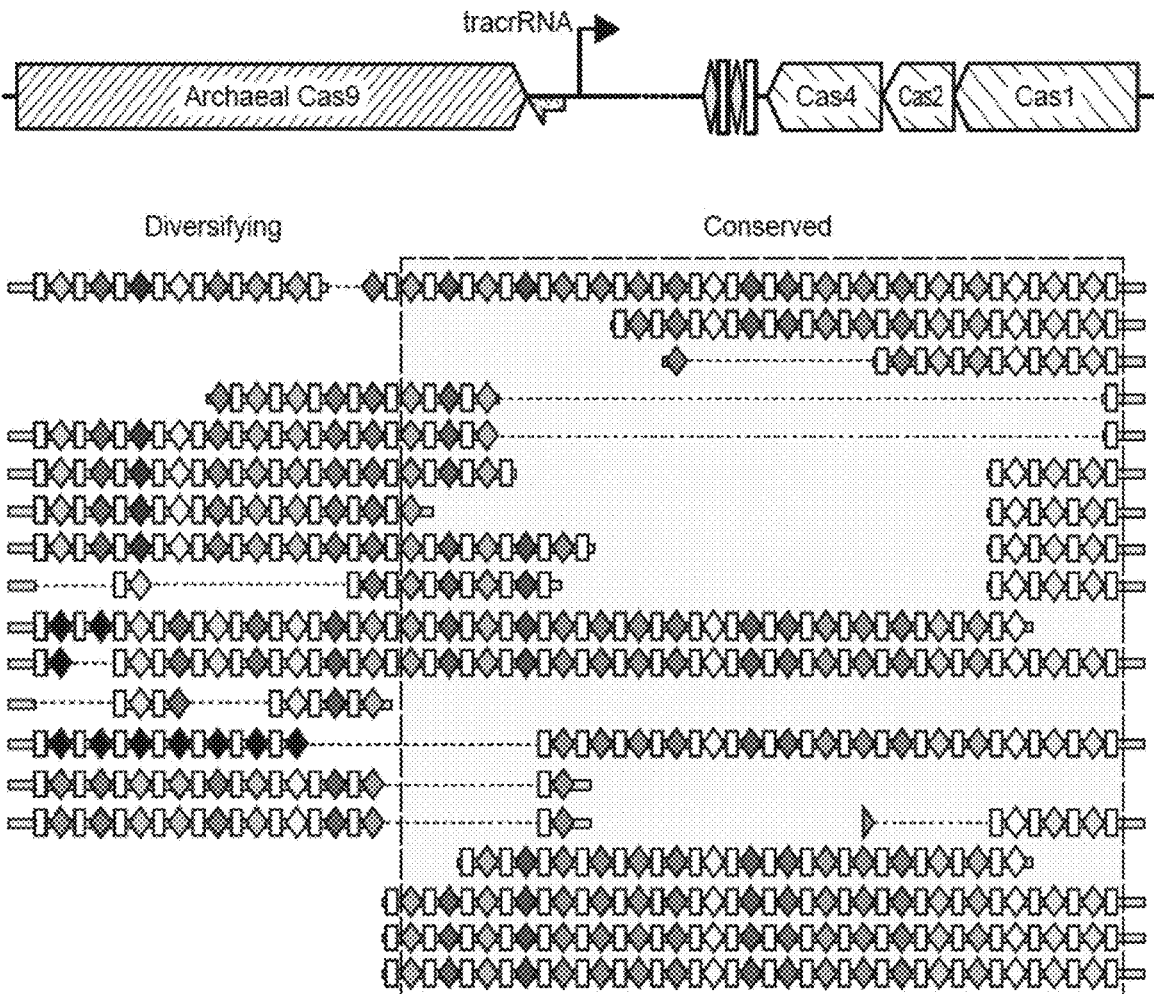
FIGS. 19A-19C present ARMAN-1 CRISPR array diversity and identification of the ARMAN-1 Cas9 PAM sequence.
Figure 19B:
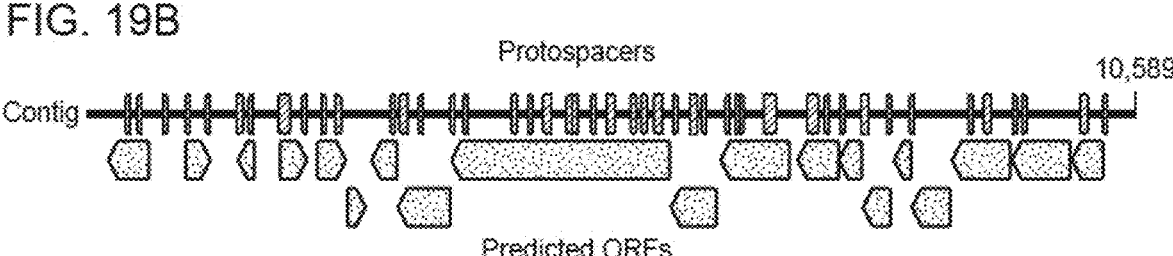

Remarkably, 56 of the putative spacer targets (protospacers) of the ARMAN-1 CRISPR-Cas9 system were located on a single 10 kbp genome fragment that is likely an ARMAN-1 virus, given that it encodes a high density of short hypothetical proteins (FIG. 19B). Indeed, cryo-electron tomographic reconstructions often identified viral particles attached to ARMAN cells. ARMAN-1 protospacers also derived from a putative transposon within the genome of ARMAN-2 (another nanoarchaeon) and a putative mobile element in the genomes of Thermoplasmatales archaea, including that of I-plasma from the same ecosystem (FIG.

26). Direct cytoplasmic "bridges" were observed between ARMAN and Thermoplasmatales cells, implying a close relationship between them. The ARMAN-1 CRISPR-Cas9 may thus defend against transposon propagation between these organisms, a role that is reminiscent of piRNA-mediated defense against transposition in the eukaryotic germ line.

Figure 19C:
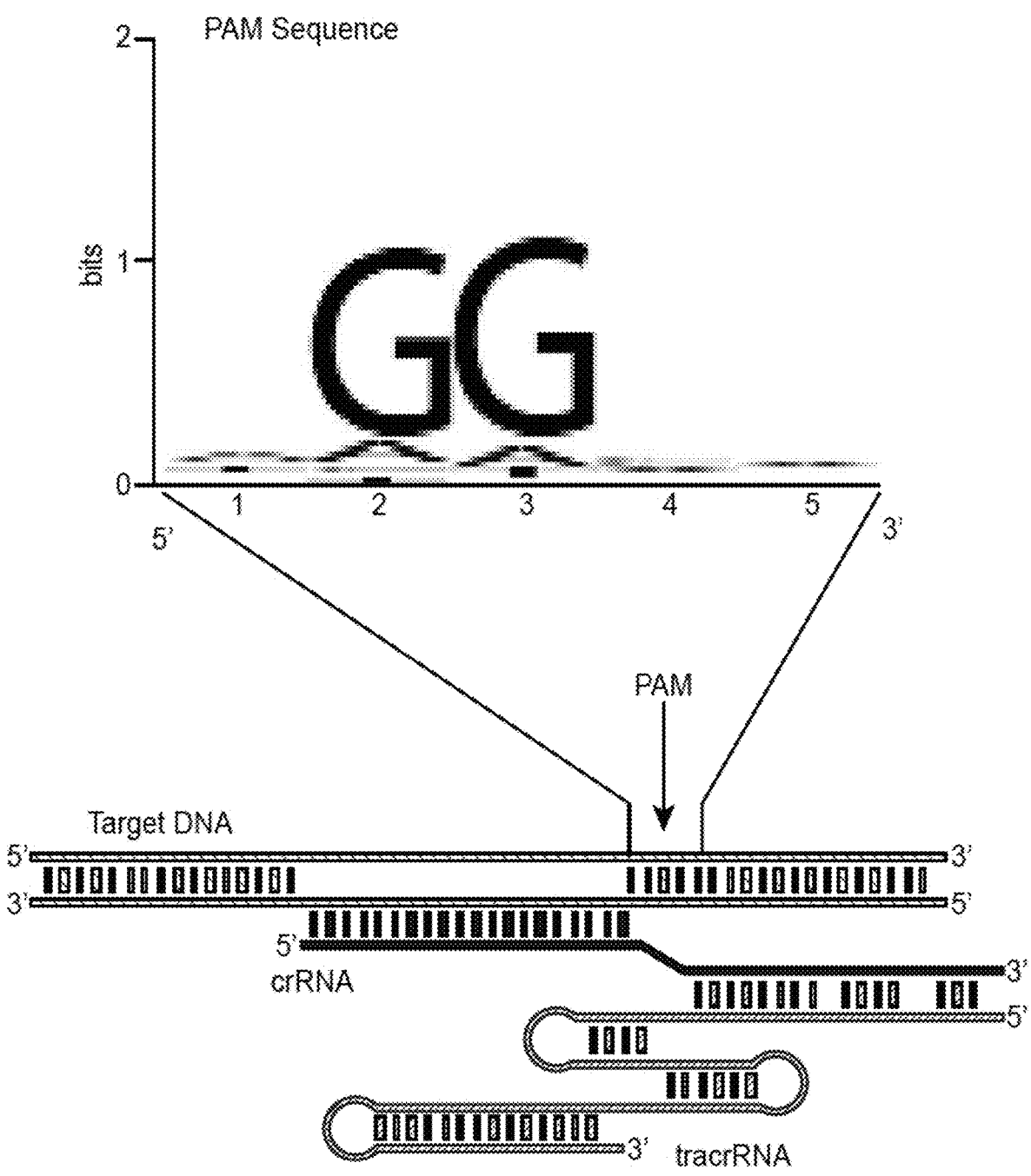
Figure 27A:
FIGS. 27A-27E present predicted secondary structure of ARMAN-1 crRNA and tracrRNA.
Figure 27B:
Figures 27C, 27D, 27E:
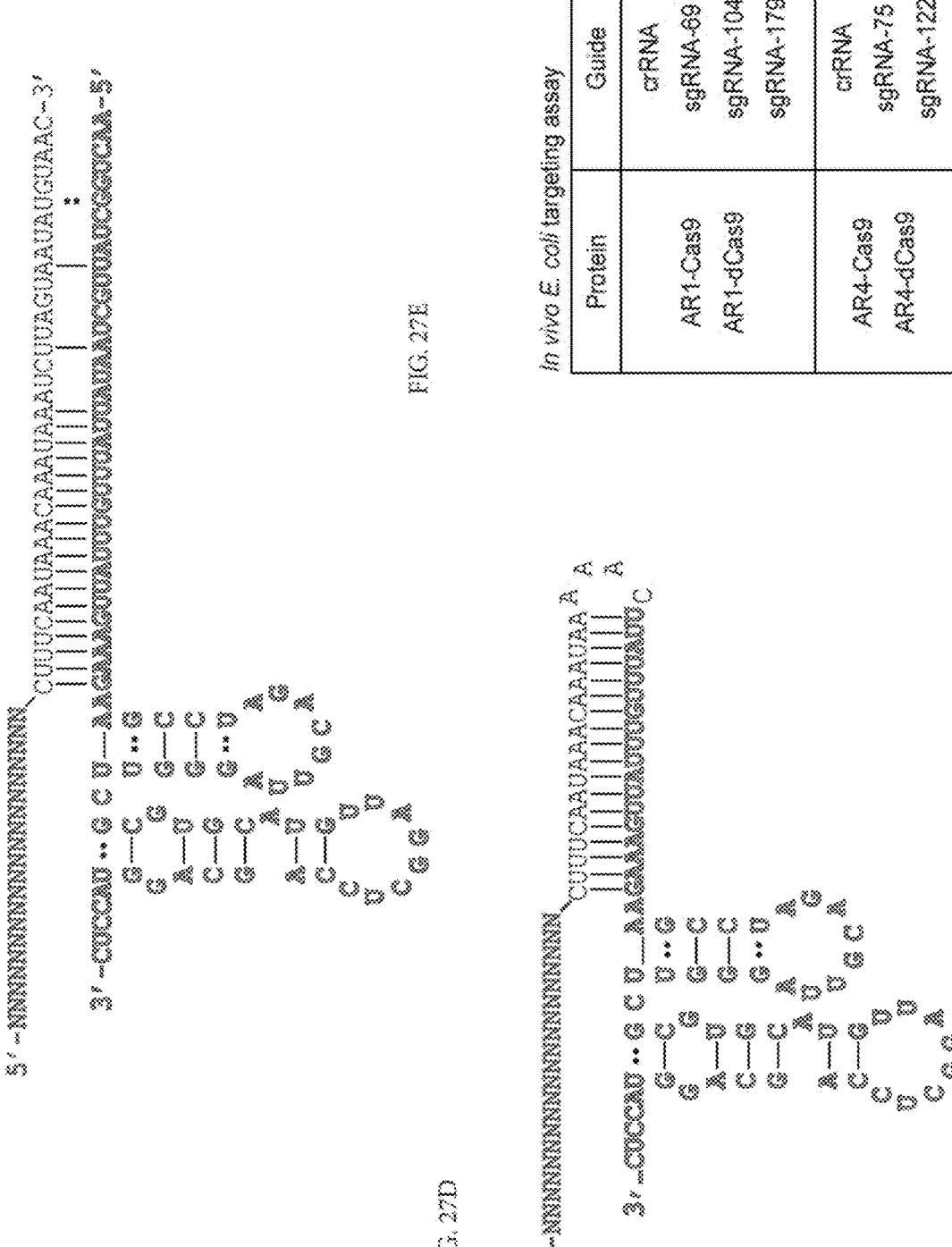

Active DNA-targeting CRISPR-Cas systems use 2 to 4 bp protospacer-adjacent motifs (PAMs) located next to target sequences for self versus non-self discrimination. Examining sequences adjacent to the genomic target sequences indeed revealed a strong 'NGG' PAM preference in ARMAN-1 (FIG. 19c). Cas9 also employs two separate transcripts, CRISPR RNA (crRNA) and trans-activating CRISPR RNA (tracrRNA), for RNA-guided DNA cleavage. A putative tracrRNA was identified in the vicinity of both ARMAN-1 and ARMAN-4 CRISPR-Cas9 systems (FIG. 27). Previously, it was suggested that type II CRISPR systems were absent in archaea due to a lack of the host factor, RNase III, responsible for crRNA-tracrRNA guide complex maturation. Notably, no RNase III homologs have been identified in the ARMAN-1 genome (estimated to be 95% complete) and no internal promoters are predicted for the CRISPR array, suggesting an as-yet undetermined mechanism of guide RNA production. Biochemical experiments to test cleavage activity of ARMAN-1 and ARMAN-4 Cas9 proteins purified from both E. coli and yeast and in vivo E. coli targeting assays did not reveal any detectable activity (see FIG. 32 and FIGS. 28A-28B).

CRISPR-CasX is a New Dual-RNA-Guided CRISPR System

In addition to Cas9, only three families of class 2 Cas effector proteins have been discovered and experimentally validated: Cpf1, C2c1, and C2c2. Another gene, c2c3, which was identified only on small DNA fragments, has been suggested to also encode such a protein family. A new type of class 2 CRISPR-Cas system was found in the genomes of two bacteria recovered repeatedly from groundwater and sediment samples. The high conservation of this system in two organisms belonging to different phyla, Deltaproteobacteria and Planctomycetes, suggests a recent cross-phyla transfer. This newly described system includes Cas1, Cas2, Cas4 and an uncharacterized ~980 aa protein, referred to herein as CasX. The CRISPR arrays associated with each CasX had highly similar repeats of 37 base pairs, spacers of 33-34 base pairs, and a putative tracrRNA between the Cas operon and the CRISPR array (FIG. 18B). BLAST searches revealed only weak similarity (e-value >$1 \times 10^{-4}$) to transposases, with similarity restricted to specific regions of the CasX C-terminus. Distant homology detection and protein modeling identified a RuvC domain near the CasX C-terminal end, with organization reminiscent of that found in type V CRISPR-Cas systems (FIG. 29). The rest of the CasX protein (630 N-terminal amino acids) showed no detectable similarity to any known protein, suggesting this is a novel class 2 effector. The combination of tracrRNA and separate Cas1, Cas2 and Cas4 proteins is unique among type V systems. Further, CasX is considerably smaller than any known type V proteins: 980 aa compared to a typical size of larger than 1,200 aa for Cpf1, C2c1 and C2c3.

Figure 20D:
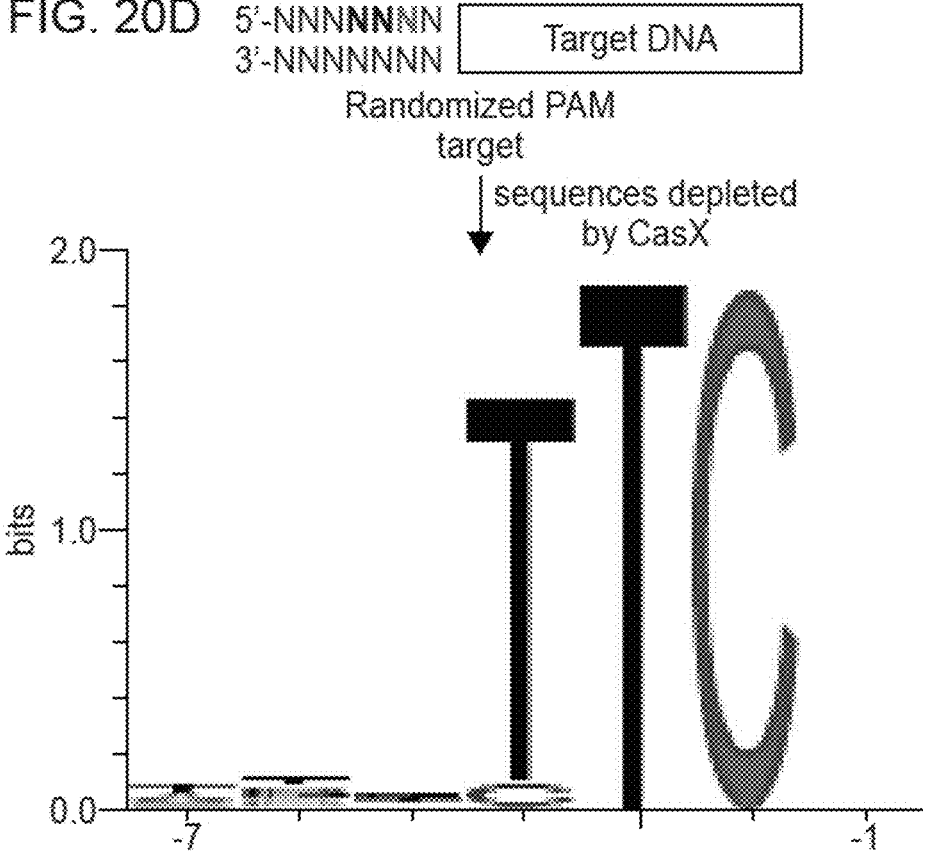

It was next wondered whether, despite its small size and non-canonical locus content, CasX would be capable of RNA-guided DNA targeting analogous to Cas9 and Cpf1 enzymes. To test this possibility, a plasmid encoding a minimal CRISPR-CasX locus including casX, a short repeat-spacer array and intervening noncoding regions was synthesized. When expressed in E. coli, this minimal locus blocked transformation by a plasmid bearing a target sequence identified by metagenomic analysis (FIG. 20A-20C, FIGS. 30A-30F). Furthermore, interference with transformation occurred only when the spacer sequence in the mini-locus matched the protospacer sequence in the plasmid target. To identify a PAM sequence for CasX, the transformation assay was repeated in E. coli using a plasmid containing either a 5' or 3' randomized sequence adjacent to the target site. This analysis revealed a stringent preference for the sequence 'TTCN' located immediately 5' of the protospacer sequence (FIG. 20D). No 3' PAM preference was observed (FIGS. 30A-30F). Consistent with this finding, 'TTCA' was the sequence found upstream of the putative Deltaproteobacteria CRISPR-CasX protospacer that was identified in the environmental samples. Notably, both CRISPR-CasX loci share the same PAM sequence, in line with their high degree of CasX protein homology.

Figure 21A:
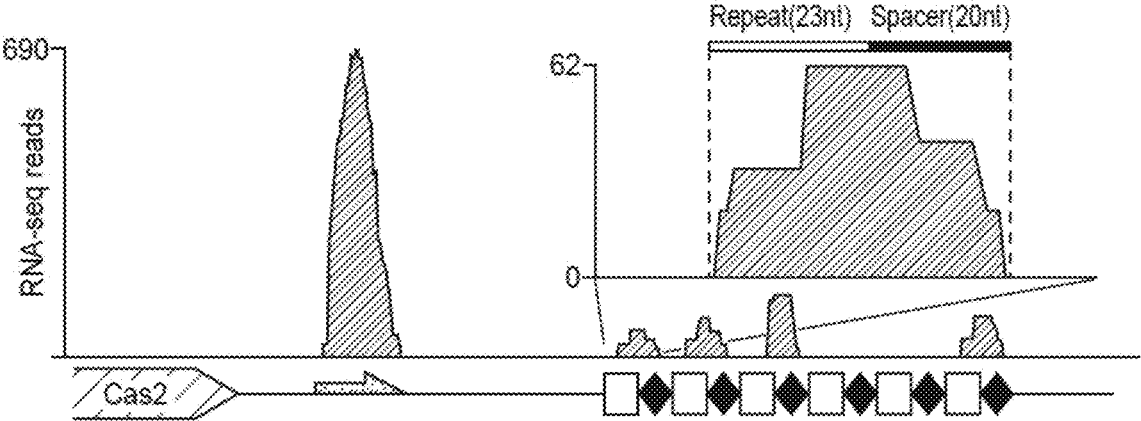
FIGS. 21A-21C present data showing CasX is a dual-guided CRISPR complex.
Figure 21B:
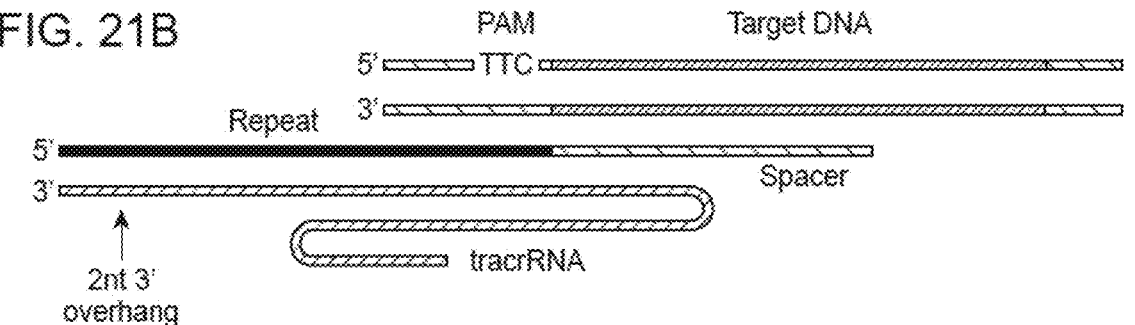
Figure 21C:
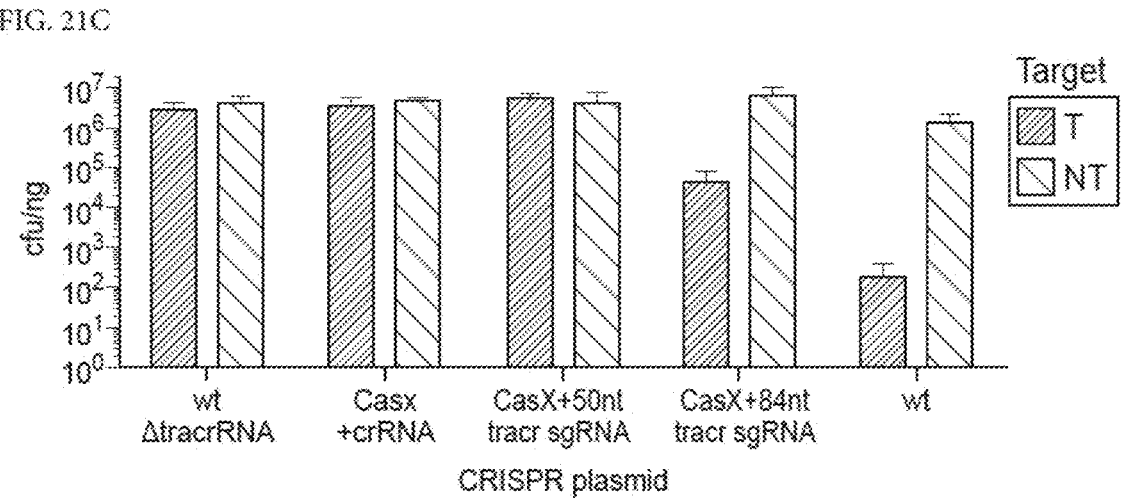

Examples of both single-RNA and dual-RNA guided systems exist among type V CRISPR loci. Environmental meta-transcriptomic data was used to determine whether CasX requires a tracrRNA for DNA targeting activity. This analysis revealed a non-coding RNA transcript with a sequence complementary to the CRISPR repeat encoded between the Cas2 open reading frame and the CRISPR array (FIG. 21A). To check for expression of this non-coding RNA in E. coli expressing the CasX locus, Northern blots were conducted against this transcript in both directions (FIGS. 30A-30F). The results showed expression of a transcript of ~110 nt encoded on the same strand as the casX gene, with a more heterogeneous transcript of ~60-70 nt, suggesting that the leader sequence for the CRISPR array lies between the tracrRNA and the array. Transcriptomic mapping further suggests that the CRISPR RNA (crRNA) is processed to include 22 nts (or about 23 nt) of the repeat and 20 nts of the adjacent spacer, similar to the crRNA processing that occurs in CRISPR-Cas9 systems (FIG. 21A). Furthermore, a 2-nt 3' overhang was identified, consistent with RNase III-mediated processing of the crRNA-tracrRNA duplex (FIG. 21B). To determine the dependence of CasX activity on the putative tracrRNA, this region was deleted from the minimal CRISPR-CasX locus described above, and the plasmid interference assays were repeated. Deletion of the putative tracrRNA-encoding sequence from the CasX plasmid abolished the robust transformation interference observed in its presence (FIG. 21C). This putative tracrRNA was joined with the processed crRNA using a tetraloop to form a single-guide RNA (sgRNA). While expression using a heterologous promoter of the crRNA alone or a shortened version of the sgRNA did not have any significant plasmid interference, expression of the full-length sgRNA conferred resistance to plasmid transformation (FIG. 21C). Together, these results establish CasX as a new functional DNA-targeting, dual-RNA guided CRISPR enzyme. These results further demonstrate that CasX can function as a single-RNA guided CRISPR enzyme.

CRISPR-CasY, a System Found Exclusively in Bacterial Lineages Lacking Isolates

Figure 22A:
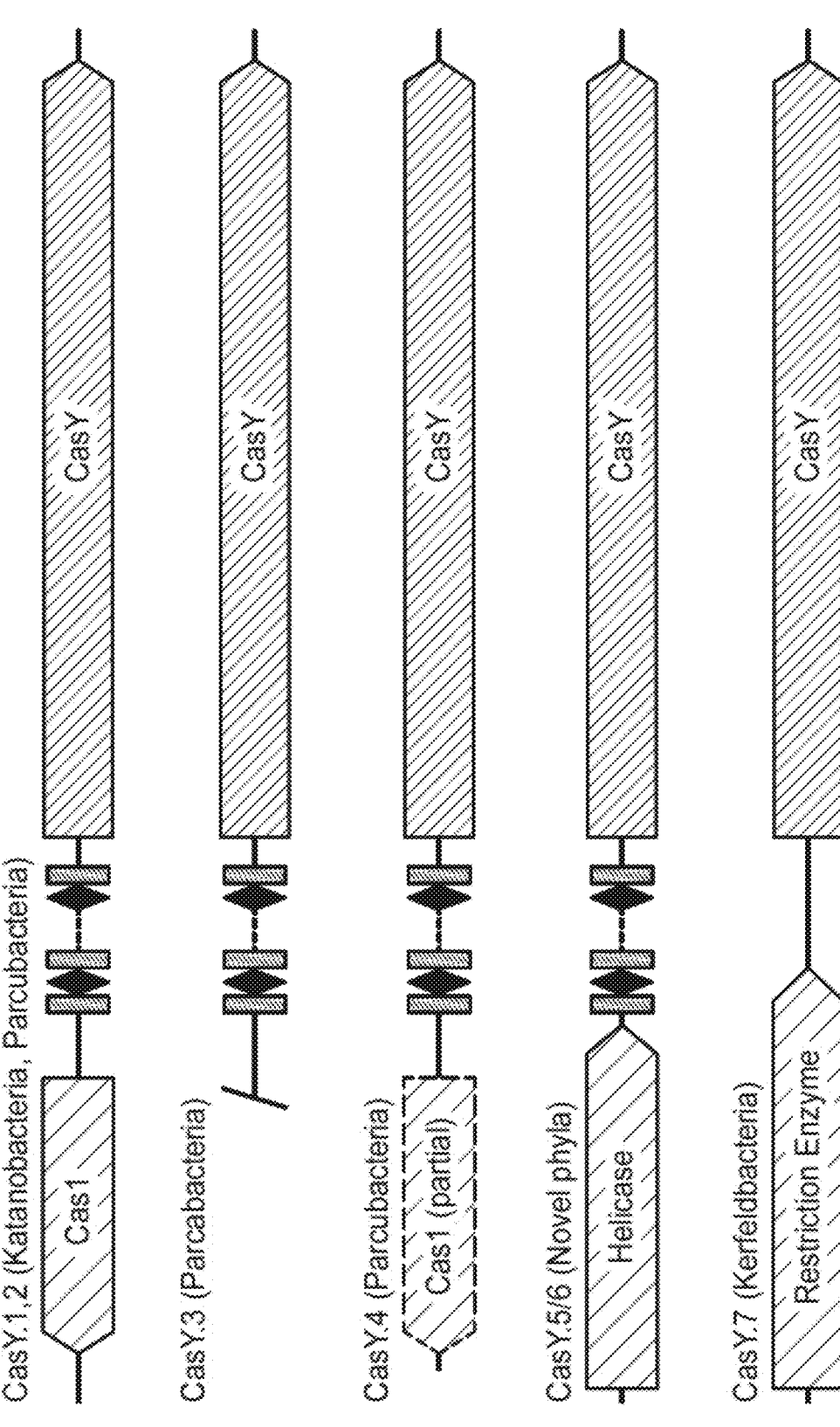
FIGS. 22A-22C present data showing expression of a CasY locus in *E. coli* is sufficient for DNA interference.

Another new class 2 Cas protein encoded in the genomes of certain candidate phyla radiation (CPR) bacteria was identified. These bacteria typically have small cell sizes (based on cryo-TEM data and enrichment via filtration), very small genomes and a limited biosynthetic capacity, indicating they are most likely symbionts. The new ~1,200 aa Cas protein, referred to herein as CasY, appears to be part of a minimal CRISPR-Cas system that includes, at most, Cas1 and a CRISPR array (FIG. 22A). Most of the CRISPR arrays have unusually short spacers of 17-19 nts, but one system, which lacks Cas1 (CasY.5), has longer spacers (27-29 nts). The six examples of CasY proteins identified had no significant sequence similarity to any protein in public databases. A sensitive search using profile models (HMMs) built from published Cas proteins[3,4] indicated that four of the six CasY proteins had local similarities (e-values $4\times10^{-11}$-$3\times10^{-18}$) to C2c3 in the C-terminal region overlapping the RuvC domains and a small region (~45 aa) of the N-terminus (see FIG. 29). C2c3 are putative type V Cas effectors that were identified on short contigs with no taxonomic affiliation, and have not been validated experimentally. Like CasY, the C2c3 were found next to arrays with short spacers and Cas1, but with no other Cas proteins. Notably, two of the CasY proteins identified in the current study had no significant similarity to C2c3, despite sharing significant sequence similarity (best Blast hits: e-values $6\times10^{-85}$, $7\times10^{-75}$) with the other CasY proteins.

Figures 22B, 22C:
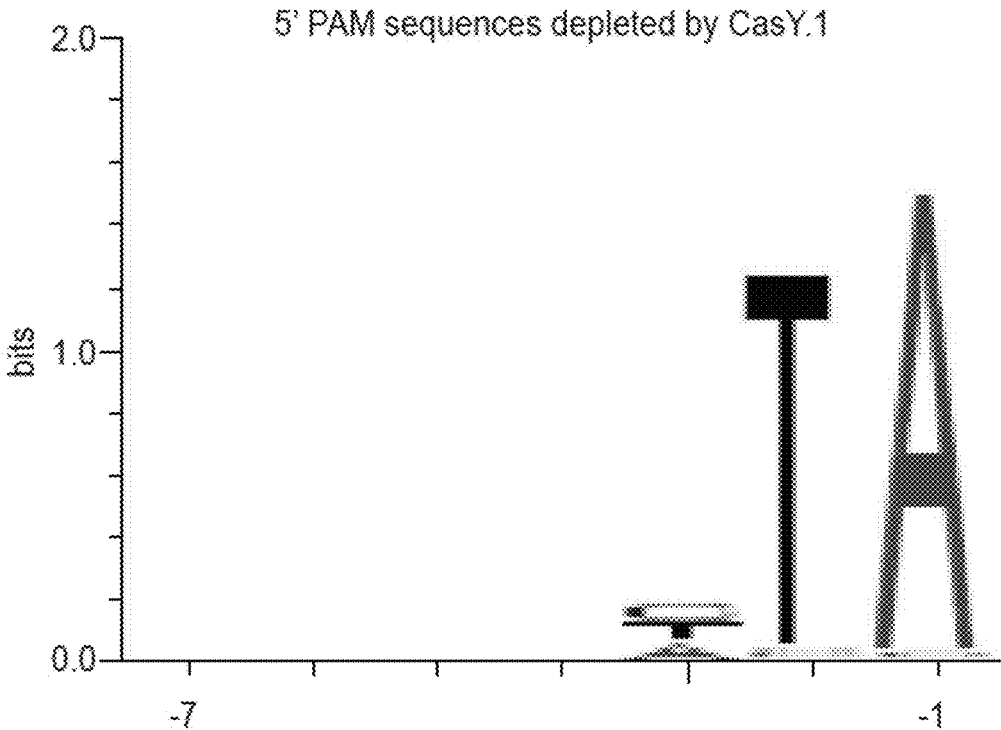

Given the low homology of CRISPR-CasY to any experimentally validated CRISPR loci, it was next wondered whether this system confers RNA-guided DNA interference, but due to the short spacer length reliable information did not exist about a possible PAM motif that might be required for such activity. To work around this, the entire CRISPR-CasY.1 locus was synthesized with a shortened CRISPR array and introduced into *E. coli* on a plasmid vector. These cells were then challenged in a transformation assay using a target plasmid with a sequence matching a spacer sequence in the array and containing an adjacent randomized 5' or 3' region to identify a possible PAM. Analysis of transformants revealed depletion of sequences containing a 5' TA directly adjacent to the targeted sequence (FIG. 22B). Using this identified PAM sequence, the CasY.1 locus was tested against plasmids containing a single PAM. Plasmid interference was demonstrated only in the presence of a target containing the identified 5' TA PAM sequence (FIG. 22C). Thus, these data show that CRISPR-CasY has DNA interference activity.

Discussion

Figure 23A:
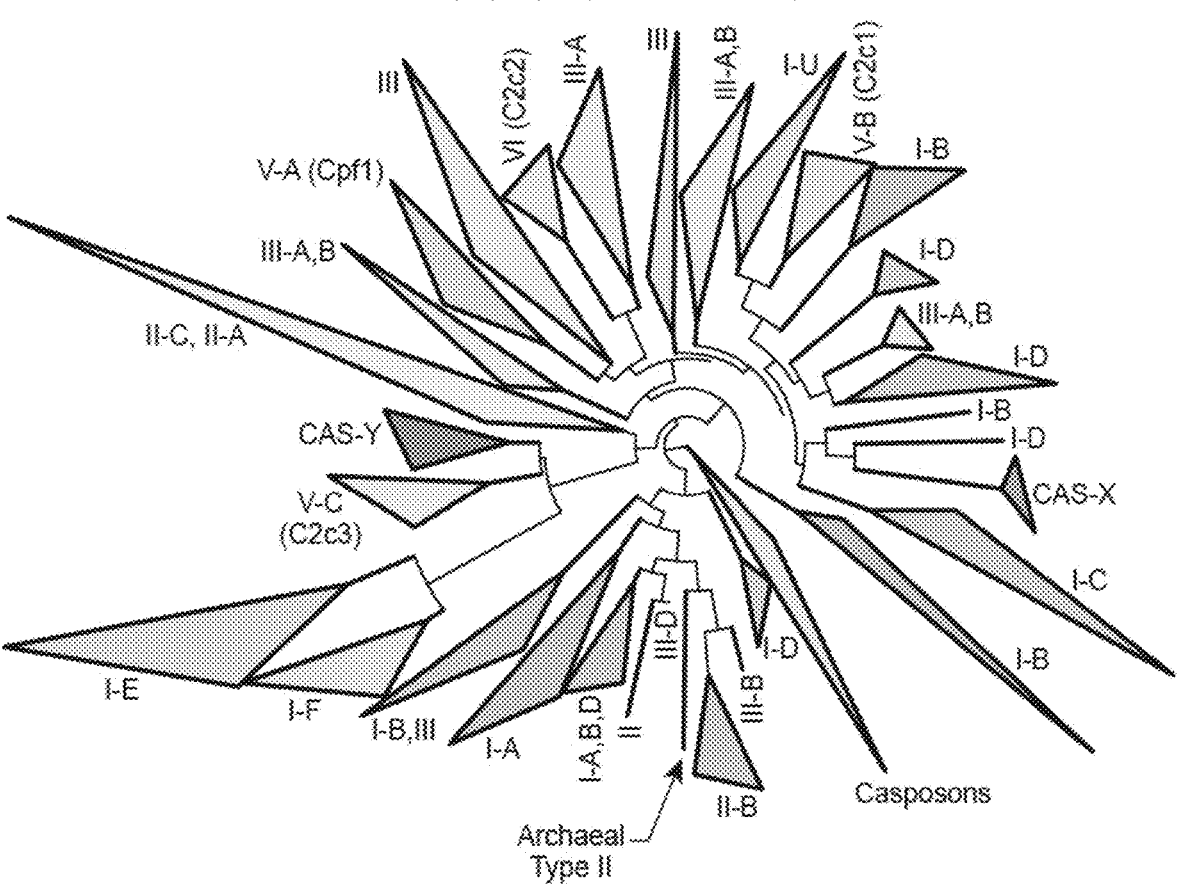
FIGS. 23A-23B present newly identified CRISPR-Cas in context of known systems.
Figure 23B:
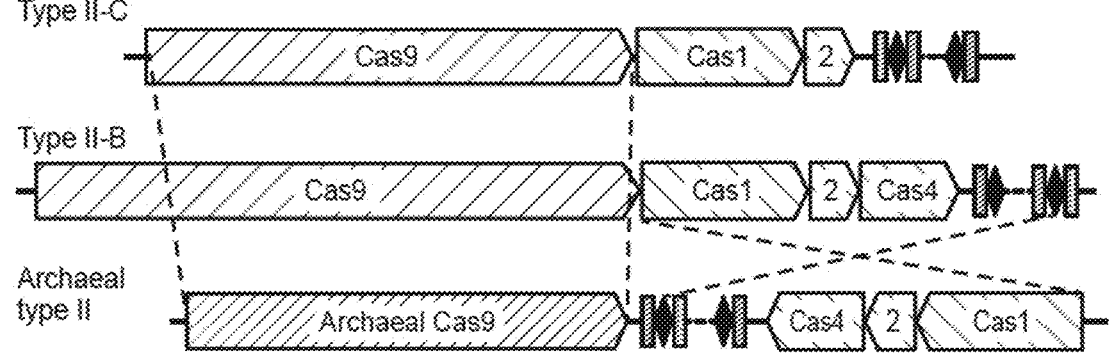
Figure 24A:
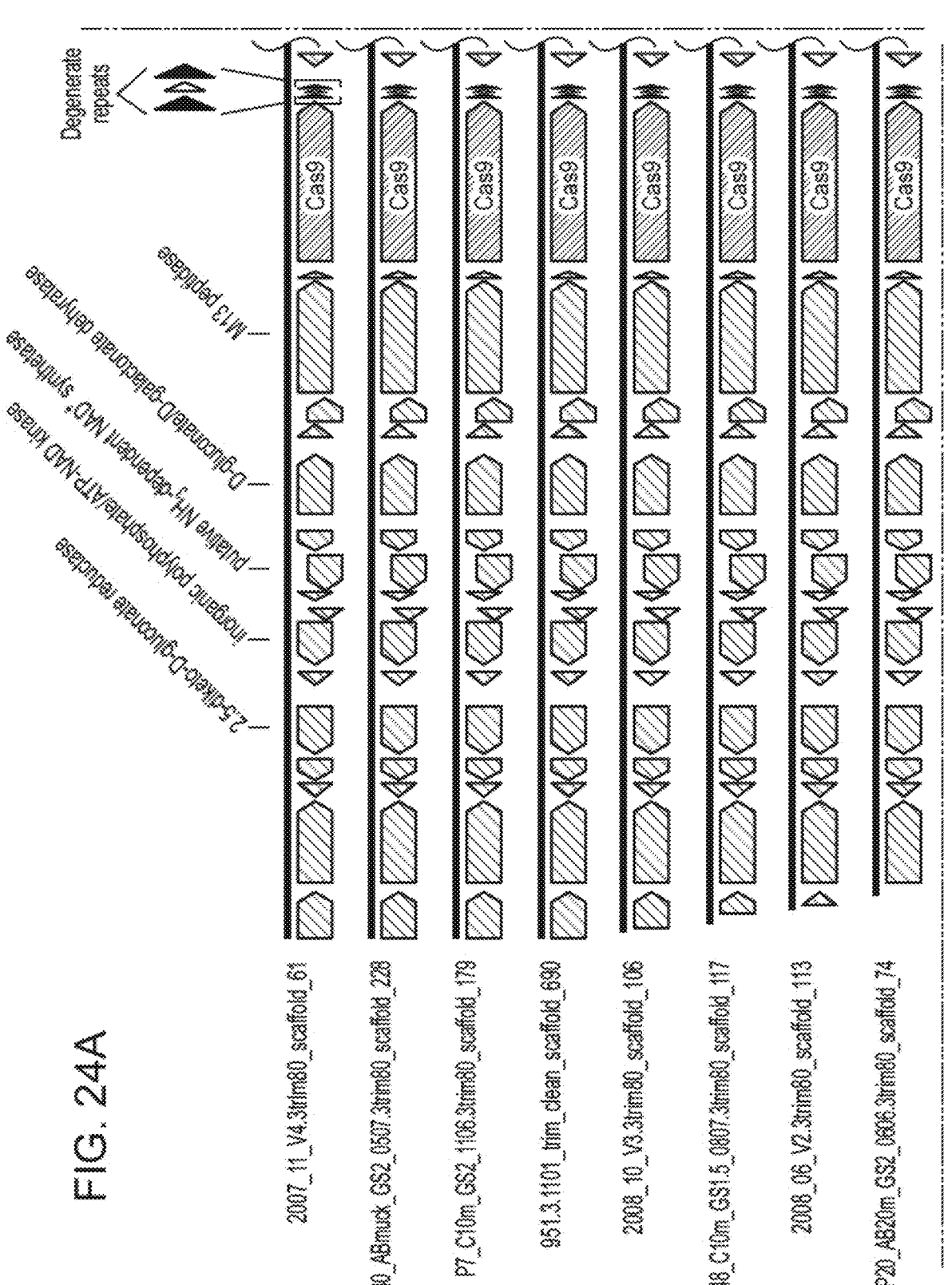
Figure 24B:
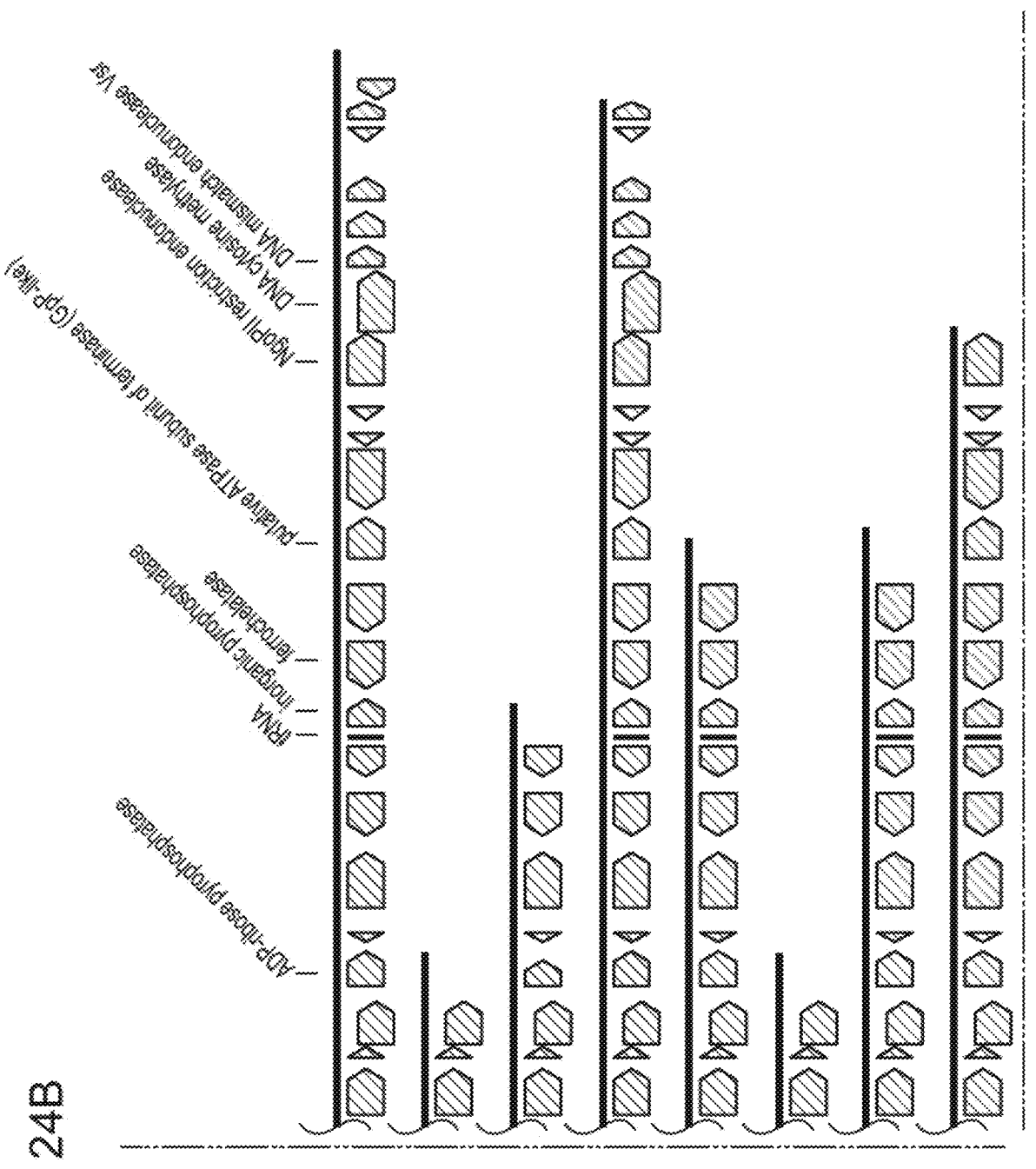
FIG. 24B, Proposed evolutionary scenario that gave rise to the archaeal type II system as a result of a recombination between type II-B and type II-C loci.
Figure 24C:
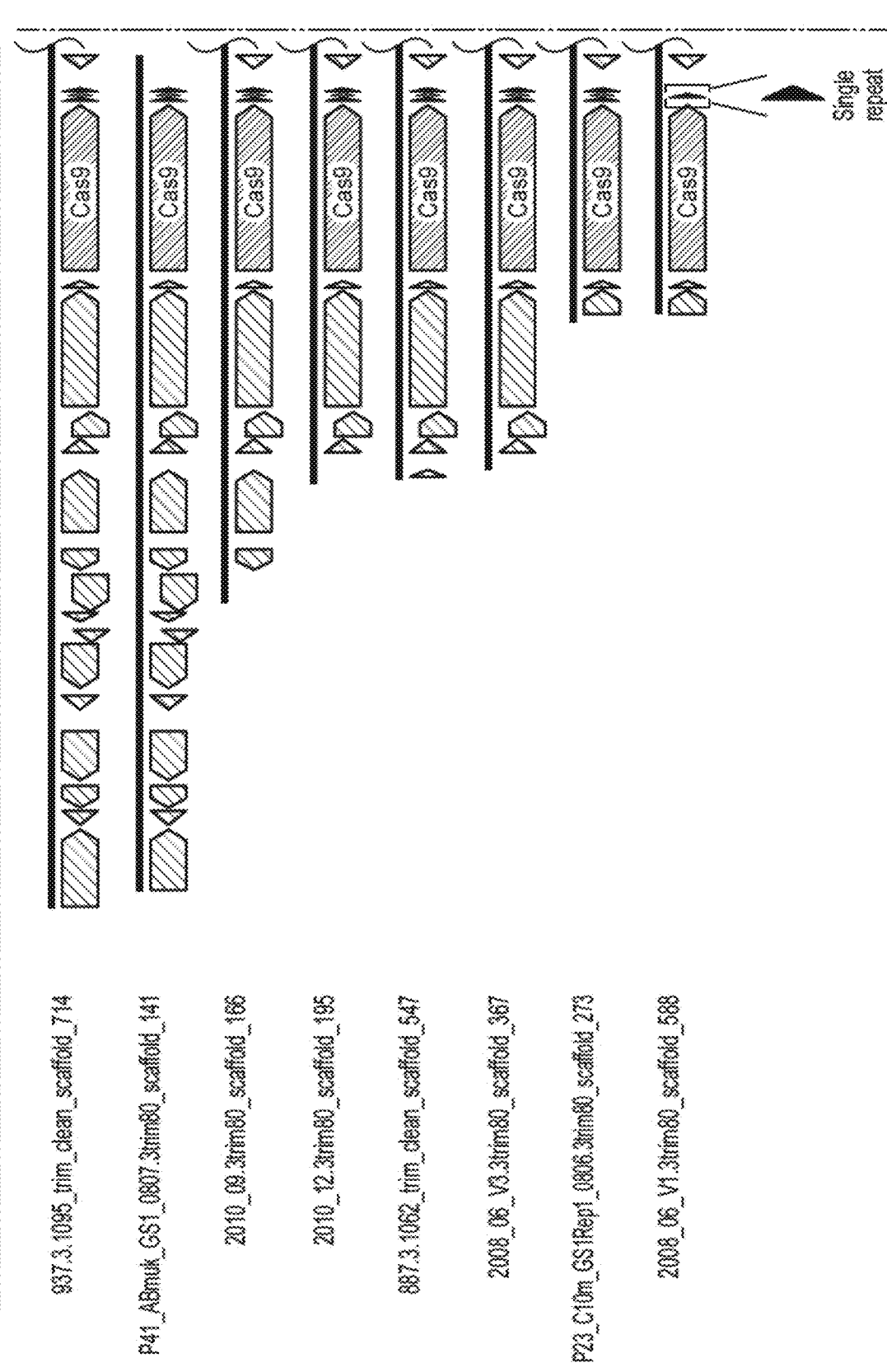
Figure 24D:
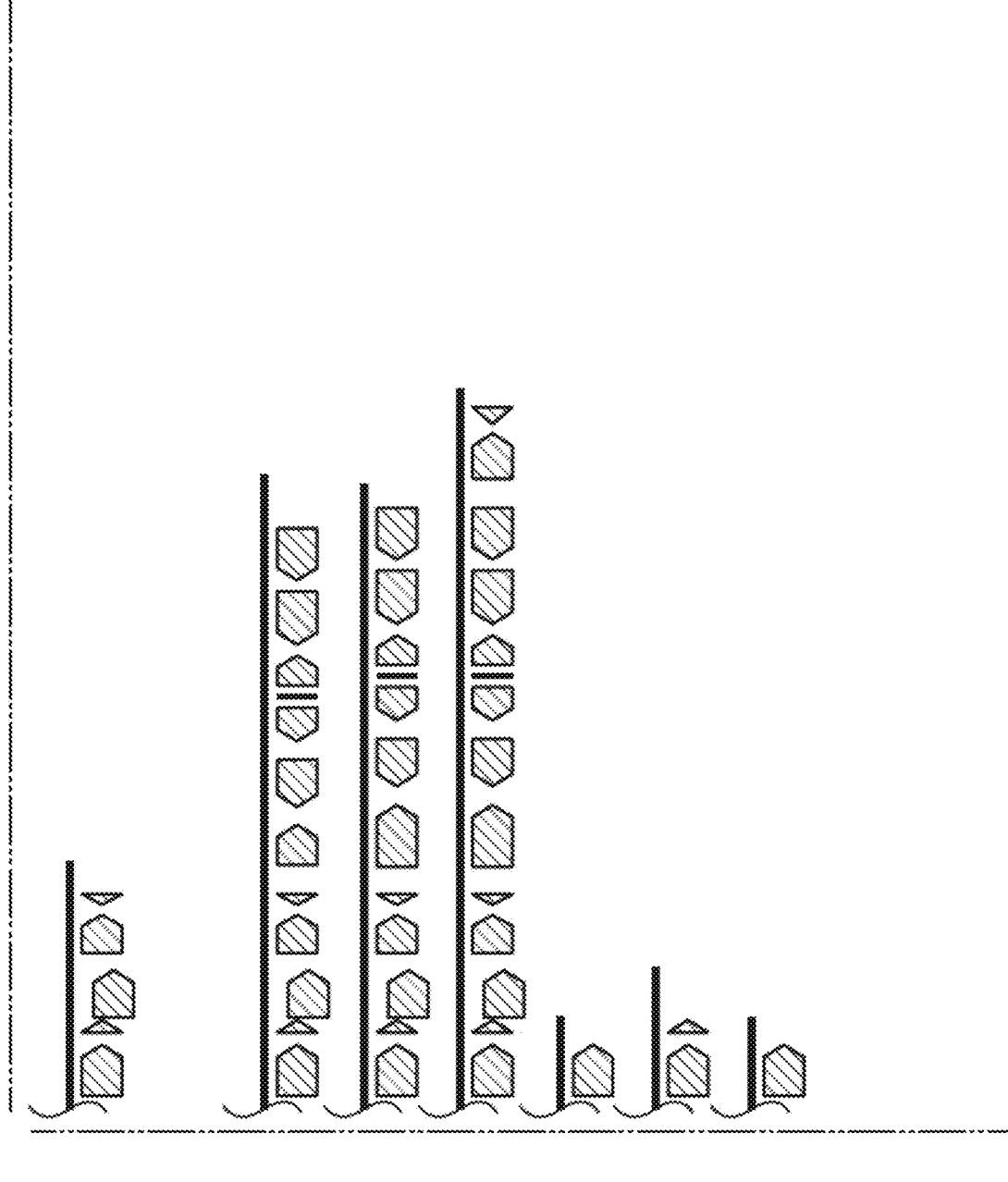
Figure 25A:
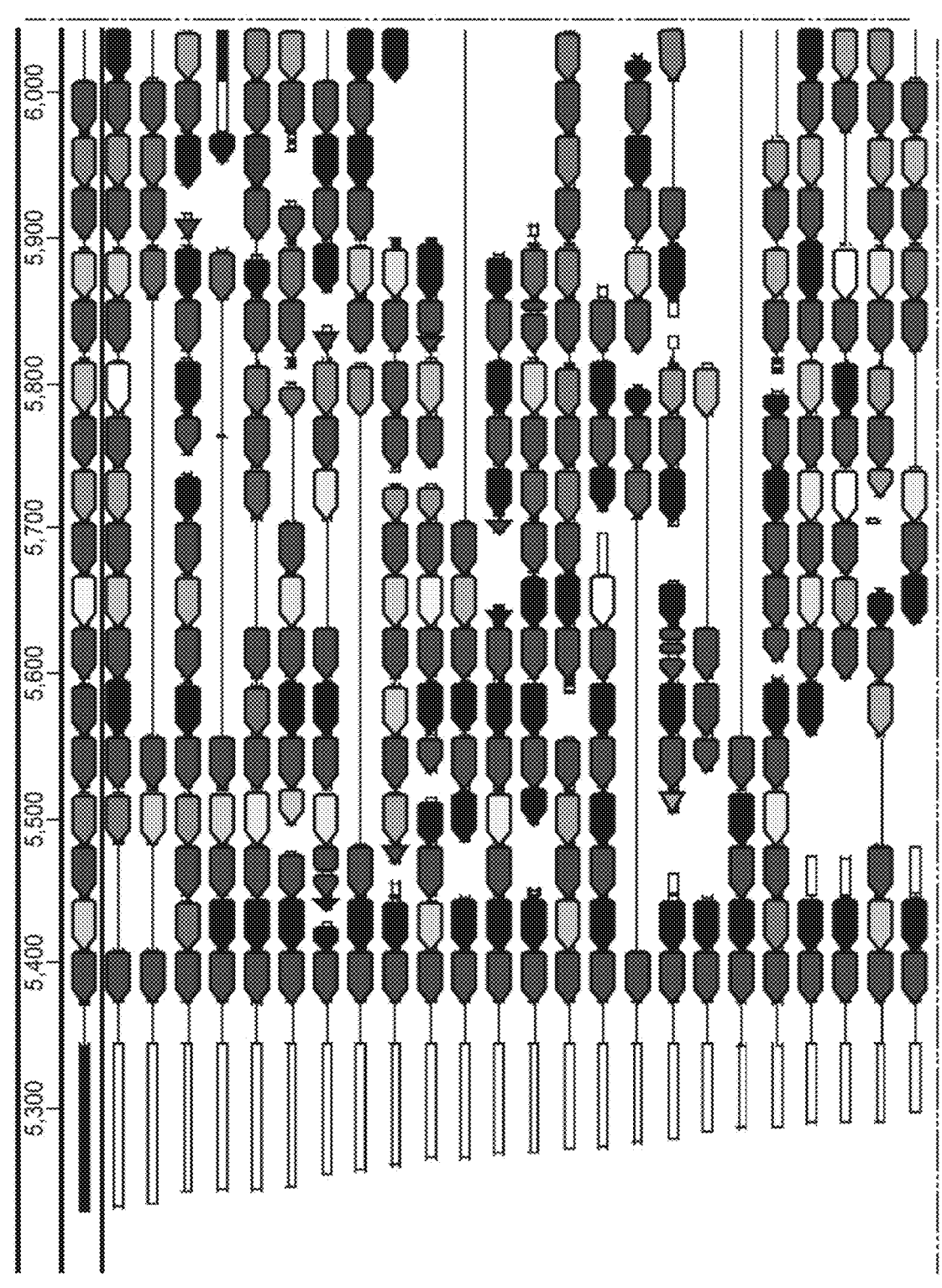
Figure 25B:
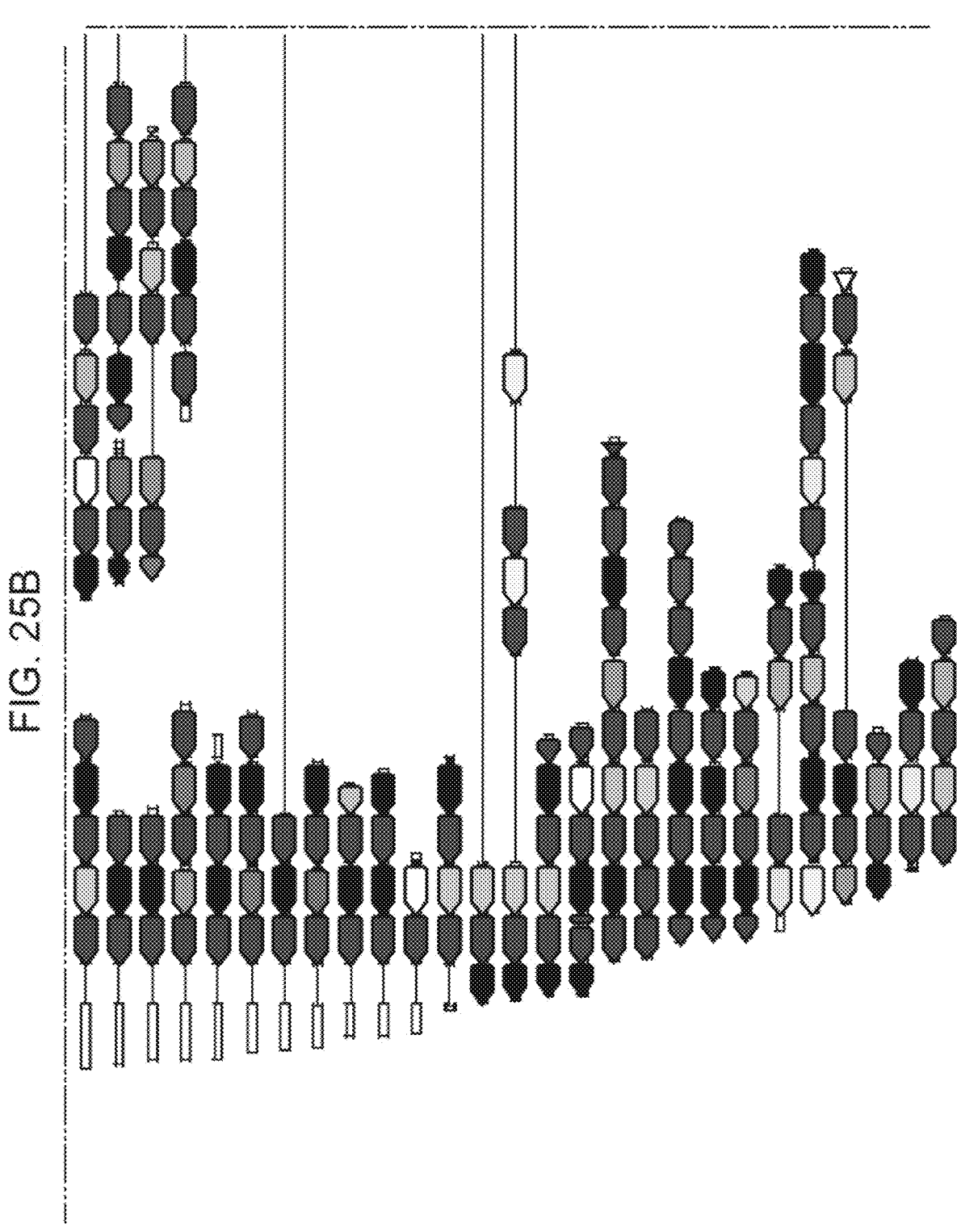
Figure 25C:
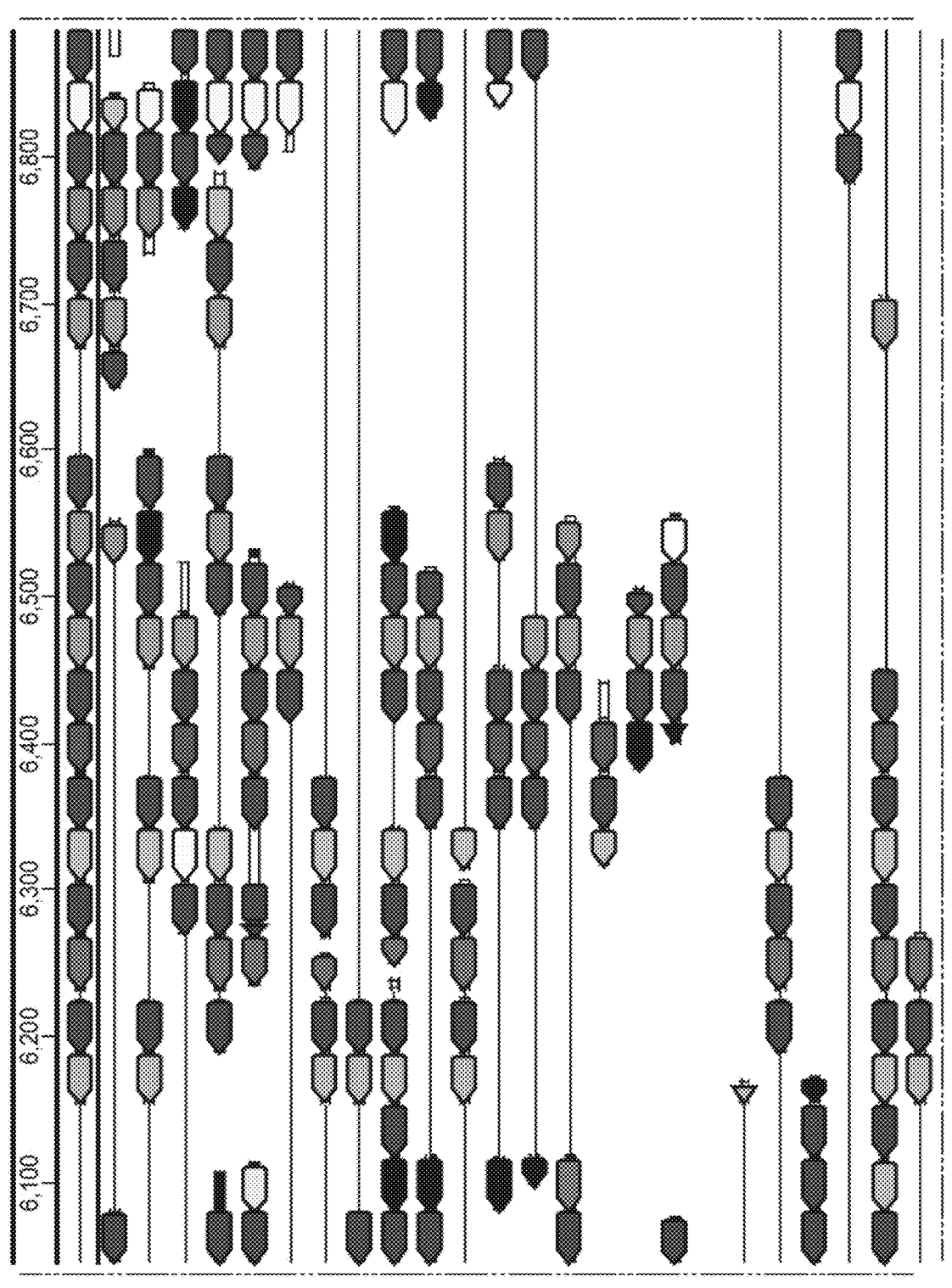
Figure 25D:
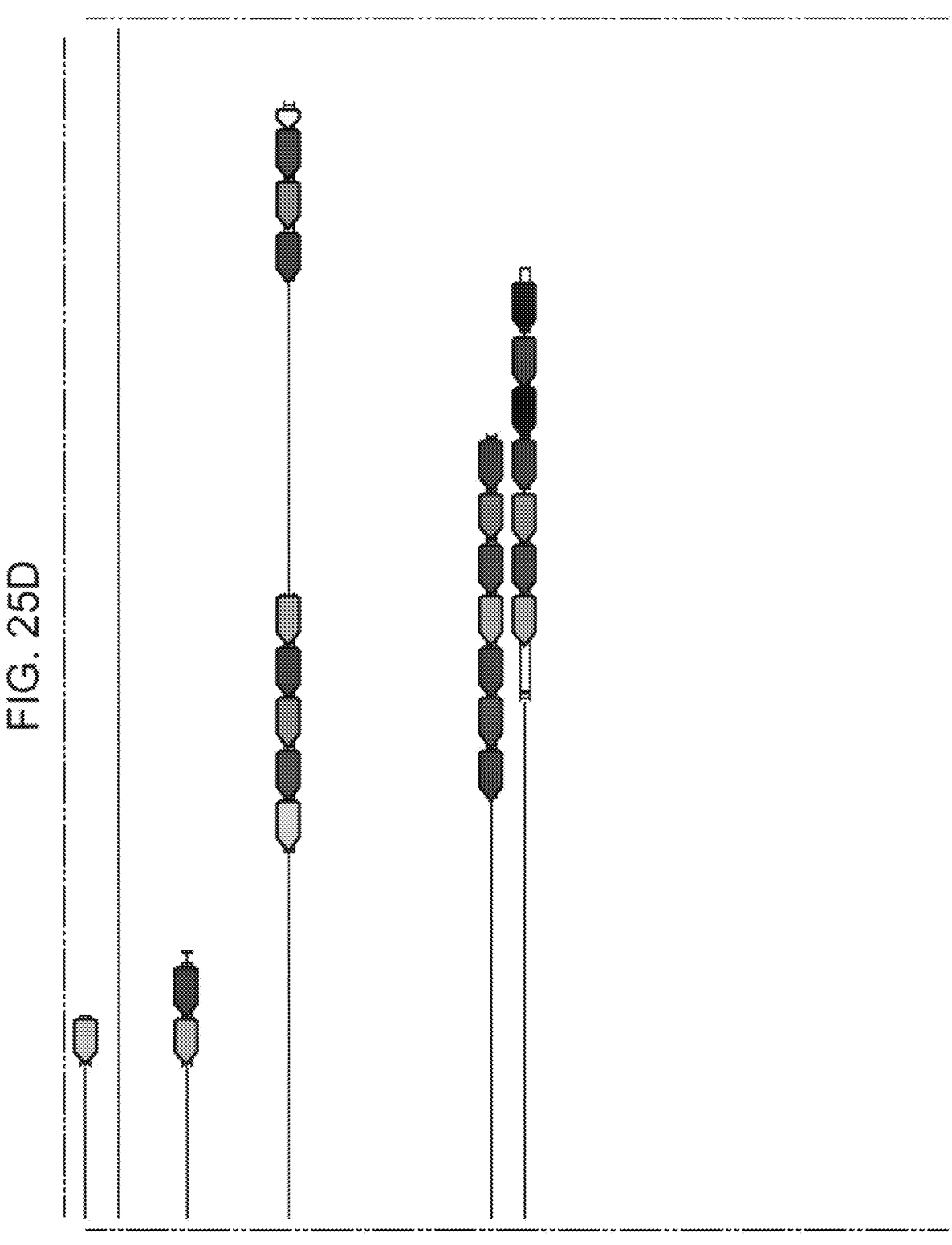
Figure 25F:
Figures 26A, 26B:
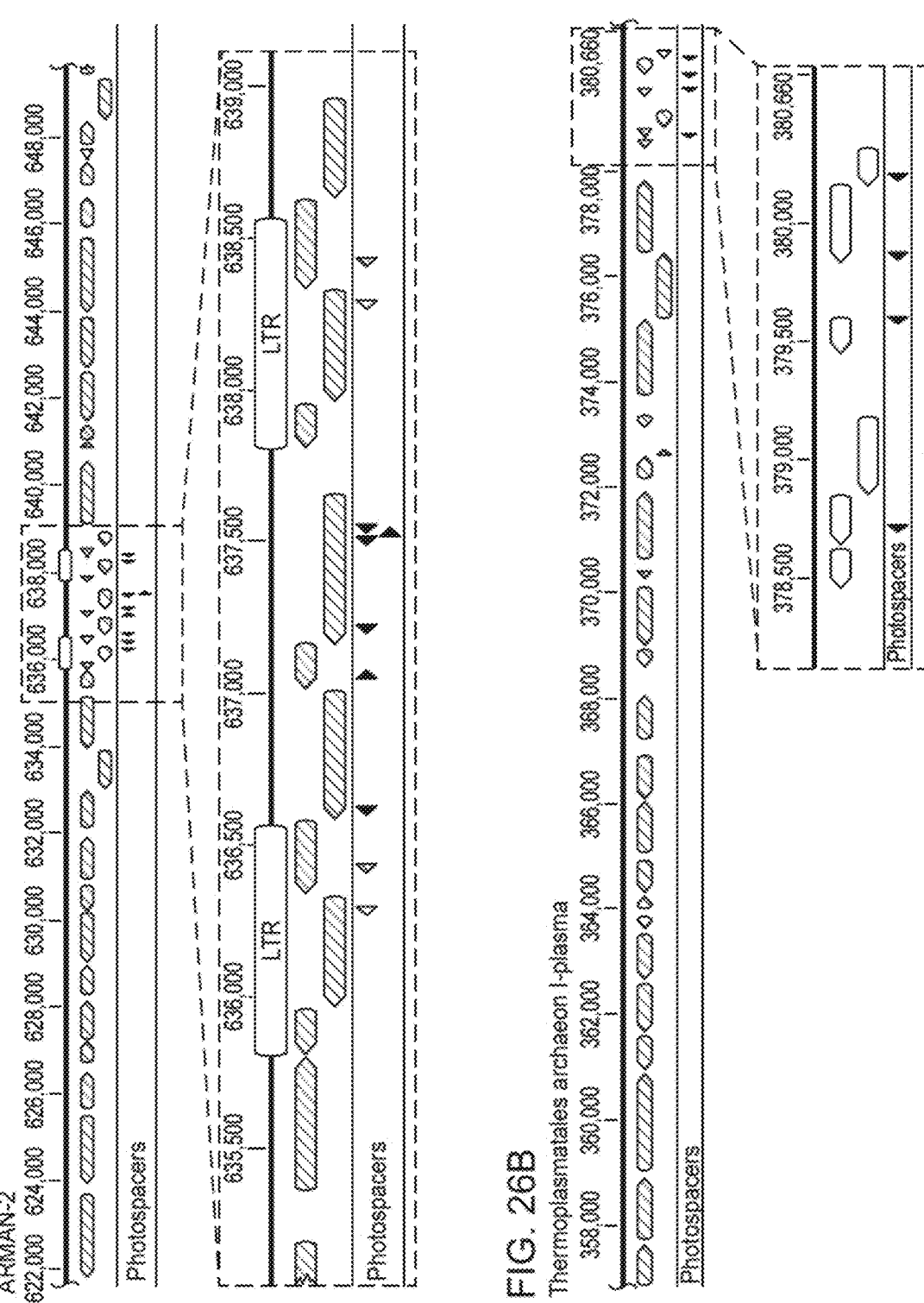
FIGS. 26A-26B show that ARMAN-1 spacers map to genomes of archaeal community members.

New class 2 CRISPR-Cas adaptive immune systems in genomes from uncultivated bacteria and archaea were identified and characterized. Evolutionary analysis of Cas1 (FIG. 23A), which is universal to active CRISPR loci, suggested that the archaeal Cas9 system described here does not clearly fall into any existing type II subtype. The Cas1 phylogeny (as well as the existence of cas4) clustered it together with type II-B systems, yet the sequence of Cas9 was more similar to type II-C proteins (FIG. 31). Thus, the archaeal type II system may have arisen as a fusion of type II-C and II-B systems (FIG. 23B). Likewise, Cas1 phylogenetic analyses indicated that the Cas1 from the CRISPR-CasX system is distant from any other known type V system. Type V systems have been suggested to be the result of the fusion of a transposon with the adaptation module (Cas1-Cas2) from an ancestral type I system. It is therefore hypothesized that the CRISPR-CasX system emerged following a fusion event different from those that gave rise to the previously described type V systems. Strikingly, both CRISPR-CasY and the putative C2c3 systems seem to lack Cas2, a protein thought to be essential for integrating DNA into the CRISPR locus. Given that all CRISPR-Cas systems are thought be descendants of an ancestral type I system that contained both Cas1 and Cas2, CRISPR-CasY and C2c3 systems may either have different ancestry than the rest of the CRISPR-Cas systems, or alternatively, Cas2 might have been lost during their evolutionary history.

The discovery described herein of Cas9 in archaea and two previously unknown CRISPR-Cas systems in bacteria used extensive DNA and RNA sequence datasets obtained from complex natural microbial communities. In the case of CasX and CasY, genome context was critical to prediction of functions that would not have been evident from unassembled sequence information. Further, the identification of a putative tracrRNA as well as targeted viral sequences uncovered through analysis of the metagenomic data guided functional testing. Interestingly, some of the most compact CRISPR-Cas loci identified to date were discovered in organisms with very small genomes. A consequence of small genome size is that these organisms likely depend on other community members for basic metabolic requirements, and thus they have remained largely outside the scope of traditional cultivation-based methods. The limited number of proteins that are required for interference make these minimal systems especially valuable for the development of new genome editing tools. Importantly, it is shown herein that metagenomic discoveries related to CRISPR-Cas systems are not restricted to in silico observations, but can be introduced into an experimental setting where their function can be tested. Given that virtually all environments where life exists can now be probed by genome-resolved metagenomic methods, it is anticipated that the combined computational-experimental approach described herein will greatly expand the diversity of known CRISPR-Cas systems, providing new technologies for biological research and clinical applications.

Methods

Metagenomics and Metatranscriptomics

Metagenomic samples from three different sites were analyzed: (1) Acid mine drainage (AMD) samples collected between 2006 and 2010 from the Richmond Mine, Iron Mountain, California (2) Groundwater and sediment samples collected between 2007 and 2013 from the Rifle Integrated Field Research (IFRC) site, adjacent to the Colorado River near Rifle, Colorado. (3) Groundwater collected in 2009 and 2014 from Crystal Geyser, a cold, $CO_2$-driven geyser on the Colorado Plateau in Utah.

For the AMD data, DNA extraction methods and short read sequencing were reported by Denef and Banfield (2012) and Miller et al. (2011). For the Rifle data, DNA and RNA extraction, as well as sequencing, assembly, and genomic reconstructed were described by Anantharaman et al. (2016) and Brown et al. (2015). For samples from Crystal Geyser, methods follow those described by Probst et al (2016) and Emerson et al. (2015). Briefly, DNA was extracted from samples using the PowerSoil DNA Isolation Kit (MoBio Laboratories Inc., Carlsbad, CA, USA). RNA was extracted from 0.2 m filters collected from six 2011 Rifle groundwater samples, as described by Brown et al. (2015). DNA was sequenced on Illumina HiSeq2000 platform, and Metatranscriptomic cDNA on 5500XL SOLiD platform. For the newly reported Crystal Geyser data and reanalysis of the AMD data, sequences were assembled using IDBA-UD. DNA and RNA (cDNA) read-mapping used to determine sequencing coverage and gene expression, respectively, was performed using Bowtie2. Open reading frames (ORFs) were predicted on assembled scaffolds using Prodigal. Scaffolds from the Crystal Geyser dataset were binned on the basis of differential coverage abundance patterns using a combination of ABAWACA, ABAWACA2 (www(dot)github(dot)com/CK7) Maxbin2, and tetranucleotide frequency using Emergent Self-Organizing Maps (ESOM). Genomes were manually curated using % GC content, taxonomic affiliation, and genome completeness.

Scaffolding errors were corrected using ra2.py (www(dot) github(dot)com/christophertbrown).

CRISPR-Cas Computation Analysis

The assembled contigs from the various samples were scanned for known Cas proteins using Hidden Markov Model (HMMs) profiles, which were built using the HMMer suite, based on alignments from Makarova et al. and Shmakov et al. CRISPR arrays were identified using a local version of the CrisprFinder software. Loci that contained both Cas1 and a CRISPR array were further analyzed if one of the ten ORFs adjacent to the cas1 gene encoded for an uncharacterized protein larger than 800 aa, and no known cas interference genes were identified on the same contig. These large proteins were further analyzed as potential class 2 Cas effectors. The potential effectors were clustered to protein families based on sequence similarities using MCL. These protein families were expanded by building HMMs representing each of these families, and using them to search the metagenomic datasets for similar Cas proteins. To make sure that the protein families are indeed new, known homologs were searched using BLAST against NCBI's non-redundant (nr) and metagenomic (env_nr) protein databases, as well as HMM searches against the UniProt KnowledgeBase. Only proteins with no full-length hits (>25% of the protein's length) were considered novel proteins. Distant homology searches of the putative Cas proteins were performed using HHpred from the HH-suite. High scoring HHpred hits were used to infer domain architecture based on comparison to resolved crystal structures, and secondary structure that was predicted by JPred4. The HMM database, including the newly discovered Cas proteins are available in Supplementary Data 1.

Spacer sequences were determined from the assembled data using CrisprFinder. CRASS was used to locate additional spacers in short DNA reads of the relevant samples. Spacer targets (protospacers) were then identified by BLAST searches (using "-task blastn-short") against the relevant metagenomic assemblies for hits with <1 mismatch to spacers. Hits belonging to contigs that contained an associated repeat were filtered out (to avoid identifying CRISPR arrays as protospacers). Protospacer adjacent motifs (PAMs) were identified by aligning regions flanking the protospacers and visualized using WebLogo. RNA structures were predicted using mFold. CRISPR array diversity was analyzed by manually aligning spacers, repeats and flanking sequences from the assembled data. Manual alignments and contig visualizations were performed with Geneious 9.1.

For the phylogenetic analyses of Cas1 and Cas9 proteins of the newly identified systems were used along with the proteins from Makarova et al. and Shmakov et al. A non-redundant set was compiled by clustering together proteins with >90% identity using CD-HIT. Alignments were produced with MAFFT, and maximum-likelihood phylogenies were constructed using RAxML with PROTGAMMALG as the substitution model and 100 bootstrap samplings. Cas1 tree were rooted using the branch leading to casposons. Trees were visualized using FigTree 1.4.1 (wwwtree(dot) bio(dot)ed(dot)ac(dot)uk/software/figtree/) and iTOL v3.

Generation of Heterologous Plasmids

Metagenomic contigs were made into minimal CRISPR interference plasmids by removing proteins associated with acquisition for CasX and reducing the size of the CRISPR array for both CasX and CasY. The minimal locus was synthesized as Gblocks (Integrated DNA Technology) and assembled using Gibson Assembly.

PAM Depletion Assay

PAM depletion assays were conducted as previously described with modification. Plasmid libraries containing randomized PAM sequences were assembled by annealing a DNA oligonucleotide containing a target with a 7 nt randomized PAM region with a primer and extended with Klenow Fragment (NEB). The double stranded DNA was digested with EcoRI and NcoI and ligated into a pUC19 backbone. The ligated library was transformed into DH5α and >$10^8$ cells were harvested and the plasmids extracted and purified. 200 ng of the pooled library was transformed into electrocompetent E. coli harboring a CRISPR locus or a control plasmid with no locus. The transformed cells were plated on selective media containing carbenicillin (100 mg $L^{-1}$) and chloramphenicol (30 mg $L^{-1}$) for 30 hours at 25° C. Plasmid DNA was extracted and the PAM sequence was amplified with adapters for Illumina sequencing. The 7 nt PAM region was extracted and PAM frequencies calculated for each 7 nt sequence. PAM sequences depleted above the specified threshold were used to generate a WebLogo.

Plasmid Interference

Putative targets identified from metagenomic sequence analysis or PAM depletion assays were cloned into a pUC19 plasmid. 10 ng of target plasmid were transformed into electrocompetent E. coli (NEB Stable) containing the CRISPR loci plasmid. Cells were recovered for 2 hrs at 25° C. and an appropriate dilution was plated on selective media. Plates were incubated at 25° C. and colony forming units were counted. All plasmid interference experiments were performed in triplicate and electrocompetent cells were prepared independently for each replicate.

ARMAN-Cas9 Protein Expression and Purification

Expression constructs for Cas9 from ARMAN-1 (AR1) and ARMAN-4 (AR4) were assembled from gBlocks (Integrated DNA Technologies) that were codon-optimized for E. coli. The assembled genes were cloned into a pET-based expression vector as an N-terminal $His_6$-MBP or $His_6$ fusion protein. Expression vectors were transformed into BL21 (DE3) E. coli cells and grown in LB broth at 37° C. For protein expression, cells were induced during mid-log phase with 0.4 mM IPTG (isopropyl β-D-1-thiogalactopyranoside) and incubated overnight at 16° C. All subsequent steps were conducted at 4° C. Cell pellets were resuspended in lysis buffer (50 mM Tris-HCl pH 8, 500 mM NaCl, 1 mM TCEP, 10 mM Imidazole) 0.5% Triton X-100 and supplemented with Complete protease inhibitor mixture (Roche) before lysis by sonication. Lysate was clarified by centrifugation at 15000 g for 40 min and applied to Superflow Ni-NTA agarose (Qiagen) in batch. The resin was washed with extensively with Wash Buffer A (50 mM Tris-HCl pH 8, 500 mM NaCl, 1 mM TCEP, 10 mM Imidazole) followed by 5 column volumes of Wash Buffer B (50 mM Tris-HCl pH 8, IM NaCl, 1 mM TCEP, 10 mM Imidazole). Protein was eluted off of Ni-NTA resin with Elution Buffer (50 mM Tris-HCl pH 8, 500 mM NaCl, 1 mM TCEP, 300 mM Imidazole). The $His_6$-MBP tag was removed by TEV protease during overnight dialysis against Wash Buffer A. Cleaved Cas9 was removed from the affinity tag through a second Ni-NTA agarose column. The protein was dialyzed into IEX Buffer A (50 mM Tris-HCl pH 7.5, 300 mM NaCl, 1 mM TCEP, 5% glycerol) before application to a 5 mL Heparin HiTrap column (GE Life Sciences). Cas9 was eluted over a linear NaCl (0.3-1.5 M) gradient. Fractions were pooled and concentrated with a 30 kDa spin concentrator (Thermo Fisher). When applicable, Cas9 was further purified via size-exclusion chromatography on an Superdex 200 pg column (GE Life Sciences) and stored in IEX Buffer A for subsequent cleavage assays. For yeast expression, AR1-Cas9 was cloned into a GalI/10 His6-MBP TEV Ura *S. cerevisiae* expression vector (Addgene plasmid #48305). The vector was transformed into a BY4741 URA3 strain and cultures were grown in MEDIA at 30° C. At an OD600 of ~0.6, protein expression was induced with 2% w/v galactose and incubated overnight at 16° C. Protein purification was performed as above.

RNA In Vitro Transcription and Oligonucleotide Purification

In vitro transcription reactions were performed as previously described[65] using synthetic DNA templates containing a T7 promoter sequence. All in vitro transcribed guide RNAs and target RNAs or DNAs were purified via denaturing PAGE. Double-stranded target RNAs and DNAs were hybridized in 20 mM Tris HCl pH 7.5 and 100 mM NaCl by incubation at 95° C. for 1 min, followed by slow-cooling to room temperature. Hybrids were purified by native PAGE.

In Vitro Cleavage Assays

Purified DNA and RNA oligonucleotides were radiolabeled using T4 polynucleotide kinase (NEB) and [γ-32P] ATP (Perkin-Elmer) in 1×PNK buffer for 30 min at 37° C. PNK was heat inactivated at 65° C. for 20 min and free ATP was removed from the labeling reactions using illustra Microspin G-25 columns (GE Life Sciences). CrRNA and tracrRNAs were mixed in equimolar quantities in 1× refolding buffer (50 mM Tris HCl pH 7.5, 300 mM NaCl, 1 mM TCEP, 5% glycerol) and incubated at 70° C. for 5 min and then slow-cooled to room temperature. The reactions were supplemented to 1 mM final metal concentration and subsequently heated at 50° C. for 5 min. After slow-cooling to room temperature, refolded guides were placed on ice. Unless noted for buffer, salt concentration, Cas9 was reconstituted with an equimolar amount of guide in 1× cleavage buffer (50 mM Tris HCl pH 7.5, 300 mM NaCl, 1 mM TCEP, 5% glycerol, 5 mM divalent metal) at 37° C. for 10 min. Cleavage reactions were conducted in 1× cleavage buffer with a 10× excess of Cas9-guide complex over radiolabeled target at 37° C. or the indicated temperature. Reactions were quenched in an equal volume of gel loading buffer supplemented with 50 mM EDTA. Cleavage products were resolved on 10% denaturing PAGE and visualized by phosphorimaging.

In Vivo *E. coli* Interference Assays

*E. coli* transformation assays for AR1- and AR4-Cas9 were conducted as previously published. Briefly, *E. coli* transformed with guide RNAs were made electrocompetent. Cells were then transformed with 9 fmol of plasmid encoding wild-type or catalytically inactive Cas9 (dCas9). A dilution series of recovered cells was plated on LB plates with selective antibiotics. Colonies were counted after 16 hr at 37° C.

TABLE 1

Details regarding the organisms and genomic location in which the CRISPR-Cas system were identified, as well as information on the number and average length of reconstructed spacers, and repeats length (NA, not available). ARMAN-1 spacers were reconstructed from 16 samples.

| Taxonomic group | Cas effector | NCBI Accession | Coordinates | Repeat length | # spacers | Spacers avg. length |
|---|---|---|---|---|---|---|
| ARMAN-1 | Cas9 | MOEG01000017 | 1827 . . . 7130 | 36 | 271 | 34.5 |
| ARMAN-4 | Cas9 | KY040241 | 11779 . . . 14900 | 36 | 1 | 36 |
| Deltaproteobacteria | CasX | MGPG01000094 | 4319 . . . 9866 | 37 | 5 | 33.6 |
| Planctomycetes | CasX | MHYZ01000150 | 1 . . . 5586 | 37 | 7 | 32.3 |
| Candidatus Katanobacteria | CasY.1 | MOEH01000029 | 459 . . . 5716 | 26 | 14 | 17.1 |
| Candidatus Vogelbacteria | CasY.2 | MOEJ01000028 | 7322 . . . 13087 | 26 | 18 | 17.3 |
| Candidatus Vogelbacteria | CasY.3 | MOEK01000006 | 1 . . . 4657 | 26 | 12 | 17.3 |
| Candidatus Parcubacteria | CasY.4 | KY040242 | 1 . . . 5193 | 25 | 13 | 18.4 |
| Candidatus Komeilibacteria | CasY.5 | MOEI01000022 | 2802 . . . 7242 | 36 | 8 | 26 |
| Candidatus Kerfeldbacteria | CasY.6 | MHKD01000036 | 11503 . . . 15366 | NA | NA | NA |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of modulating transcription from a target DNA, modifying a target DNA, or modifying a protein associated with a target DNA, the method comprising contacting the target DNA with:
    a) a CasX fusion polypeptide comprising a CasX polypeptide fused to a heterologous polypeptide; and
    b) a CasX guide RNA comprising a guide sequence that hybridizes to a target sequence of the target DNA and binds the CasX fusion polypeptide,
    (i) wherein the method is for modifying the target DNA and wherein modifying the target DNA comprises cleavage of the target DNA and wherein the heterologous polypeptide is a nuclease, or
    (ii) wherein the method is for modulating transcription from the target DNA,
        wherein modulating transcription comprises increasing transcription and the heterologous polypeptide is a transcriptional activator, or
        wherein modulating transcription comprises decreasing transcription and the heterologous polypeptide is a transcriptional repressor, or
    (iii) wherein the method is for modifying histone associated with the target DNA and wherein the heterologous polypeptide is a histone methyltransferase, a histone demethylase, a histone acetylase transferase, or a histone deacetylase.

2. The method of claim 1, wherein the CasX guide RNA is a single guide RNA.

3. The method of claim 1, wherein the CasX guide RNA is a dual guide RNA.

4. The method of claim 1, wherein the method is for modifying the target DNA and wherein modifying the target DNA comprises cleavage of the target DNA and wherein the heterologous polypeptide is a nuclease.

5. The method of claim 1, wherein the target DNA is double stranded DNA, single stranded DNA, genomic DNA, or extrachromosomal DNA.

6. The method of claim 1, wherein said contacting takes place in vitro outside of a cell.

7. The method of claim 1, wherein said contacting takes place inside of a cell in culture.

8. The method of claim 1, wherein said contacting takes place inside of a cell in vivo.

9. The method of claim 7, wherein the cell is a eukaryotic cell.

10. The method of claim 1, wherein said contacting comprises: introducing into a cell: (a) the CasX fusion polypeptide, or a nucleic acid molecule encoding the CasX fusion polypeptide, and (b) the CasX guide RNA, or a nucleic acid molecule encoding the CasX guide RNA.

11. The method of claim 10, wherein said contacting further comprises: introducing a DNA donor template into the cell.

12. The method of claim 1, wherein the CasX guide RNA comprises one or more of: (i) a non-natural internucleoside linkage selected from a phosphorothioate, an inverted polarity linkage, and an abasic nucleoside linkage; (ii) a locked nucleic acid (LNA); and (iii) a modified sugar moiety selected from 2'-O-methoxyethyl, 2'-O-methyl, and 2'-fluoro.

13. The method of claim 1, wherein the CasX polypeptide is a catalytically inactive CasX Polypeptide (dCasX).

14. The method of claim 1, wherein the CasX polypeptide comprises one or more mutations at a position corresponding to those selected from: D672, E769, and D935 of SEQ ID NO: 1.

15. The method of claim 1, wherein the CasX polypeptide comprises an amino acid sequence having at least 95% identity to the amino acid sequence set forth in SEQ ID NO:1.

16. The method of claim 1, wherein the CasX polypeptide comprises an amino acid sequence having at least 95% identity to the amino acid sequence set forth in SEQ ID NO:2.

17. The method of claim 1, wherein the CasX polypeptide comprises one or more nuclear localization signal (NLS).

18. The method of claim 1, wherein the method is for modulating transcription from the target DNA, wherein modulating transcription comprises increasing transcription and the heterologous polypeptide is a transcriptional activator, or wherein modulating transcription comprises decreasing transcription and the heterologous polypeptide is a transcriptional repressor.

19. The method of claim 1, wherein the method is for modifying histone associated with the target DNA and wherein the heterologous polypeptide is a histone methyltransferase, a histone demethylase, a histone acetylase transferase, or a histone deacetylase.

20. The method of claim 4, wherein the CasX polypeptide is a catalytically inactive CasX polypeptide (dCasX) comprising one or more mutations at a position corresponding to those selected from: D672, E769, and D935 of SEQ ID NO: 1.

21. The method of claim 18, wherein modulating transcription comprises increasing transcription, the heterologous polypeptide is a transcriptional activator, and the transcriptional activator is VP16, VP64, VP48, or VP160.

22. The method of claim 18, wherein modulating transcription comprises decreasing transcription, the heterologous polypeptide is a transcriptional repressor, and the transcriptional repressor is DNA methyltransferase 1 (DNMT1), DNA methyltransferase 3a (DNMT3a), DNA methyltransferase 3b (DNMT3b), or Krüppel associated box (KRAB).

* * * * *